United States Patent
Witter et al.

(10) Patent No.: US 7,064,122 B2
(45) Date of Patent: Jun. 20, 2006

(54) PANCREATIC LIPASE INHIBITOR COMPOUNDS, THEIR SYNTHESIS AND USE

(75) Inventors: David Witter, Putnam Valley, NY (US); Arlindo Castelhano, New City, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 48 days.

(21) Appl. No.: 10/326,302

(22) Filed: Dec. 20, 2002

(65) Prior Publication Data

US 2003/0195199 A1 Oct. 16, 2003

Related U.S. Application Data

(60) Provisional application No. 60/342,617, filed on Dec. 20, 2001, and provisional application No. 60/357,015, filed on Feb. 13, 2002.

(51) Int. Cl.
*C07D 498/04* (2006.01)
*A61K 31/5365* (2006.01)
*A61K 1/18* (2006.01)
*A61K 3/10* (2006.01)

(52) U.S. Cl. .................. 514/230.5; 544/91; 544/48; 206/570; 549/68

(58) Field of Classification Search ............. 514/230.5; 544/91; 206/570

See application file for complete search history.

(56) References Cited

U.S. PATENT DOCUMENTS

| 4,598,089 A | | 7/1986 | Hadvary et al. |
| 4,760,063 A | * | 7/1988 | Hallenbach et al. ..... 514/230.5 |
| 5,422,335 A | | 6/1995 | Hagen et al. |
| 6,037,340 A | | 3/2000 | Castelhano et al. |

FOREIGN PATENT DOCUMENTS

| EP | 0129748 | 1/1985 |
| WO | WO9619482 | 6/1996 |
| WO | WO9727200 | 7/1997 |
| WO | WO9748707 | 12/1997 |
| WO | WO9845298 | 10/1998 |
| WO | WO9854192 | 12/1998 |
| WO | WO0030646 | 6/2000 |
| WO | WO0040247 | 7/2000 |
| WO | WO0040569 | 7/2000 |
| WO | WO0320282 | 3/2003 |

OTHER PUBLICATIONS

Gutschow et al. {J. Med. Chem. (1999) 42:5437–5447}.*
Gutschow, M. et al. "2–(Diethylamino)thieno[1,3]oxazin–4–ones as Stable Inhibitors of Human Leukocyte Elastase" *J. Med. Chem.* (1999) 42: 5437–5447 (Exhibit 2).

McKibben, B.P. et al., "Practical Synthesis of Tetrasubstituted Thiophenes for Use in Compound Libraries" *Terrahedron Lett.* (1999) 40: 5471–5474 (Exhibit 13).

Yoshisuke, T. et al., *Chem. Pharm. Bull.* (1991) 39(1): 18–22 (Exhibit 14).

Tinney, F.J. et al., "Synthesis and antiallergy activity of 4–oxo–4H–pyrido[1,2–a]thieno[2,3–d]pyrimidines" *J. Med. Chem.* (1981) 24: 878–882 (Exhibit 15).

Hadvary, P. et al., "Inhibition of pancreatic lipase in vitro by the covalent inhibitor tetrahydrolipstatin" *Biochem. J.* (1988) 256: 357–361 (Exhibit 16).

Hadvary, P. et al., "Inhibition of pancreatic lipase in vitro by the covalent inhibitor tetrahydrolipstatin" *Biochem. J.* (1988) 256: 357–361 (Exhibit 17).

(Continued)

*Primary Examiner*—Mark L. Berch
*Assistant Examiner*—Kahsay Habte
(74) *Attorney, Agent, or Firm*—John P. White, Esq.; Cooper & Dunham LLP

(57) ABSTRACT

The subject invention features compounds having the structure:

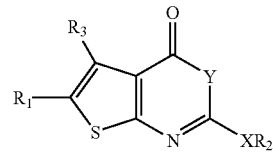

wherein X is O, S, $CH_2$ or $NR_5$; Y is O or S; $R_1$ is H, substituted or unsubstituted $C_1$–$C_{15}$ alkyl, $C_1$–$C_8$ alkylaryl, —$C(O)OR_4$, —$C(O)NR_4R_5$, —$CR_6R_6OR_4$, —$CR_6R_6OC(O)R_4$, —$CR_6R_6OC(O)NHR_7$, —$C(O)NR_{10}R_{11}$, —$C(O)NR_8R_9NR_8R_9$, —$N(R_5)C(O)NHR_5$, or $CH_2R_4$; $R_2$ is a substituted or unsubstituted, straight chain $C_1$—$C_{30}$ alkyl or branched $C_3$–$C_{30}$ alkyl, aryl, alkylaryl, arylalkyl, heteroarylalkyl or cycloalkyl; $R_3$ is H or substituted or unsubstituted $C_1$–$C_6$ alkyl or $C_3$–$C_{10}$ cycloalkyl; $R_4$ is H or a substituted or unsubstituted, straight chain or branched, $C_6$–$C_{30}$ alkyl, aryl, —$CH_2$-aryl, aryl —$C_1$–$C_{15}$ alkyl, heteroaryl-$C_1$–$C_{15}$alkyl or $C_3$–$C_{10}$ cycloalkyl; $R_5$ is H or a substituted or unsubstituted, straight chain or branched, $C_6$–$C_{30}$ alkyl, aryl $C_1$–$C_{30}$alkyl, heteroarylalkyl or cycloalkyl; $R_6$ and $R_{6'}$ are each independently H, substituted or unsubstituted $C_1$–$C_6$ alkyl, dialkyl or $C_3$–$C_{10}$ cycloalkyl or together form a 3–7 membered ring system; $R_7$ is H or substituted or unsubstituted $C_1$–$C_{12}$ alkyl or $C_3$–$C_{10}$ cycloalkyl; $R_8$ and $R_9$ are each independently H, substituted or unsubstituted $C_1$–$C_6$ alkyl, $C_1$–$C_6$ alkoxy, $C_1$–$C_6$ alkylaryl, or $NR_8R_9$ together form a substituted piperazine or piperidine ring or a dihydro-1H-isoquinoline ring system, or a specific enantiomer thereof, or a specific tautomer, or a pharmaceutically acceptable salt thereof and a method for treating diabetes or obesity by administering a therapeutically effective amount of the compounds of the invention.

27 Claims, No Drawings

OTHER PUBLICATIONS

Gutschow, M. and Neumann, U. "Novel Thieno[2,3–d][1,3]oxazin–4–ones as Inhibitors of Human Leukocyte Elastase" *J. Med. Chem.* (1998) 41(10):1729–1740 (Exhibit 18).

Wang, Z. et al., "A New Approach to the Synthesis of Heteroannulated 3,1–Oxazin–4–ones from β–Enamino Esters and Phosgeneiminium Salts" *Synthesis* (2000) 2: 255–258 (Exhibit 19); and.

Achakzi, D. et al., "Synthesis of Heterocondensed 6H–1,3–Oxazin–6–ones from N–Acylenamino Esters in the System Triphenylphosphane/Hexachloroethane/Triethylamine" *Chem. Ber.* (1981) 1 14(9): 3188–3194 (Exhibit 20).

* cited by examiner

PANCREATIC LIPASE INHIBITOR COMPOUNDS, THEIR SYNTHESIS AND USE

This application claims the benefit of U.S. Provisional Application No. 60/342,617, filed Dec. 20, 2001, and U.S. Provisional Application No. 60/357,015, filed Feb. 13, 2002, the entire contents of which are hereby incorporated by reference.

Throughout this application, various publications are referenced by full citations. The disclosures of these publications in their entireties are hereby incorporated by reference into this application in order to more fully describe the state of the art as known to those skilled therein as of the date of the invention described and claimed herein.

BACKGROUND OF THE INVENTION

During the last 20 years, obesity has become an increasingly common problem in the populations of developed countries. The increased incidence of obesity is partly due to the adoption of a westernised diet in many developed countries—which contains many foods with high fat and low fiber concentrations—and partly due to the lifestyle of westernized society. Obesity is known to increase the risk of contracting disorders such as diabetes, cardiovascular disease and hypertension.

Pharmacological approaches to the treatment of obesity either try to increase the body's energy expenditure, thereby burning more fat, or reduce the body's energy intake. The latter approach has stimulated the development of a variety of drugs which attempt to reduce the body's ability to absorb fat. These drugs target the enzymes responsible for the digestion of fat in the human digestive cycle. The most important enzymes in the digestion of fat are hydrolytic enzymes. The most significant of these enzymes are lipases, pancreatic lipase in particular. Orlistat, a derivative of lipstatin, a lipase inhibitor, is disclosed as an anti-obesity drug in European Patent Application No. EP129748. Other lipase inhibitors are disclosed in PCT International Publication Nos. WO 00/40569 and WO 00/40247, respectively.

SUMMARY OF THE INVENTION

The subject invention provides a compound having the structure:

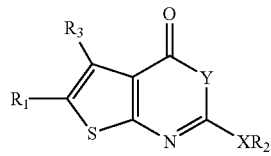

wherein,

X is O, S, $CH_2$ or $NR_5$;

Y is O or S;

$R_1$ is H, substituted or unsubstituted $C_1$–$C_{15}$ alkyl, $C_1$–$C_8$ alkylaryl, —C(O)$OR_4$, —C(O)$NR_4R_5$, —$CR_6R_6OR_4$, —$CR_6R_6OC(O)R_4$, —$CR_6R_6OC(O)NHR_7$, —C(O)$NR_{10}R_{11}$, —C(O)$NR_8R_9NR_8R_9$, —N($R_5$)C(O)$NHR_5$, or $CH_2R_4$;

$R_2$ is a substituted or unsubstituted, straight chain $C_1$–$C_{30}$ alkyl or branched $C_3$–$C_{30}$ alkyl, aryl, alkylaryl, arylalkyl, heteroarylalkyl or cycloalkyl; and $R_3$ is H or substituted or unsubstituted $C_1$–$C_6$ alkyl or $C_3$–$C_{10}$ cycloalkyl, wherein $R_4$ is H or a substituted or unsubstituted, straight chain or branched, $C_6$–$C_{30}$ alkyl, aryl, —$CH_2$-aryl, aryl —$C_1$–$C_{30}$alkyl, heteroaryl-$C_1$–$C_{30}$ alkyl or $C_3$–$C_{10}$ cycloalkyl;

$R_5$ is H or a substituted or unsubstituted, straight chain or branched, $C_6$–$C_{30}$ alkyl, aryl $C_1$–$C_{30}$alkyl, heteroarylalkyl or cycloalkyl;

$R_6$ and $R_{6'}$ are each independently H, substituted or unsubstituted $C_1$–$C_6$ alkyl, dialkyl or $C_3$–$C_{10}$ cycloalkyl or together form a 3–7 membered ring system;

$R_7$ is H or substituted or unsubstituted $C_1$–$C_{12}$ alkyl or $C_3$–$C_{10}$ cycloalkyl; and $R_8$ and $R_9$ are each independently H, substituted or unsubstituted $C_1$–$C_6$ alkyl, $C_1$–$C_6$ alkoxy, $C_1$–$C_6$ alkylaryl, or $NR_8R_9$ together form a substituted piperazine or piperidine ring or a dihydro-1H-isoquinoline ring system, or a specific enantiomer thereof, or a specific tautomer, or a pharmaceutically acceptable salt thereof.

The subject invention also provides a compound having the structure:

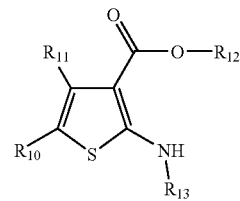

wherein, $R_{10}$ is H or substituted or unsubstituted $C_1$–$C_{15}$ alkyl, $C_1$–$C_{15}$ alkylaryl, or —C(O)$R_{14}$, wherein $R_{14}$ is hydroxyl, or a substituted or unsubstituted $C_1$–$C_{30}$ alkyl, alkylamino, dialkylamino, alkoxy, benzyloxy, cycloalkyl, alkylheteroaryl, alkylaryl, or a heterocyclic, heteroaryl or aryl ring;

$R_{11}$ is hydrogen or methyl;

$R_{12}$ is hydrogen or tert-butyl; and $R_{13}$ is hydrogen or —C(O)$ZR_{15}$, wherein Z is $CH_2$, O or N and $R_{15}$ is substituted or unsubstituted $C_1$–$C_{15}$ alkyl or aryl.

The subject invention also provides a method for treating obesity in a subject in need of such treatment, comprising administering to the subject a therapeutically effective amount of a compound of the invention so as to thereby treat obesity in the subject.

The subject invention also provides a method for treating diabetes in a subject in need of such treatment, comprising administering to the subject a therapeutically effective amount of a compound of the invention so as to thereby treat diabetes in the subject.

The subject invention also provides a method of inhibiting the hydrolytic activity of pancreatic lipase enzymes in a cell, comprising contacting the cell with an amount of a compound of the invention which is effective in inhibiting the hydrolytic activity of pancreatic lipase enzymes.

DETAILED DESCRIPTION

The subject invention provides compounds having the structure:

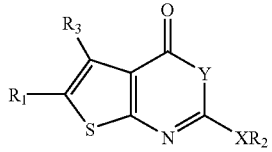

wherein,
X is O, S, CH$_2$ or NR$_5$;
Y is O or S;
R$_1$ is H, substituted or unsubstituted C$_1$–C$_{15}$ alkyl, C$_1$–C$_8$ alkylaryl, —C(O)OR$_4$, —C(O)NR$_4$R$_5$, —CR$_6$R$_6$OR$_4$, —CR$_6$R$_6$OC(O)R$_4$, —CR$_6$R$_6$OC(O)NHR$_7$, —C(O)NR$_{10}$R$_{11}$, —C(O)NR$_8$R$_9$NR$_8$R$_9$, —N(R$_5$)C(O)NHR$_5$, or CH$_2$R$_4$;
R$_2$ is a substituted or unsubstituted, straight chain C$_1$–C$_{30}$ alkyl or branched C$_3$–C$_{30}$ alkyl, aryl, alkylaryl, arylalkyl, heteroarylalkyl or cycloalkyl; and
R$_3$ is H or substituted or unsubstituted C$_1$–C$_6$ alkyl or C$_3$–C$_{10}$ cycloalkyl,
wherein
R$_4$ is H or a substituted or unsubstituted, straight chain or branched, C$_6$–C$_{30}$ alkyl, aryl, —CH$_2$-aryl, aryl —C$_1$–C$_{30}$ alkyl, heteroaryl-C$_1$–C$_{30}$ alkyl or C$_3$–C$_{10}$ cycloalkyl;
R$_5$ is H or a substituted or unsubstituted, straight chain or branched, C$_6$–C$_{30}$ alkyl, aryl C$_1$–C$_{30}$alkyl, heteroarylalkyl or cycloalkyl;
R$_6$ and R$_{6'}$ are each independently H, substituted or unsubstituted C$_1$–C$_6$ alkyl, dialkyl or C$_3$–C$_{10}$ cycloalkyl or together form a 3–7 membered ring system;
R$_7$ is H or substituted or unsubstituted C$_1$–C$_{12}$ alkyl or C$_3$–C$_{10}$ cycloalkyl; and
R$_8$ and R$_9$ are each independently H, substituted or unsubstituted C$_1$–C$_6$ alkyl, C$_1$–C$_6$ alkoxy, C$_1$–C$_6$ alkylaryl, or NR$_8$R$_9$ together form a substituted piperazine or piperidine ring or a dihydro-1H-isoquinoline ring system,
or a specific enantiomer thereof, or a specific tautomer, or a pharmaceutically acceptable salt thereof.
In one embodiment, the compound has the structure:

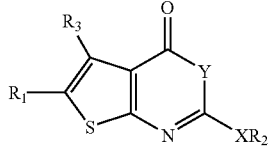

wherein,
X is O, S or NR$_5$;
Y is O or S;
R$_1$ is H, —C(O)OR$_4$, —C(O)NR$_4$R$_5$, —CR$_6$R$_6$OR$_4$, —CR$_6$R$_6$OC(O)R$_4$, —CR$_6$R$_6$OC(O)NHR$_7$, or CH$_2$R$_4$;
R$_2$ is a substituted or unsubstituted, straight chain or branched, C$_6$–C$_{30}$ alkyl, arylalkyl, heteroarylalkyl or cycloalkyl; and
R$_3$ is H or substituted or unsubstituted C$_1$–C$_6$ alkyl or cycloalkyl, wherein,
R$_4$ is H or a substituted or unsubstituted, straight chain or branched, C$_6$–C$_{30}$ alkyl, arylalkyl, heteroarylalkyl or cycloalkyl;
R$_5$ is H or a substituted or unsubstituted, straight chain or branched, C$_6$–C$_{30}$ alkyl, arylalkyl, heteroarylalkyl or cycloalkyl;
R$_6$ and R$_{6'}$ are each independently H, substituted or unsubstituted C$_1$–C$_6$ alkyl, dialkyl or cycloalkyl or together form a 3–7 membered ring system; and
R$_7$ is H or substituted or unsubstituted C$_1$–C$_{12}$ alkyl or cycloalkyl.
In a further embodiment, the compound has the structure:

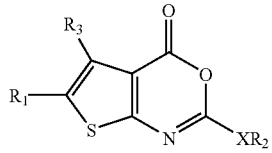

wherein,
X is O, S or NR$_5$;
R$_1$ is H, —C(O)OR$_4$, —C(O)NR$_4$R$_5$, —CR$_6$R$_6$OR$_4$, —CR$_6$R$_6$OC(O)R$_4$, —CR$_6$R$_6$OC(O)NHR$_7$, or CH$_2$R$_4$;
R$_2$ is a substituted or unsubstituted, straight chain or branched C$_6$–C$_{30}$ alkyl, arylalkyl, heteroarylalkyl or cycloalkyl; and
R$_3$ is H or substituted or unsubstituted C$_1$–C$_6$ alkyl or cycloalkyl,
wherein,
R$_4$ is H or a substituted or unsubstituted, straight chain or branched, C$_6$–C$_{30}$ alkyl, arylalkyl, heteroarylalkyl or cycloalkyl;
R$_5$ is H or a substituted or unsubstituted, straight chain or branched, C$_6$–C$_{30}$ alkyl, arylalkyl, heteroarylalkyl or cycloalkyl;
R$_6$ and R$_{6'}$ are each independently H, substituted or unsubstituted C$_1$–C$_6$ alkyl, dialkyl or cycloalkyl or together form a 3–7 membered ring system; and
R$_7$ is H or substituted or unsubstituted C$_1$–C$_{12}$ alkyl or cycloalkyl.
In a further embodiment of the above compound,
X is O or NR$_5$;
R$_1$ is —C(O)O—(C$_6$–C$_{30}$) alkyl, —C(O)NH—(C$_6$–C$_{30}$) alkyl or —C(O)OCH$_2$(C$_6$H$_5$);
R$_2$ is C$_6$–C$_{30}$ alkyl; and
R$_3$ is C$_1$–C$_6$ alkyl.
In a further embodiment, R$_3$ is H or CH$_3$.
In a further embodiment, X is O.
In a further embodiment, R$_3$ is methyl.
In a further embodiment, X is N.
In a further embodiment, R$_3$ is methyl.
In a further embodiment, the compound has the structure:

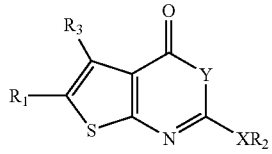

wherein,
Y is O or S;
R$_1$ is H, —(CH$_2$)$_r$CH$_3$, —CH(CH$_3$)$_2$, —CH(CH$_3$)CH$_2$C(CH$_3$)$_3$, —CH(CH$_3$)(CH$_2$)$_3$C(=CH$_2$)CH$_3$, —CH (CH₃)(CH₂)₃C(CH₃)₂OC(O)CH₃, —CH(CH₃)[CH₂]₃C(CH₃)₂OCH₃, —CH$_s$(C₆H₅), —C(O)OH, —C(O)NH(CH₂)$_r$CH₃, —C(O)O(CH₂)$_u$CH₃, —C(O)OCH[(CH₂)₃CH₃]₂, —C(O)NH(CH₂)$_v$CH₃, —C(O)N(CH₃)₂, —C(O)NHCH₂(C₆H₅), —C(O)NHCH₂(C₅H₄N), —C(O)N[(CH₂)₃CH₃]₂, —C(O)N[(CH₂)₅CH₃]₂, —C(O)N[(CH₂)₇CH₃]₂, —C(O)NH(C₆H₁₁), —C(O)(NC₄H₈N)CH₂(C₆H₅), —C(O)(NC₅H₉)CH₂(C₆H₅), —C(O)NH(CH₂)₃O(C₆H₅), —C(O)NHCH[(CH₂)₃CH₃]₂, —C(O)NH(CH₂)₃N(CH₃)₂, —C(O)NHCH₂C(O)OCH₂(C₆H₅), —C(O)N(CH₃)CH₂(C₅H₃N[CH₃]), —C(O)NH(CH₂)₂(C₅H₄N), —C(O)N(CH₂CH₃)(CH₂)₂(C₅H₄N), —C(O)NHCH₂(C₄H₃O), —C(O)(NC₄H₈N)[CH₂]₂(NC₅H₁₀), —C(O)NHCH(CH₃)₂, —C(O)NHCH₂(C₅H₄N), —C(O)NHCH₂C(CH₃)₃, —C(O)(NC₄H₈N)CH₂C(O)NHCH(CH₃)₂, —C(O)(NC₉H₈)[OCH₃]₂, —C(O)NHCH₂(C₆H₃[OCH₃]₂), —C(O)NHCH₂(C₇H₅O₂), —C(O)NH(CH₂)₂O(C₆H₅), —C(O)NH(CH₂)₂OCH₃, —C(O)NH(CH₂)₃OCH₃, —C(O)NH(CH₂)₄(C₆H₅), or —C(O)NH(CH₂)₃(C₆H₅);

r is an integer from 1 to 15;
s is an integer from 0 to 6;
t is an integer from 0 to 6;
u is an integer from 3 to 8;
v is an integer from 5 to 15;
XR₂ is —(CH₂)$_n$CH₃, —O(CH₂)$_m$CH₃, —OCH(CH₃)₂, —OCH(CH₃)(CH₂)₅CH₃, —OCH₂CH(CH₃)₂, —O(CH₂)₂OCH₃, —O(CH₂)₂OCH₂(C₆H₅), —O(CH₂)$_p$(C₆H₅), —OCH₂(C₆H₄[(CH₂)₃CH₃]), —O(C₆H₄[(CH₂)₃CH₃]), —O(CH₂)₂(C₆H₄[CH₃]), —O(CH₂)₃OCH₂(C₆H₅), —O(CH₂)₄OCH₂(C₆H₅), —N([CH₂]₇CH₃)C(O)NH(CH₂)₇CH₃, —N([CH₂]₆CH₃)C(O)NH(CH₂)₆CH₃, —NH(CH₂)$_q$CH₃, —NH(C₆H₄)O(C₆H₅), —N(CH₃)(CH₂)₅CH₃, —NHCH[(CH₂)₃CH₃]₂, —NHCH(CH₃)[CH₂]₅CH₃, or —N([CH₂]₇CH₃)₂;

n is an integer from 6 to 15;
m is an integer from 1 to 15;
p is an integer from 0 to 6;
q is an integer from 6 to 15; and
R₃ is H, —CH₃ or —CH₂OCH₃.

In a further embodiment, the compound has the structure:

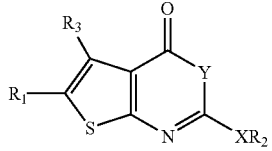

wherein,
Y is O or S;
R₁ is H, —(CH₂)₃CH₃, —(CH₂)₅CH₃, —(CH₂)₆CH₃, —(CH₂)₇CH₃, —(CH₂)₉CH₃, —(CH₂)₁₁CH₃, —CH(CH₃)₂, —CH(CH₃)CH₂C(CH₃)₃, —CH(CH₃)(CH₂)₃C(=CH₂)CH₃, —CH(CH₃)(CH₂)₃C(CH₃)₂OC(O)CH₃, —CH(CH₃)[CH₂]₃C(CH₃)₂OCH₃, —CH₂(C₆H₅), —(CH₂)₂(C₆H₅), —(CH₂)₃(C₆H₅), —(CH₂)₄(C₆H₅), —(CH₂)₅(C₆H₅), —C(O)OH, —C(O)NHCH₃, —C(O)NHCH₂CH₃, —C(O)NH(CH₂)₃CH₃, —C(O)OCH₂(C₆H₅), —C(O)O(CH₂)₅CH₃, —C(O)O(CH₂)₆CH₃, —C(O)O(CH₂)₇CH₃, —C(O)OCH[(CH₂)₃CH₃]₂, —C(O)NH(CH₂)₅CH₃, —C(O)NH(CH₂)₇CH₃, —C(O)NH(CH₂)₉CH₃, —C(O)NH(CH₂)₁₁CH₃, —C(O)NH(CH₂)₁₅CH₃, —C(O)N(CH₃)₂, —C(O)NHCH₂(C₆H₅), —C(O)NHCH₂(C₅H₄N), —C(O)N[(CH₂)₃CH₃]₂, —C(O)N[(CH₂)₅CH₃]₂, —C(O)N[(CH₂)₇CH₃]₂, —C(O)NH(C₆H₁₁), —C(O)(NC₄H₈N)CH₂(C₆H₅), —C(O)(NC₅H₉)CH₂(C₆H₅), —C(O)NH(CH₂)₃O(C₆H₅), —C(O)NHCH[(CH₂)₃CH₃]₂, —C(O)NH(CH₂)₃N(CH₃)₂, —C(O)NHCH₂C(O)OCH₂(C₆H₅), —C(O)N(CH₃)CH₂(C₅H₃N[CH₃]), —C(O)NH(CH₂)₂(C₅H₄N), —C(O)N(CH₂CH₃)(CH₂)₂(C₅H₄N), —C(O)NHCH₂(C₄H₃O), —C(O)(NC₄H₈N)[CH₂]₂(NC₅H₁₀), —C(O)NHCH₂CH(CH₃)₂, —C(O)NHCH₂(C₅H₄N), —C(O)NHCH₂C(CH₃)₃, —C(O)(NC₄H₈N)CH₂C(O)NHCH(CH₃)₂, —C(O)(NC₉H₈)[OCH₃]₂, —C(O)NHCH₂(C₆H₃[OCH₃]₂), —C(O)NHCH₂(C₇H₅O₂), —C(O)NH(CH₂)₂O(C₆H₅), —C(O)NH(CH₂)₂OCH₃, —C(O)NH(CH₂)₃OCH₃, —C(O)NH(CH₂)₄(C₆H₅), or —C(O)NH(CH₂)₃(C₆H₅);

XR₂ is —(CH₂)₆CH₃, —(CH₂)₁₀CH₃, —(CH₂)₁₄CH₃, —O(CH₂)₃CH₃, —O(CH₂)₅CH₃, —O(CH₂)₆CH₃, —O(CH₂)₇CH₃, —O(CH₂)₉CH₃, —O(CH₂)₁₁CH₃, —O(CH₂)₁₅CH₃, —OCH(CH₃)₂, —OCH(CH₃)(CH₂)₅CH₃, —OCH₂CH(CH₃)₂, —O(CH₂)₂OCH₃, —O(CH₂)₂OCH₂(C₆H₅), —O(CH₂)₄(C₆H₅), —O(CH₂)₃(C₆H₅), —O(CH₂)₂(C₆H₅), —O(C₆H₅), —OCH₂(C₆H₅), —OCH₂(C₆H₄[(CH₂)₃CH₃]), —O(C₆H₄[(CH₂)₃CH₃]), —O(CH₂)₂(C₆H₄[CH₃]), —O(CH₂)₃OCH₂(C₆H₅), —O(CH₂)₄OCH₂(C₆H₅), —N([CH₂]₇CH₃)C(O)NH(CH₂)₇CH₃, —N([CH₂]₆CH₃)C(O)NH(CH₂)₆CH₃, —NH(CH₂)₆CH₃, —NH(CH₂)₇CH₃, —NH(CH₂)₁₁CH₃, —NH(CH₂)₁₃CH₃, —NH(CH₂)₁₅CH₃, —NH(C₆H₄)O(C₆H₅), —N(CH₃)(CH₂)₅CH₃, —NHCH[(CH₂)₃CH₃]₂, —NHCH(CH₃)[CH₂]₅CH₃, or —N([CH₂]₇CH₃)₂; and R₃ is H, —CH₃ or —CH₂OCH₃.

In a further embodiment, the compound is selected from the group consisting of:
6-Heptyl-2-octyloxy-thieno[2,3-d][1,3]oxazin-4-one;
6-Hexyl-2-octyloxy-thieno[2,3-d][1,3]oxazin-4-one;
2-Octyloxy-6-(1,3,3-trimethyl-butyl)-thieno[2,3-d][1,3]oxazin-4-one;
6-Butyl-2-octyloxy-thieno[2,3-d][1,3]oxazin-4-one;
6-Heptyl-2-octylamino-thieno[2,3-d][1,3]oxazin-4-one;
6-Butyl-2-octylamino-thieno[2,3-d][1,3]oxazin-4-one;
6-Benzyl-2-octylamino-thieno[2,3-d][1,3]oxazin-4-one;
6-Heptyl-2-undecyl-thieno[2,3-d][1,3]oxazin-4-one;
6-(5-Methoxy-1,5-dimethyl-hexyl)-2-octyloxy-thieno[2,3-d][1,3]oxazin-4-one;
6-(1,5-Dimethyl-hex-4-enyl)-2-octyloxy-thieno[2,3-d][1,3]oxazin-4-one;
6-(1,5-Dimethyl-hex-5-enyl)-2-octyloxy-thieno[2,3-d][1,3]oxazin-4-one;
Trifluoro-acetic acid 1,1-dimethyl-5-(2-octyloxy-4-oxo-4H-thieno[2,3-d][1,3]oxazin-6-yl)-hexyl ester;
2-(2-Benzyloxy-ethoxy)-6-decyl-thieno[2,3-d][1,3]oxazin-4-one;
6-Heptyl-5-methyl-2-octyloxy-thieno[2,3-d][1,3]oxazin-4-one;
6-Methyl-2-octyloxy-thieno[2,3-d][1,3]oxazin-4-one;
2-Octyloxy-6-phenethyl-thieno[2,3-d][1,3]oxazin-4-one;
2-Octyloxy-6-(3-phenyl-propyl)-thieno[2,3-d][1,3]oxazin-4-one;
2-Octyloxy-6-(4-phenyl-butyl)-thieno[2,3-d][1,3]oxazin-4-one;

2-Octyloxy-6-(5-phenyl-pentyl)-thieno[2,3-d][1,3]
oxazin-4-one;
6-Decyl-2-(2-methoxy-ethoxy)-thieno[2,3-d][1,3]oxazin-
4-one;
2-(4-Butyl-phenoxy)-6-decyl-thieno[2,3-d][1,3]oxazin-4-
one;
2-(3-Benzyloxy-propoxy)-6-decyl-thieno[2,3-d][1,3]
oxazin-4-one;
2-(3-Benzyloxy-butyloxy)-6-decyl-thieno[2,3-d][1,3]
oxazin-4-one;
6-Isopropyl-2-octyloxy-thieno[2,3-d][1,3]oxazin-4-one;
6-Octyl-2-octyloxy-thieno[2,3-d][1,3]oxazin-4-one;
6-Dodecyl-2-octyloxy-thieno[2,3-d][1,3]oxazin-4-one;
2-Benzyloxy-6-Decyl-thieno[2,3-d][1,3]oxazin-4-one;
2-(4-Butylbenzyloxy)-6-Decyl-thieno[2,3-d][1,3]oxazin-
4-one;
6-Decyl-2-(2-p-tolyl-ethoxy)-thieno[2,3-d][1,3]oxazin-4-
one;
6-Decyl-2-phenethyloxy-thieno[2,3-d][1,3]oxazin-4-one;
3-Methyl-6-octyl-2-octyloxy-5H-thieno[2,3-b]pyridin-4-
one;
2-Butoxy-6-octyl-5H-thieno[2,3-b]pyridin-4-one;
2-Hexyloxy-6-octyl-5H-thieno[2,3-b]pyridin-4-one;
2-Dodecyloxy-6-octyl-5H-thieno[2,3-b]pyridin-4-one;
6-Decyl-2-phenoxy-5H-thieno[2,3-b]pyridin-4-one;
2-Decyloxy-6-octyl-5H-thieno[2,3-b]pyridin-4-one;
6-Benzyl-2-octyloxythieno[2,3-d][1,3]oxazin-4-one;
6-Decyl-2-octyloxythieno[2,3-d][1,3]oxazin-4-one;
6-Decyl-2-(1-methylheptyloxy)thieno[2,3-d][1,3]oxazin-
4-one;
6-Heptyl-2-(1-methylheptyloxy)thieno[2,3-d][1,3]
oxazin-4-one;
6-Decyl-2-(4-phenylpropoxy)thieno[2,3-d][1,3]oxazin-4-
one; and
6-Decyl-2-(4-phenylbutoxy)thieno[2,3-d][1,3]oxazin-4-
one.

The subject invention also provides compounds having the structure:

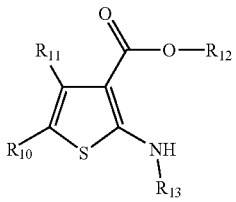

wherein,
$R_{10}$ is H or substituted or unsubstituted $C_1$–$C_{15}$ alkyl, $C_1$–$C_{15}$ alkylaryl, or —C(O)$R_{14}$,
wherein $R_{14}$ is hydroxyl, or a substituted or unsubstituted $C_1$–$C_{30}$ alkyl, alkylamino, dialkylamino, alkoxy, benzyloxy, cycloalkyl, alkylheteroaryl, alkylaryl, or a heterocyclic, heteroaryl or aryl ring;
$R_{11}$ is hydrogen or methyl;
$R_{12}$ is hydrogen or tert-butyl; and
$R_{13}$ is hydrogen or —C(O)Z$R_{15}$,
wherein Z is $CH_2$, O or N and $R_{15}$ is substituted or unsubstituted $C_1$–$C_{15}$ alkyl or aryl.

The subject invention also provides a method for treating obesity in a subject in need of such treatment, comprising administering to the subject a therapeutically effective amount of a compound of the invention so as to thereby treat obesity in the subject.

The subject invention also provides a method for treating diabetes in a subject in need of such treatment, comprising administering to the subject a therapeutically effective amount of a compound of the invention so as to thereby treat diabetes in the subject.

The subject invention also provides a method of inhibiting the hydrolytic activity of pancreatic lipase enzymes in a cell, comprising contacting the cell with an amount of a compound of the invention which is effective in inhibiting the hydrolytic activity of pancreatic lipase enzymes.

The above method may contact the cell either in vitro or in vivo.

The subject invention also provides a pharmaceutical composition comprising the a compound of the invention and a pharmaceutically acceptable carrier.

In one embodiment, the pharmaceutical composition is formulated for oral, topical, parenteral, or nasal administration.

The subject invention also provides a process for the manufacture of a pharmaceutical composition comprising admixing a compound of the invention with a pharmaceutically acceptable carrier.

The subject invention also provides an article of manufacture comprising
packaging material;
the above pharmaceutical composition; and
instructions for use of the pharmaceutical composition in the treatment of obesity.

The subject invention also provides a process of manufacturing a compound having the structure:

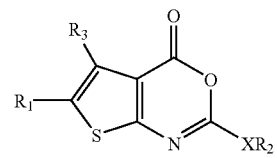

wherein,
X is O, S, $CH_2$ or $NR_5$;
$R_1$ is H, substituted or unsubstituted $C_1$–$C_{15}$ alkyl, $C_1$–$C_8$ alkylaryl, —C(O)O$R_4$, —C(O)$NR_4R_5$, —$CR_6R_{6'}OR_4$, —$CR_6R_{6'}OC(O)R_4$, —$CR_6R_{6'}OC(O)NHR_7$, —C(O)$NR_8R_9$, —C(O)$NR_8R_9NR_8R_9$, —N($R_5$)C(O)$NHR_5$, or $CH_2R_4$;
$R_2$ is a substituted or unsubstituted, straight chain $C_1$–$C_{30}$ alkyl or branched $C_3$–$C_{30}$ alkyl, aryl, alkylaryl, arylalkyl, heteroarylalkyl or cycloalkyl;
$R_3$ is H or substituted or unsubstituted $C_1$–$C_6$ alkyl or cycloalkyl;
$R_4$ is H or a substituted or unsubstituted, straight chain or branched, $C_6$–$C_{30}$ alkyl, aryl, —$CH_2$-aryl, arylalkyl, heteroarylalkyl or cycloalkyl;
$R_5$ is H or a substituted or unsubstituted, straight chain or branched, $C_6$–$C_{30}$ alkyl, arylalkyl, heteroarylalkyl or cycloalkyl;
$R_6$ and $R_{6'}$ are each independently H, substituted or unsubstituted $C_1$–$C_6$ alkyl, dialkyl or cycloalkyl or together form a 3–7 membered ring system;
$R_7$ is H or substituted or unsubstituted $C_1$–$C_{12}$ alkyl or cycloalkyl;

$R_8$ and $R_9$ are each independently H, substituted or unsubstituted $C_1$–$C_6$ alkyl, $C_1$–$C_6$ alkoxy, $C_1$–$C_6$ alkylaryl, or $NR_8R_9$ together form a substituted piperazine or piperidine ring or a dihydro-1H-isoquinoline ring system, comprising (a) reacting

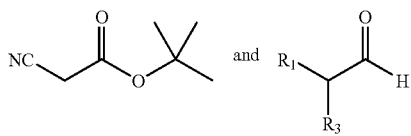

in the presence of sulfur, a base and solvent to produce:

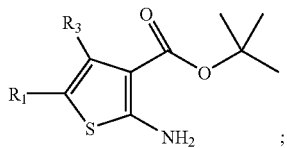

(b) reacting the product of step (a) with

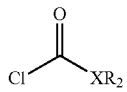

in the presence of a base to produce:

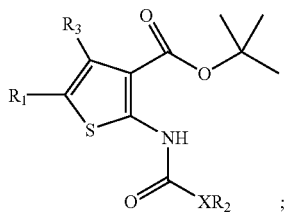

(c) reacting the product of step (b) with trifluoroacetic acid (TFA) in the presence of solvent to produce:

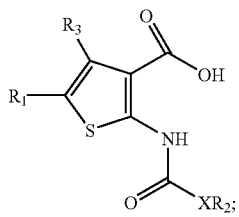

(d) reacting the product of step (c) with $SOCl_2$ in the presence of solvent to produce the compound.

In one embodiment of the above process, the base in step (a) is triethyl amine and the solvent is dimethylformamide (DMF).

In a further embodiment, the solvent in step (c) is dichloromethane.

In a further embodiment, the solvent in step (d) is pyridine:$CH_2Cl_2$.

The subject invention also provides a compound produced by the above process.

The subject invention also provides the use of the compounds of the invention for manufacturing a medicament useful for treating obesity in a subject.

The subject invention also provides the use of the compounds of the invention for manufacturing a medicament useful for treating diabetes in a subject.

The subject invention also provides the use of the compounds of the invention for manufacturing a medicament useful for inhibiting the hydrolytic activity of pancreatic lipase enzymes in a cell.

The inhibition of the cell may be effected either in vitro or in vivo.

The subject invention also provides the above compounds, wherein any heterocyclic or heteroaryl ring, if present, is a piperazine, piperidine, (1,4)diazepan, pyrazine, pyridine, pyrrolidine, pyrazole, pyrimidine, thiophene, imidazole, azetidine, pyrrole, benzothiazole, benzodioxolane, dithiolane, oxathiine, imidazolidine, quinoline, isoquinoline, dihydroisoquinoline, indole, isoindole, triazaspiro[4.5]decane, morpholine, furan or an isothiazole ring.

The subject invention also provides any of the above compounds, wherein any substituent, if present, is halogen, hydroxyl, straight chain ($C_1$–$C_{30}$)alkyl, branched chain ($C_3$–$C_{30}$)alkyl, ($C_3$–$C_{10}$)cycloalkyl, straight chain($C_1$–$C_{30}$) alkylcarbonyloxy, branched chain ($C_3$–$C_{30}$) alkylcarbonyloxy, arylcarbonyloxy, straight chain($C_1$–$C_{30}$) alkoxycarbonyloxy, branched chain($C_3$–$C_{30}$) alkoxycarbonyloxy, aryloxycarbonyloxy, carboxylate, straight chain($C_1$–$C_{30}$)alkylcarbonyl, branched chain ($C_3$–$C_{30}$)alkylcarbonyl, straight chain ($C_1$–$C_{30}$) alkoxycarbonyl, branched chain ($C_3$–$C_{30}$)alkoxycarbonyl, aminocarbonyl, straight chain ($C_1$–$C_{30}$)alkylthiocarbonyl, branched chain ($C_3$–$C_{30}$)alkylthiocarbonyl, straight chain ($C_1$–$C_{30}$)alkoxyl, branched chain ($C_1$–$C_{30}$)alkoxyl, phosphate, phosphonato, cyano, amino, straight chain ($C_1$–$C_{30}$)alkylamino, branched chain ($C_3$–$C_{30}$)alkylamino, straight chain ($C_1$–$C_{30}$)dialkylamino, branched chain ($C_3$–$C_{30}$)dialkylamino, arylamino, diarylamino, straight chain ($C_1$–$C_{30}$)alkylarylamino, branched chain ($C_3$–$C_{30}$) alkylarylamino, acylamino, straight chain ($C_1$–$C_{30}$) alkylcarbonylamino, branched chain ($C_3$–$C_{30}$) alkylcarbonylamino, arylcarbonylamino, carbamoyl, ureido, amidino, imino, sulfhydryl, straight chain ($C_1$–$C_{30}$) alkylthio, branched chain ($C_3$–$C_{30}$)alkylthio, arylthio, thiocarboxylate, sulfates, sulfonato, sulfamoyl, sulfonamido, nitro, trifluoromethyl, azido, 4–10 membered heterocyclyl, straight chain ($C_1$–$C_{30}$)alkylaryl, branched chain ($C_3$–$C_{30}$)alkylaryl, benzo(1,3)dioxole, or an aromatic or 5–6 membered heteroaromatic moiety, which substituent may be further substituted by any of the above.

The number of carbons when represented as "($C_1$–$C_{30}$)" or "($C_3$–$C_{30}$)" is intended to mean any incremental whole number between 1 and 3 and 30, e.g. 1, 2, 3, 4, 5 . . . or 30.

Additional embodiments of the compounds of this invention are described below.

| Entry | structure | MW | k 10-3.s-1 | Ymax | % inhibit MP |
|---|---|---|---|---|---|
| 1 | 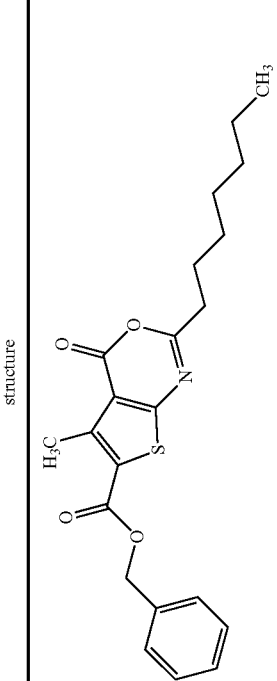 | 399.5 | | | |
| 2 | 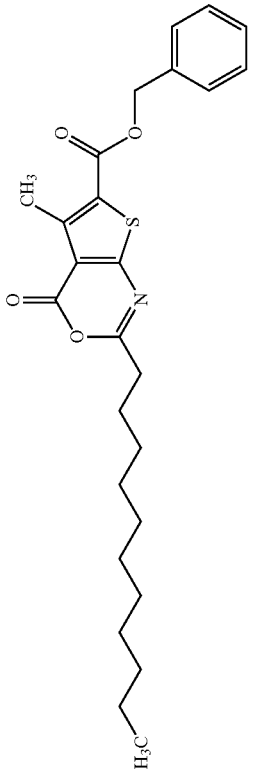 | 455.6 | | | |
| 3 | 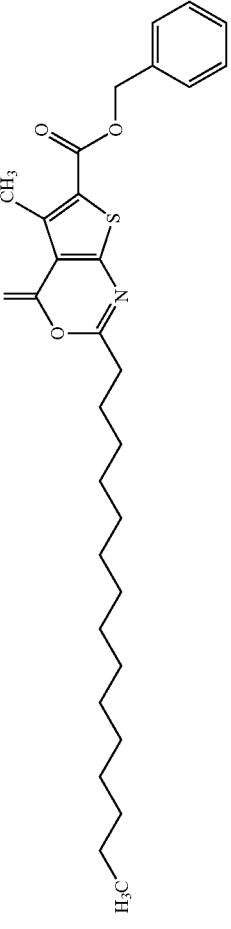 | 511.7 | | | |

-continued

| Entry | structure | MW | k 10-3.s-1 | Ymax | % inhibit | MP |
|---|---|---|---|---|---|---|
| 4 | 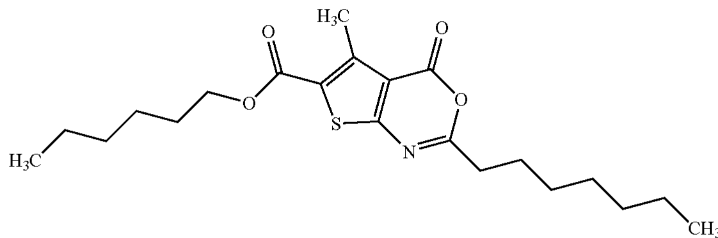 | 393.6 | | | | |
| 5 | 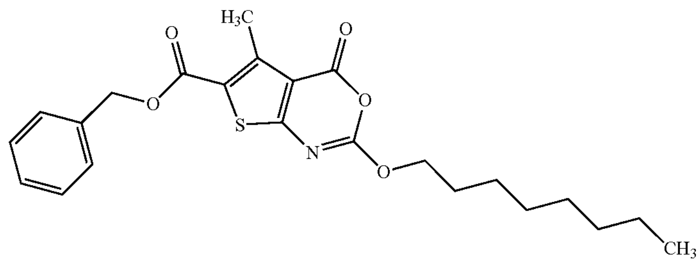 | 429.5 | 0.649 | | | |
| 6 | 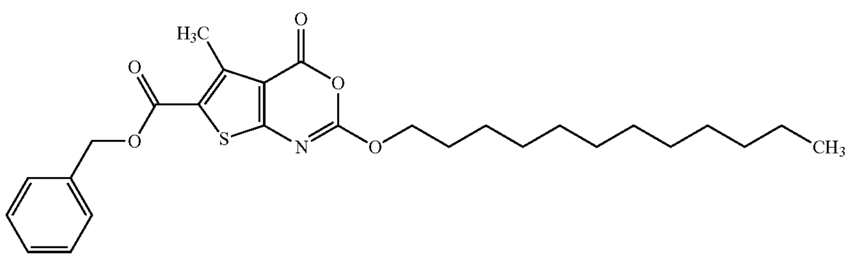 | 485.7 | | | | |

-continued

| Entry | structure | MW | k 10-3.s-1 | Ymax | % inhibit MP |
|---|---|---|---|---|---|
| 7 | 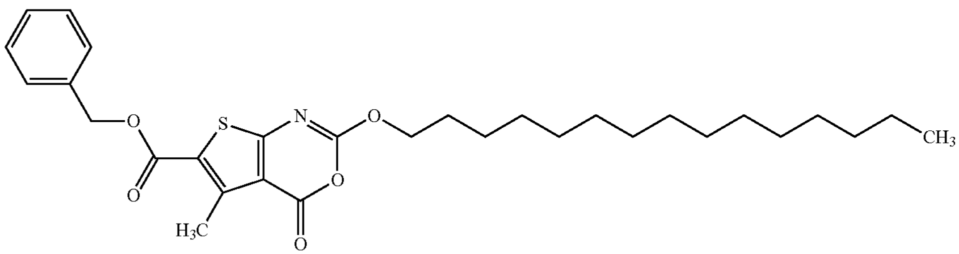 | 541.8 | 0.779 | | |
| 8 | 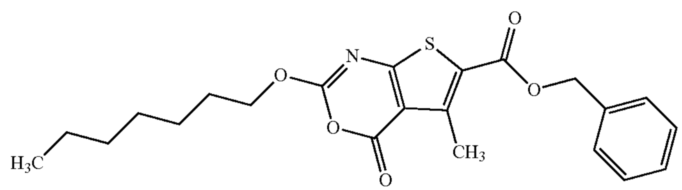 | 415.5 | 1.052 | | |
| 9 | 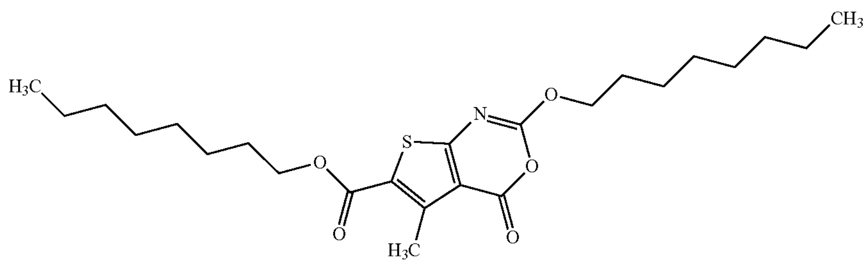 | 451.6 | 0.924 | 0.286 | 58.5–60.2 |
| 10 | 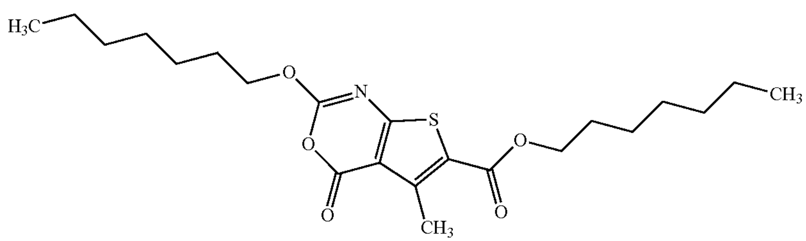 | 423.6 | 1.349 | | |

-continued
| Entry | structure | MW | k 10-3.s-1 | Ymax | % inhibit | MP |
|---|---|---|---|---|---|---|
| 11 | 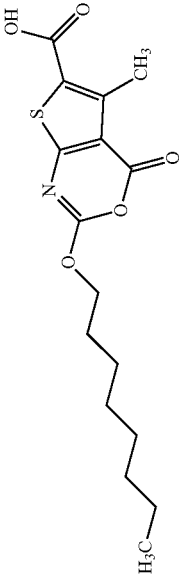 | 339.4 | 0.547 | | | |
| 12 | 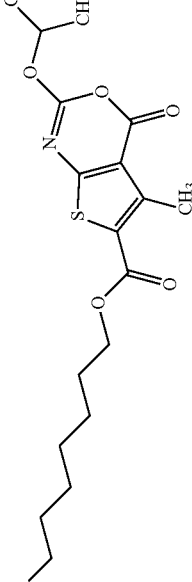 | 381.5 | 0.438 | | | 47.5–48.0 |
| 13 | 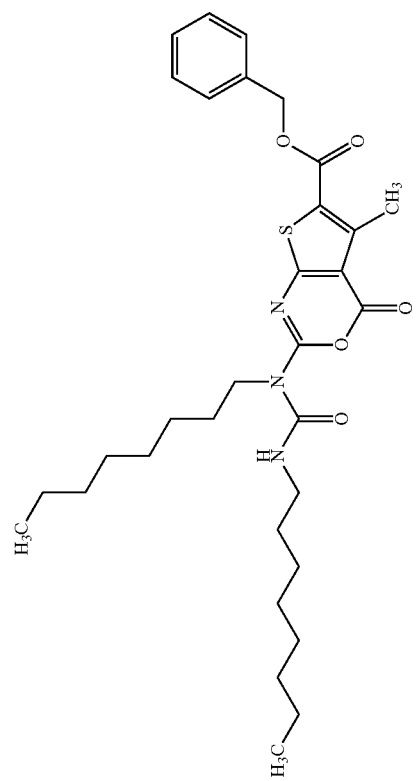 | 583.8 | 0.414 | | | |

| Entry | structure | MW | k 10-3.s-1 | Ymax | % inhibit | MP |
|---|---|---|---|---|---|---|
| 14 | 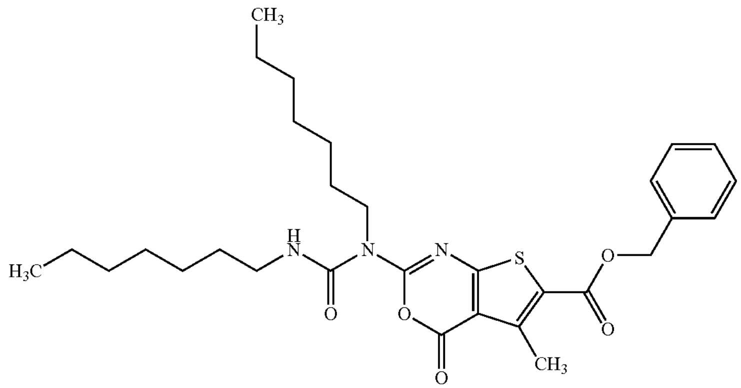 | 555.7 | 0.459 | | | |
| 15 | 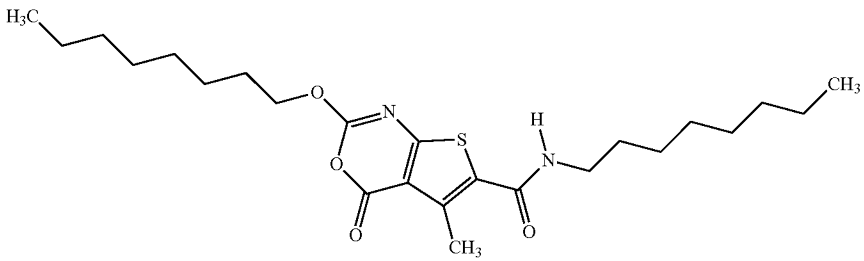 | 450.7 | 1.548 | | | |
| 16 | 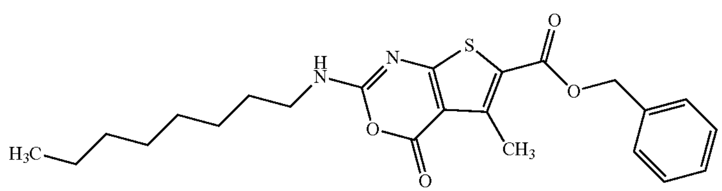 | 428.6 | 1.711 | | | 153.5–154. |

| Entry | structure | MW | k 10-3.s-1 | Ymax | % inhibit | MP |
|---|---|---|---|---|---|---|
| 17 | 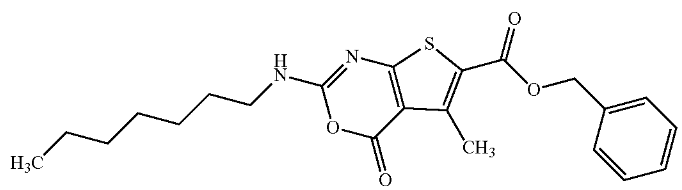 | 414.5 | 7.74 | | | |
| 18 | 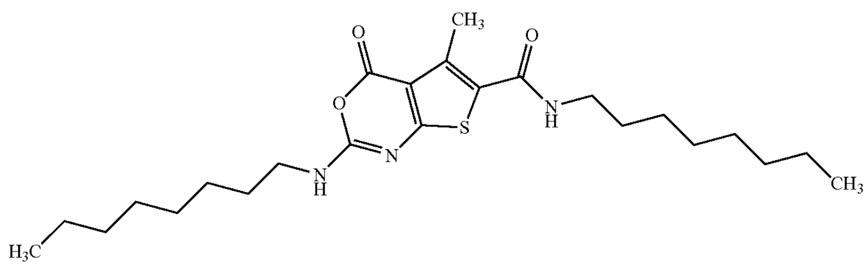 | 449.7 | 1.036 | | 18.03% | 152.0–152.8 |
| 19 | 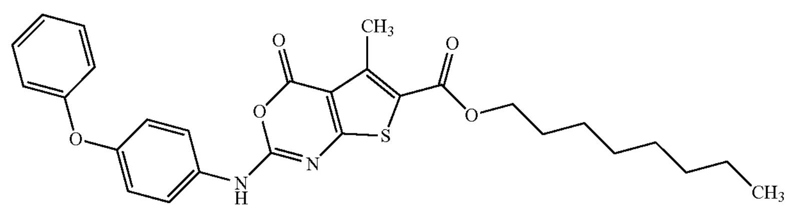 | 506.6 | 0.981 | | | |
| 20 | 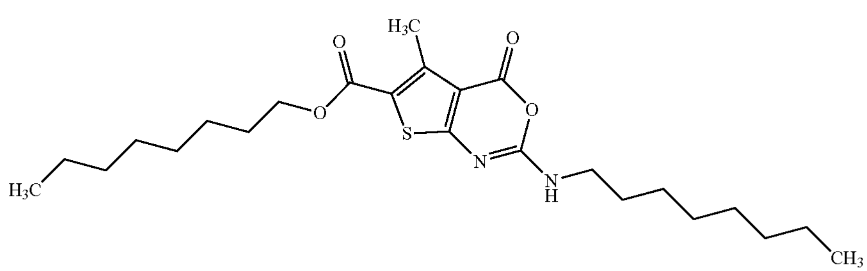 | 450.7 | 0.922 | | | |

-continued

| Entry | structure | MW | k 10-3.s-1 | Ymax | % inhibit | MP |
|---|---|---|---|---|---|---|
| 21 | 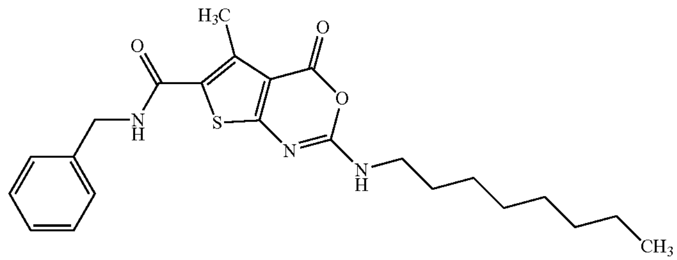 | 427.6 | 1.079 | | | |
| 22 | 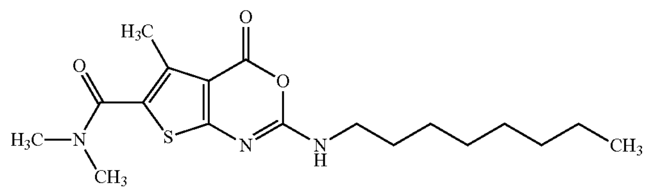 | 365.5 | 0.537 | | | |
| 23 | 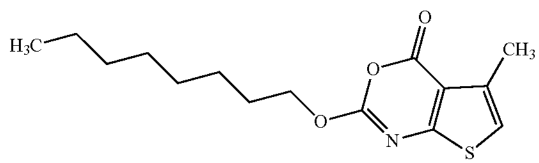 | 295.4 | 0.893 | | | |
| 24 | 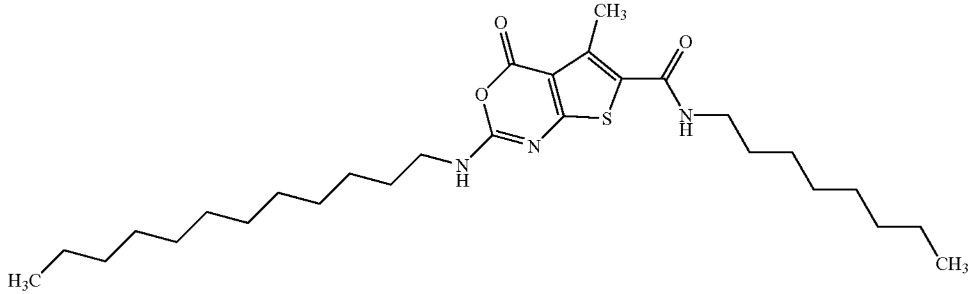 | 505.8 | 1.849 | | | 137.1–138.0 |

-continued

| Entry | structure | MW | k 10-3.s-1 | Ymax | % inhibit | MP |
|---|---|---|---|---|---|---|
| 25 | 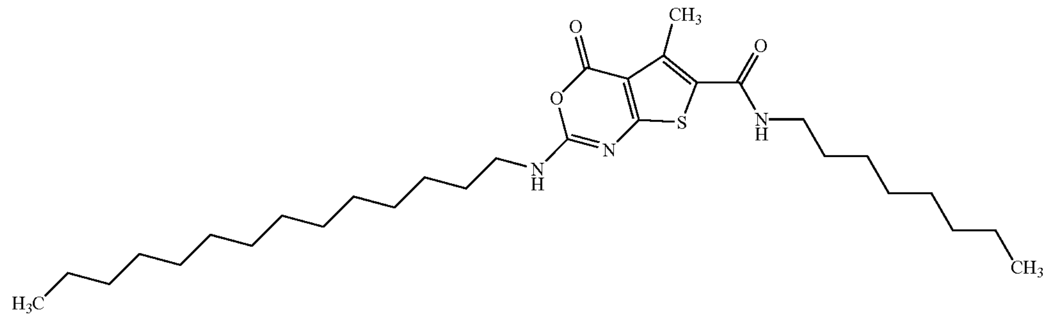 | 533.8 | 1.629 | | | 145.0–145.8 |
| 26 | 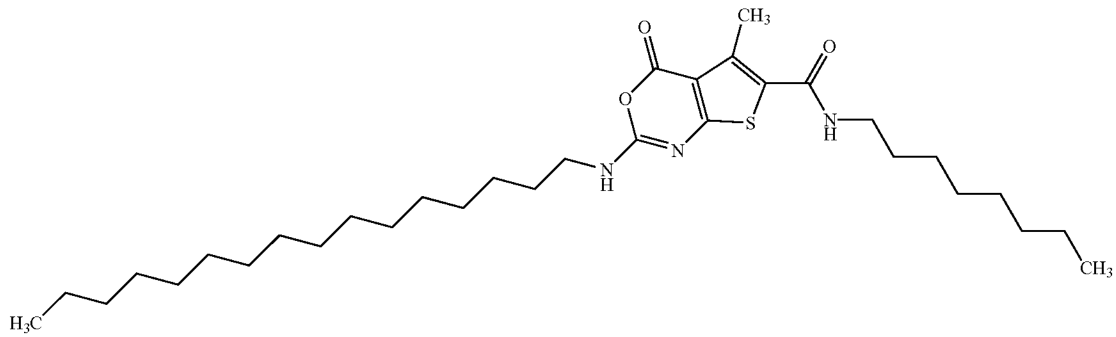 | 561.9 | 1.709 | | | 146.3–147.0 |
| 27 | 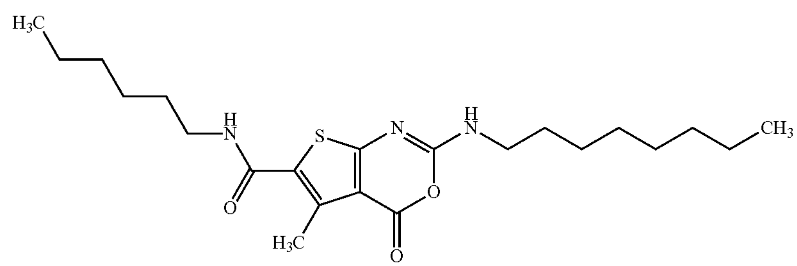 | 421.6 | 2.577 | | | |

-continued

| Entry | structure | MW | k 10-3.s-1 | Ymax | % inhibit MP |
|---|---|---|---|---|---|
| 28 | 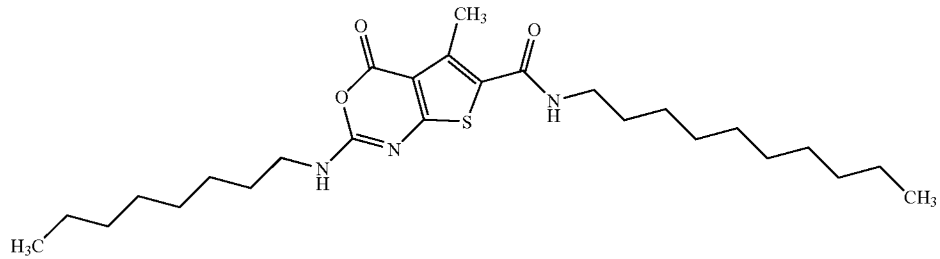 | 477.7 | 0.998 | | |
| 29 | 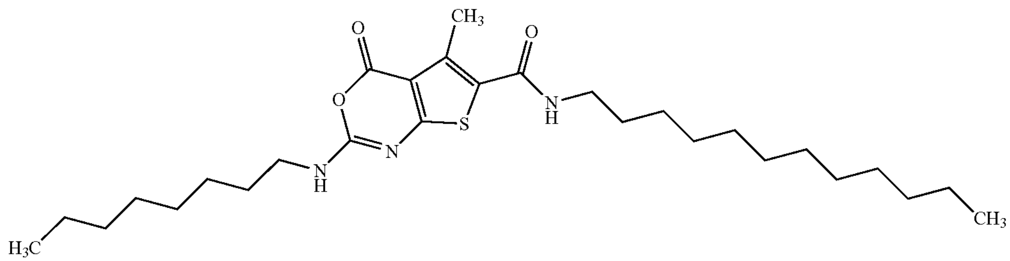 | 505.8 | 0.797 | | |
| 30 | 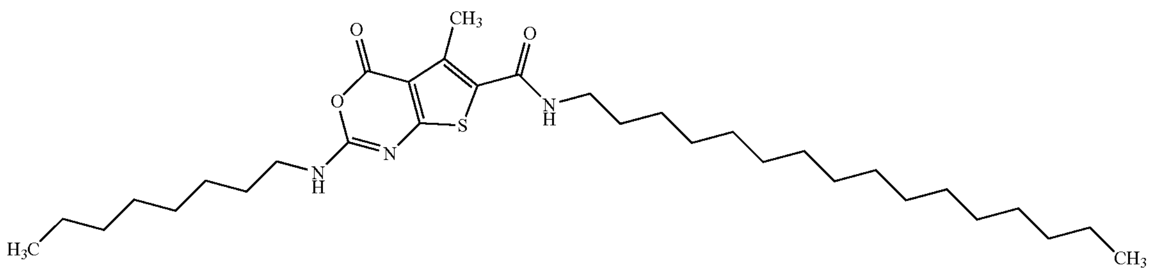 | 561.9 | 0.433 | | |

-continued

| Entry | structure | MW | k 10-3.s-1 | Ymax | % inhibit | MP |
|---|---|---|---|---|---|---|
| 31 | 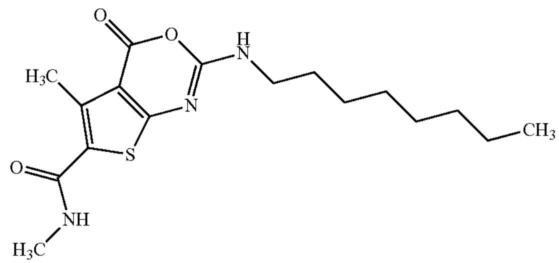 | 351.5 | 0.777 | | | 152.5–158 |
| 32 | 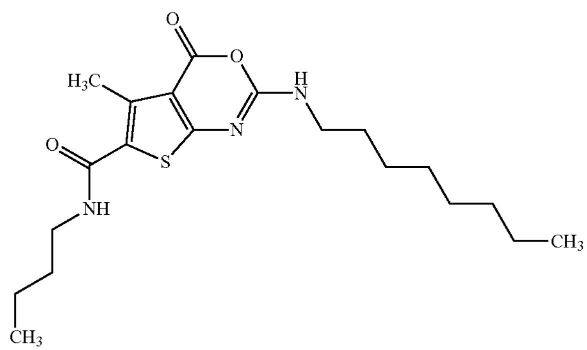 | 393.6 | 2.447 | | | |
| 33 | 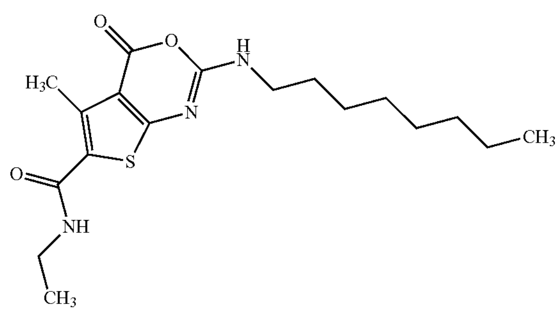 | 365.5 | 0.547 | | | |

-continued

| Entry | structure | MW | k 10-3.s-1 | Ymax | % inhibit | MP |
|---|---|---|---|---|---|---|
| 34 | 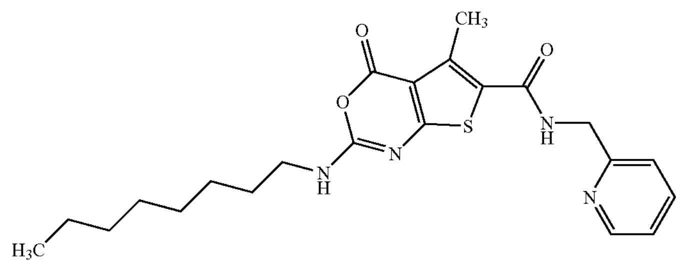 | 428.6 | 0.864 | | | |
| 35 | 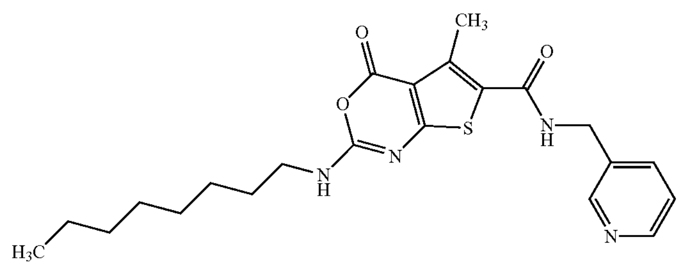 | 428.6 | 1.544 | | | 148–150 |
| 36 | 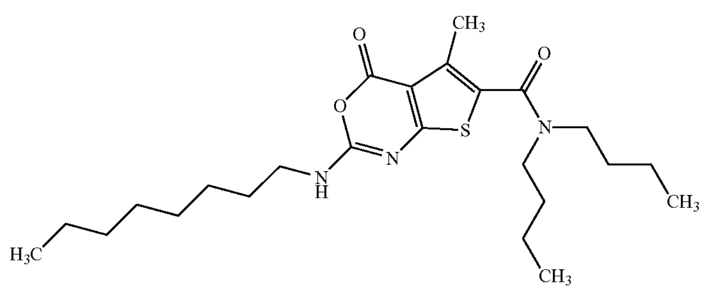 | 449.7 | 0.146 | 0.616 | | |

| Entry | structure | MW | k 10-3.s-1 | Ymax | % inhibit | MP |
|---|---|---|---|---|---|---|
| 37 | 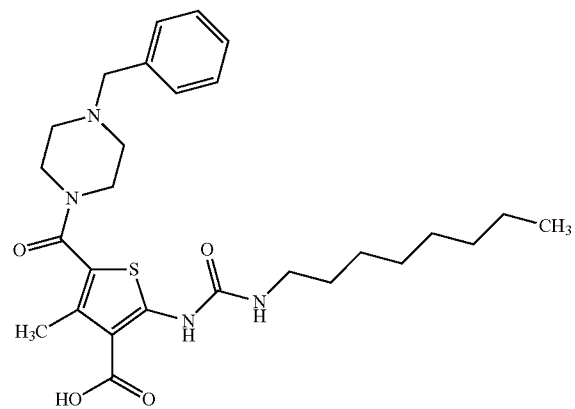 | 514.7 | 0.574 | 0.211 | | 193.5-195 (decomp) |
| 38 | 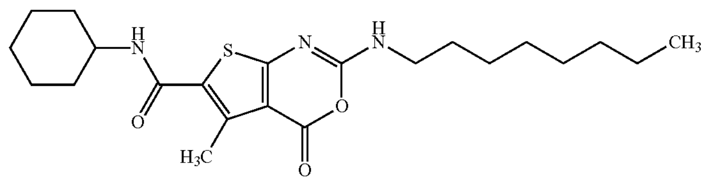 | 419.6 | 2.173 | 0.045 | | |
| 39 | 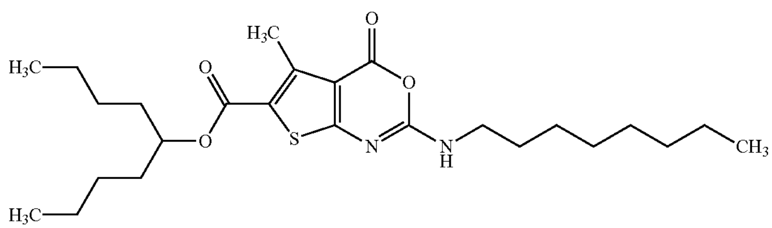 | 464.7 | 1.253 | 0.156 | | 90-92 |

| Entry | structure | MW | k 10-3.s-1 | Ymax | % inhibit MP |
|---|---|---|---|---|---|
| 40 | 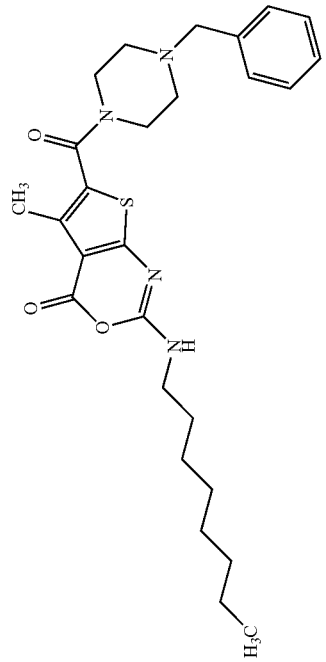 | 496.7 | 0.110 | | |
| 41 | 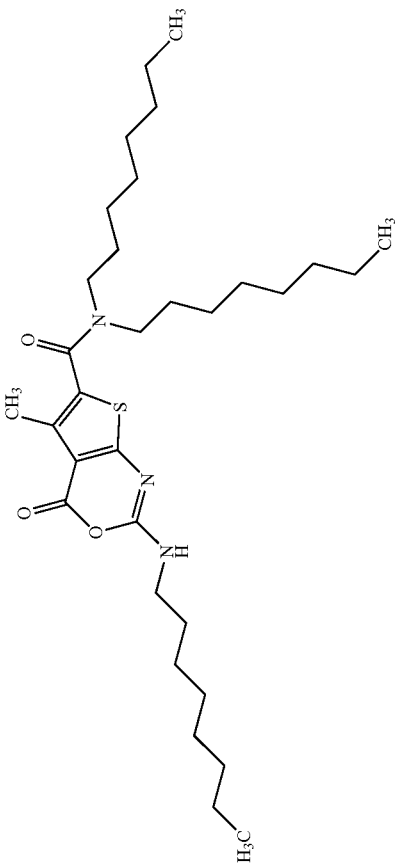 | 561.9 | 1.050 | 0.130 | 48–50 |

-continued

| Entry | structure | MW | k 10-3.s-1 | Ymax | % inhibit | MP |
|---|---|---|---|---|---|---|
| 42 | 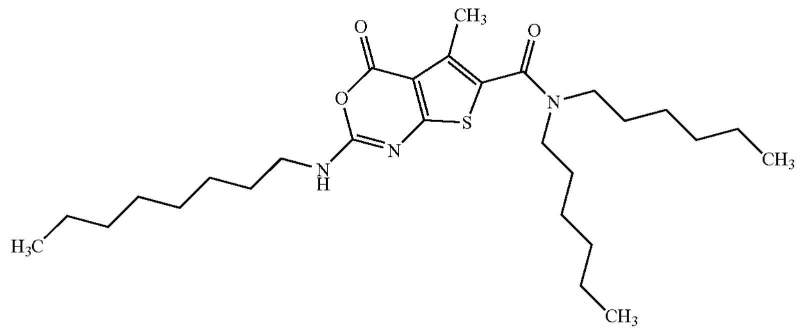 | 505.8 | 1.123 | 0.124 | | 42–45 |
| 43 | 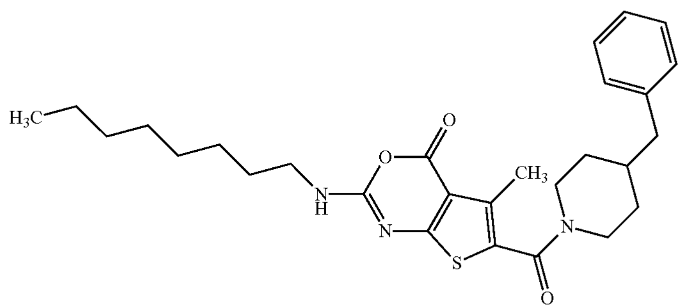 | 495.7 | 0.009 | | | 100–106 |
| 44 | 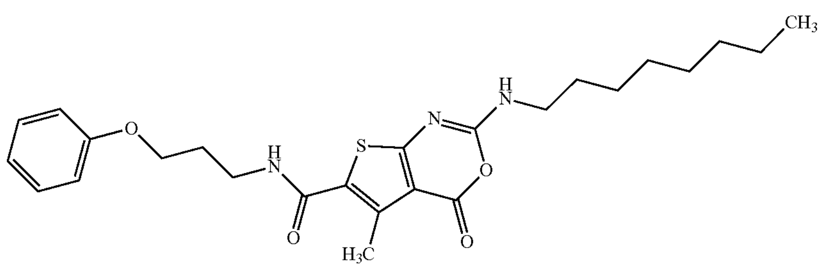 | 471.6 | 1.667 | | | |

-continued

| Entry | structure | MW | k 10-3.s-1 | Ymax | % inhibit | MP |
|---|---|---|---|---|---|---|
| 45 | 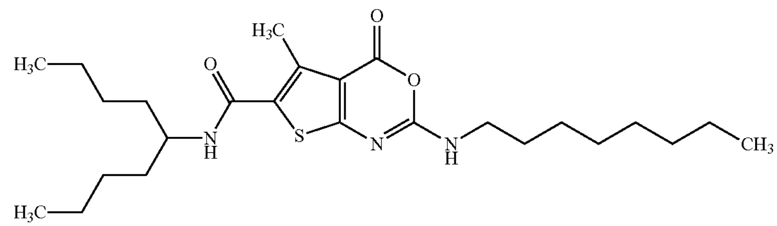 | 463.7 | 0.770 | | | |
| 46 | 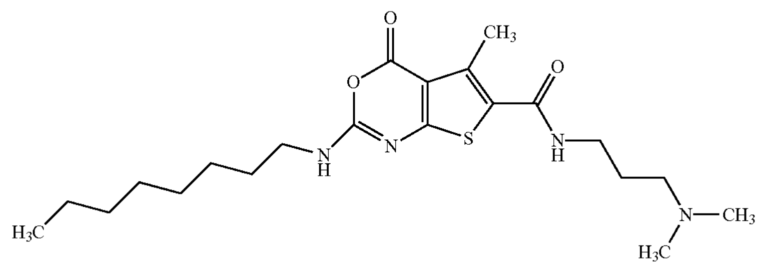 | 422.6 | 0.062 | | | |
| 47 | 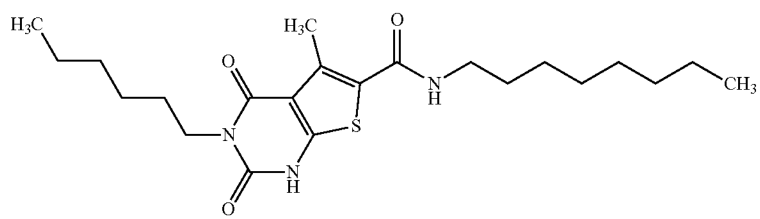 | 449.7 | 0.191 | 0.943 | | |
| 48 | 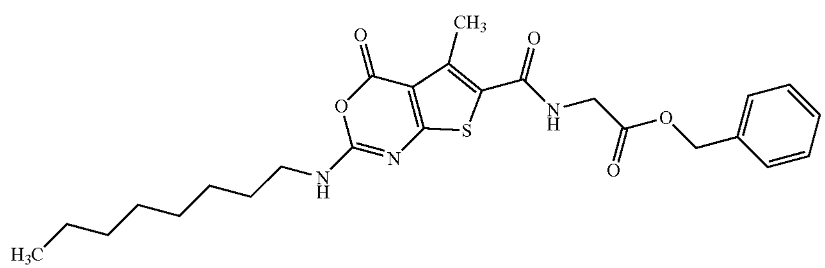 | 485.6 | 0.440 | | | 147–149 |

-continued

| Entry | structure | MW | k 10-3.s-1 | Ymax | % inhibit MP |
|---|---|---|---|---|---|
| 49 | 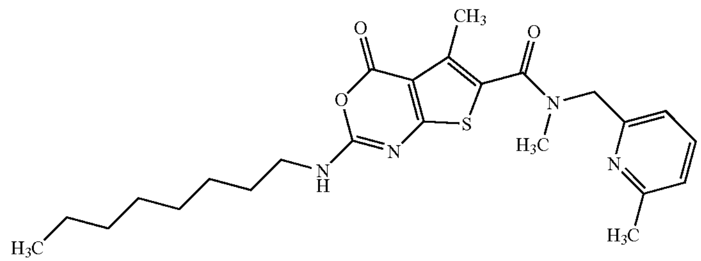 | 456.6 | 0.022 | | |
| 50 | 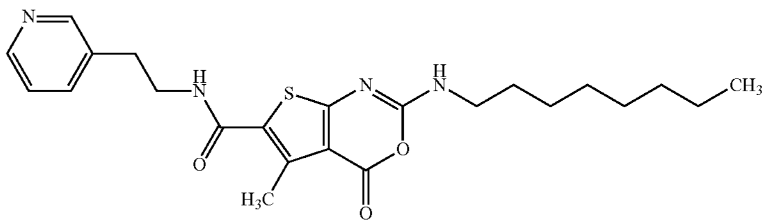 | 442.6 | 0.719 | | |
| 51 | 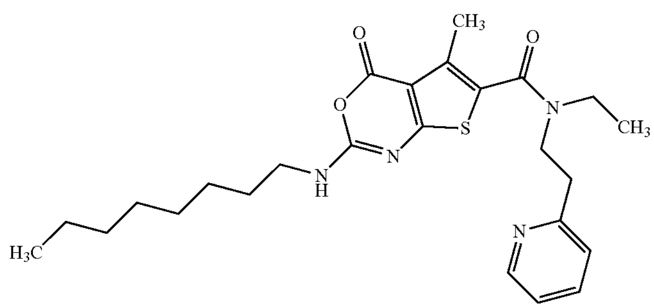 | 470.6 | 0.012 | | |

-continued

| Entry | structure | MW | k 10-3.s-1 | Ymax | % inhibit MP |
|---|---|---|---|---|---|
| 52 | (structure) | 417.5 | 1.257 | | |
| 53 | (structure) | 517.7 | 0.166 | | |
| 54 | (structure) | 393.6 | 0.702 | | |

-continued

| Entry | structure | MW | k 10-3.s-1 | Ymax | % inhibit | MP |
|---|---|---|---|---|---|---|
| 55 | 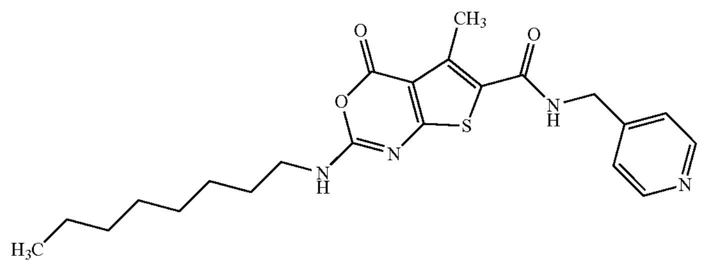 | 428.6 | 0.754 | | | |
| 56 | 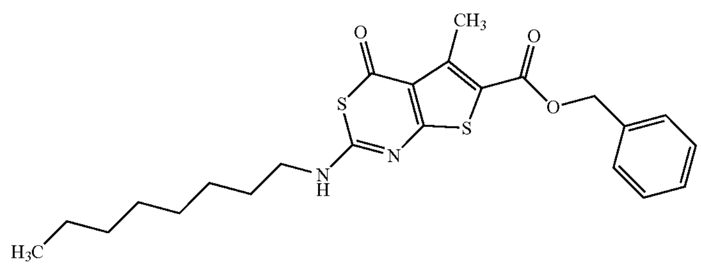 | 444.6 | 0.114 | | | |
| 57 | 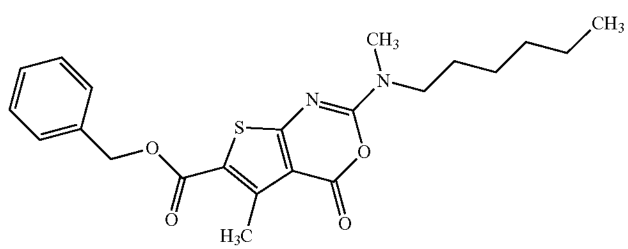 | 414.5 | 0.070 | | | 86–88 |
| 58 | 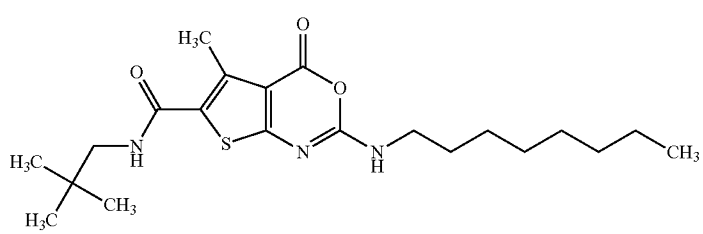 | 407.6 | 0.723 | | | 173–174.5 |

-continued

| Entry | structure | MW | k 10-3.s-1 | Ymax | % inhibit | MP |
|---|---|---|---|---|---|---|
| 59 | 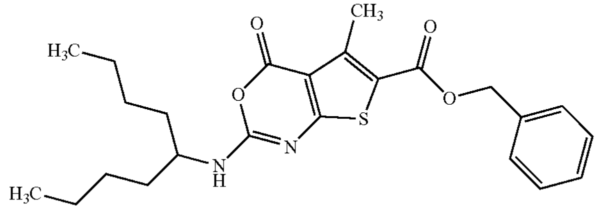 | 442.6 | 0.222 | | | 136–138 |
| 60 | 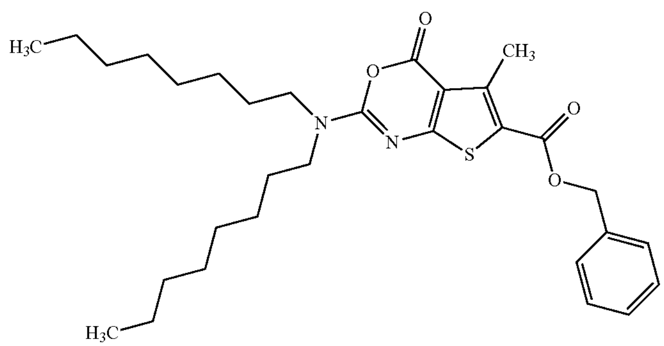 | 540.8 | 0.013 | | | |
| 61 | 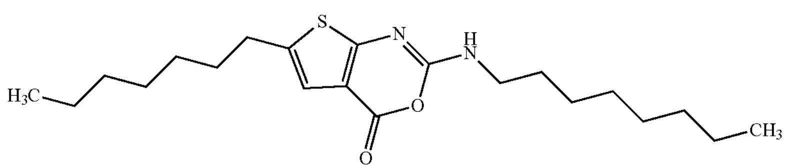 | 378.6 | 0.247 | 0.460 | | 89–91 |
| 62 | 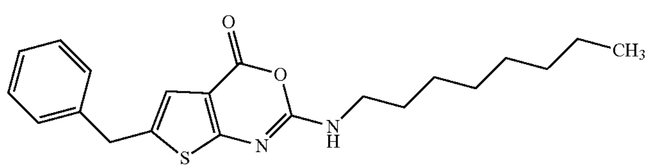 | 370.5 | 0.103 | 1.901 | | 123.0–124. |

-continued

| Entry | structure | MW | k 10-3.s-1 | Ymax | % inhibit | MP |
|---|---|---|---|---|---|---|
| 63 | 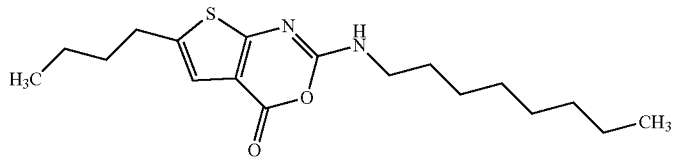 | 336.5 | 0.074 | 10.091 | | 93.0–94.0 |
| 64 | 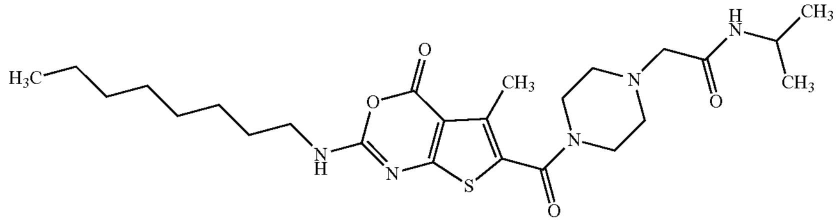 | 505.7 | 0.176 | 3.917 | | |
| 65 | 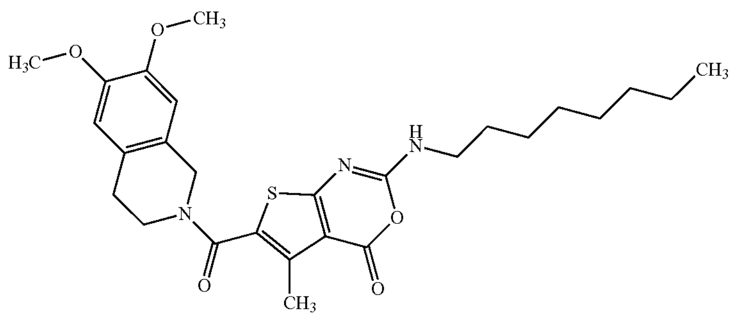 | 513.7 | 0.284 | 0.339 | | 77–80 |
| 66 | 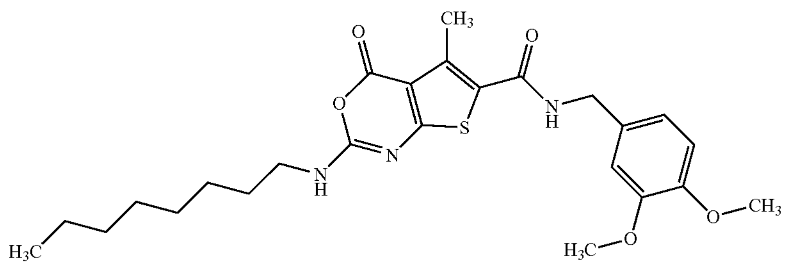 | 487.6 | 1.027 | 0.118 | | 159.0–163.0 |

-continued

| Entry | structure | MW | k 10-3.s-1 | Ymax | % inhibit | MP |
|---|---|---|---|---|---|---|
| 67 | 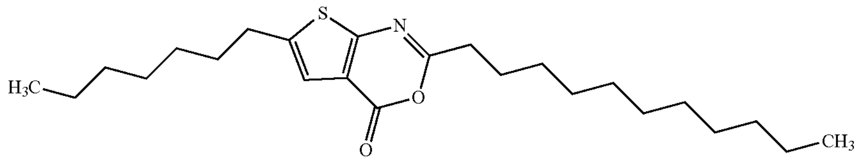 | 405.7 | 0.064 | 10.973 | | oil |
| 68 | 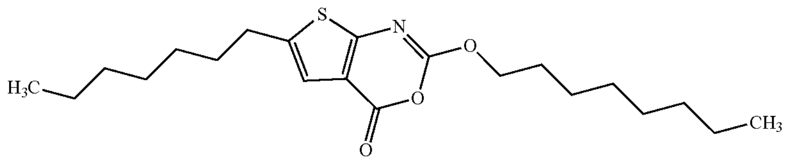 | 379.6 | 5.825 | 0.020 | 78.94% | oil |
| 69 | 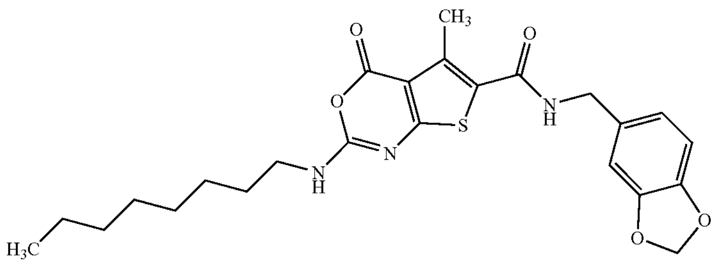 | 471.6 | 1.137 | 0.112 | | 149–152 |
| 70 | 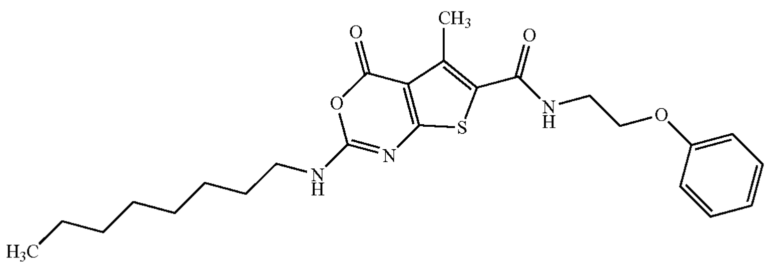 | 457.6 | 1.999 | 0.140 | | |

-continued

| Entry | structure | MW | k 10-3.s-1 | Ymax | % inhibit MP |
|---|---|---|---|---|---|
| 71 | 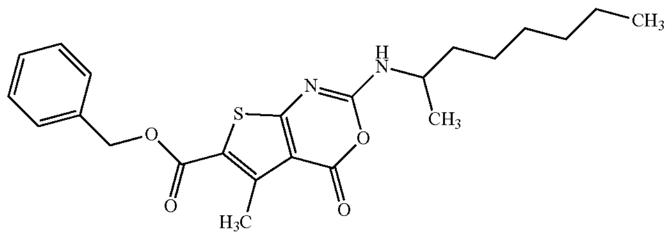 | 428.6 | 0.086 | 14.657 | |
| 72 | 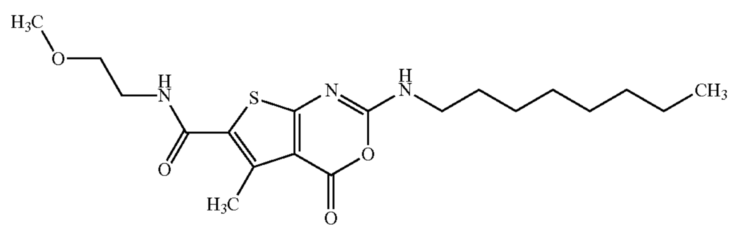 | 395.5 | 1.102 | 0.185 | |
| 73 | 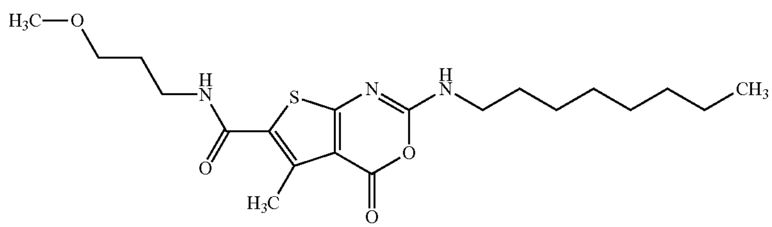 | 409.6 | 0.794 | 1.594 | |
| 74 | 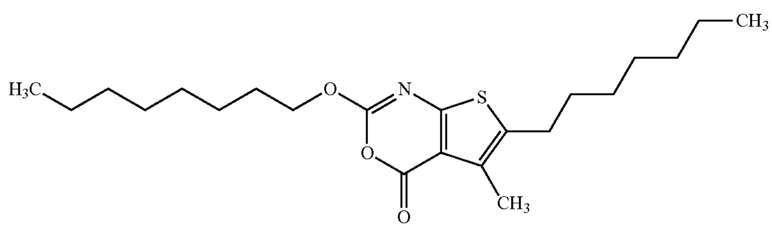 | 393.6 | 0.422 | 0.982 | oil |

| Entry | structure | MW | k 10-3.s-1 | Ymax | % inhibit | MP |
|---|---|---|---|---|---|---|
| 75 | 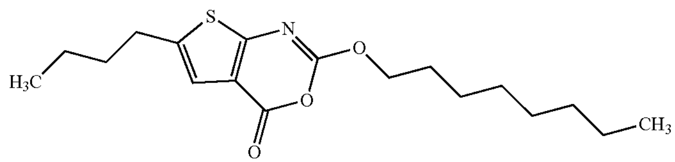 | 337.5 | 2.219 | 0.054 | | oil |
| 76 | 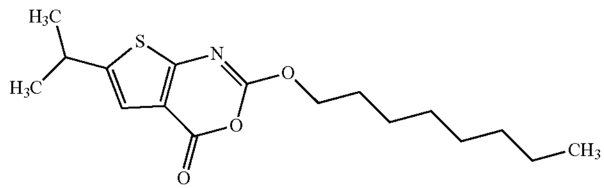 | 323.5 | 1.288 | 0.161 | | oil |
| 77 | 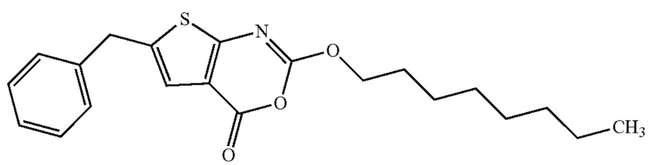 | 371.5 | 0.392 | 0.482 | | oil |
| 78 | 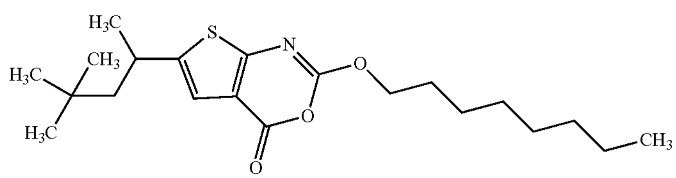 | 379.6 | 1.315 | 0.126 | 17.86% | oil |
| 79 | 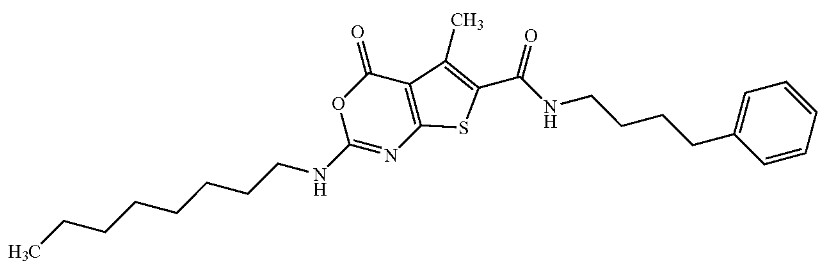 | 469.7 | | | 69.49% | 153–154 |

-continued
| Entry | structure | MW | k 10-3.s-1 | Ymax | % inhibit | MP |
|---|---|---|---|---|---|---|
| 80 | 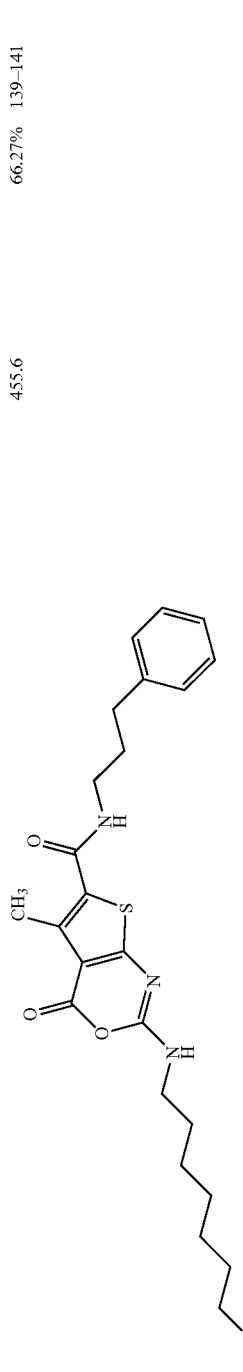 | 455.6 | | | 66.27% | 139-141 |
| 81 | 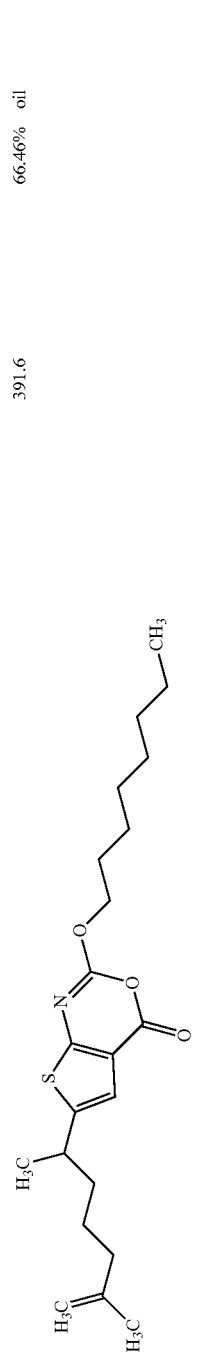 | 391.6 | | | 66.46% | oil |
| 82 | 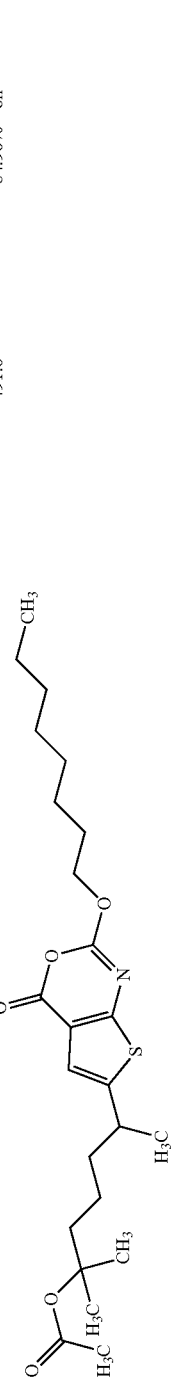 | 491.6 | | | 84.90% | oil |
| 83 | 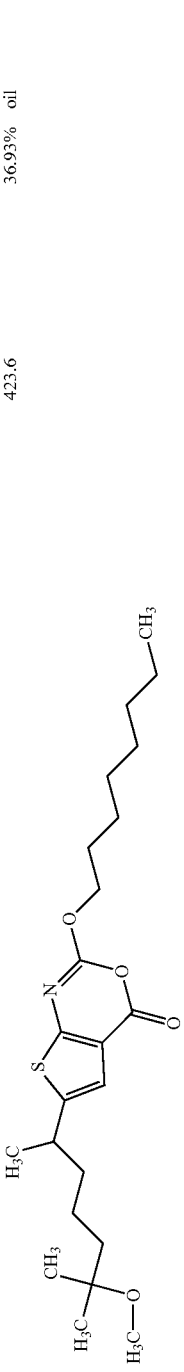 | 423.6 | | | 36.93% | oil |

-continued

| Entry | structure | MW | k 10-3.s-1 | Ymax | % inhibit | MP |
|---|---|---|---|---|---|---|
| 84 | 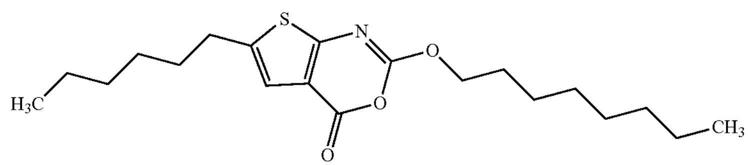 | 365.5 | 3.033 | 0.029 | 71.26% | oil |
| 85 | 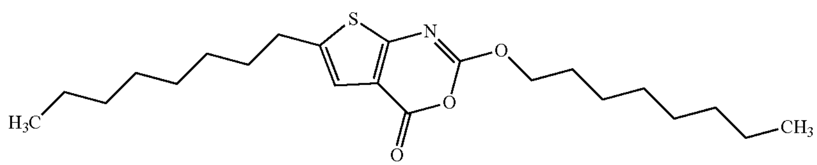 | 393.6 | | | 96.13% | oil |
| 86 | 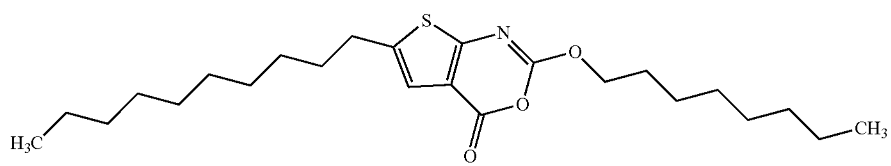 | 421.6 | | | 73.58% | oil |
| 87 | 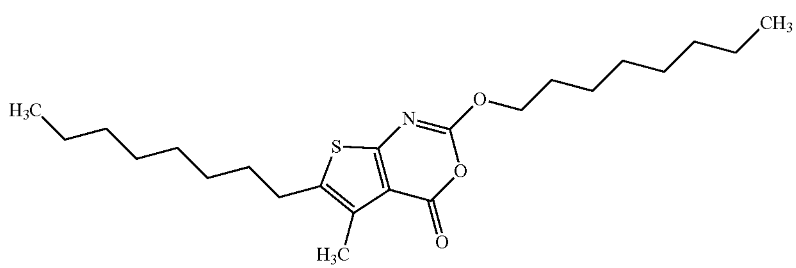 | 407.6 | | | 27.91% | 36 |
| 88 | 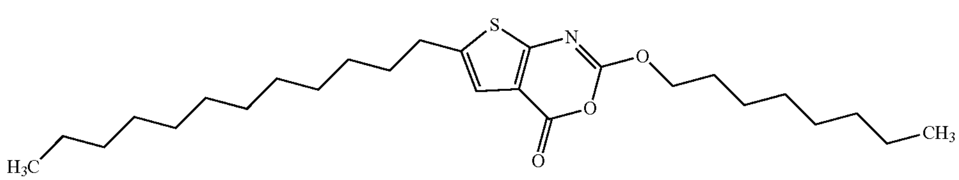 | 449.7 | | | 74.21% | |

-continued

| Entry | structure | MW | k 10-3.s-1 | Ymax | % inhibit | MP |
|---|---|---|---|---|---|---|
| 89 | 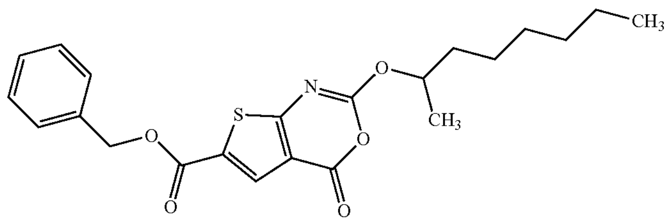 | 429.5 | | | -14.14% | oil |
| 90 | 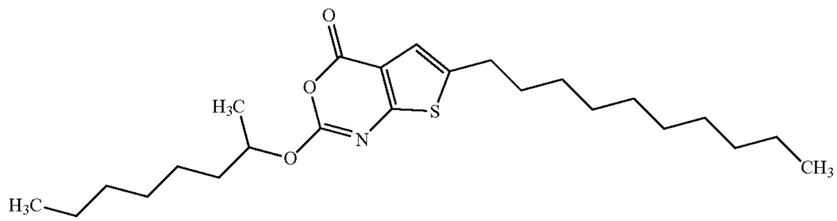 | 421.7 | | | 15.03% | oil |
| 91 | 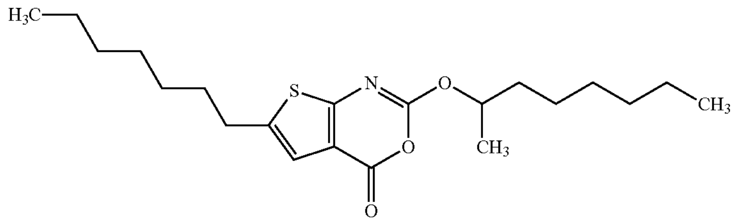 | 379.6 | | | 12.44% | oil |
| 92 | 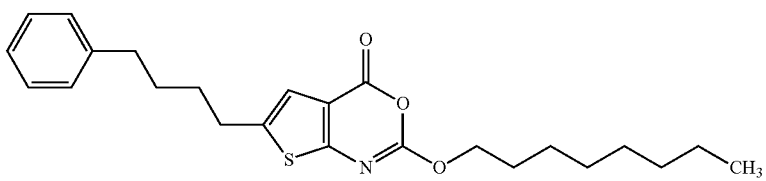 | 397.6 | | | | oil |

-continued

| Entry | structure | MW | k 10⁻³·s⁻¹ | Ymax | % inhibit | MP |
|---|---|---|---|---|---|---|
| 93 | 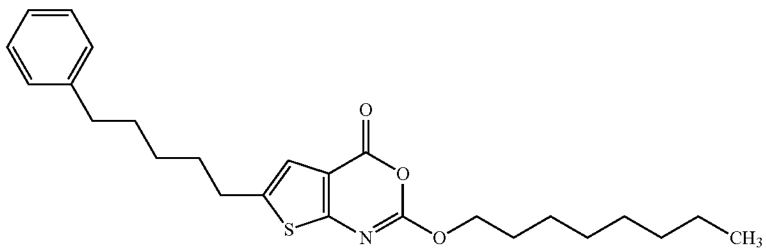 | 411.6 | | | | oil |
| 94 | 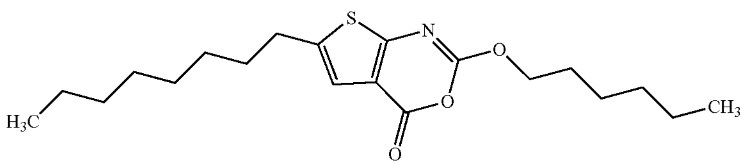 | 365.5 | | 83.03% | | oil |
| 95 | 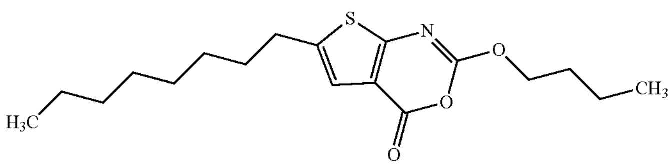 | 337.5 | | 60.26% | | oil |
| 96 | 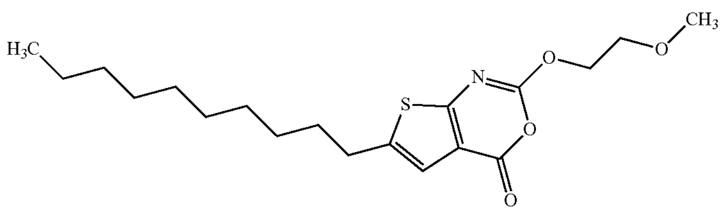 | 367.5 | | | | 38-41 |
| 97 | 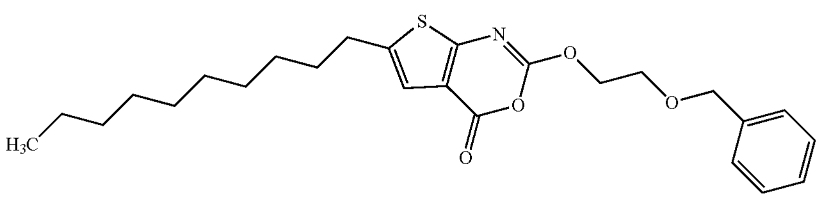 | 443.6 | | | | oil |

-continued

| Entry | structure | MW | k 10-3.s-1 | Ymax | % inhibit | MP |
|---|---|---|---|---|---|---|
| 98 | 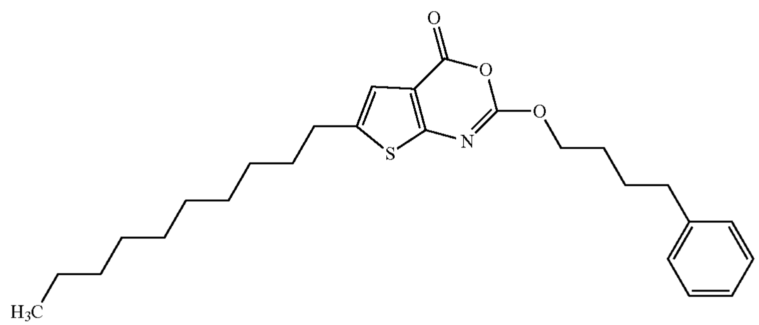 | 441.6 | | | | oil |
| 99 | 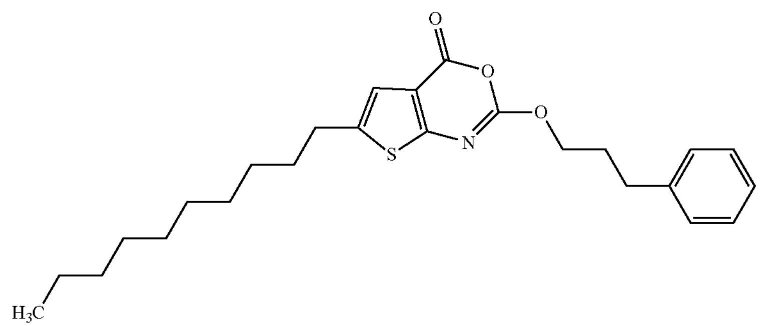 | 427.6 | | | | oil |
| 100 | 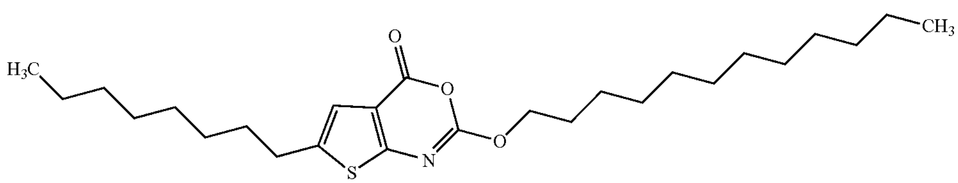 | 449.7 | | | | oil |

-continued

| Entry | structure | MW | k 10-3.s-1 | Ymax | % inhibit | MP |
|---|---|---|---|---|---|---|
| 101 | 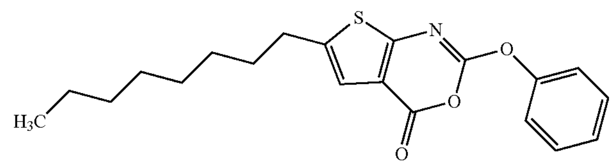 | 357.5 | | | | oil |
| 102 | 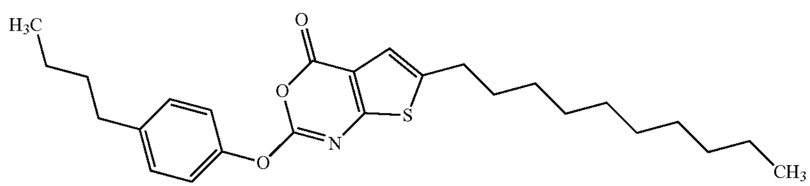 | 441.6 | | | | 55–58 |
| 103 | 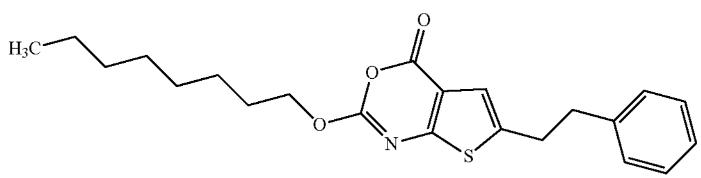 | 385.5 | | | | oil |
| 104 | 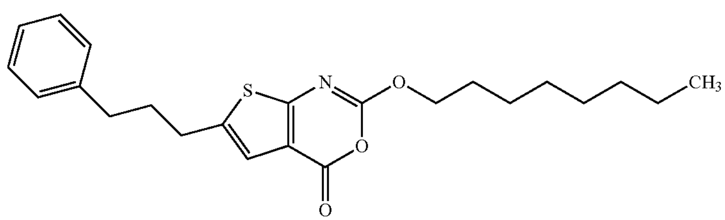 | 399.6 | | | | oil |

| Entry | structure | MW | k 10-3.s-1 | Ymax | % inhibit | MP |
|---|---|---|---|---|---|---|
| 105 | 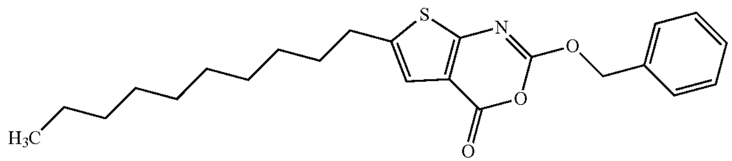 | 399.6 | | | | oil |
| 106 | 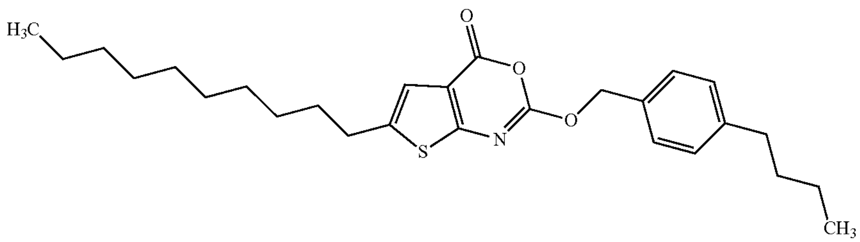 | 455.7 | | | | oil |
| 107 | 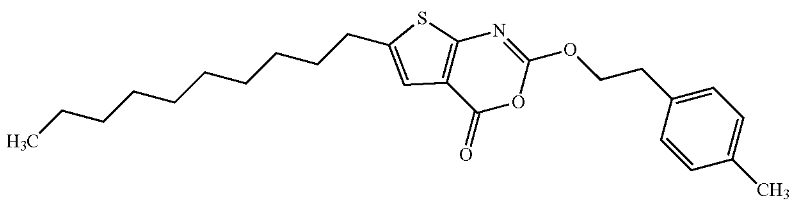 | 427.6 | | | | oil |
| 108 | 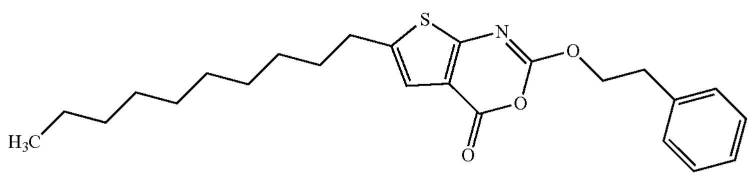 | 413.6 | | | | oil |

-continued

| Entry | structure | MW | k 10-3.s-1 | Ymax | % inhibit | MP |
|---|---|---|---|---|---|---|
| 109 | 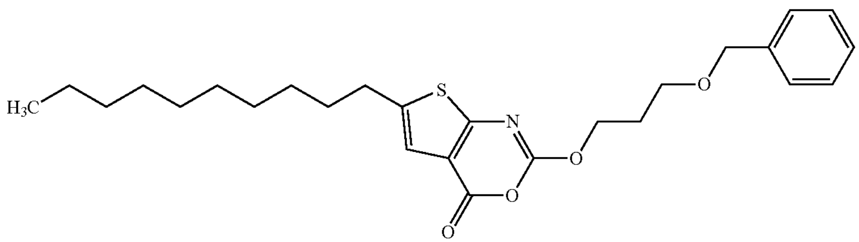 | 457.6 | | | | oil |
| 110 | 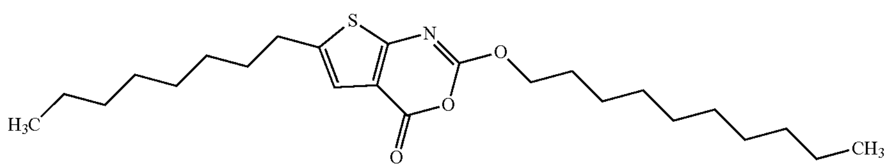 | 421.7 | | | | oil |
| 111 | 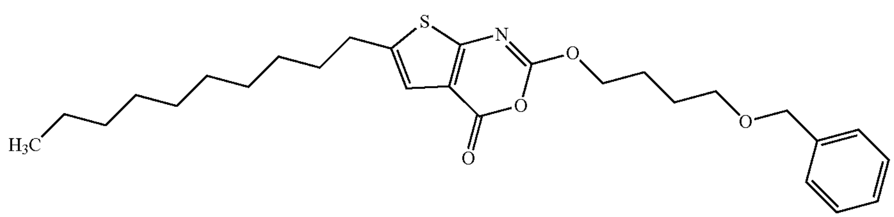 | 471.7 | | | | oil |
| 112 | 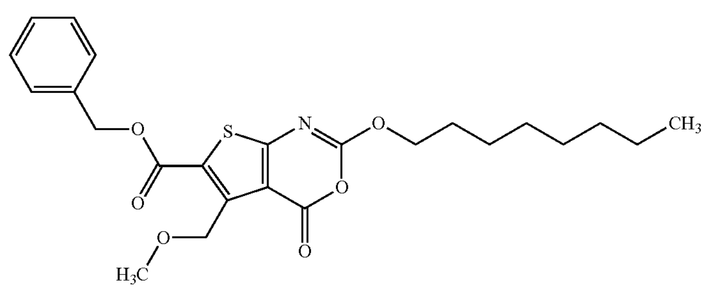 | 460.0 | | | | |

-continued

| Entry | structure | MW | k 10-3.s-1 | Ymax | % inhibit MP |
|---|---|---|---|---|---|
| 113 | 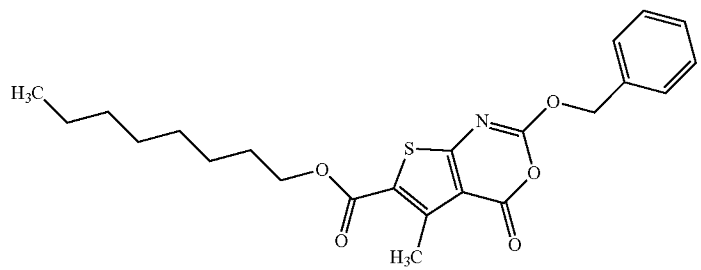 | 429.5 | | | |
| 114 | 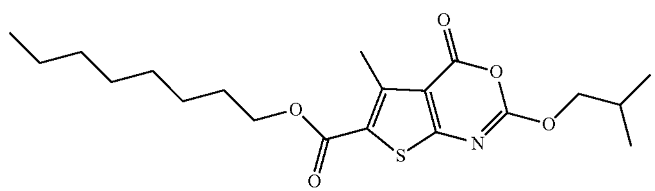 | 395.5 | | | |

"k" and "Ymax" in the above table correspond to values inn the equation appearing on page 159. All compounds listed as oils were oils at room temperature.

The language "therapeutically effective amount" of the compounds of the invention, described infra, refers to that amount of a therapeutic compound necessary or sufficient to perform its intended function within a mammal. An effective amount of the therapeutic compound can vary according to factors such as the amount of the causative agent already present in the mammal, the age, sex, and weight of the mammal, and the ability of the therapeutic compounds of the present invention to affect the desired result in the mammal. One of ordinary skill in the art would be able to study the aforementioned factors and make a determination regarding the effective amount of the therapeutic compound without undue experimentation. An in vitro or in vivo assay also can be used to determine an "effective amount" of the therapeutic compounds described infra. The ordinarily skilled artisan would select an appropriate amount of the therapeutic compound for use in the aforementioned assay or as a therapeutic treatment.

A therapeutically effective amount preferably diminishes at least one symptom or effect associated with the disorder being treated by at least about 20%, (more preferably by at least about 40%, even more preferably by at least about 60%, and still more preferably by at least about 80%) relative to untreated subjects. Assays can be designed by one skilled in the art to measure the diminishment of such symptoms and/or effects. Any art recognized assay capable of measuring such parameters are intended to be included as part of this invention.

The term "animal" includes any organism with adenosine receptors. Examples of animals include yeast, mammals, reptiles, and birds. It also includes transgenic animals.

The term "mammal" is art recognized and is intended to include an animal, more preferably a warm-blooded animal, most preferably cattle, sheep, pigs, horses, dogs, cats, rats, mice, and humans. Mammals susceptible to obesity associated disorders are included as part of this invention.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

The term "substituted alkyl", refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl. substituted with an aryl (e.g., phenylmethyl (benzyl)). The term "alkyl" also includes unsaturated aliphatic groups analogous in length and possible substitution to the alkyls described above, but that contain at least one double or triple bond respectively.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively. For example, the invention contemplates cyano and propargyl groups.

Unless the number of carbons is otherwise specified, "lower alkyl" as used herein means an alkyl group, as defined above, but having from one to ten carbons, more preferably from one to six carbon atoms in its backbone structure, even more preferably one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to the radical of two or more cyclic rings (e.g., cycloalkyls, cycloalkenyls, cycloalkynyls, aryls and/or heterocyclyls) in which two or more atoms are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "heterocycle" or "heterocyclic system" as used herein is intended to mean a stable 5, 6 or 7-membered monocyclic or 7, 8, 9, 10 or 11-membered bicyclic heterocyclic ring which is saturated or partially unsaturated.

The terms "carbocyclic" or "heterocyclic" further include spiro compounds, which denote a bicyclic compound in which the two rings have one atom in common and the atom may be carbon or a heteroatom.

The term "amino acids" includes naturally and unnaturally occurring amino acids found in proteins such as glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. Amino acid analogs include amino acids with lengthened or shortened side chains or variant side chains with appropriate functional groups. Amino acids also include D and L stereoisomers of an amino acid when the structure of the amino acid admits of stereoisomeric forms. The term "dipeptide" includes two or more amino acids linked together. Preferably, dipeptides are two amino acids linked via a peptide linkage. Particularly preferred dipeptides include, for example, alanine-alanine and glycine-alanine.

It will be noted that the structure of some of the compounds of this invention includes asymmetric carbon atoms and thus occur as racemates and racemic mixtures, single enantiomers, diastereomeric mixtures and individual diastereomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

The invention further pertains to pharmaceutical compositions for treating obesity and obesity associated disorders in a mammal. The pharmaceutical composition includes a therapeutically effective amount of a compound of the invention and a pharmaceutically acceptable carrier. It is to be understood, that all of the compounds described below are included for therapeutic treatment. It is to be further understood that the compounds of the invention can be used alone or in combination with other compounds of the invention or in combination with additional therapeutic compounds, such as antibiotics, antiinflammatories, or anticancer agents, for example.

The term "antibiotic" is art recognized and is intended to include those substances produced by growing microorganisms and synthetic derivatives thereof, which eliminate or inhibit growth of pathogens and are selectively toxic to the pathogen while producing minimal or no deleterious effects upon the infected host subject. Suitable examples of antibiotics include, but are not limited to, the principle classes of aminoglycosides, cephalosporins, chloramphenicols, fuscidic acids, macrolides, penicillins, polymixins, tetracyclines and streptomycins.

The term "antiinflammatory" is art recognized and is intended to include those agents which act on body mechanisms, without directly antagonizing the causative agent of the inflammation such as glucocorticoids, aspirin, ibuprofen, NSAIDS, etc.

The term "anticancer agent" is art recognized and is intended to include those agents which diminish, eradicate, or prevent growth of cancer cells without, preferably, adversely affecting other physiological functions. Representative examples include cisplatin and cyclophosphamide.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyl containing derivatives can be converted into esters via treatment with an esterifying agent such as alkanoyl halides. The term is further intended to include lower hydrocarbon groups capable of being solvated under physiological conditions, e.g., alkyl esters, methyl, ethyl and propyl esters. (See, for example, Berge et al., supra.)

The invention further contemplates the use of prodrugs which are converted in vivo to the therapeutic compounds of the invention (see, e.g., R. B. Silverman, 1992, "The Organic Chemistry of Drug Design and Drug Action", Academic Press, Chapter 8). Such prodrugs can be used to alter the biodistribution (e.g., to allow compounds which would not typically enter the reactive site of the protease) or the pharmacokinetics of the therapeutic compound. For example, a carboxylic acid group, can be esterified, e.g., with a methyl group or an ethyl group to yield an ester. When the ester is administered to a subject, the ester is cleaved, enzymatically or non-enzymatically, reductively or hydrolytically, to reveal the anionic group. An anionic group can be esterified with moieties (e.g., acyloxymethyl esters) which are cleaved to reveal an intermediate compound which subsequently decomposes to yield the active compound. In another embodiment, the prodrug is a reduced form of a sulfate or sulfonate, e.g., a thiol, which is oxidized in vivo to the therapeutic compound. Furthermore, an anionic moiety can be esterified to a group which is actively transported in vivo, or which is selectively taken up by target organs. The ester can be selected to allow specific targeting of the therapeutic moieties to particular reactive sites, as described below for carrier moieties.

The compounds of the invention may comprise water-soluble prodrugs which are described in WO 99/33815, International Application No. PCT/US98/04595, filed Mar. 9, 1998 and published Jul. 8, 1999. The entire content of WO 99/33815 is expressly incorporated herein by reference. The water-soluble prodrugs are metabolized in vivo to an active drug, e.g., by esterase catalyzed hydrolysis.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 per cent to about 70 percent, most preferably from about 10 percent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, acetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made, by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert dilutents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

An appropriate buffer system (e.g., sodium phosphate, sodium acetate or sodium borate) may be added to prevent pH drift under storage conditions.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 200 mg per kilogram of body weight per day, more preferably from about 0.01 to about 150 mg per kg per day, and still more preferably from about 0.2 to about 140 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The present invention also pertains to packaged pharmaceutical compositions for treating obesity or obesity associated disorders in a mammal. The packaged pharmaceutical compositions include a container holding a therapeutically effective amount of at least one compound of the invention and instructions for using the compound for treating obesity or an obesity associated disorder in the mammal.

The features and details of the invention will now be more particularly described and pointed out in the claims. It is to be understood that the particular embodiments of the invention are shown by way of illustration and not as limitations of the invention. The principle features of this invention can be employed in various embodiments without departing from the scope of the invention.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

This invention will be better understood from the Experimental Details which follow. However, one skilled in the art will readily appreciate that the specific methods and results discussed are merely illustrative of the invention as described more fully in the claims which follow thereafter.

Compounds in the examples are labeled with whole numbers if the compound appears in the table above and as X, Y, where X is the example number and Y is an index starting at 1 in each example, if they do not appear in the above table.

Experimental Details

All non-aqueous reactions requiring anhydrous conditions were performed under a positive pressure of nitrogen ($N_2$) in oven-dried glassware, which had been cooled under $N_2$. All solvents for anhydrous reactions were purchased from Aldrich. The removal of solvents refers to evaporation in vacuo on a rotary evaporator followed by evacuation to constant sample weight (<0.1 mm Hg). Solvents used for chromatography were purchased HPLC grade. All reagents employed were of American Chemical Society (ACS) grade or finer. Air sensitive reagents were handled under an atmosphere of dry $N_2$.

Where possible all reactions were followed by thin layer chromatography (TLC) and visualized using UV fluorescence, 3% $KMnO_4$ (aqueous) staining, and/or dodecamolybdophosphoric acid. Commercial thin layer and preparative layer chromatography plates were Si250F and Si500F, respectively, from J. T. Baker. Flash chromatography was performed using 40 µm 'Baker' silica gel from J. T. Baker. All solvent mixtures are listed as volume ratios.

Melting points are uncorrected and were determined on a Mel-Temp II (Laboratory Devices, USA) using open capillary tubes. Mass spectra (MS) were recorded on a Platform 2 Micromass instrument. Nuclear magnetic resonance (NMR) spectra were measured on a Varian 200 instrument in the specified solvent with tetramethylsilane (TMS) as internal standard for $^1H$ NMR. For $^{13}C$ NMR spectra, the deuterated solvent peak was used as the reference with its position set relative to TMS.

LCMS Methods: Method A=LC1 method; Method B=Polar method; Method C=Polar_Short method; Method D=Strong_Nonpolar General Procedure: Amides/Esters a. Route A. The aminothiophene was synthesized using a known protocol (McKibben, B. P., Cartwell, C. H., Castelhano, A. L. *Tetrahedron Lett.* 1999, 40, 5471–5474). Amide protection with trifluoroacetic anhydride followed by TFA deprotection and treatment with sodium carbonate generates the amino acid. Attempts to deprotect with TFA without amide protection results in decarboxylation. The amino acid was reacted with various acid chlorides, and chloroformates to afford the thienoxazinones in moderate yields (Scheme 1).

Scheme 1

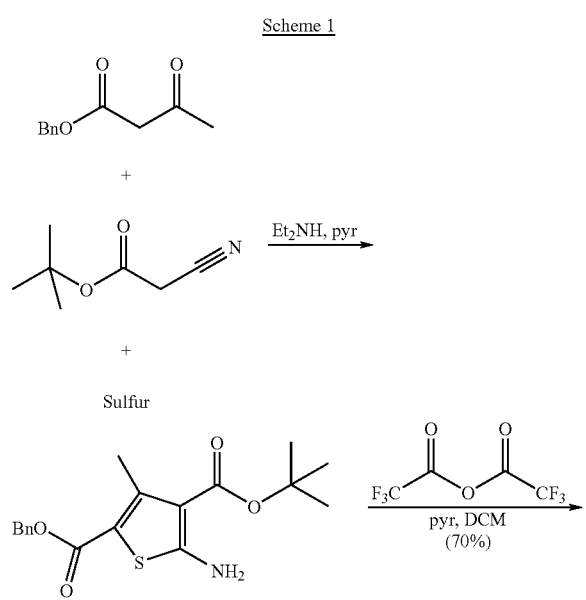

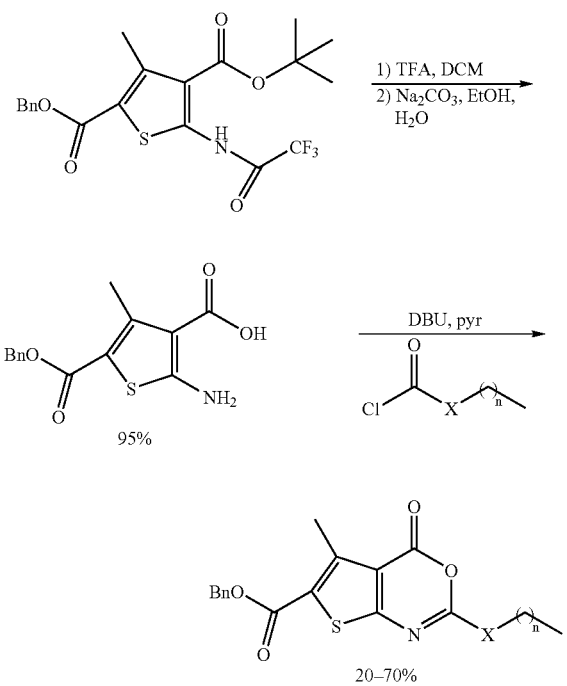

b. Route B. In general, reacting the t-Bu protected amino acid directly with a chloroformate or an isocyanate followed by TFA deprotection of the t-Bu ester and treatment with thionyl chloride gives the corresponding thienoxazinones in higher yields (Scheme 2)

Scheme 2

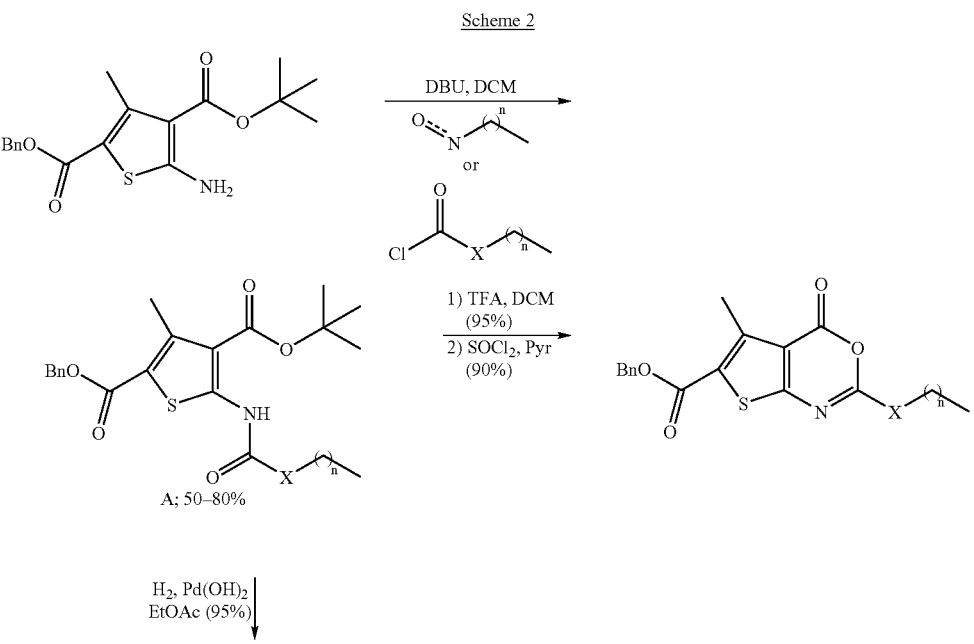

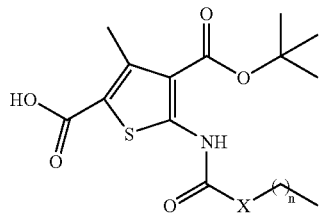 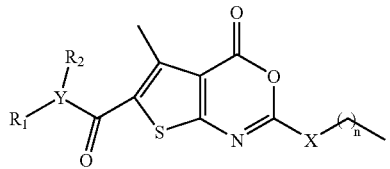

Derivation at the 5-position was achieved through either transesterification of methyl acetoacetate with various alcohols prior to thiophene formation or benzyl deprotection of the diester, followed by EDC coupling with various alcohols and amines to generate esters or amides, respectively.

EXAMPLE 1

General Procedure for Amino-Thiophene Formation

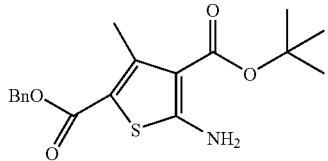

5-Amino-3-methyl-thiophene-2,4-dicarboxylic acid 2-benzyl ester 4-tert-butyl ester. (1.1) To a suspension of benzyl acetoacetate (20.0 g, 104.1 mmol), t-butyl cyanoacetate (14.7 g, 104.1 mmol), sulfur (3.5 g, 109.3 mmol) and pyridine (120 ml) was added diethyl amine dropwise. After 2 days, the black solution was concentrated under reduced pressure, dissolved in Et$_2$O and filtered through silica. The eluent was then concentrated. Chromatography (silica, 7:1 hexane/EtOAc) yielded 25.58 g (71%) of a orange oil which slowly crystallizes upon standing: $^1$H-NMR (CDCl$_3$) 1.58 (s, 9H), 2.70 (s, 3H), 5.27 (s, 2H), 7.38 (m, 5H). $^1$H NMR was consistent with published data.

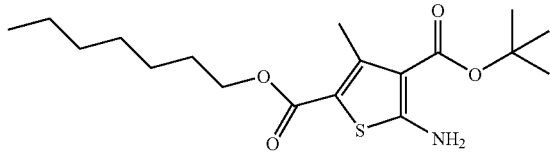

5-Amino-3-methyl-thiophene-2,4-dicarboxylic acid 2-heptyl ester 4-tert-butyl ester. (1.2) The same method as for the preparation of 5-amino-3-methyl-thiophene-2,4-dicarboxylic acid 2-benzyl ester 4-tert-butyl ester was employed. Thus, cyclization of tert-butyl cyanoacetate (10.3 mL, 72.0 mmol), heptyl acetoacetate (13.7 g, 68.0 mmol), and sulfur (4.4 g, 0.14 mol) in pyridine (80 mL) with added diethylamine (7.1 mL, 68.0 mmol) afforded 18.4 g thiophene (76%) of an oil after column chromatography (10:1; hexanes:EtOAc): $^1$H NMR (CDCl$_3$) δ 6.47 (bs, 2H), 4.19 (t, 2H, J=6.6 Hz), 2.67 (s, 3H), 1.80–1.50 (m, 2H), 1.57 (s, 9H), 1.30 (bs, 8H), 0.89 (t, 3H, J=6.6 Hz).

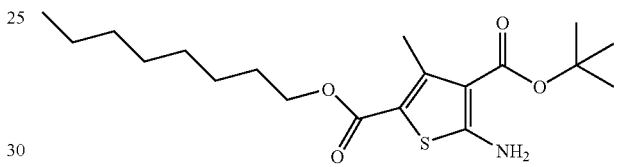

5-Amino-3-methyl-thiophene-2,4-dicarboxylic acid 2-octyl ester 4-tert-butyl ester. (1.3) The same method as for the preparation of 5-amino-3-methyl-thiophene-2,4-dicarboxylic acid 2-benzyl ester 4-tert-butyl ester was employed. Thus, cyclization of tert-butyl cyanoacetate (6.2 mL, 43.0 mmol), octyl acetoacetate (8.5 g, 41.0 mmol), and sulfur (2.6 g, 82.0 mmol) in pyridine (50 mL) with added diethylamine (4.3 mL, 41.0 mmol) afforded 10.3 g thiophene (68%) of an oil after column chromatography (10:1; hexanes:EtOAc): $^1$H NMR (CDCl$_3$) δ 6.63 (s, 2H), 4.14 (t, 2H, J=6.6 Hz), 2.63 (s, 3H), 1.72–1.50 (m, 2H), 1.52 (s, 9H), 1.22 (bs, 10H), 0.83 (t, 3H, J=6.8 Hz). $^{13}$C NMR (CDCl$_3$) δ 165.9, 165.4, 163.0, 147.9, 109.6, 108.0, 81.0, 64.4, 31.7, 29.1, 28.6, 28.4, 25.9, 22.5, 16.2, 14.0.

EXAMPLE 2

General Procedure for Cyclization from Chloroformate and Amino-acid

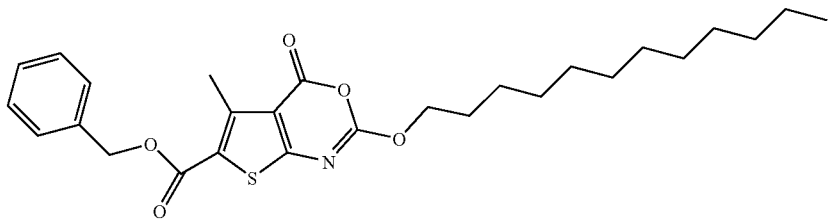

2-Dodecyloxy-5-methyl-4-oxo-4H-thieno[2,3-d][1,3] oxazine-6-carboxylic acid benzyl ester (6) To a stirring solution of 5-amino-3-methyl-thiophene-2,4-dicarboxylic acid 2-benzyl ester (1.00 g, 3.43 mmol) in pyridine (20 mL) was added dodecyl chloroformate (2.80 mL, 2.56 g, 10.3 mmol). The reaction was stirred at 0° C. for 0.5 h, then solvent was removed under reduced pressure. The product was purified by column chromatography (10:1; hexanes:EtOAc) to give 169 mg (10%) of a solid: $^1$H NMR (CDCl$_3$) δ 7.50–7.25 (m, 5H), 5.35 (s, 2H), 4.17 (t, 2H, J=6.6 Hz), 2.87 (s, 3H), 1.70–1.40 (m, 2H), 1.40–1.00 (m, 18H), 0.88 (t, 3H, J=6.4 Hz). MS (EI): 486.4 (m$^+$+H).

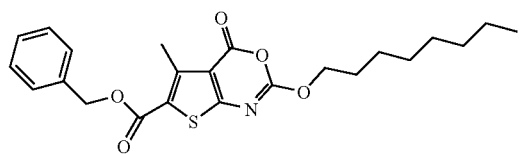

5-Methyl-2-octyloxy-4-oxo-4H-thieno[2,3-d][1,3]oxazine-6-carboxylic acid benzyl ester (5) The same method as for the preparation of 2-dodecyloxy-5-methyl-4-oxo-4H-thieno[2,3-d][1,3]oxazine-6-carboxylic acid benzyl ester was employed: $^1$H NMR (CDCl$_3$) δ 7.53–7.25 (m, 5H), 5.33 (s, 2H), 4.44 (t, 2H, J=6.6 Hz), 2.83 (s, 3H), 1.80 (quint, 2H, J=6.6 Hz), 1.26 (bs, 10H), 0.88 (t, 3H, J=6.6 Hz).

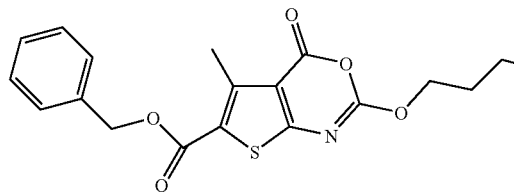

2-Hexadecyloxy-5-methyl-4-oxo-4H-thieno[2,3-d][1,3] oxazine-6-carboxylic acid benzyl ester (7) The same method as for the preparation of 2-dodecyloxy-5-methyl-4-oxo-4H-thieno[2,3-d][1,3]oxazine-6-carboxylic acid benzyl ester was employed: $^1$H NMR (CDCl$_3$) δ 7.50–7.25 (m, 5H), 5.34 (s, 2H), 4.44 (t, 2H, J=6.6 Hz), 2.83 (s, 3H), 1.80 (quint, 2H, J=6.6 Hz), 1.26 (bs, 26H), 0.88 (t, 3H, J=6.6 Hz).

EXAMPLE 3

General Procedure for Cyclization from Acyl Chloride and Amino-acid

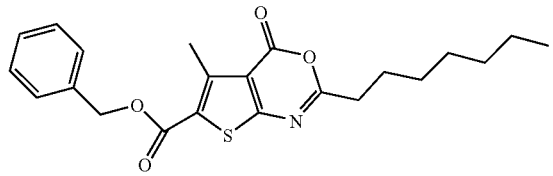

2-Heptyl-5-methyl-4-oxo-4H-thieno[2,3-d][1,3]oxazine-6-carboxylic acid benzyl ester (1) To a stirring solution of 5-amino-3-methyl-thiophene-2,4-dicarboxylic acid 2-benzyl ester (200 mg, 0.69 mmol) in pyridine (5 mL) was added octanoyl chloride (352 μL, 2.56 g, 10.3 mmol). The reaction was stirred at 0° C. for 0.5 h, then let warm to RT and stirred for 3.5 h. The solvent was removed under reduced pressure. The mixture was diluted in EtOAc, washed with H$_2$O. The organic fraction was dried (MgSO$_4$), and concentrated in vacuo. The product was purified by column chromatography (9:1; hexanes:EtOAc) to give 48 mg (18%) of a solid:): $^1$H NMR (CDCl$_3$) δ 7.32–7.48 (m, 5H), 5.35 (s, 2H), 2.86 (s, 3H), 2.69 (t, 2H, J=7.2 Hz), 1.90–1.70 (m, 2H), 1.45–1.20 (m, 8H), 0.98–0.80 (m, 3H).

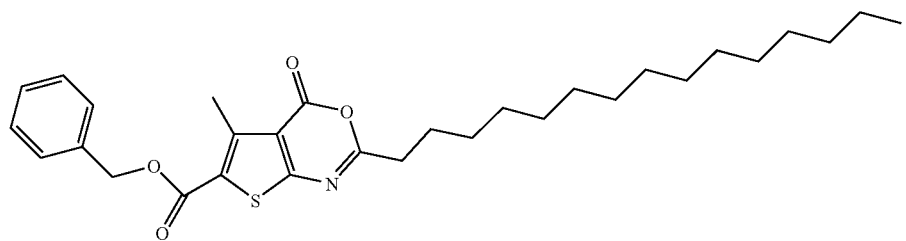

5-Methyl-4-oxo-2-pentadecyl-4H-thieno[2,3-d][1,3] oxazine-6-carboxylic acid benzyl ester (3) The same method as for the preparation of 2-heptyl-5-methyl-4-oxo-4H-thieno [2,3-d][1,3]oxazine-6-carboxylic acid benzyl ester was employed. Thus, cyclization with hexadecanoyl chloride (476 mL, 2.06 mmol) yielded 56 mg product (16%) after oil after column chromatography (9:1; hexanes:EtOAc): ¹H NMR (CDCl₃) δ 7.30–7.55 (m, 5H), 5.35 (s, 2H), 2.86 (s, 3H), 2.69 (t, 2H, J=7.2 Hz), 2.00–1.70 (m, 2H), 1.50–1.0 (m, 24H), 1.00–0.90 (m, 3H).

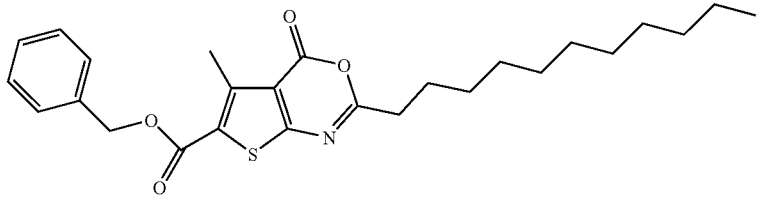

2-Undecyl-5-methyl-4-oxo-4H-thieno[2,3-d][1,3]oxazine-6-carboxylic acid benzyl ester (2) The same method as for the preparation of 2-heptyl-5-methyl-4-oxo-4H-thieno[2,3-d][1,3]oxazine-6-carboxylic acid benzyl ester was employed. Thus, cyclization with dodecanoyl chloride (476 mL, 2.06 mmol) yielded 77 mg product (24%) after oil after column chromatography (9:1; hexanes:EtOAc): ¹H NMR (CDCl₃) δ 7.30–7.50 (m, 5H), 5.35 (s, 2H), 2.86 (s, 3H), 2.69 (t, 2H, J=7.2 Hz), 1.90–1.70 (m, 2H), 1.50–1.20 (m, 16H), 1.00–0.90 (m, 3H).

EXAMPLE 4

General Procedure for Acylation with Chlorformate of Diester

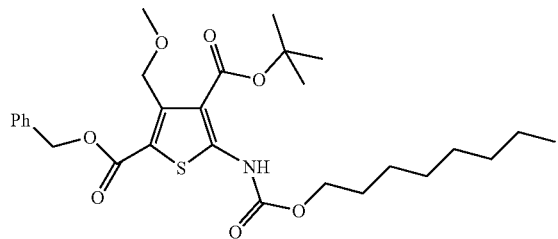

3-Methoxymethyl-5-octyloxycarbonylamino-thiophene-2,4-dicarboxylic acid 2-benzyl ester 4-tert-butyl ester. (4.1) To a stirring solution of 5-amino-3-methoxymethyl-thiophene-2,4-dicarboxylic acid 2-benzyl ester 4-tert-butyl ester (1.16 g, 3.06 mmol) in pyridine (15 mL) was added octyl chloroformate (0.9 mL, 886 mg, 4.6 mmol). The reaction was stirred at 0° C. for 1 h, then solvent was removed under reduced pressure. The product was purified by column chromatography (10:1; hexanes:EtOAc) to give 1.27 g (78%) of a solid: ¹H NMR (CDCl₃) δ 10.51 (s, 1H), 7.32 (m, 5H), 5.12 (s, 2H), 4.19 (t, 2H, J=6.6 Hz), 3.81 (s, 3H), 3.76 (s, 2H), 1.68 (quint, 2H, J=6.6 Hz), 1.45 (s, 9H), 1.44–1.21 (m, 10H), 0.89 (t, 3H, J=5.8 Hz). MS (EI): 533.9 (m⁺).

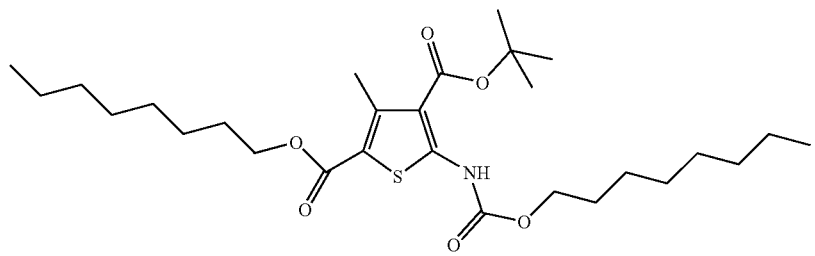

3-Methyl-5-octyloxycarbonylamino-thiophene-2,4-dicarboxylic acid 4-tert-butyl ester 2-octyl ester. (4.2) The same method as for the preparation of 3-methoxymethyl-5-octyloxycarbonylamino-thiophene-2,4-dicarboxylic acid 2-benzyl ester 4-tert-butyl ester was employed. Thus, acylation with octyl chloroformate (0.171 mL, 168 mg, 0.87 mmol) afforded 80 mg of a solid (26%) after column chromatography (9:1; hexanes:EtOAc): ¹H NMR (CDCl₃) δ 10.86 (s, 1H), 4.23 (t, 2H, J=6.6 Hz), 2.67 (s, 3H), 1.80–1.40 (m, 4H), 1.57 (s, 9H), 1.42–1.08 (m, 20H), 0.89 (t, 3H, J=6.6 Hz). MS (EI): 526.0 (m⁺).

3-Methyl-5-heptyloxycarbonylamino-thiophene-2,4-dicarboxylic acid 4-tert-butyl ester 2-heptyl ester. (4.3) To a stirring solution of 5-amino-3-methyl-thiophene-2,4-dicarboxylic acid 2-heptyl ester 4-tert-butyl ester (5.0 g, 14.0 mmol) and DBU (5.3 mL, 5.4 g, 35.0 mmol) in CH₂Cl₂ (100 mL) was added heptyl chloroformate (5.0 ml, 5.0 g, 28.0 mmol). The reaction was stirred at room temperature for 20 h, and then solvent was removed under reduced pressure. The product was purified by column chromatography (9:1; hexanes:EtOAc) to give 3.1 g (45%) of a solid: ¹H NMR (CDCl₃) δ 10.86 (s, 1H), 4.23 (t, 2H, J=6.6 Hz), 2.67 (s, 3H), 1.80–1.40 (m, 4H), 1.57 (s, 9H), 1.42–1.08 (m, 16H), 0.89 (t, 3H, J=6.6 Hz).

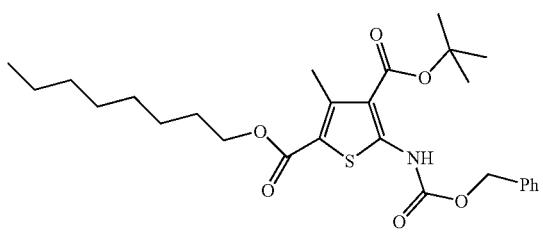

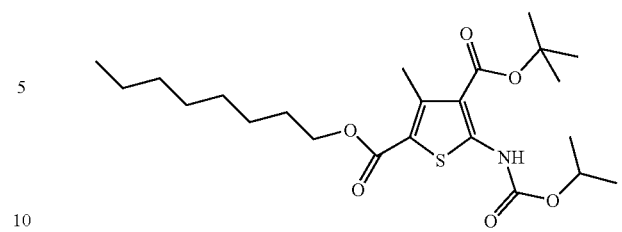

5-Benzyloxycarbonylamino-3-methyl-thiophene-2,4-dicarboxylic acid 4-tert-butyl ester 2-octyl ester. (4.4) The same method as for the preparation of 3-methyl-5-heptyloxycarbonylamino-thiophene-2,4-dicarboxylic acid 4-tert-butyl ester 2-heptyl ester was employed. Thus, acylation with benzyl chloroformate (0.154 mL, 185 mg, 1.1 mmol) afforded 138 mg of a solid (52%) after column chromatography (10:1; hexanes:EtOAc): Mp 65.0–66.0° C.; $^1$H NMR (CDCl$_3$) δ 10.97 (s, 1H), 7.50–7.30 (m, 5H), 5.28 (d, 2H, J=4.8 Hz), 4.23 (t, 2H, J=6.6 Hz), 2.72 (s, 3H), 1.80–1.55 (m, 2H), 1.58 (s, 9H), 1.28 (bs, 10H), 0.89 (t, 3H, J=6.6 Hz).

5-iso-Propoxycarbonylamino-3-methyl-thiophene-2,4-dicarboxylic acid 4-tert-butyl ester 2-octyl ester. (4.6) The same method as for the preparation of 3-methyl-5-heptyloxycarbonylamino-thiophene-2,4-dicarboxylic acid 4-tert-butyl ester 2-heptyl ester was employed. Thus, acylation with iso-propyl chloroformate in toluene (0.54 mL, 0.54 mmol), afforded 117 mg of a solid (95%) after column chromatography (9:1; hexanes:EtOAc): $^1$H NMR (CDCl$_3$) δ 10.82 (s, 1H), 5.30 (s, 1H), 5.08 (sept, 1H, J=6.2 Hz), 4.23 (t, 2H, J=6.6 Hz), 2.73 (s, 3H), 1.80–1.60 (m, 2H), 1.60 (s, 9H), 1.34 (d, 6H, J=6.2 Hz), 1.28 (bs, 10H), 0.88 (t, 3H, J=6.6 Hz).

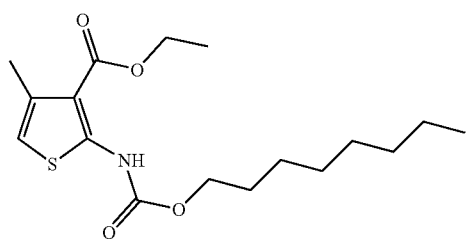

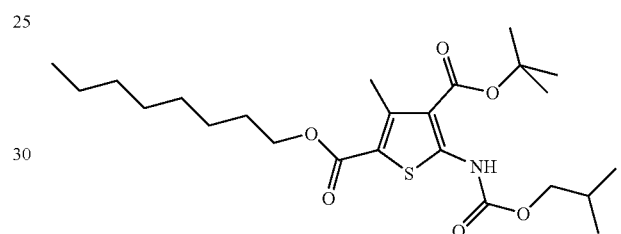

4-Methyl-2-octyloxycarbonylamino-thiophene-3-carboxylic acid ethyl ester. (4.5) The same method as for the preparation of 3-methyl-5-heptyloxycarbonylamino-thiophene-2,4-dicarboxylic acid 4-tert-butyl ester 2-heptyl ester was employed. Thus, acylation with octyl chloroformate (1.06 mL, 1.04 g, 5.4 mmol) afforded 254 mg of an oil (28%) after column chromatography (9:1; hexanes:EtOAc): $^1$H NMR (CDCl$_3$) δ 10.53 (s, 1H), 6.31 (s, 1H), 4.34 (q, 2H, J=6.8 Hz), 4.12 (t, 2H, J=6.6 Hz) 2.34 (s, 3H), 1.67 (bs, 2H), 1.37 (quint, 3H, J=6.8 Hz), 1.28 (bs, 10H), 0.88 (t, 3H, J=6.6 Hz). MS (EI): 341.9 (m+).

5-iso-Butoxycarbonylamino-3-methyl-thiophene-2,4-dicarboxylic acid 4-tert-butyl ester 2-octyl ester. (4.7) The same method as for the preparation of 3-methyl-5-heptyloxycarbonylamino-thiophene-2,4-dicarboxylic acid 4-tert-butyl ester 2-heptyl ester was employed. Thus, acylation with iso-butyl chloroformate (0.07 mL, 74.0 mg, 0.54 mmol) afforded 98 mg of a solid (77%) after column chromatography (9:1; hexanes:EtOAc): $^1$H NMR (CDCl$_3$) δ 10.86 (s, 1H), 4.23 (t, 2H, J=6.6 Hz), 4.04 (d, 2H, J=6.6 Hz), 2.73 (s, 3H), 2.02 (nonet, 1H, J=6.6 Hz), 1.80–1.50 (m, 2H), 1.06 (s, 9H), 1.28 (bs, 10H), 1.00 (d, 6H, J=6.6 Hz), 0.88 (t, 3H, J=6.2 Hz).

EXAMPLE 5

General Procedure for Acylation with Isocyanate of Diester Reaction

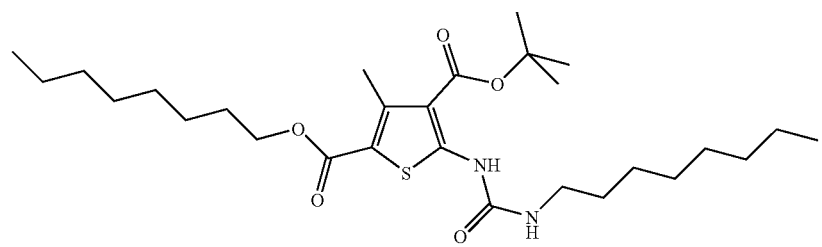

3-Methyl-5-(3-octyl-ureido)-thiophene-2,4-dicarboxylic acid 4-tert-butyl ester 2-octyl ester. (5.1) To a stirring solution of 5-amino-3-methyl-thiophene-2,4-dicarboxylic acid 2-octyl ester 4-tert-butyl ester (348 mg, 0.94 mmol) and DBU (0.35 mL, 360 mg, 2.4 mmol) in CH$_2$Cl$_2$ (10 mL) was added octyl isocyanate (0.166 mL, 146 mg, 0.94 mmol). The reaction was stirred RT for 16 h, and then solvent was removed under reduced pressure. The product was purified by column chromatography (5:1; hexanes:EtOAc) to give 431 mg of a solid (87%): Mp 92.0–94.0° C.; $^1$H NMR (CDCl$_3$) δ 12.30 (s, 1H), 8.64 (s, 1H), 5.30 (t, 1H, J=6.0 Hz), 4.25 (t, 2H, J=6.4 Hz), 3.29 (q, 2H, J=6.0 Hz), 2.74 (s, 3H), 1.90–1.50 (m, 4H), 1.61 (s, 9H), 1.28 (bs, 20H), 0.88 (m, 6H). MS (EI): 525.1 (m$^+$).

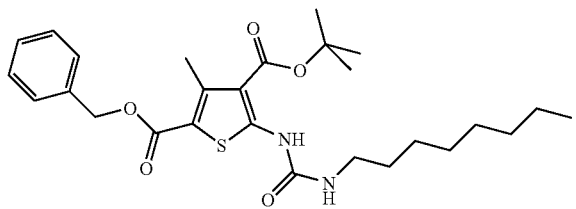

3-Methyl-5-(3-octyl-ureido)-thiophene-2,4-dicarboxylic acid 2-benzyl ester 4-tert-butyl ester. (5.2) The same method as for the preparation of 3-methyl-5-(3-octyl-ureido)-thiophene-2,4-dicarboxylic acid 4-tert-butyl ester 2-octyl ester was employed. Thus, acylation with octyl isocyanate (3.83 mL, 3.37 g, 21.7 mmol) afforded 3.42 g of a solid (38%) after column chromatography (9:1; hexanes:EtOAc): Mp 119.0–120.0° C.; $^1$H NMR (CDCl$_3$) δ 11.03 (s, 1H), 7.50–7.20 (m, 5H), 5.27 (s, 2H), 5.03 (vt, 1H), 3.29 (q, 2H, J=6.6 Hz), 2.71 (s, 3H), 1.63–1.40 (m, 2H), 1.57 (s, 9H), 1.26 (bs, 10H), 0.87 (t, 3H, J=6.6 Hz). MS (EI): 502.8 (m+).

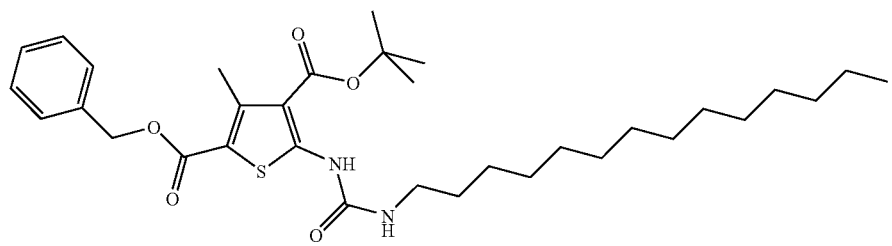

3-Methyl-5-(3-tetradecyl-ureido)-thiophene-2,4-dicarboxylic acid 2-benzyl ester 4-tert-butyl ester. (5.3) The same method as for the preparation of 3-methyl-5-(3-octyl-ureido)-thiophene-2,4-dicarboxylic acid 4-tert-butyl ester 2-octyl ester was employed. Thus, acylation with tetradecyl isocyanate (0.33 mL, 287 mg, 1.2 mmol) afforded 253 mg of a solid (36%) after column chromatography (9:1; hexanes:EtOAc): Mp 104.5–106.0° C.; $^1$H NMR (CDCl$_3$) δ 11.04 (s, 1H), 7.50–7.20 (m, 5H), 5.27 (s, 2H), 5.14 (t, 1H, J=6.2 Hz), 3.29 (q, 2H, J=6.2 Hz), 2.71 (s, 3H), 1.65–1.40 (m, 2H), 1.57 (s, 9H), 1.25 (bs, 22H), 0.88 (t, 3H, J=6.0 Hz). MS (EI): 587.1 (m$^+$).

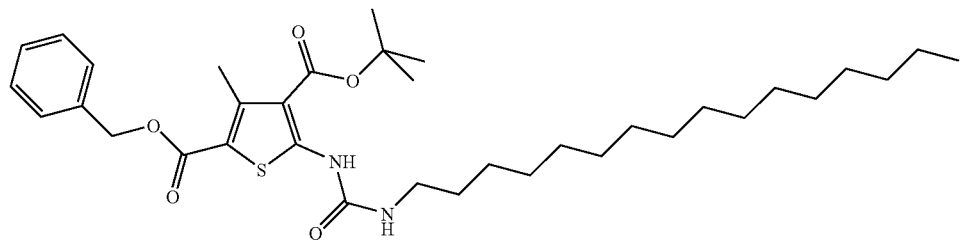

5-(3-Hexadecyl-ureido)-3-methyl-thiophene-2,4-dicarboxylic acid 2-benzyl ester 4-tert-butyl ester. (5.4) The same method as for the preparation of 3-methyl-5-(3-octyl-ureido)-thiophene-2,4-dicarboxylic acid 4-tert-butyl ester 2-octyl ester was employed. Thus, acylation with hexadecyl isocyanate (0.37 mL, 321 mg, 1.2 mmol) afforded 218 mg of a solid (30%) after column chromatography (9:1; hexanes:EtOAc): Mp 104.0–105.0° C.; $^1$H NMR (CDCl$_3$) δ 11.04 (s, 1H), 7.50–7.20 (m, 5H), 5.27 (s, 2H), 5.14 (t, 1H, J=6.2 Hz), 3.29 (q, 2H, J=6.2 Hz), 2.71 (s, 3H), 1.65–1.40 (m, 2H), 1.57 (s, 9H), 1.25 (bs, 26H), 0.88 (t, 3H, J=6.0 Hz). MS (EI): 615.1 (m$^+$).

tion of 3-methoxymethyl-5-octyloxycarbonylamino-thiophene-2,4-dicarboxylic acid 2-benzyl ester 4-tert-butyl ester (0.60 mg, 0.11 mmol) in CH$_2$Cl$_2$ (1.0 mL) was added TFA (1.0 mL). The reaction was stirred at room temperature for 12 hrs, then solvent was removed under reduced pressure to give a solid. The product was taken on without further purification: $^1$H NMR (CDCl$_3$) δ 11.98 (s, 1H), 10.09 (s, 1H), 7.45–7.20 (m, 5H), 5.14 (s, 2H), 4.22 (t, 2H, J=6.6 Hz), 3.85 (s, 3H), 3.82 (s, 2H), 1.70 (quint, 2H, J=6.6 Hz), 1.28 (bs, 10H), 0.88 (t, 3H, J=5.6 Hz).

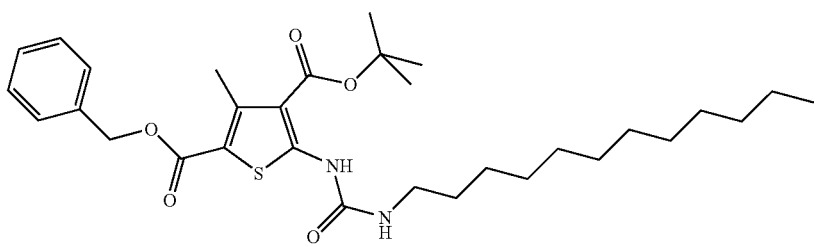

5-(3-Dodecyl-ureido)-3-methyl-thiophene-2,4-dicarboxylic acid 2-benzyl ester 4-tert-butyl ester. (5.5) The same method as for the preparation of 3-methyl-5-(3-octyl-ureido)-thiophene-2,4-dicarboxylic acid 4-tert-butyl ester 2-octyl ester was employed. Thus, acylation with decyl isocyanate

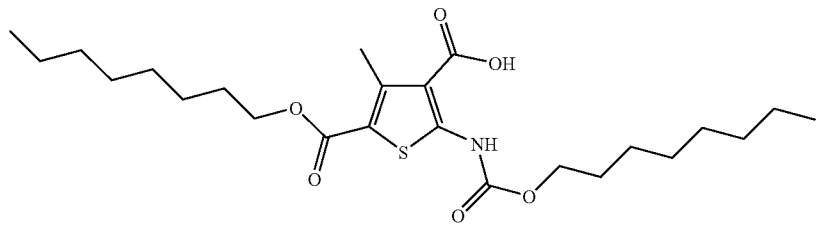

(0.29 mL, 254 mg, 1.2 mmol) afforded 265 mg of a solid (40%) after column chromatography (9:1; hexanes:EtOAc): Mp 106.8–108.0° C.). $^1$H NMR (CDCl$_3$) δ 11.04 (s, 1H), 7.45–7.26 (m, 5H), 5.27 (s, 2H), 5.24 (t, 1H, J=5.6 Hz), 3.28 (q, 2H, J=6.6 Hz), 2.72 (s, 3H), 1.60–1.40 (m, 2H), 1.57 (s, 9H), 1.25 (bs, 18H), 0.88 (t, 3H, J=6.4 Hz). MS (EI): 559.0 (m$^+$).

EXAMPLE 6

General Procedure TFA Deprotection at C-2

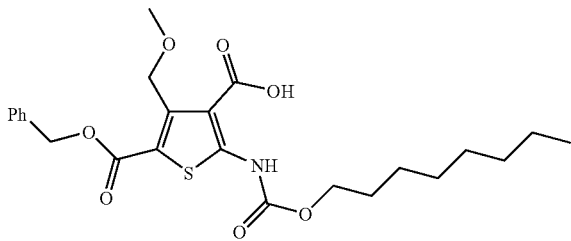

3-Methoxymethyl-5-octyloxycarbonylamino-thiophene[2,4]dicarboxylic acid 2-benzyl ester. (6.1) To a stirring solu- 3-Methoxymethyl-5-octyloxycarbonylamino-thiophene-2,4-dicarboxylic acid 2-octyl ester. (6.2) The same method as for the preparation of 3-methoxymethyl-5-octyloxycarbonylamino-thiophene[2,4]dicarboxylic acid 2-benzyl ester was employed. Thus, deprotection with TFA afforded 64 mg of a solid (68%) after column chromatography (5:1; hexanes:EtOAc): $^1$H NMR (CDCl$_3$) δ 10.56 (s, 1H), 4.27 (t, 2H, J=6.5 Hz), 4.25 (t, 2H, J=6.5 Hz), 2.81 (s, 3H), 1.80–1.53 (m, 4H), 1.50–1.15 (m, 20H), 0.89 (t, 3H, J=6.5 Hz). MS (EI): 469.9 (m$^+$).

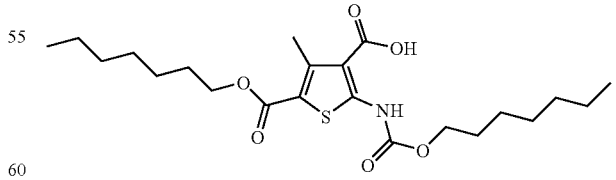

5-Heptyloxycarbonylamino-3-methoxymethyl-thiophene-2,4-dicarboxylic acid 2-heptyl ester. (6.3) The same method as for the preparation of 3-methoxymethyl-5-octyloxycarbonylamino-thiophene[2,4]dicarboxylic acid 2-benzyl ester was employed. Thus, deprotection with TFA afforded 2.7 g of a solid (96%) after tritration with hexanes:

¹H NMR (CDCl₃) δ 10.53 (s, 1H), 4.26 (t, 4H, J=6.6 Hz), 2.81 (s, 3H), 1.90–1.58 (m, 4H), 1.60–1.12 (m, 16H), 0.89 (t, 3H, J=6.6 Hz). MS (EI): 441.9 (m+).

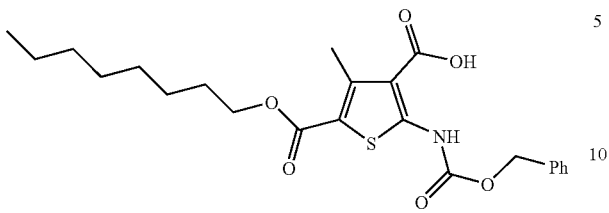

5-Benzyloxycarbonylamino-3-methyl-thiophene-2,4-dicarboxylic acid 2-octyl ester. (6.4) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: Mp 148.0–149.5° C.; ¹H NMR (CDCl₃) δ 10.56 (bs, 2H), 7.50–7.30 (m, 5H), 5.30 (d, 2H, J=4.8 Hz), 4.25 (t, 2H, J=6.6 Hz), 2.79 (s, 3H), 1.83–1.60 (m, 2H), 1.29 (bs, 10H), 0.89 (t, 3H, J=6.6 Hz).

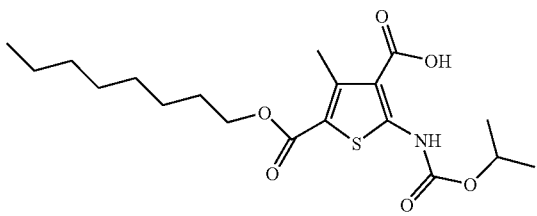

5-iso-Propoxycarbonylamino-3-methyl-thiophene-2,4-dicarboxylic acid 2-octyl ester. (6.5) The same method as for the preparation of 3-methoxymethyl-5-octyloxycarbonylamino-thiophene[2,4]dicarboxylic acid 2-benzyl ester was employed. Thus, deprotection with TFA afforded a solid, which was taken forward without further purification: Mp 152.0–153.0° C.; ¹H NMR (CDCl₃) δ 10.45 (s, 1H), 5.12 (sept, 1H, J=6.6 Hz), 4.25 (t, 2H, J=6.6 Hz), 2.82 (s, 3H), 1.73 (quint, 2H, J=6.6 Hz), 1.38 (d, 6H, J=6.6 Hz), 1.28 (bs, 10H), 0.89 (t, 3H, J=6.6 Hz).

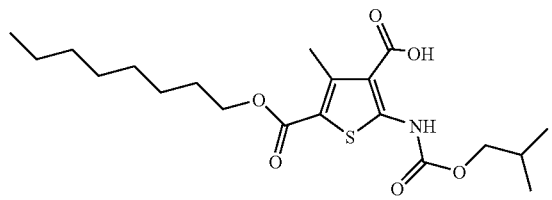

5-iso-Butoxycarbonylamino-3-methyl-thiophene-2,4-dicarboxylic acid 2-octyl ester. (6.6) The same method as for the preparation of 3-methoxymethyl-5-octyloxycarbonylamino-thiophene[2;4]dicarboxylic acid 2-benzyl ester was employed. Thus, deprotection with TFA afforded a solid, which was used without purification: ¹H NMR (CDCl₃) δ 10.53 (bs, 2H), 4.26 (t, 2H, J=6.2 Hz), 4.08 (d, 2H, J=6.6 Hz), 2.82 (s, 3H), 2.06 (nonet, 1H, J=6.6 Hz), 1.71 (quint, 2H, J=6.6 Hz), 1.29 (bs, 10H), 1.00 (d, 6H, J=6.6 Hz), 0.89 (t, 3H, J=6.6 Hz).

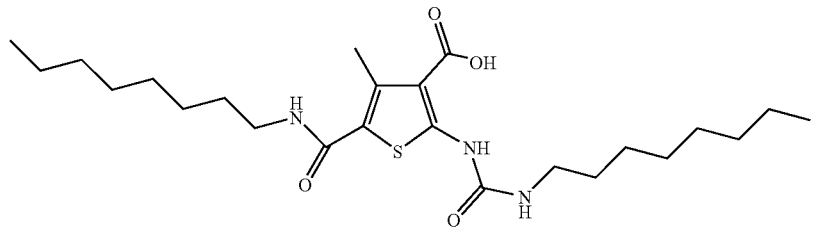

4-Methyl-5-octylcarbamoyl-2-(3-octyl-ureido)-thiophene-3-carboxylic acid. (6.7) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: ¹H NMR (CDCl₃) δ 10.90 (bs, 2H), 5.82–5.62 (m, 1H), 5.78–5.60 (m, 1H), 3.33 (q, 4H, J=6.6 Hz), 2.61 (s, 3H), 1.70–1.40 (m, 4H), 1.27 (bs, 20H), 0.88 (m, 6H).

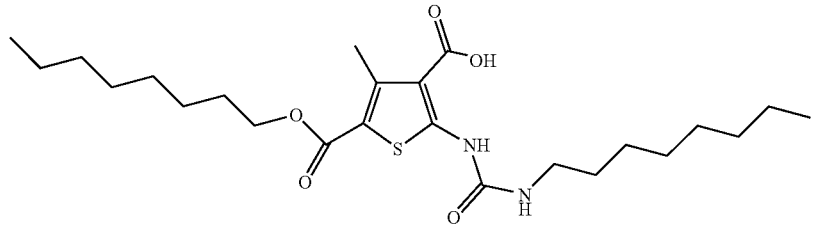

3-Methyl-5-(3-octyl-ureido)-thiophene-2,4-dicarboxylic acid 2-octyl ester. (6.8) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: $^1$H NMR (CDCl$_3$) δ 12.30 (s, 1H), 10.91 (bs, 2H), 5.30 (t, 1H, J=6.0 Hz), 4.25 (t, 2H, J=6.4 Hz), 3.29 (q, 2H, J=6.0 Hz), 2.74 (s, 3H), 1.90–1.50 (m, 4H), 1.28 (bs, 20H), 0.88 (m, 6H). MS (EI): 468.9 (m$^+$).

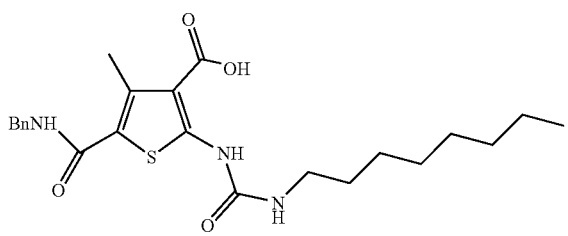

5-Benzylcarbamoyl-4-methyl-2-(3-octyl-ureido)-thiophene-3-carboxylic acid. (6.9) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: $^1$H NMR (CDCl$_3$) δ 11.16 (s, 1H), 7.40–7.10 (m, 5H), 6.19 (t, 1H, J=5.4 Hz), 4.56 (d, 2H, J=5.4 Hz), 3.25 (q, 2H, J=6.6 Hz), 2.63 (s, 3H), 1.60–1.40 (m, 2H), 1.26 (bs, 10H), 0.86 (t, 3H, J=6.2 Hz). MS (EI): 445.9 (m+).

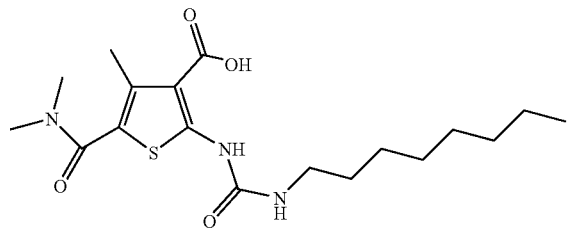

5-Dimethylcarbamoyl-4-methyl-2-(3-octyl-ureido)-thiophene-3-carboxylic acid. (6.10) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: $^1$H NMR (CDCl$_3$) δ 10.89 (s, 2H), 5.39 (t, 1H, J=6.6 Hz), 3.27 (q, 2H, J=6.6 Hz), 3.05 (s, 6H), 2.28 (s, 3H), 1.65–1.45 (m, 2H), 1.26 (s, 10H), 0.87 (t, 3H, J=6.2 Hz). MS (EI): 383.9 (m$^+$).

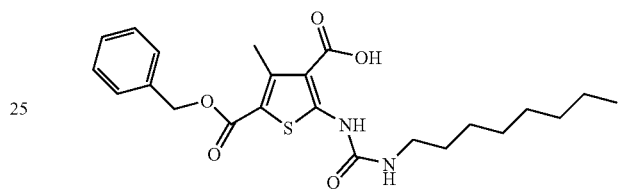

3-Methyl-5-(3-octyl-ureido)-thiophene-2,4-dicarboxylic acid 2-benzyl ester. (6.11) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: $^1$H NMR (CDCl$_3$) δ 10.57 (s, 1H), 7.45–7.25 (m, 5H), 5.30 (s, 1H), 4.26 (t, 2H, J=6.6 Hz), 2.81 (s, 3H), 1.72 (quint, 2H, J=6.6 Hz), 1.28 (bs, 10H), 0.88 (t, 3H, J=6.6 Hz).

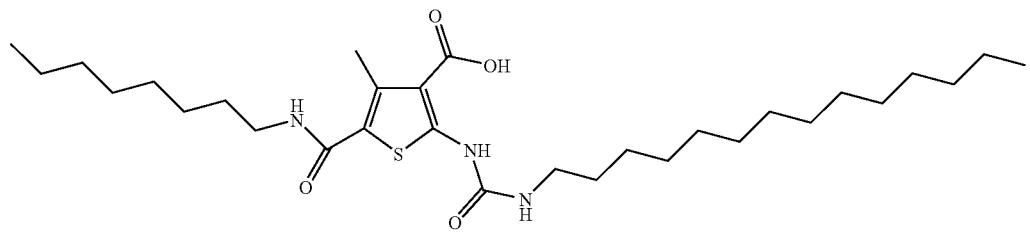

4-Methyl-5-octylcarbamoyl-2-(3-tetradecyl-ureido)-thiophene-3-carboxylic acid. (6.12) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification.

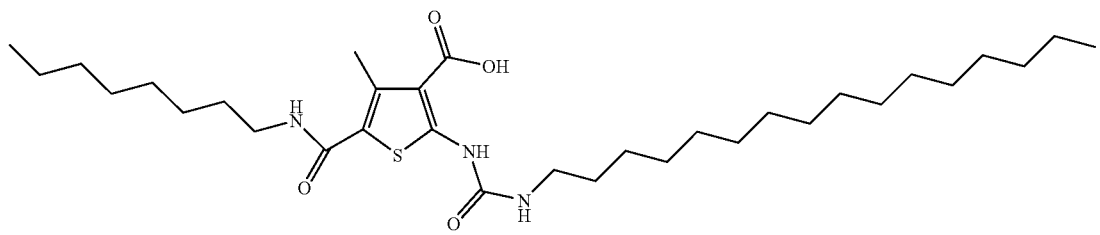

2-(3-Hexadecyl-ureido)-4-methyl-5-octylcarbamoyl-thiophene-3-carboxylic acid. (6.13) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: MS (EI): 580.2 (m⁺).

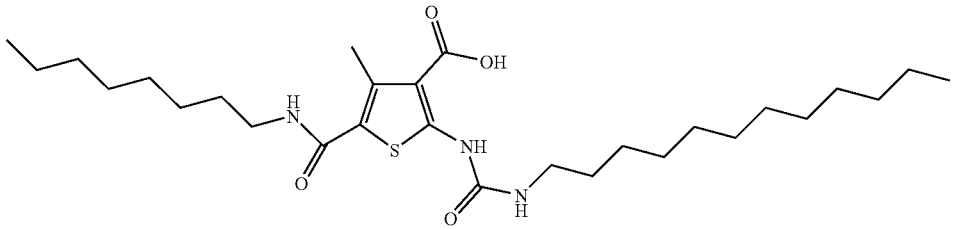

2-(3-Dodecyl-ureido)-4-methyl-5-octylcarbamoyl-thiophene-3-carboxylic acid. (6.14) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: MS (EI): 524.1 (m⁺).

EXAMPLE 7

Extra TFA Deportection

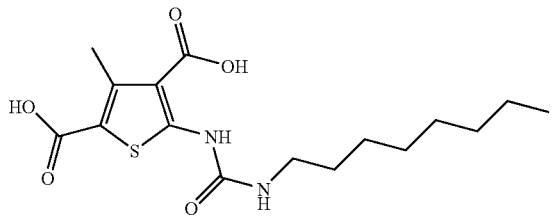

3-Methyl-5-(3-octyl-ureido)-thiophene-2,4-dicarboxylic acid. (7.1) To a stirring solution of 3-methyl-5-(3-octyl-ureido)-thiophene-2,4-dicarboxylic acid 4-tert-butyl ester (50.0 mg, 0.13 mmol) in CH$_2$Cl$_2$ (1 mL) was added TFA (1 mL). The reaction was stirred at RT for 2 h, and then solvent was removed under reduced pressure to give a solid. The product was dissolved in EtOAc, washed with sat. NaHCO$_3$ (aq.), and brine. The organic layer was dried with MgSO$_4$, filtered, and concentrated under reduced pressure to give 10.0 mg of a solid (22%): $^1$H NMR (CDCl$_3$) δ 10.45 (bs, 1H), 6.27 (bs, 1H), 5.00 (bs, 1H), 3.50–3.20 (m, 2H), 2.37 (s, 3H), 1.70–1.40 (m, 2H), 1.26 (bs, 10H), 0.88 (t, 3H, J=6.2 Hz). MS (EI): 312.9 (m+—COOH).

EXAMPLE 8

Ethyl Ester Hydrolysis

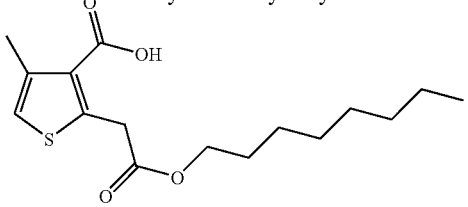

4-Methyl-2-octyloxycarbonylamino-thiophene-3-carboxylic acid. (8.1) To a stirring solution of 4-methyl-2-octyloxycarbonylamino-thiophene-3-carboxylic acid ethyl ester (254 mg, 0.74 mmol) in ethanol (2 mL) and THF (2 mL) was added LiOH—H$_2$O (31 mg, 0.74 mmol). The reaction was stirred at RT for 5 days, and then solvent was removed under reduced pressure to give a solid. The product was taken on without further purification: $^1$H NMR (CDCl$_3$) δ 6.02 (s, 1H), 4.07 (t, 2H, J=6.6 Hz), 2.32 (s, 3H), 1.60–1.40 (m, 2H), 1.27 (bs, 10H), 0.86 (t, 3H, J=6.6 Hz).

EXAMPLE 9

General Procedure for Hydrogenolysis at C-6

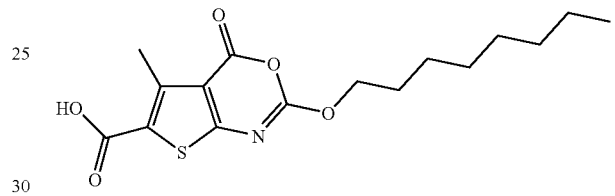

5-Methyl-2-octyloxy-4-oxo-4H-thieno[2,3-d][1,3]oxazine-6-carboxylic acid (11) To a stirring solution of 2-dodecyloxy-5-methyl-4-oxo-4H-thieno[2,3-d][1,3]oxazine-6-carboxylic acid benzyl ester (50 mg, 0.10 mmol) in EtOAc (2 mL) was added 10% Pd/C (5 mg, 10 wt %). The reaction was charged with H$_2$ and stirred at RT for 1 h. The reaction slurry was filtered through a plug of Celite, and the solvent was removed in vacuo. The product was taken on without further purification: $^1$H NMR (CDCl$_3$) δ 4.47 (t, 2H, J=6.2 Hz), 4.19 (bs, 1H), 2.85 (s, 3H), 1.80 (quint, 2H, J=6.2 Hz), 1.27 (bs, 18H), 0.88 (t, 3H, J=6.6 Hz). MS (EI): 395.4 (m⁺).

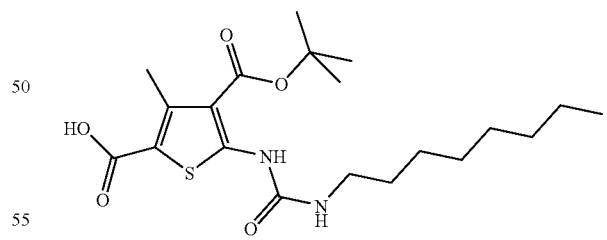

3-Methyl-5-(3-octyl-ureido)-thiophene-2,4-dicarboxylic acid 4-tert-butyl ester. (9.1) The same method as for the preparation of 2-dodecyloxy-5-methyl-4-oxo-4H-thieno[2,3-d][1,3]oxazine-6-carboxylic acid was employed. Thus, hydrogenolysis afforded a solid, which was used without purification: $^1$H NMR (CDCl$_3$) δ 11.06 (s, 1H), 5.14 (vt, 1H), 3.30 (q, 2H, J=6.0 Hz), 2.71 (s, 3H), 1.70–1.40 (m, 2H), 1.59 (s, 9H), 1.27 (bs, 10H), 0.87 (t, 3H, J=6.6 Hz). MS (EI): 412.8 (m⁺).

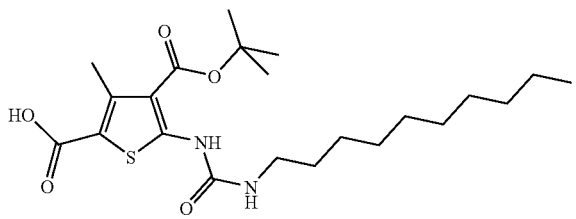

5-(3-Dodecyl-ureido)-3-methyl-thiophene-2,4-dicarboxylic acid 4-tert-butyl ester. (9.2) The same method as for the preparation of 2-dodecyloxy-5-methyl-4-oxo-4H-thieno[2,3-d][1,3]oxazine-6-carboxylic acid was employed. Thus, hydrogenolysis afforded 0.198 g of a solid (98%), which was used without purification: Mp 187.0–188.5° C.; $^1$H NMR (CDCl$_3$) δ 11.06 (s, 1H), 5.21 (bs, 1H), 3.31 (q, 2H, J=5.8 Hz), 2.72 (s, 3H), 1.65–1.40 (m, 2H), 1.60 (s, 9H), 1.26 (bs, 18H), 0.88 (t, 3H, J=6.6 Hz). MS (EI): 469.0 (m$^+$).

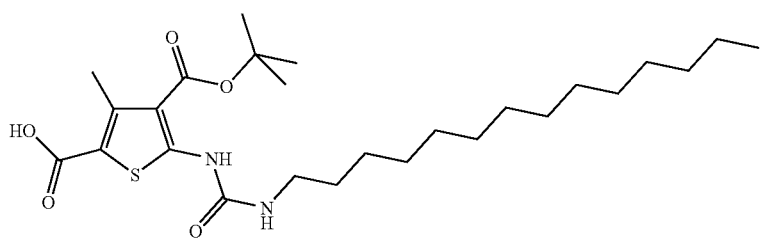

3-Methyl-5-(3-tetradecyl-ureido)-thiophene-2,4-dicarboxylic acid 4-tert-butyl ester. (9.3) The same method as for the preparation of 2-dodecyloxy-5-methyl-4-oxo-4H-thieno[2,3-d][1,3]oxazine-6-carboxylic acid was employed. Thus, hydrogenolysis afforded 123 mg of a solid (58%), which was used without purification: Mp 176.0–178.0° C.; $^1$H NMR (CDCl$_3$) δ 11.06 (s, 1H), 7.35 (t, 1H, J=6.2 Hz), 5.20 (bs, 1H), 3.30 (q, 2H, J=6.2 Hz), 2.72 (s, 3H), 1.70–1.45 (m, 2H), 1.59 (s, 9H), 1.25 (bs, 22H), 0.88 (t, 3H, J=6.6 Hz). MS (EI): 497.0 (m$^+$).

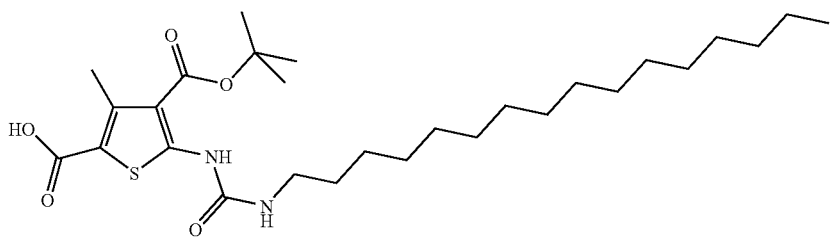

5-(3-Hexadecyl-ureido)-3-methyl-thiophene-2,4-dicarboxylic acid 4-tert-butyl ester. (9.4) The same method as for the preparation of 2-dodecyloxy-5-methyl-4-oxo-4H-thieno[2,3-d][1,3]oxazine-6-carboxylic acid was employed. Thus, hydrogenolysis afforded a solid, which was used without purification: Mp 187.5–189.0° C.; $^1$H NMR (CDCl$_3$) δ 11.07 (s, 1H), 5.18 (bs, 1H), 3.29 (q, 2H, J=6.2 Hz), 2.72 (s, 3H), 1.70–1.45 (m, 2H), 1.60 (s, 9H), 1.25 (bs, 26H), 0.88 (t, 3H, J=6.6 Hz). MS (EI): 525.0 (m$^+$).

EXAMPLE 10

General Procedure for Amide/Ester Formation at C-6

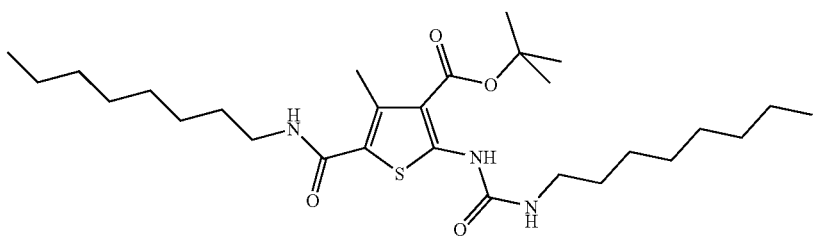

4-Methyl-5-octylcarbamoyl-2-(3-octyl-ureido)-thiophene-3-carboxylic acid tert-butyl ester. (10.1) To a stirring solution of 3-methyl-5-(3-octyl-ureido)-thiophene-2,4-dicarboxylic acid 4-tert-butyl ester (185 mg, 0.46 mmol) and octyl amine (0.112 mL, 87.3 mg, 0.69 mmol) in CH$_2$Cl$_2$ (10 mL) was added EDC (133 mg, 0.69 mmol) and DMAP (2.8 mg, 0.02 mmol). The reaction was stirred at RT for 16 h, washed with H$_2$O, 0.5N citric acid, sat. NaHCO$_3$, and brine. The organic fraction was dried (MgSO$_4$), filtered, and concentrated in vacuo. The residue was purified by column chromatography (9:1; hexanes:EtOAc) to give 290 mg of a solid (99%) $^1$H NMR (CDCl$_3$) δ 10.89 (s, 1H), 5.82–5.62 (m, 1H), 5.78–5.60 (m, 1H), 3.33 (q, 4H, J=6.6 Hz), 2.61 (s, 3H), 1.70–1.40 (m, 4H), 1.55 (s, 9H), 1.27 (bs, 20H), 0.88 (m, 6H). MS (EI): 524.1 (m$^+$).

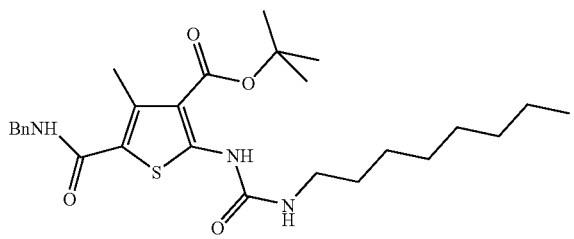

5-Benzylcarbamoyl-4-methyl-2-(3-octyl-ureido)-thiophene-3-carboxylic acid tert-butyl ester. (10.2) The same method as for the preparation of 4-methyl-5-octylcarbamoyl-2-(3-octyl-ureido)-thiophene-3-carboxylic acid tert-butyl ester was employed. Thus, coupling with benzyl amine (0.061 mL, 60 mg, 0.56 mmol) afforded 202 mg of a solid (99%) after by column chromatography (95:5; CHCl$_3$:MeOH): $^1$H NMR (CDCl$_3$) δ 10.90 (s, 1H), 7.40–7.20 (m, 5H), 6.05 (t, 1H, J=5.4 Hz), 5.33 (t, 1H, J=6.6 Hz), 4.55 (d, 2H, J=5.4 Hz), 3.26 (q, 2H, J=6.6 Hz), 2.63 (s, 3H), 1.65–1.40 (m, 2H), 1.56 (s, 9H), 1.26 (bs, 10H), 0.87 (t, 3H, J=6.2 Hz). MS (EI): 502.0 (m+).

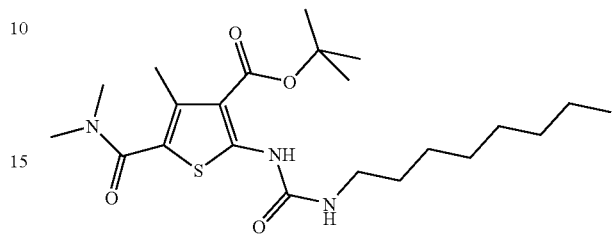

5-Dimethylcarbamoyl-4-methyl-2-(3-octyl-ureido)-thiophene-3-carboxylic acid tert-butyl ester. (10.3) The same method as for the preparation of 4-methyl-5-octylcarbamoyl-2-(3-octyl-ureido)-thiophene-3-carboxylic acid tert-butyl ester was employed. Thus, coupling with a 40% solution of dimethyl amine in H$_2$O (0.063 mL, 0.56 mmol) afforded 174 mg of a solid (99%) after by column chromatography (95:5; CHCl$_3$:MeOH): $^1$H NMR (CDCl$_3$) δ 10.78 (s, 1H), 5.39 (t, 1H, J=6.6 Hz), 3.27 (q, 2H, J=6.6 Hz), 3.05 (s, 6H), 2.28 (s, 3H), 1.65–1.45 (m, 2H), 1.56 (s, 9H), 1.26 (s, 10H), 0.87 (t, 3H, J=6.2 Hz). MS (EI): 440.0 (m+).

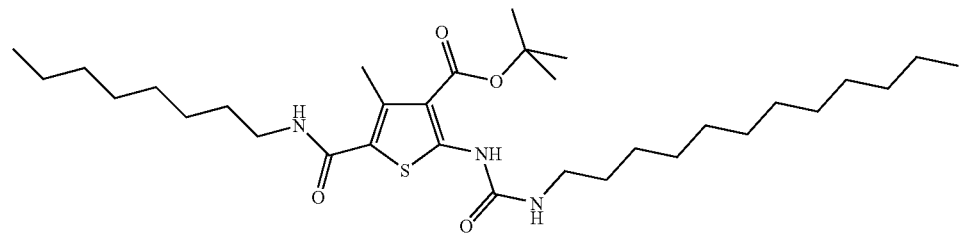

2-(3-Dodecyl-ureido)-4-methyl-5-octylcarbamoyl-thiophene-3-carboxylic acid tert-butyl ester. (10.4) The same method as for the preparation of 4-methyl-5-octylcarbamoyl-2-(3-octyl-ureido)-thiophene-3-carboxylic acid tert-butyl ester was employed. Thus, coupling with octyl amine (0.111 mL, 87.0 mg, 0.69 mmol) afforded 205 mg of a solid (81%) after by column chromatography (9:1; hexanes:EtOAc): $^1$H NMR (CDCl$_3$) δ 10.90 (s, 1H), 5.74 (t, 1H, J=5.4 Hz), 5.47 (t, 1H, J=6.2 Hz), 3.32 (vsext, 4H, J=6.6 Hz), 2.61 (s, 3H), 1.70–1.40 (m, 4H), 1.55 (s, 9H), 1.26 (bs, 28H), 0.88 (t, 6H, J=6.6 Hz). MS (EI): 580.2 (m$^+$).

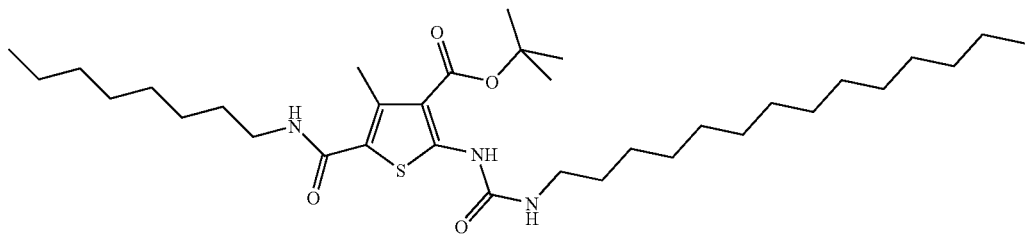

4-Methyl-5-octylcarbamoyl-2-(3-tetradecyl-ureido)-thiophene-3-carboxylic acid tert-butyl ester. (10.5) The same method as for the preparation of 4-methyl-5-octylcarbamoyl-2-(3-octyl-ureido)-thiophene-3-carboxylic acid tert-butyl ester was employed. Thus, coupling with octyl amine (0.112 mL, 87.3 mg, 0.69 mmol) afforded 290 mg of a solid (99%) after by column chromatography (9:1; hexanes:EtOAc): $^1$H NMR (CDCl$_3$) δ 10.90 (s, 1H), 5.74 (t, 1H, J=5.4), 5.44 (bs, 1H), 3.33 (vsext, 4H, J=6.2 Hz), 2.61 (s, 3H), 1.60–1.40 (m, 4H), 1.56 (s, 9H), 1.26 (bs, 32H), 0.88 (t, 6H, J=6.6 Hz). MS (EI): 608.1 (m$^+$).

preparation of 4-methyl-5-octylcarbamoyl-2-(3-octyl-ureido)-thiophene-3-carboxylic acid tert-butyl ester was employed. Thus, coupling with octyl alcohol (0.125 mL, 1.50 mmol) afforded 20 mg of a solid (21%) after by Prep. TLC (9:1; hexanes:EtOAc): $^1$H NMR (CDCl$_3$) δ 4.29 (t, 2H, J=6.6 Hz), 2.84 (s, 3H), 2.87 (t, 2H, J=7.2 Hz), 2.00–1.60 (m, 4H), 1.15–1.60 (m, 24H), 1.15–0.70 (m, 6H).

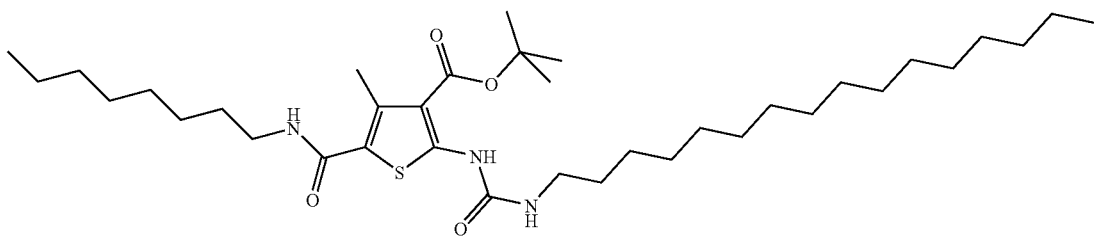

2-(3-Hexadecyl-ureido)-4-methyl-5-octylcarbamoyl-thiophene-3-carboxylic acid tert-butyl ester. (10.6) The same method as for the preparation of 4-methyl-5-octylcarbamoyl-2-(3-octyl-ureido)-thiophene-3-carboxylic acid tert-butyl ester was employed. Thus, coupling with octyl amine (0.080 mL, 62.0 mg, 0.50 mmol) afforded 195 mg of a solid (93% from BnOOC) after by column chromatography (9:1; hexanes:EtOAc): $^1$H NMR (CDCl$_3$) δ 10.90 (s, 1H), 5.73 (t, 1H, J=5.4), 5.35 (bs, 1H), 3.33 (vsext, 4H, J=6.2 Hz), 2.61 (s, 3H), 1.65–1.40 (m, 4H), 1.56 (s, 9H), 1.26 (bs, 36H), 0.88 (t, 6H, J=6.6 Hz). MS (EI): 636.2 (m$^+$).

EXAMPLE 11

General Procedure for Cyclization with EDCI

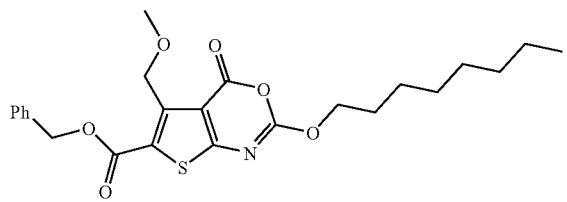

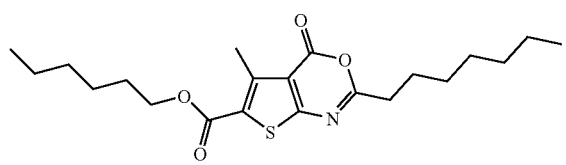

2-Heptyl-5-methyl-4-oxo-4H-thieno[2,3-d][1,3]oxazine-6-carboxylic acid hexyl ester (4) The same method as for the 5-Methoxy-2-octyloxy-4-oxo-4H-thieno[2,3-d][1,3]oxazine-6-carboxylic acid benzyl ester (112) To a stirring solution of 3-methoxymethyl-5-octyloxycarbonylamino-thiophene[2,4]dicarboxylic acid 2-benzyl ester (27 mg, 0.056 mmol) in CH$_2$Cl$_2$ (1.0 mL) was added EDC (16.0 mg, 0.084 mmol). The reaction was stirred at RT for 16 h, washed with H$_2$O and brine. The organic fraction was dried (MgSO$_4$), filtered, and concentrated in vacuo. The residue was purified by column chromatography (5:1; hexanes:EtOAc) to give 7.0 mg of a solid (27%): $^1$H NMR (CDCl$_3$) δ 7.42–7.27 (m, 5H), 5.16 (s, 2H), 4.38 (t, 2H, J=6.6 Hz), 3.89 (s, 3H), 3.85 (s, 2H), 1.78 (quint, 2H, J=6.6 Hz), 1.50–1.10 (m, 10H), 0.89 (t, 3H, J=6.6 Hz). MS (EI): 461.9 (m+H$^+$).

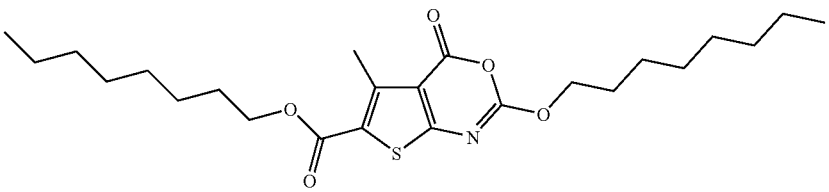

5-Methyl-2-octyloxy-4-oxo-4H-thieno[2,3-d][1,3]oxazine-6-carboxylic acid octyl ester (9) The same method as for the preparation of 5-methoxy-2-octyloxy-4-oxo-4H-thieno[2,3-d][1,3]oxazine-6-carboxylic acid benzyl ester was employed. Thus, cyclization afforded 15 mg of a solid (24%) after by column chromatography (9:1; hexanes:EtOAc): Mp 58.5–60.2° C.; $^1$H NMR (CDCl$_3$) δ 4.45 (t, 2H, J=6.6 Hz), 4.29 (t, 2H, J=6.6 Hz), 2.80 (s, 3H), 1.88–1.70 (m, 4H), 1.29 (bs, 20H), 0.89 (t, 6H, J=6.6 Hz). MS (EI): 451.8 (m$^+$).

EXAMPLE 12

General Procedure for Cyclization with SOCl$_2$

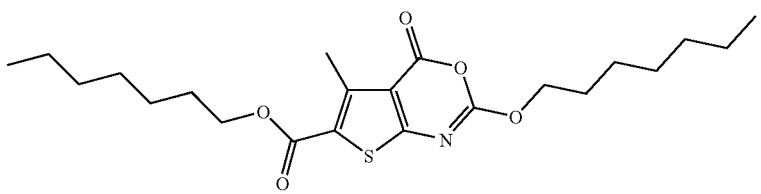

5-Methyl-2-heptyloxy-4-oxo-4H-thieno[2,3-][1,3]oxazine-6-carboxylic acid heptyl ester (10) To a stirring solution of 5-heptyloxycarbonylamino-3-methoxymethyl-thiophene-2,4-dicarboxylic acid 2-heptyl ester (2.7 g, 6.1 mmol) in pyridine (65 mL) was added thionyl chloride (0.88 mL, 1.4 g, 12.0 mmol). The reaction was stirred RT for 0.5 h, and concentrated in vacuo. The residue was dissolved in CHCl$_3$, washed with H$_2$O, 0.5 N citric acid, sat. NaHCO$_3$, and brine. The organic fraction was dried (MgSO$_4$), filtered, and concentrated in vacuo. The residue was purified by column chromatography (20:1; hexanes:EtOAc) to give 2.6 g of a solid (99%): $^1$H NMR (CDCl$_3$) δ 4.45 (t, 2H, J=6.6 Hz), 4.29 (t, 2H, J=6.6 Hz), 2.80 (s, 3H), 1.78 (dquint, 4H, J=13.2, 6.6 Hz), 1.58–1.18 (bs, 16H), 0.90 (t, 6H, J=7.0 Hz); $^{13}$C NMR (CDCl$_3$) δ 168.9, 162.1, 158.3, 154.0, 144.1, 121.4, 113.9, 71.1, 65.4, 31.6, 31.6, 28.8, 28.7, 28.6, 28.2, 25.9, 25.5, 22.5, 14.6, 14.0; MS (EI): 423.9 (m$^+$).

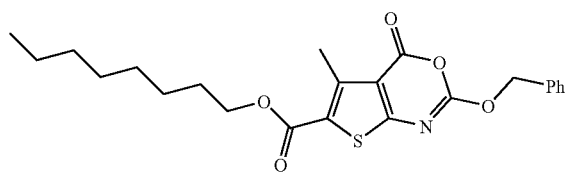

2-Benzyloxy-5-methyl-4-oxo-4H-thieno[2,3-d][1,3]oxazine-6-carboxylic acid octyl ester (113) The same method as for the preparation of 5-methyl-2-heptyloxy-4-oxo-4H-thieno[2,3-d][1,3]oxazine-6-carboxylic acid heptyl ester was employed. Thus, cyclization afforded 11.0 mg of a solid (10%) after by column chromatography (20:1; hexanes:EtOAc): $^1$H NMR (CDCl$_3$) δ 7.55–7.30 (m, 5H), 5.48 (s, 2H), 4.29 (t, 2H, J=6.6 Hz), 2.82 (s, 3H), 1.75 (quint, 2H, J=6.6 Hz), 1.29 (bs, 10H), 0.89 (t, 3H, J=6.6 Hz).

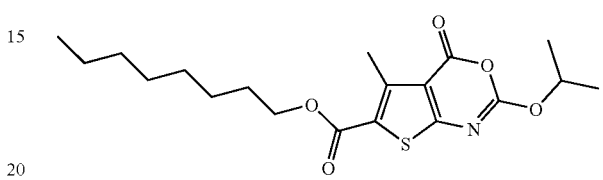

2-iso-Propoxy-5-methyl-4-oxo-4H-thieno[2,3-d][1,3]oxazine-6-carboxylic acid octyl ester (12) The same method as for the preparation of 5-methyl-2-heptyloxy-4-oxo-4H-thieno[2,3-d][1,3]oxazine-6-carboxylic acid heptyl ester was employed. Thus, cyclization afforded 108 mg of a solid (98%) after by column chromatography (20:1; hexanes:EtOAc): Mp 47.5–48.0° C.; $^1$H NMR (CDCl$_3$) δ 5.31 (sept, 1H, J=6.2 Hz), 4.29 (t, 2H, J=6.6 Hz), 2.81 (s, 3H), 1.75 (quint, 2H, J=6.6 Hz), 1.44 (d, 6H, J=6.2 Hz), 1.29 (bs, 10H), 0.89 (t, 3H, J=6.4 Hz); MS (EI): 381.9 (m$^+$).

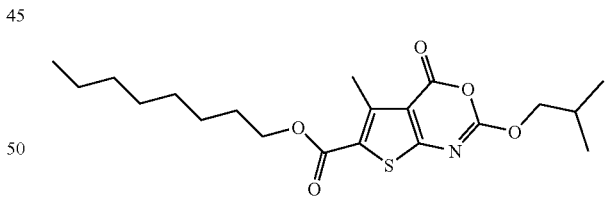

2-iso-Butoxy-5-methyl-4-oxo-4H-thieno[2,3-d][1,3]oxazine-6-carboxylic acid octyl ester (114) The same method as for the preparation of 5-methyl-2-heptyloxy-4-oxo-4H-thieno[2,3-d][1,3]oxazine-6-carboxylic acid heptyl ester was employed. Thus, cyclization afforded 15 mg of a solid (25%) after by column chromatography (20:1; hexanes:EtOAc): $^1$H NMR (CDCl$_3$) δ 4.31 (q, 2H, J=6.6 Hz), 4023 (d, 2H, J=6.6 Hz), 2.82 (s, 3H), 2.13 (nonet, 1H, J=6.6 Hz), 1.73 (quint, 2H, J=6.6 Hz), 1.29 (bs, 10H), 1.03 (d, 6H, J=6.6 Hz), 0.89 (t, 3H, J=6.6 Hz); MS (EI): 395.9 (m+).

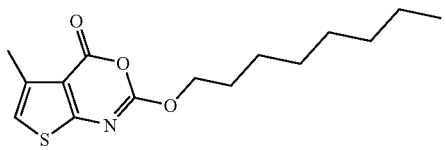

5-Methyl-2-octyloxy-thieno[2,3-d][1,3]oxazin-4-one (23) The same method as for the preparation of 5-methyl-2-heptyloxy-4-oxo-4H-thieno[2,3-d][1,3]oxazine-6-carboxylic acid heptyl ester was employed. Thus, cyclization afforded 44 mg of an oil (20%) after by column chromatography (20:1; hexanes:EtOAc): $^1$H NMR (CDCl$_3$) δ 6.59 (s, 1H), 4.41 (t, 2H, J=6.6 Hz), 2.46 (s, 3H), 1.80 (quint, 2H, J=6.6 Hz), 1.29 (bs, 10H), 0.89 (t, 3H, J=6.6 Hz); MS (EI): 295.9 (m+).

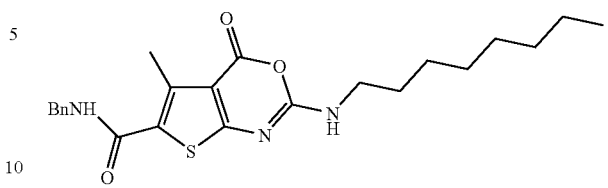

5-Methyl-2-octylamino-4-oxo-4H-thieno[2,3-d][1,3] oxazine-6-carboxylic acid benzylamide (21) The same method as for the preparation of 5-methyl-2-heptyloxy-4-oxo-4H-thieno[2,3-d][1,3]oxazine-6-carboxylic acid heptyl ester was employed. Thus, cyclization afforded 75.0 mg of a solid (49% from 3-methyl-5-(3-octyl-ureido)-thiophene-2,4-dicarboxylic acid 4-tert-butyl ester) after by column chromatography (95:5; CHCl$_3$:MeOH): $^1$H NMR (CDCl$_3$) δ 7.40–7.26 (m, 5H), 6.03 (t, 1H, J=5.4 Hz), 5.20 (bs, 1H), 4.62 (d, 2H, J=5.4 Hz), 3.50–3.30 (m, 2H), 2.72 (s, 3H), 1.73–1.43 (m, 2H), 1.28 (bs, 10H), 0.88 (t, 3H, J=6.6 Hz). MS (EI): 427.9 (m+).

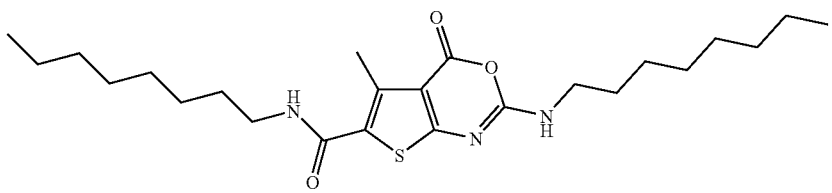

5-Methyl-2-octylamino-4-oxo-4H-thieno[2,3-d][1,3] oxazine-6-carboxylic acid octylamide (18) The same method as for the preparation of 5-methyl-2-heptyloxy-4-oxo-4H-thieno[2,3-d][1,3]oxazine-6-carboxylic acid heptyl ester was employed. Thus, cyclization afforded 106 mg of a solid (52% from 4-methyl-5-octylcarbamoyl-2-(3-octyl-ureido)-thiophene-3-carboxylic acid tert-butyl ester) after by column chromatography (95:5; CHCl$_3$:MeOH): Mp 152.0–152.8° C.; $^1$H NMR (CDCl$_3$) δ 5.70 (bs, 1H), 5.06 (bs, 1H), 3.42 (q, 6H, J=6.2 Hz), 2.71 (s, 3H), 1.70–1.42 (m, 4H), 1.54 (s, 9H), 1.28 (bs, 20H), 0.89 (t, 6H, J=6.6 Hz); MS (EI): 450.5 (m+1).

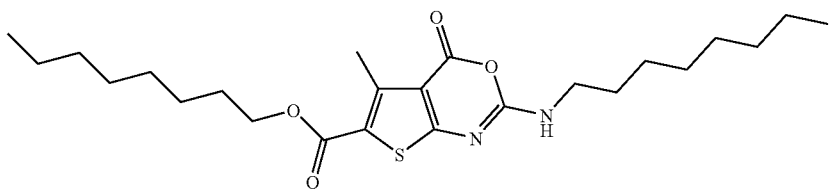

5-Methyl-2-octylamino-4-oxo-4H-thieno[2,3-d][1,3] oxazine-6-carboxylic acid octyl ester (20) The same method as for the preparation of 5-methyl-2-heptyloxy-4-oxo-4H-thieno[2,3-d][1,3]oxazine-6-carboxylic acid heptyl ester was employed. Thus, cyclization afforded 229 mg of a solid (67% from t-Bu ester) after by column chromatography (20:1; hexanes:EtOAc): $^1$H NMR (CDCl$_3$) δ 5.20 (bs, 1H), 4.26 (t, 2H, J=6.6 Hz), 3.51–3.40 (m, 2H), 2.78 (s, 3H), 1.85–1.48 (m, 4H), 1.28 (bs, 20H), 1.00–0.80 (m, 6H); MS (EI): 451.0 (m+).

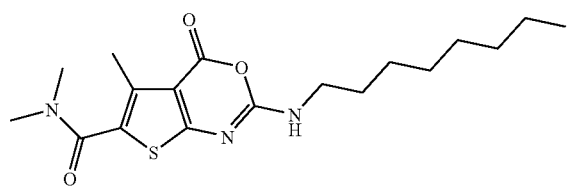

5-Methyl-2-octylamino-4-oxo-4H-thieno[2,3-d][1,3] oxazine-6-carboxylic acid dimethylamide (22) The same method as for the preparation of 5-methyl-2-heptyloxy-4-oxo-4H-thieno[2,3-d][1,3]oxazine-6-carboxylic acid heptyl ester was employed. Thus, cyclization afforded 17.0 mg of a solid (13% from 3-methyl-5-(3-octyl-ureido)-thiophene-2,4-dicarboxylic acid 4-tert-butyl ester) after by column chromatography (1:1 to 1:5; hexanes:EtOAc): $^1$H NMR (CDCl$_3$) δ 5.22 (bs, 1H), 3.41 (q, 2H, J=5.4 Hz), 3.08 (s, 6H), 2.41 (s, 3H), 1.62 (quint, 2H, J=6.6 Hz), 1.28 (bs, 10H), 0.88 (t, 3H, J=6.2 Hz); MS (EI): 365.9 (m+).

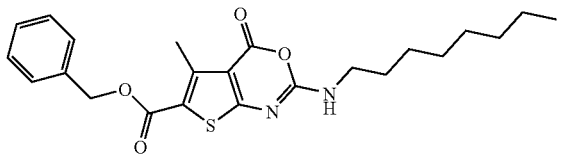

5-Methyl-2-octylamino-4-oxo-4H-thieno[2,3-d][1,3]oxazine-6-carboxylic acid benzyl ester (16) The same method as for the preparation of 5-methyl-2-heptyloxy-4-oxo-4H-thieno[2,3-d][1,3]oxazine-6-carboxylic acid heptyl ester was employed. Thus, cyclization afforded 108 mg of a solid (63% from 3-methyl-5-(3-octyl-ureido)-thiophene-2,4-dicarboxylic acid 2-benzyl ester 4-tert-butyl ester) after by column chromatography (9:1; hexanes:EtOAc): Mp 153.5–154.0° C.; $^1$H NMR (CDCl$_3$) δ 7.50–7.30 (m, 5H), 5.44 (bs, 1H), 5.32 (s, 2H), 3.42 (q, 2H, J=6.2 Hz), 2.79 (s, 3H), 1.78–1.50 (m, 2H), 1.27 (bs, 10H), 0.88 (t, 3H, J=6.4 Hz); MS (EI): 428.9 (m+).

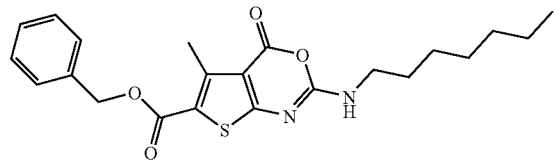

2-Heptylamino-5-methyl-4-oxo-4H-thieno[2,3-d][1,3]oxazine-6-carboxylic acid benzyl ester (17) The same method as for the preparation of 5-methyl-2-heptyloxy-4-oxo-4H-thieno[2,3-d][1,3]oxazine-6-carboxylic acid heptyl ester was employed. Thus, cyclization afforded 12 mg of a solid; $^1$H NMR (CDCl$_3$) δ 7.50–7.30 (m, 5H), 5.32 (s, 2H), 5.24 (bs, 1H), 3.42 (q, 2H, J=6.2 Hz), 2.79 (s, 3H), 1.78–1.50 (m, 2H), 1.27 (bs, 8H), 0.88 (t, 3H, J=6.4 Hz); MS (EI): 414.8 (m+).

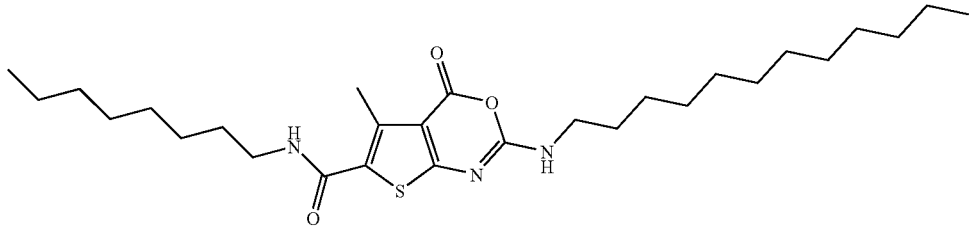

2-Dodecylamino-5-methyl-4-oxo-4H-thieno[2,3-d][1,3]oxazine-6-carboxylic acid octylamide (24) The same method as for the preparation of 5-methyl-2-heptyloxy-4-oxo-4H-thieno[2,3-d][1,3]oxazine-6-carboxylic acid heptyl ester was employed. Thus, cyclization afforded 56 mg of a solid (32% from 2-(3-decyl-ureido)-4-methyl-5-octylcarbamoyl-thiophene-3-carboxylic acid tert-butyl ester) after by column chromatography (9:1 to 5:1; hexanes:EtOAc): Mp 137.1–138.0° C.; $^1$H NMR (CDCl$_3$) δ 5.74 (bs, 1H), 5.30 (bs, 1H), 3.42 (q, 4H, J=6.6 Hz), 2.71 (s, 3H), 1.75–1.45 (m, 4H), 1.27 (bs, 28H), 0.89 (t, 6H, J=6.0 Hz); MS (EI): 506.1 (m+).

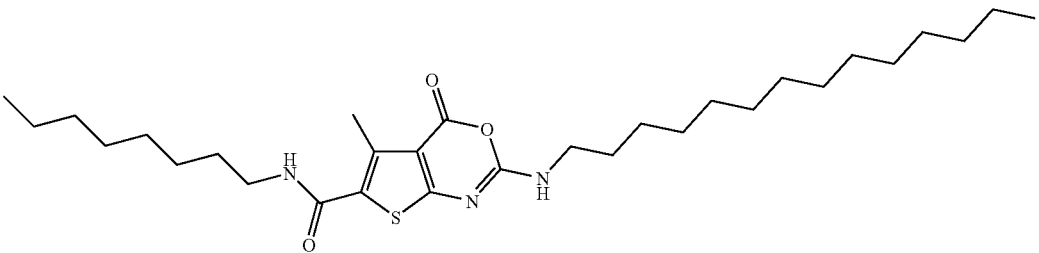

5-Methyl-4-oxo-2-tetradecylamino-4H-thieno[2,3-d][1,3]oxazine-6-carboxylic acid octylamide (25) The same method as for the preparation of 5-methyl-2-heptyloxy-4-oxo-4H-thieno[2,3-d][1,3]oxazine-6-carboxylic acid heptyl ester was employed. Thus, cyclization afforded 25 mg of a solid (19% from 4-methyl-5-octylcarbamoyl-2-(3-tetradecyl-ureido)-thiophene-3-carboxylic acid tert-butyl ester) after by column chromatography (5:1; hexanes:EtOAc): Mp 145.0–145.8° C.; $^1$H NMR (CDCl$_3$) δ 5.74 (bs, 1H), 5.30 (bs, 1H), 3.42 (q, 4H, J=6.6 Hz), 2.71 (s, 3H), 1.75–1.45 (m, 4H), 1.27 (bs, 32H), 0.89 (t, 6H, J=6.0 Hz); MS (EI): 534.1 (m+).

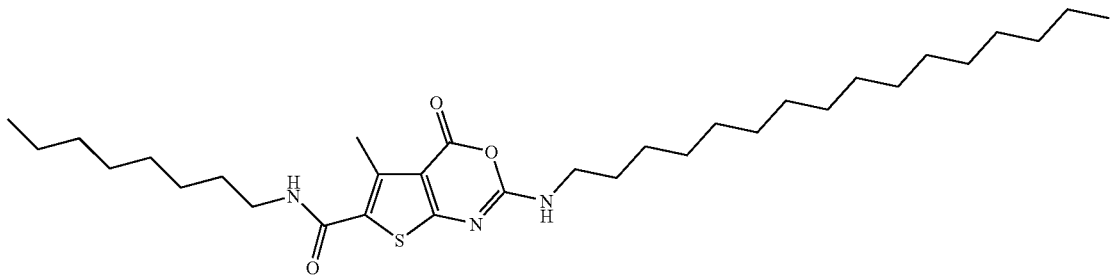

2-Hexadecylamino-5-methyl-4-oxo-4H-thieno[2,3-d][1,3]oxazine-6-carboxylic acid octylamide (26) The same method as for the preparation of 5-methyl-2-heptyloxy-4-oxo-4H-thieno[2,3-d][1,3]oxazine-6-carboxylic acid heptyl ester was employed. Thus, cyclization afforded 24 mg of a solid (14% from 2-(3-hexadecyl-ureido)-4-methyl-5-octylcarbamoyl-thiophene-3-carboxylic acid tert-butyl ester) after by column chromatography (5:1; hexanes:EtOAc): Mp 146.3–147.0° C.; $^1$H NMR (CDCl$_3$) δ 5.74 (bs, 1H), 5.30 (bs, 1H), 3.42 (q, 4H, J=6.6 Hz), 2.71 (s, 3H), 1.75–1.45 (m, 4H), 1.27 (bs, 36H), 0.89 (t, 6H, J=6.0 Hz); MS (EI): 562.1 (m$^+$).

7.40–6.90 (m, 5H), 4.27 (t, 2H, J=6.6 Hz), 2.81 (s, 3H), 1.73 (dt, 2H, J=6.6 Hz), 1.27 (m, 10H), 0.89 (t, 3H, J=6.0 Hz).

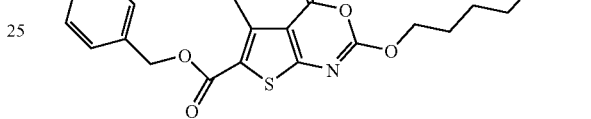

2-Heptyloxy-5-methyl-4-oxo-4H-thieno[2,3-d][1,3]oxazine-6-carboxylic acid benzyl ester (8) The same method as for the preparation of 5-methyl-2-heptyloxy-4-oxo-4H-thieno[2,3-d][1,3]oxazine-6-carboxylic acid heptyl ester was employed. Thus, cyclization afforded 116 mg of a solid (63%) after by column chromatography (4:1; hexanes:EtOAc): $^1$H NMR (CDCl$_3$) δ 7.50–7.30 (m, 5H), 5.33 (s, 2H), 4.44 (t, 2H, J=6.2 Hz), 1.90–1.70 (m, 2H), 1.45–1.15 (m, 10H), 1.00–0.80 (m, 3H).

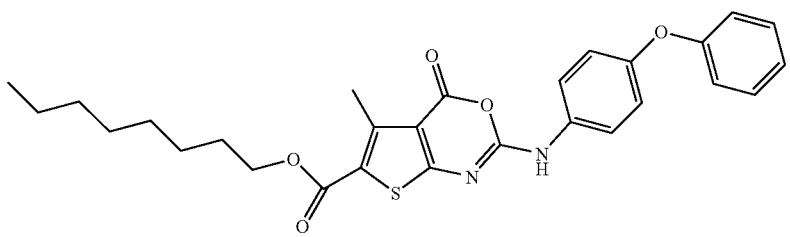

5-Methyl-4-oxo-2-(4-phenoxy-phenylamino)-4H-thieno[2,3-d][1,3]oxazine-6-carboxylic acid octyl ester (19) The same method as for the preparation of 5-methyl-2-heptyloxy-4-oxo-4H-thieno[2,3-d][1,3]oxazine-6-carboxylic acid heptyl ester was employed. Thus, cyclization afforded a solid, which was purified by recrystalization from EtOAc/Hexanes to give 25 mg of a solid (24%): $^1$H NMR (CDCl$_3$) δ 7.50 (d, 2H, J=8.8 Hz), 7.25–7.45 (m, 2H),

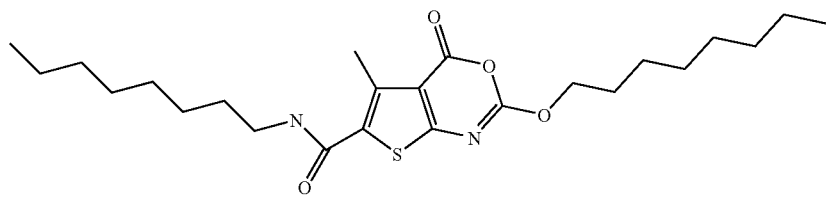

5-Methyl-2-octyloxy-4-oxo-4H-thieno[2,3-d][1,3]oxazine-6-carboxylic acid octylamide (15) The same method as for the preparation of 5-methyl-2-heptyloxy-4-oxo-4H-thieno[2,3-d][1,3]oxazine-6-carboxylic acid heptyl ester was employed. Thus, cyclization afforded 44.0 mg of a solid (44%) after by column chromatography (4:1; hexanes:EtOAc): $^1$H NMR (CDCl$_3$) δ 5.90–5.70 (m, 1H), 4.43 (t, 2H, J=6.6 Hz), 3.42 (q, 2H, J=6.6 Hz), 2.72 (s, 3H), 1.90–1.70 (m, 2H), 1.70–1.50 (m, 2H), 1.50–1.15 (m, 20H), 0.95–0.80 (m, 6H).

EXAMPLE 13

Carbamate/Urea Intermediates

4-Methyl-2-(3-octyl-ureido)-5-[(pyridin-4-ylmethyl)-carbamoyl]-thiophene-3-carboxylic acid tert-butyl ester (13.1) The compound was purified by column chromatography (100% EtOAc) to yield 175 mg (70%) of a white foam.: (70%). $^1$H NMR (CDCl$_3$, 200 MHz) δ 0.86 (m, 3H), 1.25 (brs, 10H), 1.56 (brs, 11H), 2.64 (s, 3H), 3.28 (dt, 2H, J=6.2 Hz, J=6.6 Hz), 4.56 (d, 2H, J=5.8 Hz), 5.16 (t, 1H, J=5.4 Hz), 6.17 (t, 1H, J=5.8 Hz), 7.24 (d, 2H, J=5.8 Hz), 8.54 (d, 2H, J=5.8 Hz), 10.94 (s, 1H)

4-Methyl-5-[methyl-(6-methyl-pyridin-2-ylmethyl)-carbamoyl]-2-(3-octyl-ureido)-thiophene-3-carboxylic acid tert-butyl ester (13.2): (84%). $^1$H NMR (CDCl$_3$, 200 MHz) δ 0.87 (m, 3H), 1.25 (brs, 10H), 1.56 (brs, 11H), 2.32 (s, 3H), 2.52 (s, 3H), 3.01 (s, 3H), 3.28 (dt, 2H, J=6.2 Hz, J=6.6 Hz), 4.74 (s, 2H), 4.95 (t, 1H, J=5.4 Hz), 7.03 (d, 2H, J=7.8 Hz), 7.55 (t, 1H, J=7.6 Hz), 10.75 (s, 1H)

5-[Ethyl-(2-pyridin-2-yl-ethyl)-carbamoyl]-4-methyl-2-(3-octyl-ureido)-thiophene-3-carboxylic acid tert-butyl ester (13.3): (99%). $^1$H NMR (CDCl$_3$, 200 MHz) δ 0.87 (m, 3H), 1.11 (t, 3H, J=7.0 Hz), 1.25 (brs, 10H), 1.56 (brs, 11H), 2.20 (s, 3H), 3.09 (t, 2H, J=7.0 Hz), 3.26 (m, 4H), 3.80 (t, 2H, J=7.0 Hz), 5.08 (t, 1H, J=5.0 Hz), 7.15 (m, 2H), 7.59 (ddd, 1H, J=7.6 Hz, J=7.6 Hz, J=1.4 Hz), 8.51 (d, 1H, J=4.4 Hz), 10.76 (s, 1H)

5-(Benzyloxycarbonylmethyl-carbamoyl)-4-methyl-2-(3-octyl-ureido)-thiophene-3-carboxylic acid tert-butyl ester (13.4): (95%). $^1$H NMR (CDCl$_3$, 200 MHz) δ 0.86 (m, 3H), 1.25 (brs, 10H), 1.58 (brs, 11H), 2.56 (s, 3H), 3.25 (dt, 2H, J=6.2 Hz, J=6.6 Hz), 4.21 (d, 2H, J=5.4 Hz), 5.21 (s, 2H), 5.49 (brs, 1H), 6.51 (t, 1H, J=5.6 Hz), 7.36 (s, 5H), 10.71 (s, 1H)

5-(6,7-Dimethoxy-3,4-dihydro-1H-isoquinoline-2-carbonyl)-4-methyl-2-(3-octyl-ureido)-thiophene-3-carboxylic acid tert-butyl ester (13.5): (97%). $^1$H NMR (CDCl$_3$, 200 MHz) δ 0.87 (brs, 3H), 1.27 (brs, 10H), 1.57 (s, 11H), 2.30 (s, 3H), 2.83 (t, 2H, J=5.8 Hz), 3.29 (dt, 2H, J=6.2 Hz, J=6.6 Hz), 3.80 (m, 8H), 4.69 (s, 2H), 4.87 (t, 1H, J=5.6 Hz), 6.55 (s, 1H), 6.60 (s, 1H), 10.83 (s, 1H)

5-(3,4-Dimethoxy-benzylcarbamoyl)-4-methyl-2-(3-octyl-ureido)-thiophene-3-carboxylic acid tert-butyl ester (13.6): (97%). $^1$H NMR (CDCl$_3$, 200 MHz) δ 0.86 (brs, 3H), 1.25 (brs, 10H), 1.56 (s, 11H), 2.63 (s, 3H), 3.25 (dt, 2H, J=6.2 Hz, J=6.6 Hz), 3.86 (s, 6H), 4.47 (d, 2H, J=5.6 Hz), 5.05 (t, 1H, J=5.8 Hz), 5.95 (t, 1H, J=5.0 Hz), 6.84 (m, 3H), 10.90 (s, 1H)

5-(2-Acetylamino-ethylcarbamoyl)-4-methyl-2-(3-octyl-ureido)-thiophene-3-carboxylic acid tert-butyl ester (13.7): (58%). $^1$H NMR (CDCl$_3$, 200 MHz) δ 0.87 (s, 3H), 1.27 (brs, 10H), 1.57 (brs, 11H), 2.04 (s, 3H), 2.60 (s, 3H), 3.29 (dt, 2H, J=6.2 Hz, J=6.6 Hz), 3.50 (m, 4H), 4.90 (brs, 1H), 6.29 (brm, 2H), 10.92 (s, 1H)

5-[4-(Isopropylcarbonyl-methyl)-piperazine-1-carbonyl]-4-methyl-2-(3-octyl-ureido)-thiophene-3-carboxylic acid tert-butyl ester (13.8): (61%). $^1$H NMR (CDCl$_3$, 200 MHz) δ 0.86 (brs, 3H), 1.10–1.28 (m, 16H), 1.56 (s, 11H), 2.29 (s, 3H), 2.51 (s, 4H), 2.99 (s, 3H), 3.27 (dt, 2H, J=6.2 Hz, J=6.6 Hz), 3.63 (s, 4H), 4.10 (m, 1H), 5.05 (brs, 1H), 6.81 (d, 1H, J=8.0 Hz), 10.79 (s, 1H)

3-Methyl-5-(3-octyl-thioureido)-thiophene-2,4-dicarboxylic acid 2-benzyl ester 4-tert-butyl ester (13.9): $^1$H NMR (CDCl$_3$, 200 MHz) δ 0.88 (m, 3H), 1.28 (brs, 10H), 1.59 (m, 11H), 2.72 (s, 3H), 3.47 (m, 2H), 5.30 (s, 2H), 6.31 (brs, 1H), 7.36 (m, 5H).

4-Methyl-2-(3-octyl-ureido)-5-[(pyridin-3-yl-methyl)-carbamoyl]-thiophene-3-carboxylic acid tert-butyl ester (13.10). The reaction was passed through a plug of silica gel with ethyl acetate to yield 13.10, 3.42 g (94% crude yield) of an off white solid.

5-[(Furan-2-ylmethyl)-carbamoyl]-4-methyl-2-(3-octyl-ureido)-thiophene-3-carboxylic acid tert-butyl ester (13.11) white solid (97% yield): $^1$H NMR (CDCl$_3$, 200 MHz) δ 0.86 (t, 3H, J=6.6 Hz), 1.24–1.27 (m, 10H), 1.54 (bs, 11H), 2.61 (s, 3H), 3.26 (dt, 2H, J=6.4, 5.8 Hz), 4.54 (d, 2H, J=5.4 Hz), 5.31 (bs, 1H), 6.02 (t, 1H, J=5.3 Hz), 6.27 (1H, dd, J=11.4, 3.2 Hz), 6.30, (d, 1H, J=3.2 Hz), 7.34 (s, 1H), 10.89 (bs, 1H). $^{13}$C NMR (CDCl$_3$) δ 14.0, 16.0, 22.6, 26.8, 28.4, 29.1, 29.2, 29.9, 31.7, 36.9, 40.8, 82.3, 107.6, 11.0.4, 112.9, 118.7, 140.5, 142.3, 151.0, 152.7, 153.6, 163.2, 166.4. MS (ES+) 491.95 (M+1), 493.00 (M+2).

4-Methyl-2-(3-octyl-ureido)-5-[(2-pyridin-3-yl-ethyl)-carbamoyl]-thiophene-3-carboxylic acid tert-butyl ester (13.12) white solid (73% yield): $^1$H NMR (CDCl$_3$, 200 MHz) δ 0.85 (t, 3H, J=6.6 Hz), 1.21–1.28 (m, 10H), 1.52 (bs, 11H), 2.54 (s, 3H), 2.89 (t, 2H, J=6.9 Hz), 3.27 (dt, 2H, J=6.4, 6.2 Hz), 3.61 (dt, 2H, J=6.6, 6.2 Hz), 5.69 (bs, 1H), 5.92 (t, 1H, J=5.9 Hz), 7.23 (dd, 1H, J=6.2, 5.2 Hz), 7.55, (ddd, 1H, J=7.6, 1.8, 1.8 Hz), 8.46 (d, 1H, J=4.8 Hz), 8.47 (s, 1H), 10.81 (bs, 1H). $^{13}$C NMR (CDCl$_3$) δ 14.0, 15.9, 22.6, 26.8, 28.3, 29.1, 29.2, 29.9, 31.7, 33.0, 40.7, 40.9, 82.2, 112.7, 118.9, 123.5, 134.4, 136.3, 139.9, 147.9, 150.1, 152.6, 153.6, 163.7, 166.3. MS (ES+) 516.98 (M+1), 518.05 (M+2).

4-Methyl-2-(3-octyl-ureido)-5-[4-(2-piperidin-1-yl-ethyl)-piperazine-1-carbonyl]-thiophene-3-carboxylic acid tert-butyl ester (13.13) yellow oil (80% yield): $^1$H NMR (CDCl$_3$, 200 MHz) δ 0.84 (t, 3H, J=6.4 Hz), 1.22 (bs, 12H), 1.53 (m, 15H), 2.25, (s, 3H), 2.33–2.52 (m, 8H), 3.23 (dt, 2H, J=6.6, 6.4 Hz), 3.57 (bs, 2H), 5.63 (bs, 1H), 10.73 (bs, 1H). MS (ES+) 592.07 (M+1), 593.13 (M+2).

5-(3-Hexyl-3-methyl-ureido)-3-methyl-thiophene-2,4-dicarboxylic acid 2-benzyl ester 4-tert-butyl ester (13.14). $^1$H NMR (CDCl$_3$, 200 MHz) δ 0.87 (t, 3H, J=6.4 Hz), 1.25–1.32 (m, 6H), 1.58 (s, 11H), 2.72 (s, 3H), 3.04 (s, 3H), 3.36 (t, 2H, J=7.7 Hz), 5.26 (s, 2H), 7.27–7.43 (m, 5H), 11.53 (bs, 1H). $^{13}$C NMR (CDCl$_3$) δ 13.9, 15.8, 22.5, 26.3, 27.7, 28.3, 31.4, 34.4, 49.3, 65.8, 82.3, 113.1, 115.2, 127.9, 128.4, 136.1, 145.5, 153.6, 156.6, 163.0, 166.7. MS (ES+) 557 (M+68).

5-[3-(1-Butyl-pentyl)-ureido]-3-methyl-thiophene-2,4-dicarboxylic acid 2-benzyl ester 4-tert-butyl ester (13.15). $^1$H NMR (CDCl$_3$, 200 MHz) δ 0.86 (t, 6H, J=6.6 Hz), 1.25–1.31 (m, 12H), 1.55 (s, 9H), 2.70 (s, 3H), 3.58–3.78 (m, 1H), 5.04 (bd, 1H, J=8.8 Hz), 5.25 (s, 2H), 7.27–7.41 (m, 5H), 10.98 (bs, 1H). $^{13}$C NMR (CDCl$_3$) δ 13.9, 14.0, 15.8, 22.6, 22.7, 28.0, 28.1, 28.3, 35.1, 35.6, 65.9, 82.3, 112.8, 115.2, 127.9, 128.4, 136.1, 145.5, 153.1, 156.3, 163.0, 166.4, 186.4. MS (ES+) 585 (M+68).

5-(3,3-Dioctyl-ureido)-3-methyl-thiophene-2,4-dicarboxylic acid 2-benzyl ester 4-tert-butyl ester (13.16). $^1$H NMR (CDCl$_3$, 200 MHz) δ 0.87 (t, 6H, J=6.6 Hz), 1.26–1.30 (m, 20H), 1.58 (bs, 13H), 2.72 (s, 3H), 3.32 (t, 4H, J=7.7 Hz), 5.25 (s, 2H), 7.28–7.43 (m, 5H), 11.58 (bs, 1H). ¹³C NMR (CDCl₃) δ 14.0, 15.8, 22.6, 26.9, 28.3, 28.5, 29.2, 29.3, 31.8, 47.9, 65.9, 82.3, 113.0, 115.1, 127.9, 128.0, 128.5, 136.1, 145.6, 153.3, 156.7, 163.0, 166.7.

5-Isobutylcarbamoyl-4-methyl-2-(3-octyl-ureido)-thiophene-3-carboxylic acid tert-butyl ester (13.17). MS (ES): m/z 467.9 [MH⁺]. ¹H NMR (CDCl₃, 200 MHz): δ=0.83 (m, 9H), 1.26–1.57 (m, 20H), 1.87 (m, 1H, 6.6 Hz), 2.62 (s, 3H), 3.16–3.30 (m, 4H), 5.11 (brs, 1H), 5.64 (m, 1H).

5-(2,2-Dimethyl-propylcarbamoyl)-4-methyl-2-(3-octyl-ureido)-thiophene-3-carboxylic acid tert-butyl ester (13.18). MS (ES): m/z 481.7 [MH⁺]. ¹H NMR (CDCl₃, 200 MHz): δ=0.83 (m, 9H), 1.26–1.57 (m, 23H), 2.62 (s, 3H), 3.16–3.30 (m, 4H), 5.11 (brs, 1H), 5.64 (m, 1H).

5-[(2,3-Dihydro-benzofuran-5-ylmethyl)-carbamoyl]-4-methyl-2-(3-octyl-ureido)-thiophene-3-carboxylic acid tert-butyl ester (13.19). MS (ES): m/z 543.87 [MH⁺].

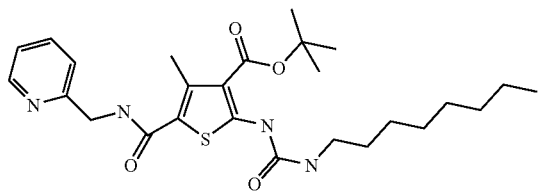

4-Methyl-2-(3-octyl-ureido)-5-[(pyridin-2-yl methyl)-carbamoyl]-thiophene-3-carboxylic acid tert-butyl ester (13.20) The same method as for the preparation of 4-methyl-5-octylcarbamoyl-2-(3-octyl-ureido)-thiophene-3-carboxylic acid tert-butyl ester was employed. Thus, coupling with 2-(aminomethyl)pyridine (31.5 mg, 0.36 mmol) afforded 86.9 mg of a solid (71%) after by column chromatography (EtOAc): ¹H NMR (CDCl₃) δ 0.87 (m, 3H), 1.45–1.20 (m, 10H), 1.70–1.45 (m, 11H), 2.64 (s, 3H), 3.29 (dt, 4H, J=6.7, 6.6 Hz), 4.68 (d, 2H, J=5.8 Hz), 4.91 (m, 1H), 7.02 (m, 1H), 7.35–7.10 (m, 1H), 7.65 (t, 1H, J=8.0 Hz), 8.53 (d, 1H, J=5.0 Hz), 10.92 (s, 1H); MS (EI): cal'd 502.86, exp 502.94 (MH⁺).

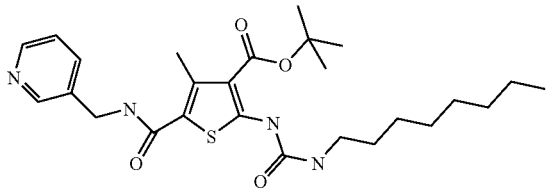

4-Methyl-2-(3-octyl-ureido)-5-[(pyridin-3-yl methyl)-carbamoyl]-thiophene-3-carboxylic acid tert-butyl ester (13.21) The same method as for the preparation of 4-methyl-5-octylcarbamoyl-2-(3-octyl-ureido)-thiophene-3-carboxylic acid tert-butyl ester was employed. Thus, coupling with 3-(aminomethyl)pyridine (31.5 mg, 0.36 mmol) afforded 93.1 mg of a solid (76%) after by column chromatography (EtOAc): ¹H NMR (CDCl₃) δ 0.87 (m, 3H), 1.45–1.20 (m, 10H), 1.70–1.45 (m, 11H), 2.65 (s, 3H), 3.29 (dt, 4H, J=6.7, 6.6 Hz), 4.57 (d, 2H, J=5.6 Hz), 4.89 (m, 1H), 6.05 (t, 1H, J=7.0, 5.0 Hz), 7.68 (d, 1H, J=7.0 Hz), 8.53 (d, 1H, J=5.0 Hz), 8.58 (s, 1H), 10.92 (s, 1H); MS (EI): cal'd 502.86, exp 502.94 (MH⁺).

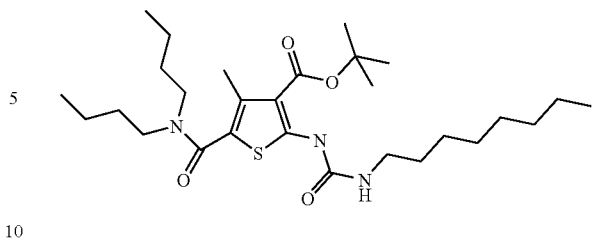

5-Dibutylcarbamoyl-4-methyl-2-(3-octyl-ureido)-thiophene-3-carboxylic acid tert-butyl ester (13.22) The same method as for the preparation of 4-methyl-5-octylcarbamoyl-2-(3-octyl-ureido)-thiophene-3-carboxylic acid tert-butyl ester was employed. Thus, coupling with dibutylamine (37.6 mg, 0.36 mmol) afforded 56.9 mg of a solid (45%) after by column chromatography (8:2; hexanes:EtOAc): ¹H NMR (CDCl₃) δ 0.87 (m, 9H), 1.18–1.40 (m, 14H), 1.45–1.68 (m, 15H), 2.23 (s, 3H), 3.20–3.46 (m, 6H), 5.11 (m, 1H), 10.74 (s, 1H); MS (EI): cal'd 523.77, exp 524.02 (MH⁺).

5-(4-Benzyl-piperidine-1-carbonyl)-4-methyl-2-(3-octyl-ureido)-thiophene-3-carboxylic acid tert-butyl ester (13.23): ¹H NMR (CDCl₃, 200 MHz) δ 0.87 (s, 3H), 1.26 (brs, 11H), 1.56 (brs, 15H), 2.27 (s, 3H), 2.54 (d, 2H, J=6.6 Hz), 2.80 (m, 2H), 3.27 (dt, 2H, J=6.2 Hz, J=6.6 Hz), 4.20 (m, 2H), 5.06 (t, 1H, J=5.2 Hz), 7.05–7.30 (m, 5H), 10.77 (s, 1H); MS (ES) 570.1 (M+1)

3-Methyl-5-(3-octyl-ureido)-thiophene-2,4-dicarboxylic acid 4-tert-butyl ester 2-(1-butyl-pentyl) ester (13.24): (60%). ¹H NMR (CD₃OD, 200 MHz) δ 0.89 (s, 9H), 1.32 (s, 18H), 1.60 (s, 15H), 2.69 (s, 3H), 3.19 (t, 2H, J=6.4 Hz), 5.00 (p, 1H, J=6 Hz), 10.95 (s, 1H); MS (ES) 539.2 (M+1)

4-Methyl-2-(3-octyl-ureido)-5-(3-phenoxy-propylcarbamoyl)-thiophene-3-carboxylic acid tert-butyl ester (13.25): (55%). ¹H NMR (CDCl₃, 400 MHz) δ 0.88 (m, 3H), 1.27 (m, 10H), 1.55 (m, 11H), 2.07 (m, 2H), 2.62 (s, 3H), 3.30 (dt, 2H, J=5.6 Hz, J=7.2 Hz), 3.59 (dt, 2H, J=5.6 Hz, J=6.4 Hz), 4.07 (t, 2H, J=5.6 Hz), 4.82 (brs, 1H), 6.14 (brs, 1H), 6.95 (m, 3H), 7.25 (m, 2H), 10.95 (s, 1H); MS (ES) 545.95 (M)

5-(1-Butyl-pentylcarbamoyl)-4-methyl-2-(3-octyl-ureido)-thiophene-3-carboxylic acid tert-butyl ester (13.26): (92%). ¹H NMR (CDCl₃, 200 MHz) δ 0.87 (m, 9H), 1.29 (m, 18H), 1.56 (s, 11H), 2.61 (s, 3H), 3.29 (dt, 2H, J=6.6 Hz, J=6.6 Hz), 4.02 (brs, 1H), 5.04 (t, 1H, J=5.6 Hz), 5.40 (d, 1H, J=8.8 Hz), 10.91 (s, 1H)

5-[(Furan-2-ylmethyl)-carbamoyl]-4-methyl-2-(3-octyl-ureido)-thiophene-3-carboxylic acid tert-butyl ester (13.27): MS (ES+) 491.88 (M+1).

4-Methyl-2-(3-octyl-ureido)-5-(thiazol-2-ylcarbamoyl)-thiophene-3-carboxylic acid tert-butyl ester (13.28): MS (ES+) 494.84 (M+1).

4-Methyl-2-(3-octyl-ureido)-5-(2-pyridin-3-yl-ethylcarbamoyl)-thiophene-3-carboxylic acid tert-butyl ester (13.29): MS (ES+) 516.93 (M+1).

4-Methyl-2-(3-octyl-ureido)-5-[4-(2-piperidin-1-yl-ethyl)-piperazine-1-carbonyl]-thiophene-3-carboxylic acid tert-butyl ester (13.30): MS (ES+) 592.04 (M+1).

4-Methyl-2-(3-octyl-ureido)-5-(4-phenyl-piperazine-1-carbonyl)-thiophene-3-carboxylic acid tert-butyl ester (13.31): MS (ES+) 556.94 (M+1).

5-([1,4']Bipiperidinyl-1'-carbonyl)-4-methyl-2-(3-octyl-ureido)-thiophene-3-carboxylic acid tert-butyl ester (13.32): MS (ES+) 563.01 (M+1).

5-(3-Imidazol-1-yl-propylcarbamoyl)-4-methyl-2-(3-octyl-ureido)-thiophene-3-carboxylic acid tert-butyl ester (13.33): MS (ES+) 519.95 (M+1).

5-Dihexylcarbamoyl-4-methyl-2-(3-octyl-ureido)-thiophene-3-carboxylic acid tert-butyl ester (13.34): (40%). $^1$H NMR (CD$_3$Cl, 200 MHz) δ 0.85 (s, 9H), 1.24 (s, 22H), 1.56 (s, 15H), 2.24 (s, 3H), 3.31 (m, 6H), 4.83 (t, 1H, J=5.2 Hz), 10.76 (s, 1H); MS (ES) 580.21 (M+1)

5-Dioctylcarbamoyl-4-methyl-2-(3-octyl-ureido)-thiophene-3-carboxylic acid tert-butyl ester (13.35): (65%). $^1$H NMR (CD$_3$Cl, 200 MHz) δ 0.86 (m, 9H), 1.23 (s, 32H), 1.56 (s, 15H), 2.25 (s, 3H), 3.31 (m, 6H), 4.80 (t, 1H, J=5.6 Hz), 10.77 (s, 1H); MS (ES) 637.00 (M+1)

5-Cyclohexylcarbamoyl-4-methyl-2-(3-octyl-ureido)-thiophene-3-carboxylic acid tert-butyl ester (13.36): (75%). $^1$H NMR (CD$_3$Cl, 200 MHz) δ 0.87 (t, 3H, J=6.4 Hz), 1.26 (m, 16H), 1.56 (m, 15H), 2.60 (s, 3H), 3.28 (dt, 2H, J=6.6 Hz, J=6.2 Hz), 3.88 (m, 1H), 4.97 (t, 1H, J=5.4 Hz), 5.57 (d, 1H, J=7.2 Hz), 10.78 (s, 1H); MS (ES) 494.12 (M+1)

5-(4-Benzyl-piperazine-1-carbonyl)-4-methyl-2-(3-octyl-ureido)-thiophene-3-carboxylic acid tert-butyl ester (13.37): (72%). $^1$H NMR (CD$_3$Cl, 200 MHz) δ 0.87 (m, 3H), 1.26 (brs, 10H), 1.56 (brs, 11H), 2.28 (s, 3H), 2.44 (brs, 4H), 3.27 (dt, 2H, J=6.6 Hz, J=6.6 Hz), 3.52 (s, 2H), 3.60 (brs, 4H), 4.88 (t, 1H, J=5.0 Hz), 7.30 (brs, 5H), 10.78 (s, 1H); MS (ES) 571.16 (M+1)

4-Methyl-2-(3-octyl-ureido)-5-[(pyridin-3-ylmethyl)-carbamoyl]-thiophene-3-carboxylic acid tert-butyl ester (13.38). The crude solid was then flashed through a plug of silica gel with ethyl acetate to yield 13.38, 3.84 g (98% crude yield) of a tan solid.

5-(3-Dimethylamino-propylcarbamoyl)-4-methyl-2-(3-octyl-ureido)-thiophene-3-carboxylic acid tert-butyl ester (13.39): MS (ES+) 496.95 (M+1).

3-Methyl-5-(3-octyl-ureido)-thiophene-2,4-dicarboxylic acid 2-benzyl ester 4-tert-butyl ester (13.40). Mp 119.0–120.0° C.; $^1$H NMR (CDCl$_3$) δ 11.03 (s, 1H), 7.50–7.20 (m, 5H), 5.27 (s, 2H), 5.03 (vt, 1H), 3.29 (q, 2H, J=6.6 Hz), 2.71 (s, 3H), 1.63–1.40 (m, 2H), 1.57 (s, 9H), 1.26 (bs, 10H), 0.87 (t, 3H, J=6.6 Hz). MS (EI): 502.8 (m+).

3-Methyl-5-(3-octyl-ureido)-thiophene-2,4-dicarboxylic acid 4-tert-butyl ester 2-octyl ester (13.41) Mp 92.0–94.0° C.; $^1$H NMR (CDCl$_3$) δ 12.30 (s, 1H), 8.64 (s, 1H), 5.30 (t, 1H, J=6.0 Hz), 4.25 (t, 2H, J=6.4 Hz), 3.29 (q, 2H, J=6.0 Hz), 2.74 (s, 3H), 1.90–1.50 (m, 4H), 1.61 (s, 9H), 1.28 (bs, 20H), 0.88 (m, 6H). MS (EI): 525.1 (m$^+$).

4-Methyl-5-octylcarbamoyl-2-(3-octyl-ureido)-thiophene-3-carboxylic acid tert-butyl ester (13.42). $^1$H NMR (CDCl$_3$) δ 10.89 (s, 1H), 5.82–5.62 (m, 1H), 5.78–5.60 (m, 1H), 3.33 (q, 4H, J=6.6 Hz), 2.61 (s, 3H), 1.70–1.40 (m, 4H), 1.55 (s, 9H), 1.27 (bs, 20H), 0.88 (m, 6H). MS (EI): 524.1 (m$^+$).

4-Methyl-2-(3-octyl-ureido)-5-(4-phenyl-butylcarbamoyl)-thiophene-3-carboxylic acid tert-butyl ester (13.43): $^1$H NMR (CDCl$_3$, 200 MHz) δ 0.87 (m, 3H), 1.21–1.43 (m, 10H), 1.57 (s, 15H), 2.60 (m, 5H), 3.24–3.43 (m, 4H), 5.22 (brs, 1H), 5.70 (t, 1H, J=5.0 Hz), 7.25 (m, 5H), 10.90 (s, 1H).

4-Methyl-2-(3-octyl-ureido)-5-(3-phenyl-propylcarbamoyl)-thiophene-3-carboxylic acid tert-butyl ester (13.44) $^1$H NMR (CDCl$_3$, 200 MHz) δ 0.87 (m, 3H), 1.21–1.45 (m, 10H), 1.57 (s, 11H), 1.89 (tt, 2H, J=7.4 Hz, J=7.6 Hz), 2.65 (m, 5H), 3.24–3.45 (m, 4H), 5.14 (brs, 1H), 5.73 (t, 1H, J=5.2 Hz), 7.17–7.31 (m, 5H), 10.90 (s, 1H).

4-Methyl-2-(3-octyl-ureido)-5-(2-phenoxy-ethylcarbamoyl)-thiophene-3-carboxylic acid tert-butyl ester (13.45): $^1$H NMR (CDCl$_3$, 200 MHz) δ 0.87 (m, 3H), 1.22–1.49 (m, 10H), 1.56 (s, 11H), 2.61 (s, 3H), 3.28 (dt, 2H, J=6.2 Hz, J=6.6 Hz), 3.78 (dt, 2H, J=5.2 Hz, J=5.4 Hz), 4.09 (t, 2H, J=5.2 Hz), 5.08 (t, 1H, J=5.0 Hz), 6.21 (t, 1H, J=5.4 Hz), 6.29 (m, 3H), 7.28 (m, 2H), 10.91 (s, 1H).

5-(2-Methoxy-ethylcarbamoyl)-4-methyl-2-(3-octyl-ureido)-thiophene-3-carboxylic acid tert-butyl ester (13.46): $^1$H NMR (CDCl$_3$, 200 MHz) δ 0.87 (m, 3H), 1.27–1.45 (m, 10H), 1.57 (brs, 11H), 2.60 (s, 3H), 3.24–3.37 (m, 5H), 3.54 (m, 4H), 5.05 (t, 1H, J=5.2 Hz), 6.12 (brs, 1H), 10.88 (s, 1H).

5-(3-Methoxy-propylcarbamoyl)-4-methyl-2-(3-octyl-ureido)-thiophene-3-carboxylic acid tert-butyl ester (13.47): $^1$H NMR (CDCl$_3$, 200 MHz) δ 0.87 (m, 3H), 1.21–1.49 (m, 10H), 1.57 (brs, 11H), 1.83 (tt, 2H, J=5.8 Hz, J=6.2 Hz), 2.60 (s, 3H), 3.24–3.35 (m, 5H), 3.49 (m, 4H), 5.13 (t, 1H, J=5.6 Hz), 6.31 (t, 1H, J=5.6 Hz), 10.90 (s, 1H).

5-((Benzo(1,3)dioxol-5-ylmethyl)-carbamoyl)-4-methyl-2-(3-octyl-ureido)-thiophene-3-carboxylic acid tert-butyl ester (13.48): $^1$H NMR (CDCl$_3$, 200 MHz) δ 0.87 (m, 3H), 1.26–1.43 (brs, 10H), 1.57 (brs, 11H), 2.63 (s, 3H), 3.27 (dt, 2H, J=6.2 Hz, J=6.6 Hz), 4.44 (d, 2H, J=5.6 Hz), 4.92 (t, 1H, J=5.6 Hz), 5.94 (s, 2H), 6.76 (s, 2H), 6.81 (s, 1H), 10.91 (s, 1H).

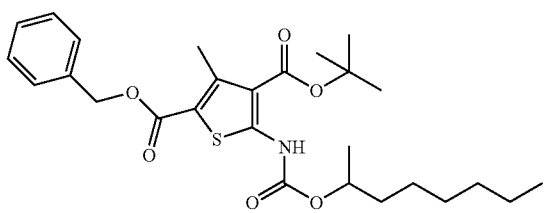

3-Methyl-5-(1-methylheptyloxycarbonylamino)thiophene-2,4-dicarboxylic acid 2-benzyl ester 4-tert-butyl ester (13.49)

Light brownish oil in 82% yield as mixture of two rotatmers (2:1 ratio).

$^1$H NMR (CDCl$_3$, 200 MHz): δ 7.35–7.40 (m, 5H), 6.49 (brs, 1H), 5.25 and 5.28 (s, 2H), 4.70–4.80 and 4.80–5.05 (m, 1H), 2.68 and 2.73 (s, 3H), 1.50–1.61 (m, 9H), 1.20–1.40 (m, 8H), 0.87 (m, 3H).

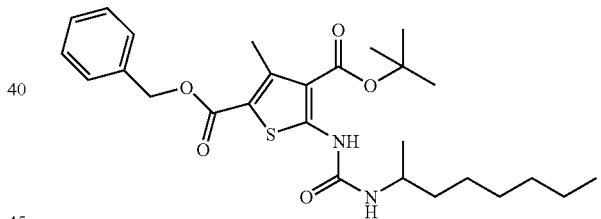

3-Methyl-5-[3-(1-methylheptyl)ureido]thiophene-2,4-dicarboxylic acid 2-benzyl ester 4-tert-butyl ester (13.50)

Light yellow oil in 99% yield as mixture of two rotatmers.

$^1$H NMR (CDCl$_3$, 200 MHz): δ 11.00 (brs, 1H), 7.29–7.43 (m, 5H), 5.24 and 5.26 (s, 2H), 4.60 and 4.68 (brs, 1H), 3.80–3.95 (brs, 1H), 3.45–3.90 (m, 1H), 2.65 and 2.70 (s, 3H), 1.55 and 1.57 (s, 9H), 1.40–1.50 (m, 2H), 1.20–1.40 (m, 8H), 1.17 (d, 2H, J=6.6 Hz), 1.09 (d, 1H, J=6.2 Hz), 0.80–0.95 (m, 3H).

EXAMPLE 14

Acid Intermediates

4-Methyl-2-(3-octyl-ureido)-5-[(pyridin-4-ylmethyl)-carbamoyl]-thiophene-3-carboxylic acid (14.1): (99%). $^1$H NMR (CD$_3$OD, 200 MHz) δ 0.86 (m, 3H), 1.25 (brs, 10H), 1.56 (m, 2H), 2.64 (s, 3H), 3.28 (m, 2H), 4.56 (d, 2H, J=5.8 Hz) 7.24 (d, 2H, J=5.8 Hz), 8.54 (d, 2H, J=5.8 Hz)

4-Methyl-5-[methyl-(6-methyl-pyridin-2-ylmethyl)-carbamoyl]-2-(3-octyl-ureido)-thiophene-3-carboxylic acid (14.2): (99%). $^1$H NMR (CD$_3$OD, 200 MHz) δ 0.86 (m, 3H), 1.28 (brs, 10H), 1.50 (brs, 2H), 2.38 (s, 3H), 2.50 (s, 3H), 3.04 (s, 3H), 3.17 (brs, 2H), 4.74 (s, 2H), 7.15 (m, 2H), 7.55 (t, 1H, J=7.6 Hz)

5-[Ethyl-(2-pyridin-2-yl-ethyl)-carbamoyl]-4-methyl-2-(3-octyl-ureido)-thiophene-3-carboxylic acid (14.3): (99%). ¹H NMR (CD₃OD, 200 MHz) δ 0.85 (m, 3H), 1.20 (brs, 13H), 1.49 (brs, 2H), 2.20 (s, 3H), 3.19 (m, 4H), 3.41 (m, 2H), 3.83 (brs, 2H), 7.38 (m, 2H), 7.84 (t, 1H, J=7.2 Hz), 8.49 (d, 1H, J=3.6 Hz)

5-(Benzyloxycarbonylmethyl-carbamoyl)-4-methyl-2-(3-octyl-ureido)-thiophene-3-carboxylic acid (14.4): (99%). ¹H NMR (CD₃OD, 200 MHz) δ 0.86 (m, 3H). 1.28 (brs, 10H), 1.50 (brs, 2H), 2.57 (s, 3H), 3.18 (m, 2H), 4.09 (s, 2H), 7.31 (brs, 5H)

3-Methyl-5-(3-octyl-thioureido)-thiophene-2,4-dicarboxylic acid 2-benzyl ester (14.5): (99%). ¹H NMR (CD₃OD, 200 MHz) δ 0.89 (brs, 3H), 1.29 (brs, 10H), 1.61 (brs, 2H), 2.74 (s, 3H), 3.48 (brs, 2H), 5.29 (s, 2H), 7.38 (m, 5H).

4-Methyl-2-(3-octyl-ureido)-5-[(pyridin-3-yl-methyl)-carbamoyl]-thiophene-3-carboxylic acid (14.6) Thiophene (3.42 g, 6.8 mmol) was dissolved in 40 mL CH₂Cl₂. Trifluoroacetic acid (10 mL) was added slowly and the reaction was stirred for 4 h at rt. The reaction was concentrated in-vacuo. The residue was dissolved in methanol and saturated NaHCO₃ was added until pH~7. The solution was concentrated in vacuo and then resuspended in hot ethyl acetate. The insoluble salts were filtered and the filtrate was concentrated in vacuo to yield 14.6, 2.19 g (72% crude yield) of a tan solid.

5-[(Furan-2-yl-methyl)-carbamoyl]-4-methyl-2-(3-octyl-ureido)-thiophene-3-carboxylic acid (14.7) white solid (73% yield): ¹H NMR (CD₃OD, 200 MHz) δ 0.90 (t, 3H, J=6.4 Hz), 1.30–1.39 (m, 10H), 1.50–1.60 (m, 2H), 2.56 (s, 3H), 3.20 (t, 2H, J=6.9 Hz), 4.49 (s, 2H), 6.27 (1H, d, J=3.0 Hz), 6.35 (dd, 1H, J=3.2, 1.8 Hz), 7.34 (d, 1H, J=1.8 Hz). MS (ES+) 435.76 (M+1), 436.66 (M+2).

4-Methyl-2-(3-octyl-ureido)-5-[(2-pyridin-3-yl-ethyl)-carbamoyl]-thiophene-3-carboxylic acid (14.8) light pink solid (100% yield): ¹H NMR (CD₃OD, 200 MHz) δ 0.90 (t, 3H, J=9.9 Hz), 1.32 (bs, 10H), 1.51–1.60 (m, 2H), 2.58 (s, 3H), 2.96 (t, 2H, J=7.0 Hz), 3.20 (t, 2H, J=6.7 Hz), 3.59 (t, 2H, J=7.0 Hz), 7.39 (dd, 1H, J=7.8, 4.8 Hz), 7.78 (d, 1H, J=7.8 Hz), 8.39 (d, 1H, J=4.8 Hz), 8.46 (s, 1H). MS (ES−) 458.92 (M−1).

4-Methyl-2-(3-octyl-ureido)-5-[4-(2-piperidin-1-yl-ethyl)-piperazine-1-carbonyl]-thiophene-3-carboxylic acid (14.9) peach solid (80% yield): MS (ES−) 534.04 (M−1).

5-(3-Hexyl-3-methyl-ureido)-3-methyl-thiophene-2,4-dicarboxylic acid 2-benzyl ester (14.10) light pink solid (100% yield): ¹H NMR (CDCl₃, 200 MHz) δ 0.87 (t, 3H, J=6.4 Hz), 1.25–1.31 (m, 6H), 1.58–1.62 (m, 2H), 2.78 (s, 3H), 3.05 (s, 3H), 3.36 (t, 2H, J=7.5 Hz), 5.29 (s, 2H), 7.29–7.44 (m, 5H), 10.39 (bs, 1H), 11.18 (bs, 1H). ¹³C NMR (CDCl₃) δ 13.9, 15.4, 22.4, 26.3, 27.7, 31.4, 34.7, 49.7, 66.4, 110.8, 116.4, 127.9, 128.1, 128.5, 135.7, 146.1, 153.5, 158.6, 162.9, 171.3. MS (ES+) 432.74 (M+1).

5-(3,3-Dioctyl-ureido)-3-methyl-thiophene-2,4-dicarboxylic acid 2-benzyl ester (14.11) light pink solid (84% yield): ¹H NMR (CDCl₃, 200 MHz) δ 0.86 (t, 6H, J=6.6 Hz), 1.26–1.30 (m, 20H), 1.63 (bs, 4H), 2.80 (s, 3H), 3.33 (t, 4H, J=7.0 Hz), 5.28 (s, 2H), 7.30–7.43 (m, 5H), 11.20 (s, 1H), 11.92 (bs, 1H).

5-Isobutylcarbamoyl-4-methyl-2-(3-octyl-ureido)-thiophene-3-carboxylic acid (14.12). MS (ES): m/z 411.8 [MH⁺].

5-(2,2-Dimethyl-propylcarbamoyl)-4-methyl-2-(3-octyl-ureido)-thiophene-3-carboxylic acid (14.13). MS (ES): m/z 425.8 [MH⁺]. ¹H NMR (CDCl₃, 200 MHz): □=1.26–1.57 (m, 23H), 2.62 (s, 3H), 3.16–3.30 (m, 4H), 5.11 (brs, 1H), 5.64 (m, 1H).

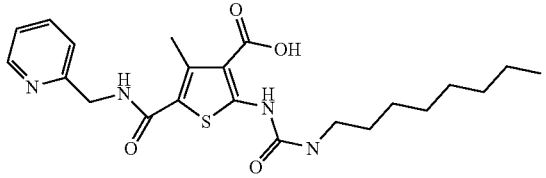

4-Methyl-2-(3-octyl-ureido)-5-[(pyridin-2-ylmethyl)-carbamoyl]-thiophene-3-carboxylic acid (14.14) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: ¹H NMR (CDCl₃+1 drop of CD₃OD) δ 0.86 (m, 3H), 1.32–1.20 (m, 10H), 1.60–1.32 (m, 2H), 2.59 (s, 3H), 3.22 (dt, 4H, J=6.7, 6.6 Hz), 4.76 (s, 2H), 7.40–7.15 (m, 2H), 7.76 (t, 1H, J=7.9 Hz), 8.53 (d, 1H, J=5.0 Hz).

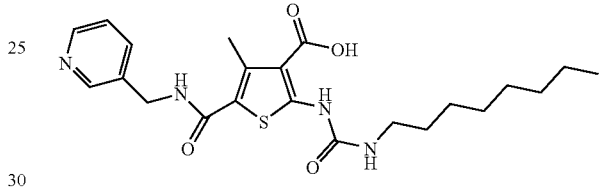

4-Methyl-2-(3-octyl-ureido)-5-[(pyridin-3-ylmethyl)-carbamoyl]-thiophene-3-carboxylic acid (14.15) The same method as for the preparation of 3-methoxymethyl-5-octyloxycarbonylamino-thiophene[2,4]dicarboxylic acid 2-benzyl ester was employed. Thus, deprotection with TFA afforded a solid, which was used without purification: ¹H NMR (CDCl₃+1 drop of CD₃OD) δ 0.82 (m, 3H), 1.45–1.20 (m, 10H), 1.70–1.45 (m, 2H), 2.02 (m, 3H), 2.92 (m, 2H), 4.39 (m, 1H), 7.11 (m, 1H), 7.55 (m, 1H), 8.31 (m, 1H), 8.49 (m, 1H).

5-(4-Benzyl-piperidine-1-carbonyl)-4-methyl-2-(3-octyl-ureido)-thiophene-3-carboxylic acid (14.16): (100%). ¹H NMR (CD₃OD, 200 MHz) δ 0.87 (s, 3H), 1.26 (brs, 11H), 1.56 (brs, 6H), 2.27 (s, 3H), 2.54 (d, 2H, J=6.6 Hz), 2.90 (m, 2H), 3.27 (t, 2H, J=6.6 Hz), 4.20 (brs, 2H), 7.05–7.30 (m, 5H)

3-Methyl-5-(3-octyl-ureido)-thiophene-2,4-dicarboxylic acid 2-(1-butyl-pentyl) ester (14.17): (95%). ¹H NMR (CD₃OD, 400 MHz) δ 0.89 (m, 9H), 1.33 (m, 18H), 1.50–1.70 (m, 6H), 2.73 (s, 3H), 3.19 (t, 2H, J=6.6 Hz), 5.02 (m, 1H)

5-(1-Butyl-pentylcarbamoyl)-4-methyl-2-(3-octyl-ureido)-thiophene-3-carboxylic acid (14.18): (100%). ¹H NMR (CDCl₃, 200 MHz) δ 0.87 (m, 9H), 1.29 (m, 18H), 1.56 (s, 6H), 2.52 (s, 3H), 3.35 (t, 2H, J=6.6 Hz), 3.90 (brs, 1H)

4-Methyl-2-(3-octyl-ureido)-5-(3-phenoxy-propylcarbamoyl)-thiophene-3-carboxylic acid (14.19): (100%). ¹H NMR (CD₃OD, 200 MHz) δ 0.89 (m, 3H), 1.32 (s, 10H), 1.55 (brs, 2H), 2.06 (tt, 2H, J=6.0 Hz, J=6.0 Hz), 2.55 (s, 3H), 3.19 (t, 2H, J=7.0 Hz), 3.51 (t, 2H, J=6.8 Hz), 6.90 (m, 3H), 7.24 (m, 2H).

4-Methyl-2-(3-octyl-ureido)-5-(pyridin-3-ylmethyl)-carbamoyl)-thiophene-3-carboxylic acid (14.20): 14.20, 110 mg (100% crude yield) of a tan solid.

5-(3-Dimethylamino-propylcarbamoyl)-4-methyl-2-(3-octyl-ureido)-thiophene-3-carboxylic acid (14.21): MS (ES−) 438.70 (M−1).

5-[(Furan-2-ylmethyl)-carbamoyl]-4-methyl-2-(3-octyl-ureido)-thiophene-3-carboxylic acid (14.22): MS (ES−) 434.03 (M−1).

4-Methyl-2-(3-octyl-ureido)-5-(thiazol-2-ylcarbamoyl)-thiophene-3-carboxylic acid (14.23): MS (ES−) 436.23 (M−1).

4-Methyl-2-(3-octyl-ureido)-5-(2-pyridin-3-yl-ethylcarbamoyl)-thiophene-3-carboxylic acid (14.24): MS (ES−) 459.03 (M−1).

4-Methyl-2-(3-octyl-ureido)-5-[4-(2-piperidin-1-yl-ethyl)-piperazine-1-carbonyl]-thiophene-3-carboxylic acid (14.25): MS (ES−) 534.20 (M−1).

4-Methyl-2-(3-octyl-ureido)-5-(4-phenyl-piperazine-1-carbonyl)-thiophene-3-carboxylic acid (14.26): MS (ES−) 499.03 (M−1).

5-([1,4']Bipiperidinyl-1'-carbonyl)-4-methyl-2-(3-octyl-ureido)-thiophene-3-carboxylic acid (14.27): MS (ES−) 505.08 (M−1).

5-(3-Imidazol-1-yl-propylcarbamoyl)-4-methyl-2-(3-octyl-ureido)-thiophene-3-carboxylic acid (14.28): MS (ES−) 462.09 (M−1).

3-Methyl-5-(3-octyl-ureido)-thiophene-2,4-dicarboxylic acid 4-tert-butyl ester (14.29) $^1$H NMR (CDCl$_3$) δ 11.06 (s, 1H), 5.14 (vt, 1H), 3.30 (q, 2H, J=6.0 Hz), 2.71 (s, 3H), 1.70–1.40 (m, 2H), 1.59 (s, 9H), 1.27 (bs, 10H), 0.87 (t, 3H, J=6.6 Hz). MS (EI): 412.8 (m$^+$).

2-Dodecyloxy-5-methyl-4-oxo-4H-thieno[2,3-d][1,3]oxazine-6-carboxylic acid (14.30) $^1$H NMR (CDCl$_3$) δ 4.47 (t, 2H, J=6.2 Hz), 4.19 (bs, 1H), 2.85 (s, 3H), 1.80 (quint, 2H, J=6.2 Hz), 1.27 (bs, 18H), 0.88 (t, 3H, J=6.6 Hz). MS (EI): 395.4 (m$^+$).

4-Methyl-5-octylcarbamoyl-2-(3-octyl-ureido)-thiophene-3-carboxylic acid (14.31) $^1$H NMR (CDCl$_3$) δ 10.90 (bs, 2H), 5.82–5.62 (m, 1H), 5.78–5.60 (m, 1H), 3.33 (q, 4H, J=6.6 Hz), 2.61 (s, 3H), 1.70–1.40 (m, 4H), 1.27 (bs, 20H), 0.88 (m, 6H).

3-Methoxymethyl-5-octyloxycarbonylamino-thiophene[2,4]dicarboxylic acid 2-benzyl ester (14.32) $^1$H NMR (CDCl$_3$) δ 11.98 (s, 1H), 10.09 (s, 1H), 7.45–7.20 (m, 5H), 5.14 (s, 2H), 4.22 (t, 2H, J=6.6 Hz), 3.85 (s, 3H), 3.82 (s, 2H), 1.70 (quint, 2H, J=6.6 Hz), 1.28 (bs, 10H), 0.88 (t, 3H, J=5.6 Hz).

5-(4-(Isopropylcarbamoyl-methyl)-piperazine-1-carbonyl)-4-methyl-2-(3-octyl-ureido)-thiophene-3-carboxylic acid (14.33): $^1$H NMR (CDCl$_3$, 200 MHz) δ 0.89 (brs, 3H), 1.15–1.34 (m, 16H), 1.56 (m, 2H), 2.37 (s, 3H), 3.05–3.49 (m, 10H), 3.95 (m, 1H).

5-((Benzo(1,3)dioxol-5-ylmethyl)-carbamoyl)-4-methyl-2-(3-octyl-ureido)-thiophene-3-carboxylic acid (14.34): $^1$H NMR (CDCl$_3$, 200 MHz) δ 0.86 (m, 3H), 1.32–1.45 (m, 10H), 1.53 (m, 2H), 2.56 (s, 3H), 3.19 (m, 2H), 4.4 (d, 2H, J=6.0 Hz), 5.91 (s, 2H), 6.80 (m, 3H).

5-(3,4-Dimethoxy-benzylcarbamoyl)-4-methyl-2-(3-octyl-ureido)-thiophene-3-carboxylic acid (14.35): $^1$H NMR (CDCl$_3$, 200 MHz) δ 0.88 (brs, 3H), 1.31–1.45 (m, 10H), 1.56 (m, 2H), 2.56 (s, 3H), 3.18 (dt, 2H, J=6.2 Hz, J=6.6 Hz), 3.80 (s, 3H), 3.82 (s, 3H), 4.43 (s, 2H), 6.89 (s, 2H), 6.97 (s, 1H).

5-(6,7-Dimethoxy-3,4-dihydro-1H-isoquinoline-2-carbonyl)-4-methyl-2-(3-octyl-ureido)-thiophene-3-carboxylic acid (14.36): $^1$H NMR (CDCl$_3$, 200 MHz) δ 0.89 (m, 3H), 1.31–1.45 (m, 10H), 1.51 (brs, 2H), 2.31 (s, 3H), 2.85 (t, 2H, J=6.0 Hz), 3.18 (t, 2H, J=7.0 Hz), 3.79 (s, 8H), 6.71 (s, 1H), 6.74 (s, 1H).

4-Methyl-2-(3-octyl-ureido)-5-(4-phenyl-butylcarbamoyl)-thiophene-3-carboxylic acid (14.37): $^1$H NMR (CDCl$_3$, 200 MHz) δ 0.89 (brs, 3H), 1.26–1.45 (m, 10H), 1.59 (m, 6H), 2.54 (s, 3H), 2.65 (t, 2H, J=7.0 Hz), 3.19 (m, 4H), 7.21 (m, 5H).

4-Methyl-2-(3-octyl-ureido)-5-(3-phenyl-propylcarbamoyl)-thiophene-3-carboxylic acid (14.38): $^1$H NMR (CDCl$_3$, 200 MHz) δ 0.89 (m, 3H), 1.25–1.45 (m, 10H), 1.57 (brs, 2H), 1.89 (tt, 2H, J=7.4 Hz, J=7.6 Hz), 2.55 (s, 3H), 3.17–3.39 (m, 4H), 7.23 (m, 5H).

4-Methyl-2-(3-octyl-ureido)-5-(2-phenoxy-ethylcarbamoyl)-thiophene-3-carboxylic acid (14.39): $^1$H NMR (CDCl$_3$, 200 MHz) δ 0.87 (m, 3H), 1.25–1.41 (m, 10H), 1.56 (brs, 2H), 2.56 (s, 3H), 3.19 (dt, 2H, J=6.2 Hz, J=6.6 Hz), 3.71 (dt, 2H, J=5.2 Hz, J=5.4 Hz), 4.12 (t, 2H, J=5.2 Hz), 6.95 (m, 3H), 7.25 (m, 2H).

5-(2-Methoxy-ethylcarbamoyl)-4-methyl-2-(3-octyl-ureido)-thiophene-3-carboxylic acid (14.40): $^1$H NMR (CDCl$_3$, 200 MHz) δ 0.89 (brs, 3H), 1.25–1.43 (m, 10H), 1.53 (m, 2H), 2.56 (s, 3H), 3.19 (t, 2H, J=7.0 Hz), 3.37 (s, 3H), 3.51 (m, 4H).

5-(3-Methoxy-propylcarbamoyl)-4-methyl-2-(3-octyl-ureido)-thiophene-3-carboxylic acid (14.41): $^1$H NMR (CDCl$_3$, 200 MHz) δ 0.89 (brs, 3H), 1.27–1.44 (m, 10H), 1.51 (brs, 2H), 1.84 (tt, 2H, J=6.2 Hz, J=6.6 Hz), 2.56 (s, 3H), 3.19 (t, 2H, J=7.0 Hz), 3.34 (s, 3H), 3.39 (t, 2H, J=7.0 Hz), 3.49 (t, 2H, J=6.2 Hz).

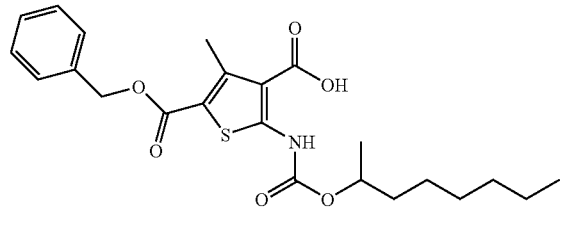

5-Methyl-2-(1-methylheptyloxy)-4-oxo-4H-thieno[2,3-d]oxazine-6-carboxylic acid benzyl ester (14.42)

Light yellow oil in 32% yield.

$^1$HNMR (CDCl$_3$, 200 MHz): δ 10.70 (brs, 1H), 8.31 (brs, 2H), 7.29–7.43 (m, 5H), 5.27 (s, 2H), 3.45–3.90 (m, 1H), 2.75 (s, 3H), 1.40–1.60 (m, 2H), 1.10–1.40 (m, 11H), 0.85 (t, 3H, J=6.6 Hz).

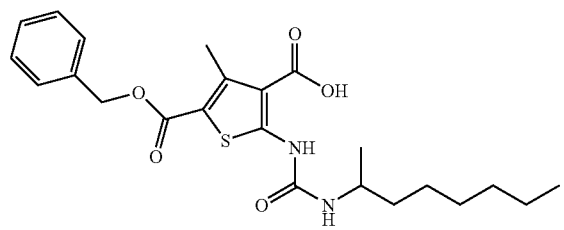

3-Methyl-5-[3-(1-methylheptyl)ureido]thiophene-2,4-dicarboxylic acid 2-benzyl ester (14.43)

Light brownish solid in 99% yield.

$^1$HNMR (CDCl$_3$, 200 MHz): δ 10.52 (s, 1H), 9.00 (brs, 1H), 7.35–7.39 (m, 5H), 5.28 (s, 2H), 4.70–5.05 (m, 1H), 2.79 (s, 3H), 1.42–1.62 (m, 2H), 1.10–1.40 (m, 8H), 0.87 (t, 3H, J=6.6 Hz), MS (ES) [M−1] 444.96.

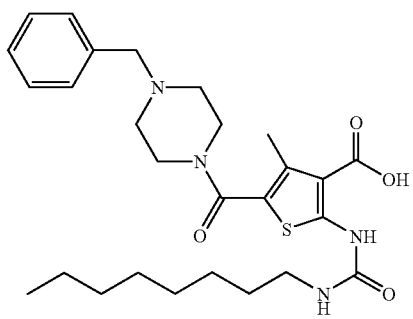

5-(4-Benzyl-piperazine-1-carbonyl)-4-methyl-2-(3-octyl-ureido)-thiophene-3-carboxylic acid (37) $^1$H NMR (DMSO, 200 MHz) δ 0.83 (brm, 3H), 1.18–1.41 (brm, 12H), 2.26 (s, 3H), 2.33 (brs, 4H), 2.99 (dt, 2H, J=5.8 Hz, J=5.8 Hz), 3.29 (s, 2H), 3.43 (brm, 4H), 7.21–7.41 (m, 5H)

EXAMPLE 15

Thienoxazinones

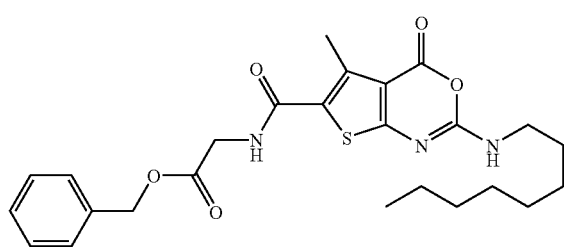

[(5-Methyl-2-octylamino-4-oxo-4H-thieno[2,3-d][1,3]oxazine-6-carbonyl)-amino]-acetic acid benzyl ester (48): $^1$H NMR (CDCl$_3$, 200 MHz) δ 0.88 (m, 3H), 1.30 (brs, 10H), 1.61 (m, 2H), 2.74 (s, 3H), 3.42 (dt, 2H, J=6.2 Hz, J=7.0 Hz), 4.25 (d, 2H, J=5.0 Hz), 5.08 (brs, 1H), 5.23 (s, 2H), 6.29 (brs, 1H), 7.37 (s, 5H)

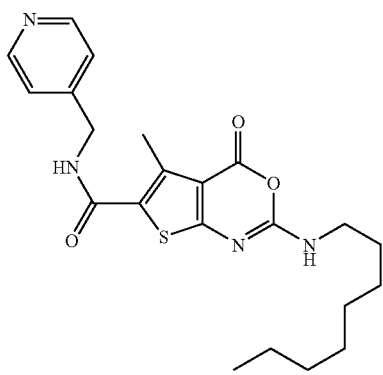

5-Methyl-2-octylamino-4-oxo-4H-thieno[2,3-d][1,3]oxazine-6-carboxylic acid (pyridin-4-ylmethyl)-amide (55): (15%). $^1$H NMR (CDCl$_3$, 200 MHz) δ 0.88 (brs, 3H), 1.25 (brs, 10H), 1.55 (brs, 2H), 2.75 (s, 3H), 3.38 (dt, 2H, J=6.4 Hz, J=6.6 Hz), 4.60 (d, 2H, J=5.8 Hz), 6.17 (s, 1H), 7.24 (s, 2H), 8.54 (d, 2H, J=5.8 Hz)

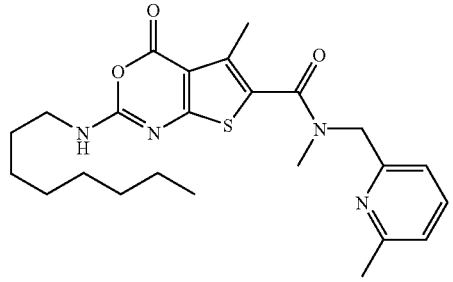

5-Methyl-2-octylamino-4-oxo-4H-thieno[2,3-d][1,3]oxazine-6-carboxylic acid methyl-(6-methyl-pyridin-2-ylmethyl)-amide (49): (20%). $^1$H NMR (CDCl$_3$, 200 MHz) δ 0.86 (m, 3H), 1.26 (brs, 10H), 1.58 (m, 2H), 2.45 (s, 3H), 2.52 (s, 3H), 3.06 (s, 3H), 3.38 (dt, 2H, J=6.4 Hz, J=6.6 Hz), 4.73 (s, 2H), 5.28 (brs, 1H), 7.05 (d, 2H, J=7.6 Hz), 7.56 (t, 1H, J=7.8 Hz)

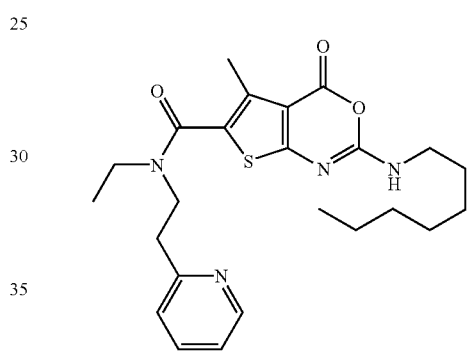

5-Methyl-2-octylamino-4-oxo-4H-thieno[2,3-d][1,3]oxazine-6-carboxylic acid ethyl-(2-pyridin-2-yl-ethyl)-amide (51): (58%). $^1$H NMR (CDCl$_3$, 200 MHz) δ 0.87 (m, 3H), 1.14 (t, 3H, J=7.0 Hz), 1.26 (brs, 10H), 1.59 (m, 2H), 2.31 (s, 3H), 3.10 (t, 2H, J=7.0 Hz), 3.38 (dt, 4H, J=6.2 Hz, J=7.0 Hz), 3.84 (t, 2H, J=7.6 Hz), 5.26 (brs, 1H), 7.14 (m, 2H), 7.59 (ddd, 1H, J=7.4 Hz, J=7.6 Hz, J=1.6 Hz), 8.52 (d, 1H, J=4.4 Hz)

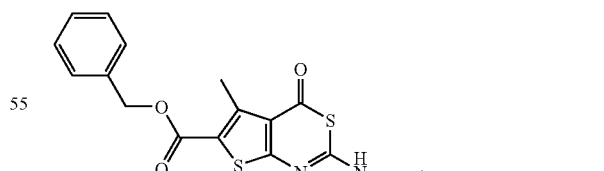

5-Methyl-2-octylamino-4-oxo-4H-thieno[2,3-d][1,3]thiazine-6-carboxylic acid benzyl ester (56): $^1$H NMR (CD$_3$OD, 200 MHz) δ 0.87 (brs, 3H), 1.27 (brs, 10H), 1.61 (m, 2H), 2.82 (s, 3H), 3.45 (dt, 2H, J=6.2 Hz, J=6.6 Hz), 5.31 (s, 2H), 5.42 (brs, 1H), 7.35 (m, 5H)

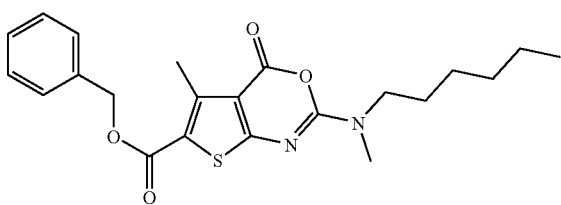

2-(Hexyl-methyl-amino)-5-methyl-4-oxo-4H-thieno[2,3-d]
[1,3]oxazine-6-carboxylic acid benzyl ester (57): $^1$H NMR
(CDCl$_3$, 200 MHz) δ 0.89 (t, 3H, J=6.6 Hz), 1.30 (bs, 6H),
1.58–1.64 (m, 2H), 2.77 (s, 3H), 3.11 (s, 3H), 3.47–3.50 (m,
2H), 5.29 (s, 2H), 7.30–7.44 (m, 5H). MS (ES+) 414.70
(M+1).

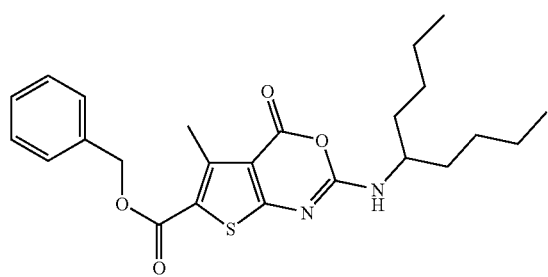

2-(1-Butyl-pentylamino)-5-methyl-4-oxo-4H-thieno[2,3-d]
[1,3]oxazine-6-carboxylic acid benzyl ester (59). $^1$H NMR
(CDCl$_3$, 200 MHz) δ 0.89 (t, 6H, J=6.4 Hz), 1.22–1.40 (bs,
8H), 1.48–1.66 (m, 4H), 2.79 (s, 3H), 3.90–4.00 (m, 1H),
5.32 (s, 2H), 5.77 (d, J=8.4 Hz), 7.31–7.45 (m, 5H).

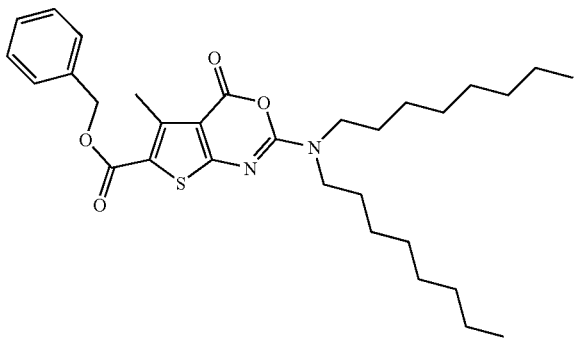

2-Dioctylamino-5-methyl-4-oxo-4H-thieno[2,3-d][1,3]
oxazine-6-carboxylic acid benzyl ester (60) $^1$H NMR
(CDCl$_3$, 200 MHz) δ 0.88 (t, 6H, J=6.6 Hz), 1.26–1.37 (m,
20H), 1.58–1.64 (m, 4H), 2.79 (s, 3H), 3.39–3.53 (m, 4H),
5.31 (s, 2H), 7.29–7.45 (m, 5H).

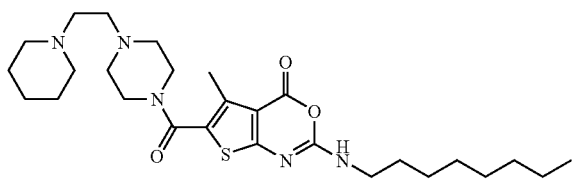

5-Methyl-2-octylamino-6-[4-(2-piperidin-1-yl-ethyl)-
piperazine-1-carbonyl]-thieno[2,3-d][1,3]oxazin-4-one (53).
MS (ES): m/z 517.9 [MH$^+$]. $^1$H NMR (CDCl$_3$, 200 MHz):
δ=0.87–1.59 (m, 9H), 1.18–1.59 (m, 14H), 2.54 (s, 3H),
2.23–2.51 (m, 4H), 3.34 (dt, 2H, J=7 Hz), 3.61 (m, 3H), 5.21
(brs, 1H)

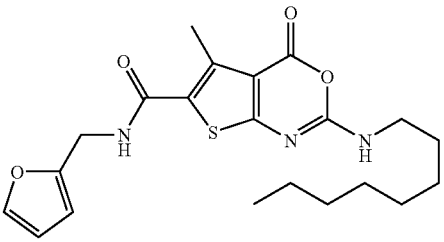

5-Methyl-2-octylamino-4-oxo-4H-thieno[2,3-d][1,3]
oxazine-6-carboxylic acid (furan-2-ylmethyl)-amide (52)
MS (ES): m/z 417.3 [MH$^+$].

$^1$H NMR (CDCl$_3$, 200 MHz): δ=1.18–1.41 (m, 14H), 2.67
(s, 3H), 3.43 (t, 2H, J=8.4 Hz), 4.48 (m, 2H, J=5.6 Hz), 5.12
(brs, 1H), 6.02–6.57 (m, 3H).

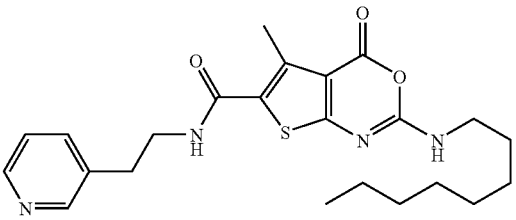

5-Methyl-2-octylamino-4-oxo-4H-thieno[2,3-d][1,3]
oxazine-6-carboxylic acid (2-pyridin-3-yl-ethyl)-amide (50)
MS (ES): m/z 443.5 [MH$^+$]. $^1$H NMR (CDCl$_3$, 200 MHz):
δ=1.25–1.68 (m, 14H), 2.60 (s, 3H), 2.99 (t, 2H, J=7.4 Hz),
3.39 (dt, 2H, J=6.6 Hz), 5.25 (brs, 1H), 5.77 (s, 1H), 7.25 (m,
2H), 7.61 (d, 1H, J=19.4 Hz), 8.51 (m, 1H).

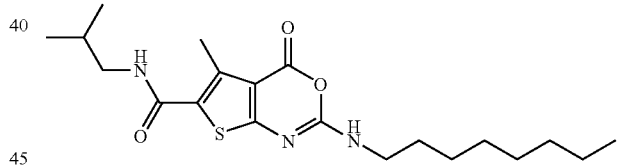

5-Methyl-2-octylamino-4-oxo-4H-thieno[2,3-d][1,3]
oxazine-6-carboxylic acid isobutyl-amide (54). MS (ES):
m/z 393.8 [MH$^+$].

$^1$H NMR (CDCl$_3$, 200 MHz): δ=0.84–0.88 (m, 20H),
0.95–0.99 (d, 6H,), 1.41 (m, 14H), 2.67 (s, 3H), 3.43 (t, 2H,
J=8.4 Hz), 4.48 (m, 2H, J=5.6 Hz), 5.12 (brs, 1H).

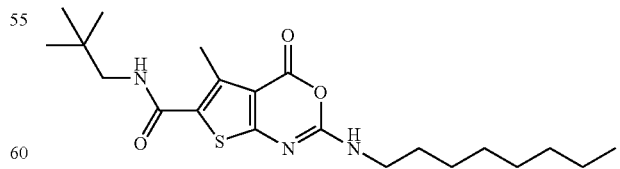

5-Methyl-2-octylamino-4-oxo-4H-thieno[2,3-d][1,3]
oxazine-6-carboxylic acid (2,2-dimethyl-propyl-amide (58).
MS (ES): m/z 407.86 [MH$^+$]. $^1$H NMR (CDCl$_3$, 200 MHz):
δ=0.84–0.93 (m, 14H), 0.96 (s, 9H), 2.72 (s, 3H), 3.24 (s,
2H), 3.42 (m, 2H, J=6.2 Hz), 5.12 (brs, 1H), 5.76 (brs, 1H).

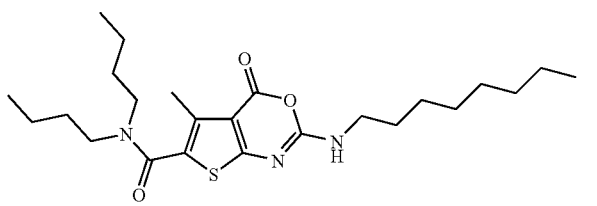

5-Methyl-2-octylamino-4-oxo-4H-thieno[2,3-d][1,3]
oxazine-6-carboxylic acid dibutylamide (36). The same
method as for the preparation of 5-methyl-2-heptyloxy-4-
oxo-4H-thieno[2,3-d][1,3]oxazine-6-carboxylic acid heptyl
ester was employed. Thus, cyclization afforded 20 mg of a
solid after column chromatography (7:3; hexanes:EtOAc)
(40% from tert-butyl ester): $^1$H NMR (CDCl$_3$) δ 0.88 (m,
9H), 1.18–1.40 (m, 14H), 1.45–1.68 (m, 6H), 2.37 (s, 3H),
3.30–3.46 (m, 6H), 5.19 (br s, 1H); MS (EI): cal'd 449.66,
exp 449.95 (MH$^+$).

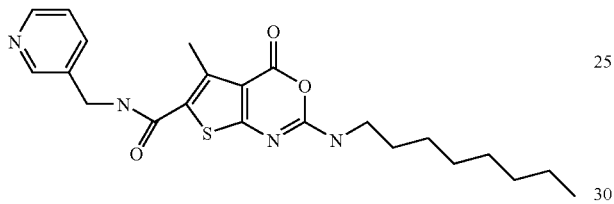

5-Methyl-2-octylamino-4-oxo-4H-thieno[2,3-d][1,3]
oxazine-6-carboxylic acid (pyridin-3-ylmethyl)amide (35).
The same method as for the preparation of 5-methyl-2-
heptyloxy-4-oxo-4H-thieno[2,3-d][1,3]oxazine-6-
carboxylic acid heptyl ester was employed. Thus, cycliza-
tion afforded 46 mg of a solid (36.6% from tert-butyl ester)
after tritration: $^1$H NMR (CDCl$_3$) δ 0.87 (m, 3H), 1.42–1.20
(m, 10H), 1.68–1.45 (m, 2H), 2.72 (s, 3H), 3.41 (dt, 4H,
J=6.7, 6.6 Hz), 4.62 (d, 2H, J=6.0 Hz), 5.15 (m, 1H), 6.07
(m, 1H), 7.38–7.20 (m, 1H), 7.70 (d, 1H, J=8.6 Hz),
8.65–8.52 (m, 2H); MS (EI): cal'd 428.56, exp 428.88
(MH$^+$).

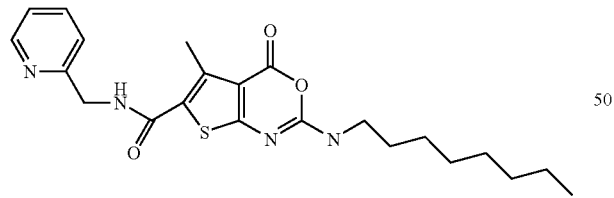

5-Methyl-2-octylamino-4-oxo-4H-thieno[2,3-d][1,3]
oxazine-6-carboxylic acid (pyridin-2-ylmethyl)amide (34).
The same method as for the preparation of 5-methyl-2-
heptyloxy-4-oxo-4H-thieno[2,3-d][1,3]oxazine-6-
carboxylic acid heptyl ester was employed. Thus, cycliza-
tion afforded 46 mg of a solid (36.6% from tert-butyl ester)
after tritration: $^1$H NMR (CDCl$_3$) δ 0.87 (m, 3H), 1.45–1.20
(m, 10H), 1.80–1.50 (m, 2H), 2.79 (s, 3H), 3.41 (dt, 4H,
J=6.7, 6.6 Hz), 4.72 (d, 2H, J=4.4 Hz), 5.25 (m, 1H),
7.45–7.18 (m, 2H), 7.69 (t, 1H, J=7.6 Hz), 8.55 (d, 1H, J=4.6
Hz); MS (EI): cal'd 428.56, exp 428.88 (MH$^+$).

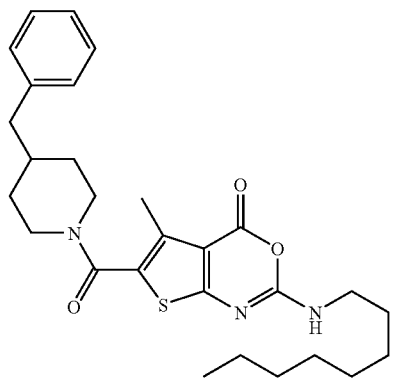

6-(4-Benzyl-piperidine-1-carbonyl)-5-methyl-2-
octylamino-thieno[2,3-d][1,3]oxazin-4-one (43)

$^1$H NMR (CDCl$_3$, 200 MHz) δ 0.88 (brs, 3H), 1.27 (brs,
11H), 1.54–1.70 (m, 6H), 2.40 (s, 3H), 2.57 (d, 2H, J=7.0
Hz), 2.86 (m, 2H), 3.40 (dt, 2H, J=6.4 Hz, J=6.4 Hz), 4.20
(brs, 2H), 5.09 (s, 1H), 7.11–7.35 (m, 5H); MS (ES) 496.69
(M+1).

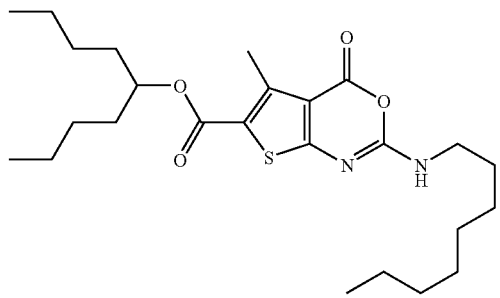

5-Methyl-2-octylamino-4-oxo-4H-thieno[2,3-d][1,3]
oxazine-6-carboxylic acid 1-butyl-pentyl ester (39): (73%).
$^1$H NMR (CDCl$_3$, 200 MHz) δ 0.89 (s, 9H), 1.31 (s, 18H),
1.61 (m, 6H), 2.78 (s, 3H), 3.42 (dt, 2H, J=6.2 Hz, J=6.6 Hz),
5.00–5.20 (m, 2H); MS (ES) 465.67 (M+1)

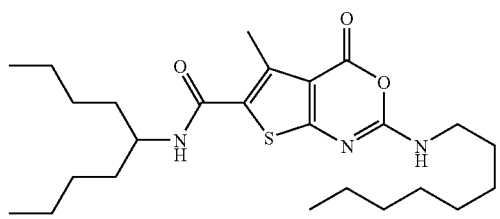

5-Methyl-2-octylamino-4-oxo-4H-thieno[2,3-d][1,3]
oxazine-6-carboxylic acid (1-butyl-pentyl)-amide (45):
(28%). $^1$H NMR (CDCl$_3$, 200 MHz) δ 0.87 (m, 9H), 1.29
(m, 18H), 1.56 (s, 2H), 2.65 (s, 3H), 3.40 (dt, 2H, J=6.6 Hz,
J=6.6 Hz), 4.02 (brs, 1H), 5.04 (brs, 1H), 5.40 (d, 1H, J=8.8
Hz); MS (ES) 464.6 (M+1)

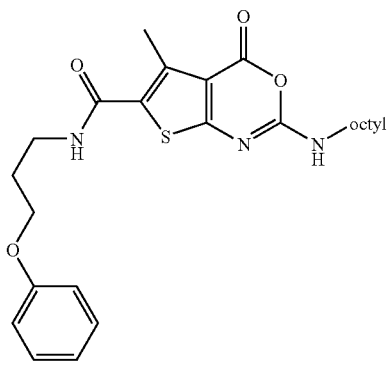

5-Methyl-2-octylamino-4-oxo-4H-thieno[2,3-d][1,3]oxazine-6-carboxylic acid (3-phenoxy-propyl)-amide (44): (22%). ¹H NMR (CDCl$_3$, 200 MHz) δ 0.88 (m, 3H), 1.27 (m, 10H), 1.55 (m, 2H), 2.07 (m, 2H), 2.62 (s, 3H), 3.40 (dt, 2H, J=5.6 Hz, J=7.2 Hz), 3.65 (dt, 2H, J=5.6 Hz, J=6.4 Hz), 4.12 (t, 2H, J=5.6 Hz), 5.05 (brs, 1H), 6.30 (brs, 1H), 6.95 (m, 3H), 7.25 (m, 2H); MS (ES) 471.81 (M+1)

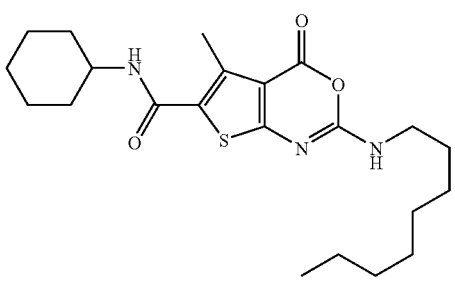

5-Methyl-2-octylamino-4-oxo-4H-thieno[2,3-d][1,3]oxazine-6-carboxylic acid cyclohexylamide (38): (21%). ¹H NMR (CDCl$_3$, 400 MHz) δ 0.87 (s, 3H), 1.26 (m, 16H), 1.56 (m, 6H), 2.60 (s, 3H), 3.40 (dt, 2H, J=6.6 Hz, J=6.2 Hz), 3.88 (m, 1H), 5.07 (brs, 1H), 5.57 (d, 1H, J=7.2 Hz); MS (ES) 420.12 (M+1)

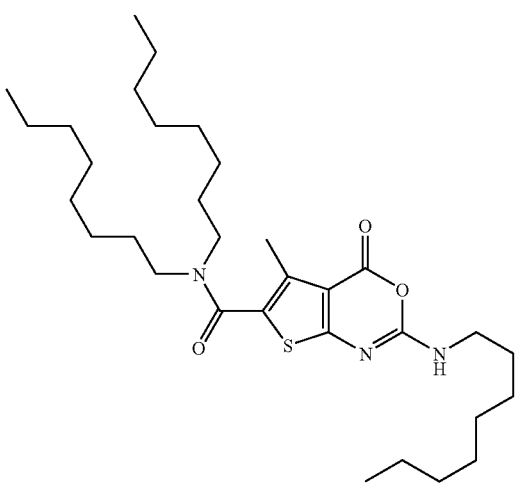

5-Methyl-2-octylamino-4-oxo-4H-thieno[2,3-d][1,3]oxazine-6-carboxylic acid dioctylamide (41): (61%). ¹H NMR (CDCl$_3$, 400 MHz) δ 0.87 (m, 9H), 1.25 (brs, 30H), 1.58 (m, 6H), 2.38 (s, 3H), 3.39 (m, 6H), 5.12 (brs, 1H); MS (ES) 562.15 (M+1)

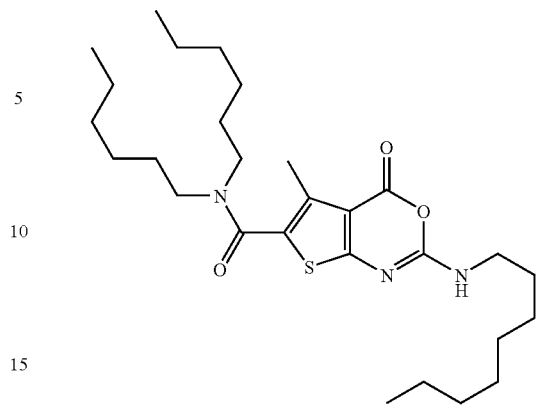

5-Methyl-2-octylamino-4-oxo-4H-thieno[2,3-d][1,3]oxazine-6-carboxylic acid dihexylamide (42): (56%). ¹H NMR (CDCl$_3$, 400 MHz) δ 0.87 (m, 9H), 1.27 (brs, 22H), 1.56 (m, 6H), 2.38 (s, 3H), 3.40 (m, 6H), 5.05 (brs, 1H); MS (ES) 506.03 (M+1).

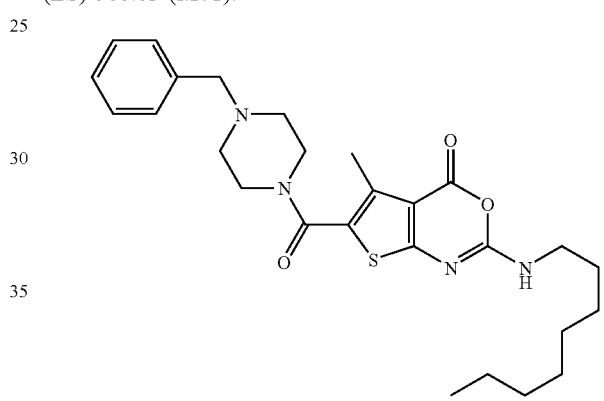

6-(4-Benzyl-piperazine-1-carbonyl)-5-methyl-2-octylamino-thieno[2,3-d][1,3]oxazin-4-one (40): (67%). ¹H NMR (CD$_3$Cl, 200 MHz) δ 0.87 (t, 3H, J=5 Hz), 1.27 (brs, 10H), 1.58 (brs, 2H), 2.40 (s, 3H), 2.46 (t, 4H, J=4.8 Hz), 3.39 (dt, 2H, J=6.6 Hz, J=6.6 Hz), 3.52 (s, 2H), 3.62 (brs, 4H), 5.19 (brs, 1H), 7.30 (s, 5H); MS (ES) 497.11 (M+1)

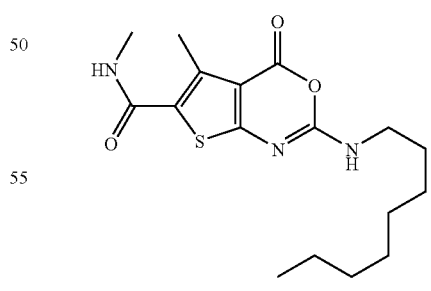

5-Methyl-2-octylamino-4-oxo-4H-thieno[2,3-d][1,3]oxazine-6-carboxylic acid methylamide (31): (70%, off-white solid). ¹H NMR (CDCl$_3$, 200 MHz) δ 0.88 (m, 3H), 1.25–1.4 (m), 1.59–1.65 (m), 2.71 (s, 3H), 2.99 (d, 3H (J=5.2)), 3.41 (q, 2H, J=7 Hz), 5.32 (bs, 1H), 5.76 (bs, 1H). MS (ES+) 351.93 (M+1), 352.99 (M+2).

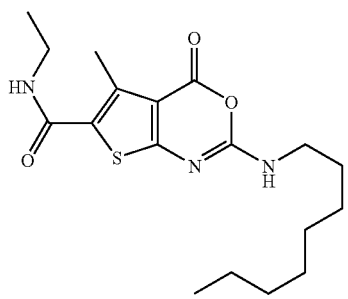

5-Methyl-2-octylamino-4-oxo-4H-thieno[2,3-d][1,3]
oxazine-6-carboxylic acid ethylamide (33): (off-white
solid). $^1$H NMR (CDCl$_3$, 200 MHz) δ 0.88 (t, 3H, J=6.5 Hz),
1.21–1.31 (m, 13H), 1.59–1.65 (m, 2H), 2.71 (s, 3H),
3.36–3.53 (m, 4H), 5.27 (bs, 1H), 5.72 (bs, 1H). MS (ES+)
365.95 (M+1), 367.01 (M+2).

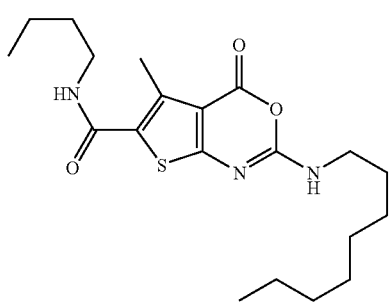

5-Methyl-2-octylamino-4-oxo-4H-thieno[2,3-d][1,3]
oxazine-6-carboxylic acid butylamide (32): (off-white
solid). $^1$H NMR (CDCl$_3$, 200 MHz) δ 0.85–1.00 (m, 6H),
1.28–1.50 (m, 12H), 1.53–1.63 (m, 4H), 2.70 (s, 3H),
3.41–3.43 (m, 4H), 5.53 (bs, 1H), 5.78 (bs, 1H). MS (ES+)
393.98 (M+1), 395.05 (M+2).

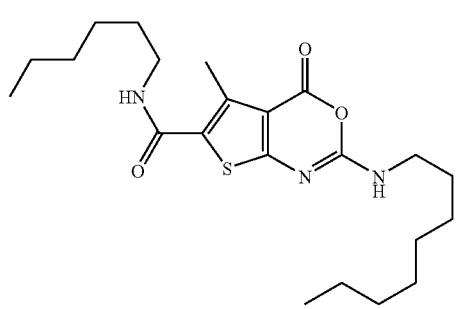

5-Methyl-2-octylamino-4-oxo-4H-thieno[2,3-d][1,3]
oxazine-6-carboxylic acid hexylamide (27): (off-white
solid). $^1$H NMR (CDCl$_3$, 200 MHz) δ 0.88–0.89 (m, 6H),
1.27–1.32 (m, 16H), 1.61 (bs, 4H), 2.70 (s, 3H), 3.41 (2xdt,
4H), 5.44 (bs, 1H), 5.76 (bs, 1H). MS (ES+) 422.05 (M+1),
423.13 (M+2).

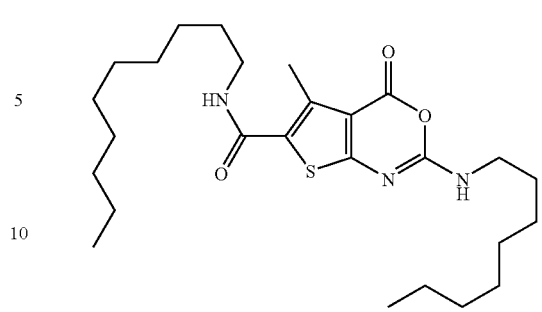

5-Methyl-2-octylamino-4-oxo-4H-thieno[2,3-d][1,3]
oxazine-6-carboxylic acid decylamide (28): (off-white
solid). $^1$H NMR (CDCl$_3$, 200 MHz) δ 0.85–0.88 (m, 6H),
1.26–1.31 (m, 24H), 1.61 (bs, 4H), 2.70 (s, 3H), 3.41 (2xdt,
4H), 5.27 (bs, 1H), 5.73 (bs, 1H). MS (ES+) 478.08 (M+1),
479.10 (M+2).

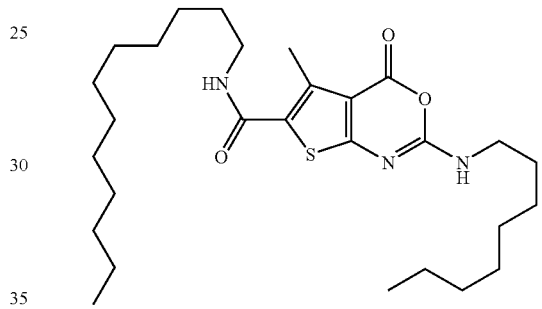

5-Methyl-2-octylamino-4-oxo-4H-thieno[2,3-d][1,3]
oxazine-6-carboxylic acid dodecylamide (29): (off-white
solid). $^1$H NMR (CDCl$_3$, 200 MHz) δ 0.85–0.91 (m, 6H),
1.26–1.31 (m, 24H), 1.61 (bs, 4H), 2.70 (s, 3H), 3.41 (2xdt,
4H), 5.30 (bs, 1H), 5.73 (bs, 1H). MS (ES+) 506.14 (M+1),
507.14 (M+2).

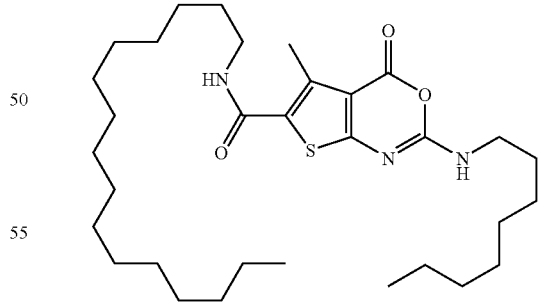

5-Methyl-2-octylamino-4-oxo-4H-thieno[2,3-d][1,3]
oxazine-6-carboxylic acid hexadecylamide (30): (off-white
solid). $^1$H NMR (CDCl$_3$, 200 MHz) δ 0.84–0.91 (m, 6H),
1.26–1.32 (m, 34H), 1.61 (bs, 4H), 2.70 (s, 3H), 3.41 (2xdt,
4H), 5.21 (bs, 1H), 5.72 (bs, 1H). MS (ES+) 562.19 (M+1),
563.22 (M+2).

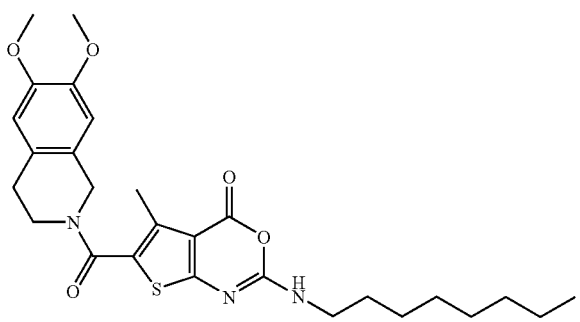

6-(6,7-Dimethoxy-3,4-dihydro-1H-isoquinoline-2-carbonyl)-5-methyl-2-octylamino-thieno(2,3-d)(1,3)oxazin-4-one (65): $^1$H NMR (CDCl$_3$, 200 MHz) δ 0.88 (brs, 3H), 1.28–1.45 (m, 10H), 1.62 (m, 2H), 2.43 (s, 3H), 2.85 (t, 2H, J=5.6 Hz), 3.41 (dt, 2H, J=6.6 Hz, J=6.6 Hz), 3.84 (m, 8H), 4.69 (s, 2H), 5.20 (brs, 1H), 6.56 (s, 1H), 6.63 (s, 1H).

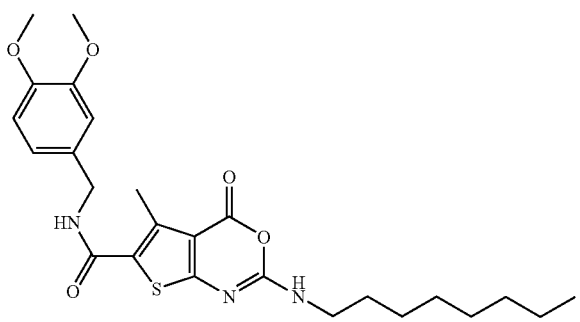

5-Methyl-2-octylamino-4-oxo-4H-thieno(2,3-d)(1,3)oxazine-6-carboxylic acid (2-(3,4-dimethoxy-phenyl)-methyl)-amide (66): $^1$H NMR (CDCl$_3$, 200 MHz) δ 0.88 (brs, 3H), 1.28–1.43 (m, 10H), 1.59 (m, 2H), 2.71 (s, 3H), 3.41 (dt, 2H, J=6.6 Hz, J=6.6 Hz), 3.88 (s, 6H), 4.55 (d, 2H, J=5.4 Hz), 5.10 (brs, 1H), 5.96 (brs, 1H), 6.88 (m, 3H).

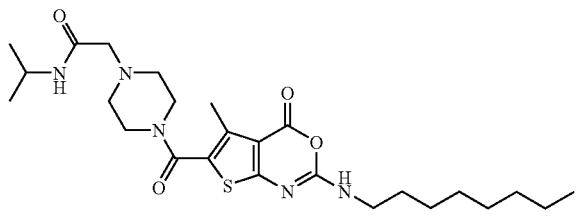

N-Isopropyl-2-(4-(5-methyl-2-octylamino-4-oxo-4H-thieno(2,3-d)(1,3)oxazine-6-carbonyl)-piperazin-1-yl)-acetamide (64): $^1$H NMR (CDCl$_3$, 200 MHz) δ 0.88 (m, 3H), 1.28–1.45 (m, 16H), 1.60 (m, 2H), 2.41 (s, 3H), 2.54 (m, 4H), 3.25 (s, 2H), 3.40 (dt, 2H, J=6.6 Hz, J=6.6 Hz), 3.59 (m, 4H), 4.61 (m, 1H), 5.08 (brs, 1H).

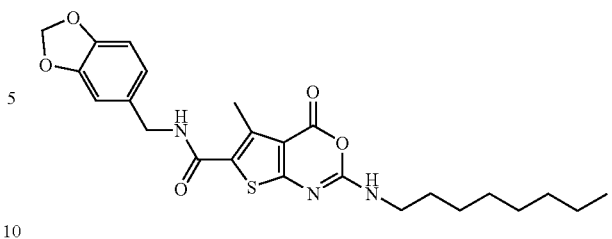

5-Methyl-2-octylamino-4-oxo-4H-thieno(2,3-d)(1,3)oxazine-6-carboxylic acid (2-benzo(1,3)dioxol-5-yl-methyl)-amide (69): $^1$H NMR (CDCl$_3$, 200 MHz) δ 0.88 (t, 3H, J=7.0 Hz), 1.27–1.45 (m, 10H), 1.60 (m, 2H), 2.71 (s, 3H), 3.44 (dt, 2H, J=6.4 Hz, J=6.4 Hz), 4.51 (d, 2H, J=5.6 Hz), 5.08 (brs, 1H), 5.96 (s, 3H), 6.79 (m, 3H).

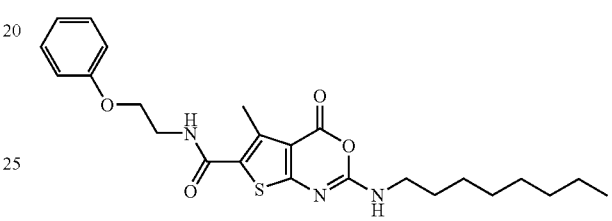

5-Methyl-2-octylamino-4-oxo-4H-thieno(2,3-d)(1,3)oxazine-6-carboxylic acid (2-phenoxy-ethyl)-amide (70): $^1$H NMR (CDCl$_3$, 200 MHz) δ 0.88 (t, 3H, J=7.0 Hz), 1.27–1.42 (m, 10H), 1.60 (m, 2H), 2.72 (s, 3H), 3.41 (dt, 2H, J=6.6 Hz, J=6.6 Hz), 3.84 (dt, 2H, J=5.0 Hz, J=5.2 Hz), 4.15 (t, 2H, J=5.0 Hz), 5.08 (brs, 1H), 6.25 (brs, 1H), 6.93 (m, 3H), 7.30 (m, 2H).

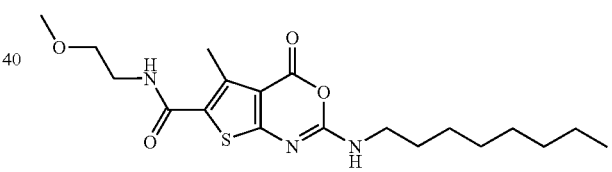

5-Methyl-2-octylamino-4-oxo-4H-thieno(2,3-d)(1,3)oxazine-6-carboxylic acid (2-methoxy-ethyl)-amide (72): $^1$H NMR (CDCl$_3$, 200 MHz) δ 0.88 (t, 3H, J=6.8 Hz), 1.28–1.45 (m, 10H), 1.61 (m, 2H), 2.71 (s, 3H), 3.93 (m, 5H), 3.58 (m, 4H), 5.08 (brs, 1H), 6.15 (brs, 1H).

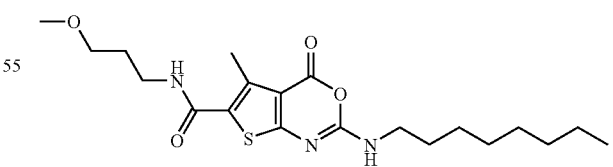

5-Methyl-2-octylamino-4-oxo-4H-thieno(2,3-d)(1,3)oxazine-6-carboxylic acid (3-methoxy-propyl)-amide (73): $^1$H NMR (CDCl$_3$, 200 MHz) δ 0.88 (t, 3H, J=6.8 Hz), 1.28–1.44 (m, 10H), 1.61 (m, 2H), 1.87 (tt, 2H, J=5.8 Hz, J=6.0 Hz), 2.70 (s, 3H), 3.40 (m, 5H), 3.57 (m, 4H), 5.09 (brs, 1H), 6.77 (brs, 1H).

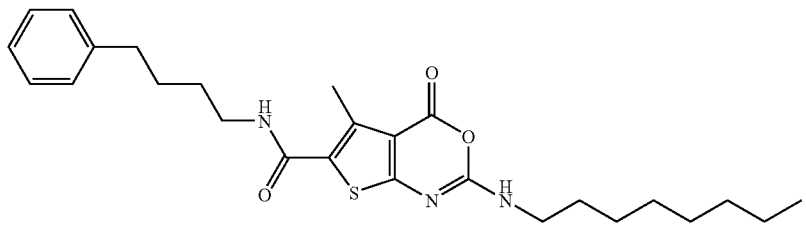

5-Methyl-2-octylamino-4-oxo-4H-thieno(2,3-d)(1,3)oxazine-6-carboxylic acid (4-phenyl-butyl)-amide (79): $^1$H NMR (CDCl$_3$, 200 MHz) δ 0.88 (t, 3H, J=6.6 Hz), 1.28–1.45 (m, 10H), 1.66 (m, 6H), 2.69 (m, 5H), 3.43 (m, 4H), 5.07 (brs, 1H), 5.68 (brs, 1H), 7.20 (m, 5H).

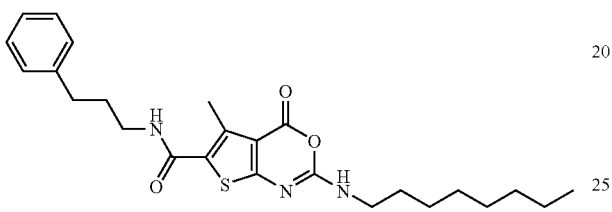

5-Methyl-2-octylamino-4-oxo-4H-thieno(2,3-d)(1,3)oxazine-6-carboxylic acid (3-phenyl-propyl)-amide (80): $^1$H NMR (CDCl$_3$, 200 MHz) δ 0.88 (t, 3H, J=6.6 Hz), 1.27–1.44 (m, 10H), 1.58 (m, 2H), 1.96 (tt, 2H, J=7.0 Hz, J=7.4 Hz), 2.72 (m, 5H), 3.43 (m, 4H), 5.71 (brs, 1H), 7.22 (m, 5H).

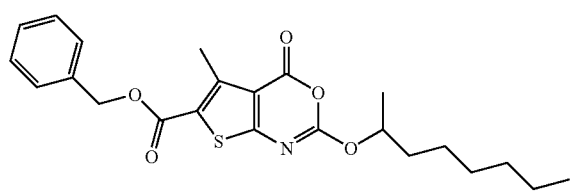

5-Methyl-2-(1-methylheptyloxy)-4-oxo-4H-thieno[2,3-d][1,3]oxazine-6-carboxylic acid benzyl ester (89)

Light yellow oil in 22% yield.

$^1$H NMR (CDCl$_3$, 200 MHz): δ 7.31–7.50 (m, 5H), 5.34 (s, 2H), 5.18 (tq, 1H, J=6.2, 6.2 Hz), 2.82 (s, 3H), 1.58–1.83 (m, 2H), 1.40 (d, 3H, J=6.2 Hz), 1.10–1.34 (m, 8H), 0.88 (t, 3H, J=6.6 Hz).

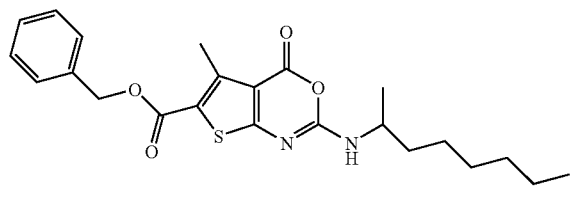

5-Methyl-2-(1-methylheptylamino)-4-oxo-4H-thieno[2,3-d][1,3]oxazine-6-carboxylic acid benzyl ester (71)

Light yellow oil in 40% yield.

$^1$H NMR (CDCl$_3$, 200 MHz): δ 7.31–7.43 (m, 5H), 5.32 (s, 2H), 5.13 (d, 1H, J=6.2 Hz), 4.00 (m, 1H), 2.79 (s, 3H), 1.42–1.62 (m, 2H), 1.10–1.40 (m, 8H), 0.87 (t, 3H, J=6.6 Hz). MS (ES) [M$^+$+1] 429.10.

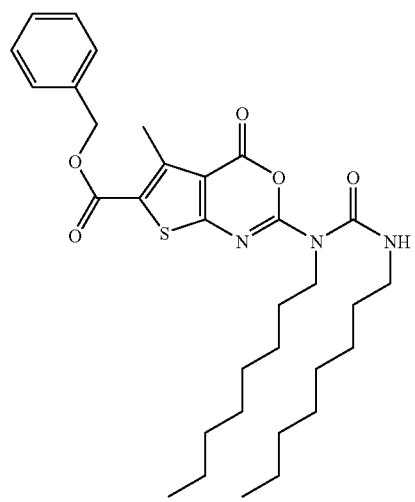

2-(1,3-Dioctyl-ureido)-5-methyl-4-oxo-4H-thieno[2,3-d][1,3]oxazine-6-carboxylic acid benzyl ester (13): $^1$H NMR (CDCl$_3$, 200 MHz): δ 9.25 (m, 1H), 7.31–7.43 (m, 5H), 5.32 (s, 2H), 3.99 (m, 2H), 3.35 (dt, 2H, J=5.6, 5.6 Hz), 2.83 (s, 3H), 1.70–1.5 (m, 4H), 1.50–1.20 (m, 20H), 0.87 (m, 6H, J=6.6 Hz). MS (ES) [M$^+$+1] 583.99.

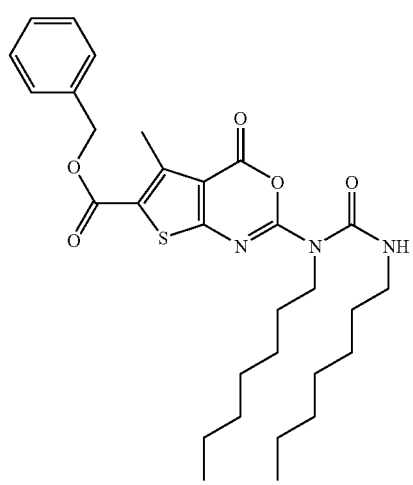

2-(1,3-Diheptyl-ureido)-5-methyl-4-oxo-4H-thieno[2,3-d][1,3]oxazine-6-carboxylic acid benzyl ester (14): $^1$H NMR (CDCl$_3$, 200 MHz): δ 9.25 (m, 1H), 7.31–7.43 (m, 5H), 5.32 (s, 2H), 3.99 (m, 2H), 3.35 (dt, 2H, J=5.6, 5.6 Hz), 2.83 (s, 3H), 1.70–1.5 (m, 4H), 1.50–1.20 (m, 16H), 0.87 (m, 6H, J=6.6 Hz). MS (ES) [M$^+$+1] 555.97.

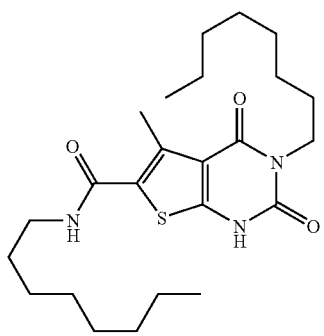

5-Methyl-3-octyl-1H-thieno[2,3-d]pyrimidine-2,4-dione-6-carboxylic acid octylamide (47): Compound 18 (100 mg, 0.22 mmol) was dissolved in 1.8 mL absolute ethanol. Sodium ethoxide (21% by wt in ethanol, 1.1 mL, 2.9 mmol) was added and the solution was refluxed for 1 h. Once cooled to room temperature, the solution was poured into 10 mL of a 1N HCl solution. The resultant precipitate was filtered to provide 47 (116 mg) as an off-white solid (100% yield). $^1$H NMR (CDCl$_3$, 200 MHz) δ 0.87 (m, 6H), 1.27–1.32 (m, 20H), 1.54–1.70 (m, 4H), 2.78 (s, 3H), 3.44 (dt, 2H, J=7.0, 6.2 Hz), 3.97 (t, 2H, J=7.7 Hz), 5.86 (t, 1H, J=5.4 Hz), 10.39 (s, 1H).

EXAMPLE 16

Procedure for reduction of carboxylic acid: 5-Hydroxymethyl-4-methyl-2-(3-octyl-ureido)-thiophene-3-carboxylic acid tert-butyl ester (2) 3-Methyl-5-(3-octyl-ureido)-thiophene-2,4-dicarboxylic acid 4-tert-butyl ester (1.0 g, 2.40 mmol) was dissolved in 25 mL of CH$_2$Cl$_2$ and 0.25 mL of DMF. Thionyl chloride added as a 2M solution in CH$_2$Cl$_2$ (1.2 mL, 2.4 mmol) and the reaction was stirred for 2 h. The reaction was rotovaped to a white solid, which was dissolved in 20 mL of dioxane. Sodium borohydride (910 mg, 24.0 mmol) added and the reaction stirred for 2 h. The reaction was poured into 100 mL of H$_2$O and extracted with EtOAc. The organic layer was washed with 1N HCl (aq), H$_2$O, dried with MgSO$_4$, and the solvent rotovaped off. The residue was recrystalized from EtOAc/Hexanes to give 600 mg of the title compound.: (62%). $^1$H NMR (CDCl$_3$, 200 MHz) δ 0.87 (m, 3H), 1.26 (brs, 10H), 1.57 (brs, 11H), 2.30 (s, 3H), 3.28 (dt, 2H, J=6.2 Hz, J=6.6 Hz), 4.64 (s, 2H), 4.74 (t, 2H, J=5.6 Hz), 10.77 (s, 1H)

Scheme 3

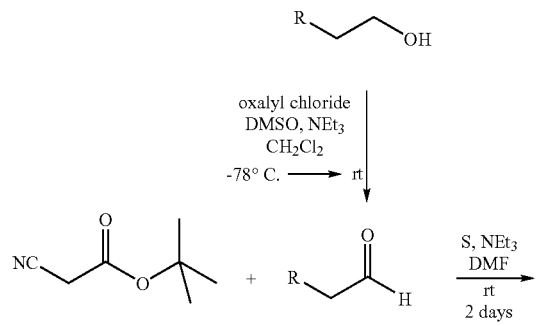

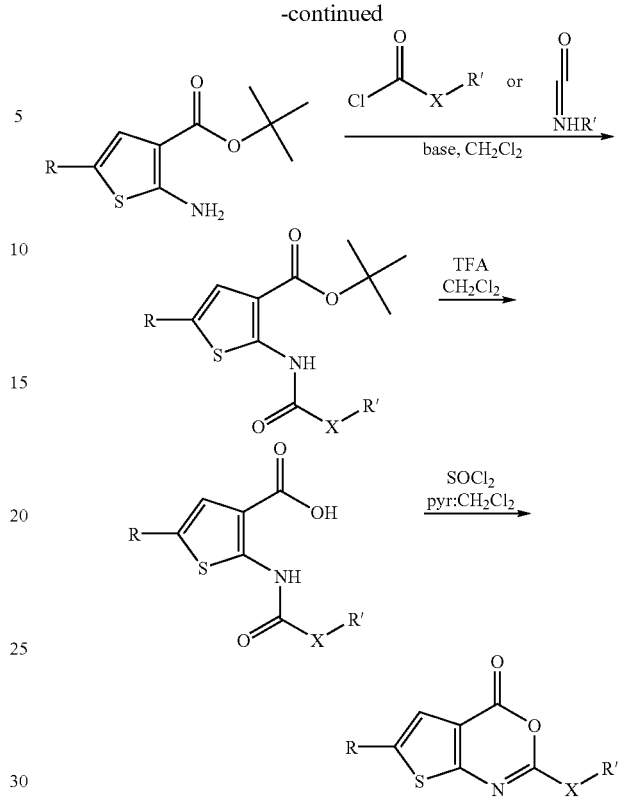

EXAMPLE 17

Aldehyde Intermediates

For a general procedure to synthesize non-commercial aldehydes 17.1–17.4 see Yoshisuke, Tsuda et al, *Chem. Pharm. Bull.* 1991, 39(1), 18–22

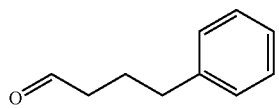

4-Phenyl-butyraldehyde (17.1) clear liquid (860 mg, 87% yield) $^1$H NMR (CDCl$_3$, 200 MHz) δ 1.99 (tt, 2H, J=7.8, 7.4 Hz), 2.45 (dt, 2H, J=7.0, 1.2 Hz), 2.67 (t, 2H, J=7.4 Hz), 7.26 (m, 5H), 9.76 (t, 1H, J=1.4 Hz).

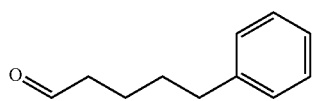

5-Phenyl-pentanal (17.2) clear liquid (470 mg, 48% yield) $^1$H NMR (CDCl$_3$, 200 MHz) δ 1.67 (m, 4H), 2.45 (dt, 2H, J=4.8, 1.8 Hz), 2.64 (brs, 2H), 7.25 (m, 5H), 9.75 (t, 1H, J=1.8 Hz).

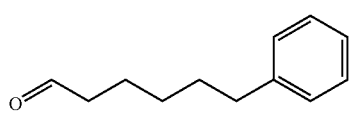

6-Phenyl-hexanal (17.3) pale yellow oil (2.49 g, 84% yield) $^1$H NMR (CDCl$_3$, 200 MHz) δ 1.20–1.43 (m, 4H), 1.44–1.76 (m, 4H), 2.41 (dt, 2H, J=7.0, 7.6 Hz), 2.60 (t, 2H, J=7.2 Hz), 7.06–7.35 (m, 5H), 9.75 (t, 1H, J=1.8 Hz); MS (ES) No ionization and no LC was found

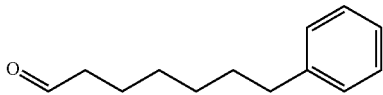

5-Phenyl-heptanal (17.4) pale yellow oil (401 mg, 81% yield) $^1$H NMR (CDCl$_3$, 200 MHz) δ 1.20–1.50 (m, 2H), 1.50–1.80 (m, 4H), 2.41 (dt, 2H, J=7.0, 7.4 Hz), 2.61 (t, 2H, J=7.4 Hz), 7.00–7.20 (m, 5H), 9.75 (t, 1H, 2 Hz), MS (ES) No ionization and no LC was found.

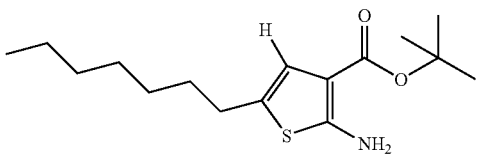

EXAMPLE 18

Aminothiophenes

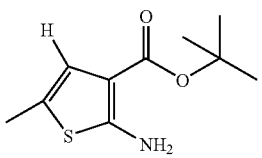

2-Amino-5-methyl-thiophene-3-carboxylic acid tert-butyl ester (18.1): $^1$H NMR (CDCl$_3$) δ 1.54 (s, 9H), 2.24 (s, 3H), 5.65 (br d, 2H), 7.25 (s, 1H); MS (EI): cal'd 213.70, exp 213.96 (MH$^+$).

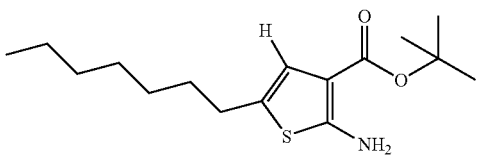

2-Amino-5-heptyl-thiophene-3-carboxylic acid tert-butyl ester (18.2) yellow oil (5.808 g, 46% yield): 0.88 (t, 3H, J=6.4 Hz), 1.24–1.32 (m, 8H), 1.54–1.57 (m, 11H), 2.56 (t, 2H, J=7.5 Hz), 5.69 (bs, 2H), 6.56 (s, 1H). MS (ES+) 297.

For a general procedure to synthesize 2-amino-5-alkyl-thiophene-3-carboxylic acid tert-butyl esters from aldehydes, see Tinney, F. J.; et al. *J. Med. Chem.* 1981, 24, 878–882.

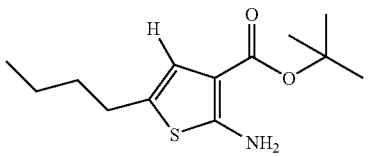

2-Amino-5-butyl-thiophene-3-carboxylic acid tert-butyl ester (18.3) yellow oil (372 mg, 41% yield): $^1$H NMR (CDCl$_3$, 200 MHz) δ 0.91 (t, 3H, J=7.1 Hz), 1.26–1.41 (m, 4H), 1.53 (bs, 9H), 2.56 (t, 2H, J=7.3 Hz), 5.77 (bs, 2H), 6.56 (t, 1H, J=1.1 Hz). $^{13}$C NMR (CDCl$_3$, 50 MHz) δ 13.7, 22.0, 28.4, 29.3, 33.2, 79.7, 107.7, 121.8, 126.3, 160.4, 164.9. MS (ES+) 340.4 (M+1).

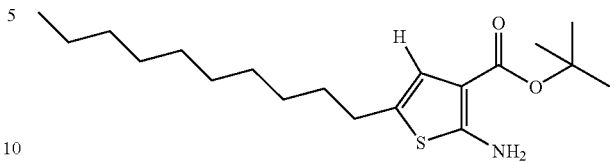

2-Amino-5-decyl-thiophene-3-carboxylic acid tert-butyl ester (18.4) yellow oil (11.32 g, 79% yield): $^1$H NMR (CDCl$_3$, 400 MHz) δ 0 88 (t, 3H, J=6.8 Hz), 1.26–1.30 (m, 14H), 1.52–1.55 (m, 11H), 2.56 (t, 2H, J=7.4 Hz), 5.68 (bs, 2H), 6.56 (s, 1H).

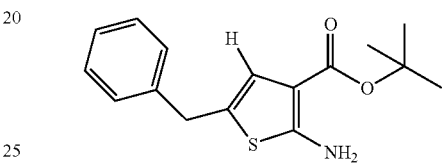

2-Amino-5-benzyl-thiophene-3-carboxylic acid tert-butyl ester (18.5) yellow oil (520 mg, 51% yield): $^1$H NMR (CDCl$_3$, 200 MHz) δ 1.53 (s, 9H), 3.89 (s, 2H), 5.71 (bs, 2H), 6.66 (t, 1H, J=1.1 Hz), 7.16–7.33 (m, 5H). $^{13}$C NMR (CDCl$_3$, 50 MHz) δ 28.4, 35.9, 79.9, 107.8, 123.4, 124.7, 126.5, 128.4, 128.5, 140.0, 161.3, 164.9. MS (ES+) 289.9 (M+1).

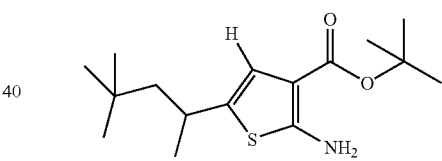

2-Amino-5-(1,3,3-trimethyl-butyl)-thiophene-3-carboxylic acid tert-butyl ester (18.6) yellow oil (846 mg, 79% yield): $^1$H NMR (CDCl$_3$, 200 MHz) δ 0.89 (s, 9H), 1.22 (d, 3H, J=7.0 Hz), 1.39 (dd, 1H, J=13.8, 4.6 Hz), 1.54 (s, 9H), 1.59 (dd, 1H, J=14.0, 7.0 Hz), 2.80–2.96 (m, 1H), 5.67 (bs, 2H), 6.55 (s, 1H).

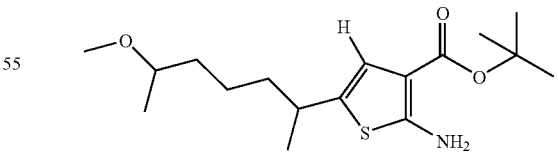

2-Amino-5-(5-methoxy-1,5-dimethyl-hexyl)-thiophene-3-carboxylic acid tert-butyl ester (18.7) yellow oil (2.328 g, 80% yield): $^1$H NMR (CDCl$_3$, 200 MHz) δ 1.12 (s, 6H), 1.22 (d, 3H, J=6.8 Hz), 1.22–1.54 (m, 18H), 2.74 (dq, 1H, J=7.0, 6.2 Hz), 3.16 (s, 3H), 5.70 (bs, 2H), 6.57 (s, 1H). MS (ES+) 341.93 (M+1).

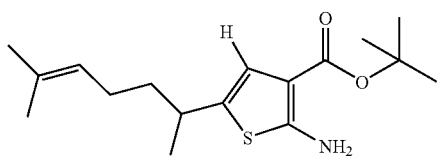

2-Amino-5-(1,5-dimethyl-hex-4-enyl)-thiophene-3-carboxylic acid tert-butyl ester (18.8) yellow oil (2.029 mg, 77% yield): $^1$H NMR (CDCl$_3$, 200 MHz) δ 1.21 (d, 3H, J=6.6 Hz), 1.51–1.54 (m, 11H), 1.57 (s, 3H), 1.68 (s, 3H), 1.96 (dt, 2H, J=7.2, 7.0 Hz), 2.75 (tq, 1H, J=7.0, 6.6 Hz), 5.08 (t, 1H, J=6.4 Hz), 5.69 (bs, 2H), 6.56 (s, 1H). MS (ES+) 309.9 (M+1).

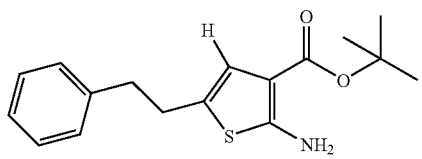

2-Amino-5-phenethyl-thiophene-3-carboxylic acid tert-butyl ester (18.9) yellow solid (1.5 g, 85% yield) $^1$H NMR (CDCl$_3$, 200 MHz) δ 1.53 (s, 9H), 2.88 (s, 4H), 5.70 (s, 2H), 6.59 (s, 1H), 7.26 (m, 5H)

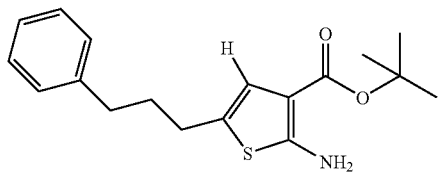

2-Amino-5-(3-phenyl-propyl)-thiophene-3-carboxylic acid tert-butyl ester (18.10) yellow oil (440 mg, 48% yield) $^1$H NMR (CDCl$_3$, 200 MHz) δ 1.54 (s, 9H), 1.90 (tt, 2H, J=7.8, 7.2 Hz), 2.62 (m, 4H), 5.70 (s, 2H), 6.58 (s, 1H), 7.26 (m, 5H)

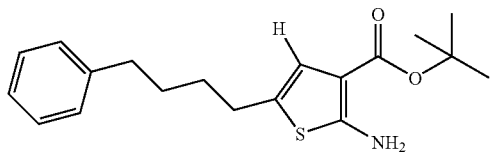

2-Amino-5-(4-phenyl-butyl)-thiophene-3-carboxylic acid tert-butyl ester (18.11) yellow oil (1.22 g, 67% yield) $^1$H NMR (CDCl$_3$, 200 MHz) δ 0.88 (bt, 2H, J=6.6 Hz), 1.16–1.31 (m, 2H), 1.54 (s, 9H), 1.57–1.74 (m, 2H), 2.52–2.70 (m, 2H), 5.69 (bs, 2H), 6.56 (t, 1H, J=1.2 Hz), 7.11–7.22 (m, 3H), 7.22–7.34 (m, 2H); MS (ES) No Ionization (M+1), t$_R$(method D)=9.11 min.

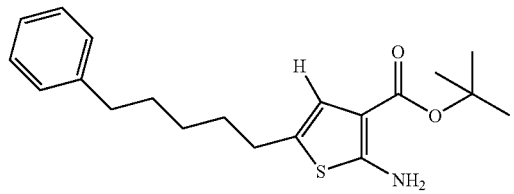

2-Amino-5-(5-phenyl-pentyl)-thiophene-3-carboxylic acid tert-butyl ester (18.12) yellow oil (638 mg, 36% yield) $^1$H NMR (CDCl$_3$, 200 MHz) δ 1.21–1.50 (m, 2H), 1.50–1.76 (m, 14H), 2.44–2.72 (m, 4H), 5.69 (bs, 2H), 6.56 (t, 1H, J=1.2 Hz), 7.07–7.37 (m, 5H); MS (ES) No Ionization (M+1), t$_R$(method D)=No LC trace observed

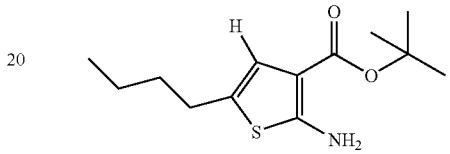

2-Amino-5-butyl-thiophene-3-carboxylic acid tert-butyl ester (18.13): $^1$H NMR (CDCl$_3$, 200 MHz): δ=0.91 (t, J=7.1 Hz, 3H), 1.10–1.80 (m, 13H), 2.56 (td, J=0.8, 7.4 Hz, 2H), 5.68 (brs, 2H), 6.56 (t, J=1.1 Hz, 1H).

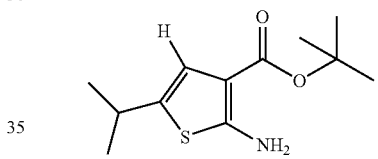

2-Amino-5-isopropyl-thiophene-3-carboxylic acid tert-butyl ester (18.14): $^1$H NMR (CDCl$_3$, 200 MHz); δ=1.23 (dd, J=2.2, 6.8 Hz, 6H), 1.54 (s, 9H), 2.78–3.02 (m, 1H), 5.68 (brs, 2H), 6.57 (d, J=1.2 Hz, 1H).

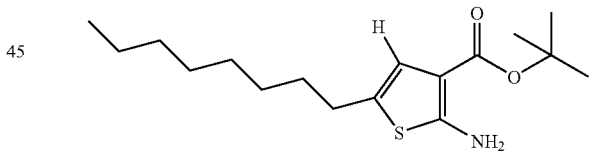

2-Amino-5-octyl-thiophene-3-carboxylic acid tert-butyl ester (18.15): $^1$H NMR (CDCl$_3$, 200 MHz): δ=0.88 (t, J=6.6 Hz, 3H), 1.14–1.43 (m, 10H), 1.44–1.68 (m, 11H), 2.56 (t, J=7.1 Hz, 2H), 5.67 (brs, 2H), 6.56 (s, 1H).

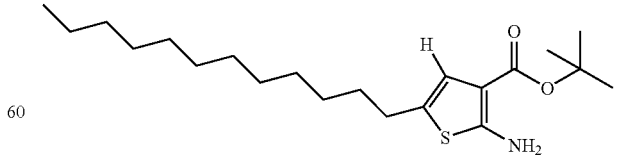

2-Amino-5-dodecyl-thiophene-3-carboxylic acid tert-butyl ester (18.16): $^1$H NMR (CDCl$_3$, 200 MHz): δ=0.88 (t, J=6.6 Hz, 3H), 1.16–1.42 (m, 18H), 1.46–1.68 (m, 11H), 2.55 (t, J=7.5 Hz, 2H), 5.68 (brs, 2H), 6.55 (t, J=1.2 Hz, 1H).

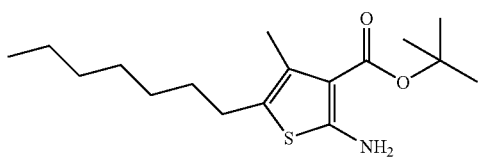

2-Amino-5-heptyl-4-methyl-thiophene-3-carboxylic acid tert-butyl ester (18.17): 9.561 g (61%). $^1$H NMR (CDCl$_3$, 200 MHz): δ 0.87 (t, J=6.6 Hz, 3H), 1.16–1.40 (m, 10H, 1.55 (s, 9H), 2.12 (s, 3H), 2.41 (t, J=7.4 Hz, 2H).

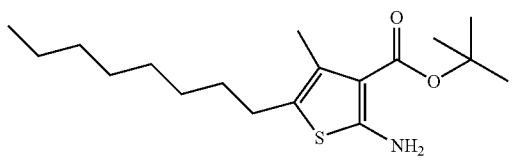

2-Amino-5-octyl-4-methyl-thiophene-3-carboxylic acid tert-butyl ester (18.18): 10.202 g (63%). $^1$H NMR (CDCl$_3$, 200 MHz): δ 0.87 (t, J=6.8 Hz, 3H), 1.20–1.38 (m, 12H), 1.55 (s, 9H), 2.12 (s, 3H), 2.41 (t, J=7.2 Hz, 2H).

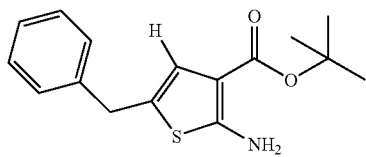

2-Amino-6-benzylthiophene-3-carboxylic acid t-butyl ester (18.19)

Light yellow oil in 62% yield.

$^1$H NMR (CDCl$_3$, 200 MHz): δ 7.18–7.38 (m, 5H), 6.66 (t, 1H, J=1.0 Hz), 5.70 (brs, 2H), 3.90 (s, 2H), 1.54 (s, 9H).

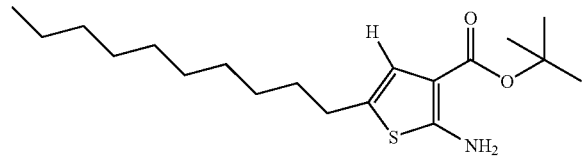

2-Amino-6-decylthiophene-3-carboxylic acid t-butyl ester (18.20)

Dark brownish oil in 74% yield.

$^1$H NMR (CDCl$_3$, 200 MHz): δ 6.56 (t, 1H, J=1.2 Hz), 5.68 (brs, 2H), 2.56 (dt, 2H, J=7.6, 1.2 Hz), 1.54 (s, 9H), 1.20–1.40 (m, 8H), 0.89 (t, 3H, J=7.6 Hz).

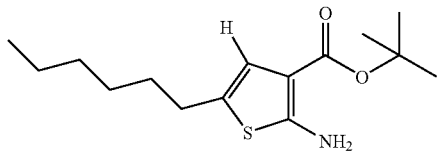

2-Amino-6-hexylthiophene-3-carboxylic acid t-butyl ester (18.21)

Dark brownish oil in 99% yield.

$^1$H NMR (CDCl$_3$, 200 MHz): δ 6.56 (t, 1H, J=1.2 Hz), 5.68 (brs, 2H), 2.55 (dt, 2H, J=8.0, 1.2 Hz), 1.54 (s, 9H), 1.20–1.40 (m, 16H0, 0.88 (t, 3H, J=7.0 Hz).

EXAMPLE 19

Carbamate/Urea Intermediates

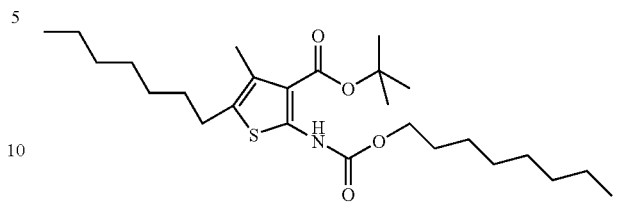

5-Heptyl-4-methyl-2-octyloxycarbonylamino-thiophene-3-carboxylic acid tert-butyl ester (19.1): $^1$H NMR (CDCl$_3$) δ 0.83–0.92 (m, 6H), 1.20–1.40 (m, 18H), 1.50–1.60 (m, 11H), 1.64–1.72 (m, 2H), 2.20 (s, 3H), 2.62 (t, 2H, J=7.6 Hz), 4.19 (t, 2H, J=7.2 Hz); MS (EI): cal'd 467.72, exp, did not ionize.

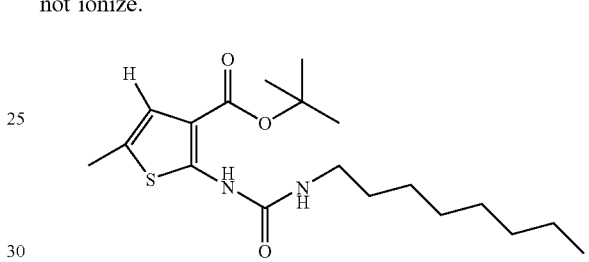

5-Methyl-2-(3-octyl-ureido)-thiophene-3-carboxylic acid tert-butyl ester (19.2): $^1$H NMR (CDCl$_3$) δ 0.87 (t, 3H, J=7.2 Hz), 1.20–1.42 (m, 10H), 1.45–1.68 (m, 11H), 2.32 (s, 3H), 3.27 (dt, 2H, J=7.2, 7.2 Hz), 4.79 (m, 1H), 6.70 (s, 1H), 10.2 (br s, 1H); MS (EI): cal'd 368.5, exp 368.87 (MH$^+$).

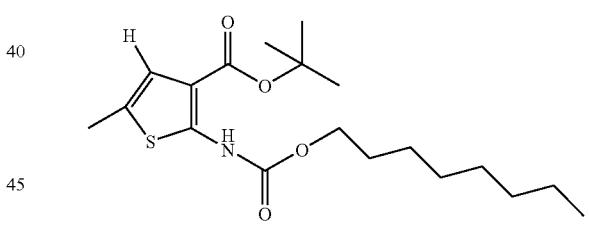

5-Methyl-2-octyloxycarbonylamino-thiophene-3-carboxylic acid tert-butyl ester (19.3): $^1$H NMR (CDCl$_3$) δ 0.88 (t, 3H, J=7.2 Hz), 1.20–1.42 (m, 10H), 1.55 (s, 9H), 1.62–1.72 (m, 2H), 2.34 (s, 3H), 4.19 (t, 2H, J=6.8 Hz), 6.74 (s, 1H), 10.12 (br s, 1H); MS (EI): cal'd 369.5, exp, did not ionize.

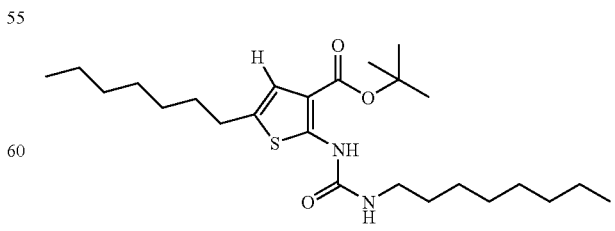

General Procedure for Urea Formation (19.4–19.6):

5-Heptyl-2-(3-octyl-ureido)-thiophene-3-carboxylic acid tert-butyl ester (19.4) Amino-thiophene 18.2 (200 mg, 0.67 mmol) was dissolved in 3 mL CH₂Cl₂ and cooled to 0° C. Under N₂ atmosphere, DBU (0.25 mL, 1.68 mmol) was added slowly followed by octyl-isocyanate (104 mg, 0.67 mmol). The reaction slowly warmed to rt and was stirred at room temperature for 5 h. The reaction was then diluted with 20 mL CH₂Cl₂ and washed with 1N HCl and brine. The organic solution was then dried with MgSO₄ and concentrated in vacuo. The crude mixture purified by silica gel chromatography (15:1 hexanes:ethyl acetate) to yield 19.4, 73 mg (24% yield) of an off-white solid: $^1$H NMR (CDCl₃, 200 MHz) δ 0.88 (t, 6H, J=6.4 Hz), 1.27–1.29 (m, 18H), 1.54–1.58 (m, 13H), 2.64 (t, 2H, J=7.5 Hz), 3.26 (dt, 2H, J=7.0, 5.8 Hz), 4.85 (t, 1H, J=5.7 Hz), 6.69 (s, 1H), 10.25 (s, 1H). MS (ES+) 453.1 (M+1).

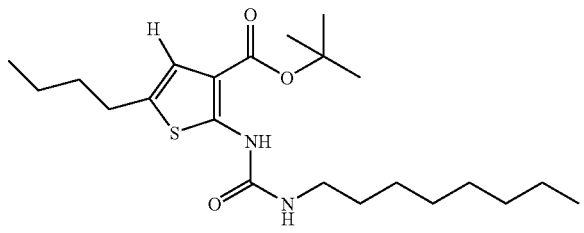

5-Butyl-2-(3-octyl-ureido)-thiophene-3-carboxylic acid tert-butyl ester (19.5) off-white solid (353 mg, 59% yield): $^1$H NMR (CDCl₃, 200 MHz) δ 0.87 (t, 3H, J=7.1 Hz), 0.90 (t, 3H, J=7.1 Hz), 1.25–1.41 (m, 12H), 1.53–1.64 (m, 13H), 2.64 (t, 2H, J=7.5 Hz), 3.27 (dt, 2H, J=7.0, 6.2 Hz), 5.29 (t, 1H, J=5.7 Hz), 6.69 (s, 1H), 10.27 (bs, 1H). $^{13}$C NMR (CDCl₃, 50 MHz) δ 13.7, 14.0, 22.1, 22.6, 26.8, 28.3, 29.1, 29.2, 29.3, 30.0, 31.7, 33.4, 40.8, 80.7, 110.7, 119.8, 133.0, 149.9, 153.7, 165.6.

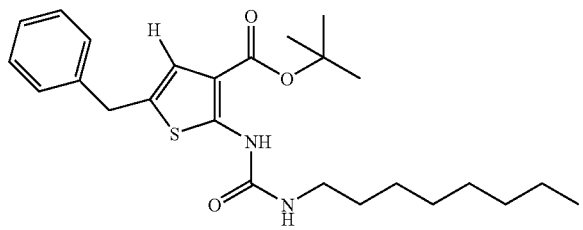

5-Benzyl-2-(3-octyl-ureido)-thiophene-3-carboxylic acid tert-butyl ester (19.6) pale yellow solid (394 mg, 49% yield): $^1$H NMR (CDCl₃, 200 MHz) δ 0.87 (t, 3H, J=6.4 Hz), 1.27 (bs, 10H), 1.54 (s, 11H), 3.25 (dt, 2H, J=7.0, 5.8 Hz), 3.97 (s, 2H), 4.88 (t, 1H, J=5.6 Hz), 6.48 (t, 1H, J=1.0 Hz), 7.16–7.32 (m, 5H), 10.26 (bs, 1H).

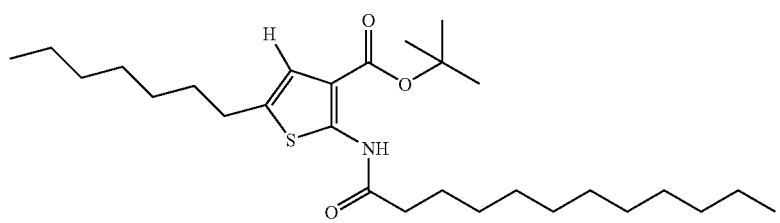

General Procedure for Amide and Carbamate Formation (19.7–19.17):

2-Dodecanoylamino-5-heptyl-thiophene-3-carboxylic acid tert-butyl ester (19.7) Amino-thiophene 18.2 (171 mg, 0.57 mmol) was dissolved in 3 mL CH₂Cl₂ and 2 mL pyridine. Under N₂ atmosphere, lauroyl chloride (126 mg, 0.57 mmol) was added and the reaction was stirred at room temperature for 6 h. The reaction was then diluted with 10 mL CH₂Cl₂ and washed with water, 5% citric acid, and brine. The organic solution was then dried with MgSO₄ and concentrated in vacuo. The crude mixture purified by silica gel chromatography (40:1 hexanes:ethyl acetate) to yield 19.7, 175 mg (63% yield) of a yellow oil: $^1$H NMR (CDCl₃, 200 MHz) δ 0.87 (t, 6H, J=6.4 Hz), 1.25–1.44 (m, 24H), 1.51–1.73 (m, 13H), 2.45 (t, 2H, J=7.5 Hz), 2.67 (t, 2H, J=7.5 Hz), 6.77 (s, 1H), 10.94 (bs, 1H). $^{13}$C NMR (CDCl₃, 50 MHz) δ 14.0, 14.1, 22.5, 22.6, 25.3, 28.3, 28.9, 29.0, 29.1, 29.2, 29.3, 29.4, 29.5, 29.6, 31.3, 31.7, 31.9, 36.7, 81.2, 113.3, 120.1, 134.8, 146.3, 165.1, 169.9.

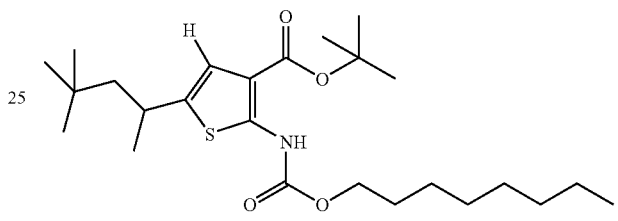

2-Octyloxycarbonylamino-5-(1,3,3-trimethyl-butyl)-thiophene-3-carboxylic acid tert-butyl ester (19.8) yellow oil (185 mg, 34% yield): $^1$H NMR (CDCl₃, 200 MHz) δ 0.85–0.91 (m, 12H), 1.26–1.76 (m, 26H), 2.90–3.03 (m, 1H), 4.20 (t, 2H, J=6.8 Hz), 6.73 (s, 1H), 10.15 (bs, 1H). $^{13}$C NMR (CDCl₃, 50 MHz) δ 14.0, 22.6, 25.8, 26.3, 28.3, 28.8, 29.1, 29.2, 29.8, 31.2, 31.8, 32.0, 52.6, 66.3, 81.2, 112.3, 118.9, 142.1, 147.7, 153.3, 164.9.

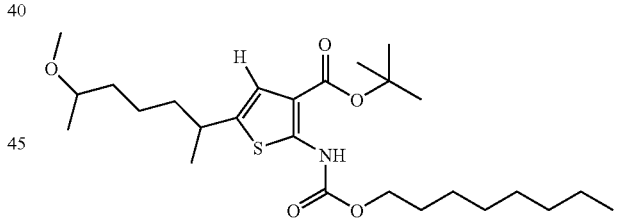

5-(5-Methoxy-1,5-methyl-hexyl)-2-octyloxycarbonylamino-thiophene-3-carboxylic acid tert-butyl ester (19.9) pale yellow oil: $^1$H NMR (CDCl₃, 200 MHz) δ 0.89 (t, 3H, J=6.4 Hz), 1.11 (s, 6H), 1.26–1.48 (m, 19H), 1.50–1.71 (m, 11H), 2.74 (dq, 1H, J=7.0, 7.0 Hz), 3.15

(s, 3H), 4.20 (t, 2H, J=6.6 Hz), 6.74 (s, 1H), 10.17 (s, 1H). $^{13}$C NMR (CDCl$_3$, 50 MHz) δ 14.0, 21.5, 22.5, 22.6, 24.9, 25.7, 28.2, 28.7, 29.1, 31.7, 35.1, 39.3, 39.5, 48.9, 60.2, 66.2, 74.3, 81.1, 112.2, 119.3, 139.7, 147.9, 153.1, 164.8.

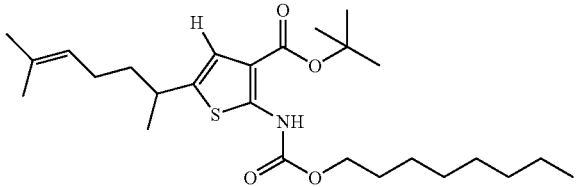

5-(1,5-Dimethyl-hex-4-enyl)-2-octyloxycarbonylamino-thiophene-3-carboxylic acid tert-butyl ester (19.10) brown oil (630 mg, 90% yield): $^1$H NMR (CDCl$_3$, 200 MHz) δ 0.89 (t, 3H, J=6.6 Hz), 1.26–1.42 (m, 13H), 1.55–1.73 (m, 19H), 1.96 (dt, 2H, J=7.8, 7.2 Hz), 2.86 (tq, 1H, J=7.2, 6.6 Hz), 4.20 (t, 3H, J=6.6 Hz), 5.08 (t, 1H, J=7.2 Hz), 6.74 (s, 1H), 10.16 (bs, 1H).

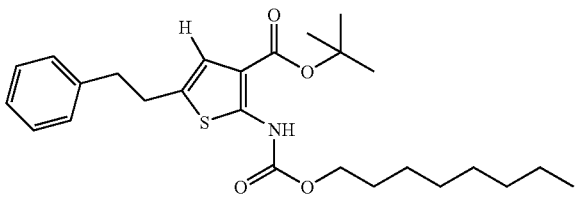

2-Octyloxycarbonylamino-5-phenethyl-thiophene-3-carboxylic acid tert-butyl ester (19.11) white solid (740 mg, 98% yield) $^1$H NMR (CDCl$_3$, 200 MHz) δ 0.88 (t, 3H, J=6.6 Hz), 1.28 (brs, 10H), 1.56 (s, 9H), 1.68 (m, 2H), 2.96 (s, 4H); 4.20 (t, 2H, J=6.6 Hz), 6.75 (s, 1H), 7.26 (m, 5H), 10.15 (s, 1H)

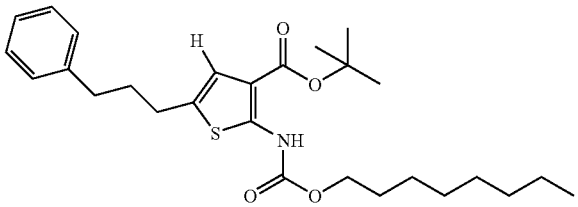

2-Octyloxycarbonylamino-5-(3-phenyl-propyl)-thiophene-3-carboxylic acid tert-butyl ester (19.12) yellow oil (270 mg, 90% yield) $^1$H NMR (CDCl$_3$, 200 MHz) δ 0.88 (t, 3H, J=6.6 Hz), 1.28 (brs, 10H), 1.64 (brs, 11H), 1.97 (tt, 2H, J=7.8, 7.2 Hz), 2.69 (m, 4H), 4.20 (t, 2H, J=6.6 Hz), 6.76 (s, 1H), 7.26 (m, 5H), 10.15 (s, 1H)

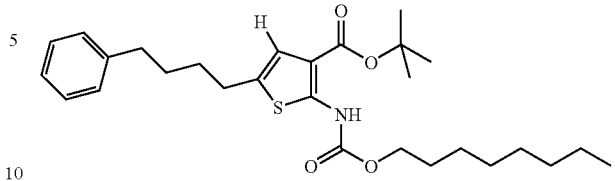

2-Octyloxycarbonylamino-5-(4-phenyl-butyl)-thiophene-3-carboxylic acid tert-butyl ester (19.13) clear colorless oil (401 mg, 88% yield) $^1$H NMR (CDCl$_3$, 200 MHz) δ 0.88 (bt, 3H, J=6.2 Hz), 1.15–1.42 (m, 11H), 1.56 (s, 9H), 1.61–1.80 (m, 6H), 2.52–2.80 (m, 4H), 4.20 (t, 2H, J=6.6 Hz), 6.74 (s, 1H), 7.09–7.35 (m, 5H), 10.15 (s, 1H); MS (ES) no ionization or LC was observed.

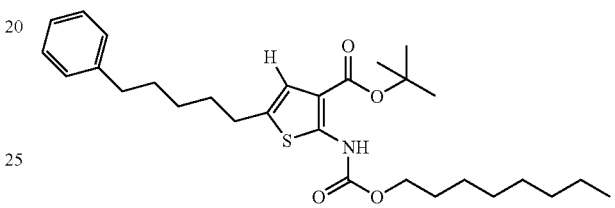

2-Octyloxycarbonylamino-5-(5-phenyl-pentyl)-thiophene-3-carboxylic acid tert-butyl ester (19.14) clear/colorless oil (331 mg, 75% yield) $^1$H NMR (CDCl$_3$, 200 MHz), δ 0.88 (bt, 3H, J=6.2 Hz), 1.20–1.50 (m, 14H), 1.50–1.75 (m, 15H), 2.50–2.75 (m, 4H), 4.19 (t, 2H, J=7.0 Hz), 6.74 (t, 1H, J=1.0 Hz), 7.08–7.36 (m, 5H); MS (ES) No LC trace and no ionization came out.

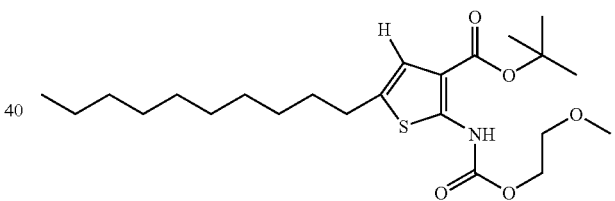

5-Decyl-2-(2-methoxy-ethoxycarbonylamino)-thiophene-3-carboxylic acid tert-butyl ester (19.15) pale yellow oil (307 mg, 76% yield) $^1$H NMR (CDCl$_3$, 200 MHz) δ 0.88 (bt, 3H, J=6.2 Hz), 1.16–1.43 (m, 14H), 1.55 (s, 9H), 1.57–1.73 (m, 2H), 2.66 (t, 2H, J=7.8 Hz), 3.41 (s, 3H), 3.58–3.70 (m, 2H), 4.25–4.44 (m, 2H), 6.74 (s, 1H), 10.27 (bs, 1H); MS (ES) 442.64 (M+1), $t_R$(method D)=12.91 min.

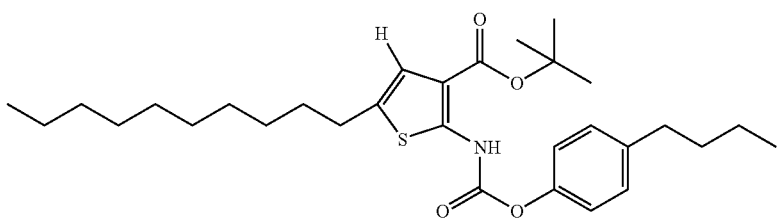

2-(4-Butyl-phenoxycarbonylamino)-5-decyl-thiophene-3-carboxylic acid tert-butyl ester (19.16) Amino thiophene 18.4 (300 mg, 0.92 mmol) was dissolved in anhydrous THF (4 mL). Under a nitrogen atmosphere was added 4-nitrophenyl chloroformate (184 mg, 0.92 mmol) and was stirred overnight at room temperature. Without any isolation of the 4-nitrophenyl carbamate intermediate the sodium salt of 4-butyl phenol (200 mg, 1.26 mmol) was dropwise added to the solution of the intermediate and was stirred at room temperature for 2 hours followed by heating to 40° C. for an additional hour. The sodium salt of the phenol was prepared by dissolving 4-butyl phenol (174 mg, 1.16 mmol) in anhydrous THF (3 mL) and cooling to 0° C. Then NaH(60% dispersion in mineral oil) (45 mg, 1.16 mmol) was added to reaction mixture and stirred at 0° C. for ½ hour and was used as stated above. The reaction mixture was partitioned between CHCl$_3$ and H$_2$O and separated. The H$_2$O layer was extracted again with CHCl$_3$ (3×) and separated. The combined CHCl$_3$ layers was washed with 2M NaOH (1×), 1M HCl (1×), brine (1×) and dried with Na$_2$SO$_4$ filtered and concentrated resulting in 490 mg of a dark orange oil. The crude material was further purified by flash silica chromatography (2% EtOAc in Hexanes) which resulted in 241 mg of a yellow oil (50% yield). $^1$H NMR (CDCl$_3$, 200 MHz) δ 0.83–0.93 (m, 6H), 1.19–1.45 (m, 18H), 1.47–1.72 (m, 14H), 2.55–2.75 (m, 4H), 6.80 (s, 1H), 7.11 (d, 2H, J=8.8 Hz), 7.19 (d, 2H, J=8.8 Hz), 10.58 (s, 1H).

EXAMPLE 20

Tert-butyl Ester Intermediates

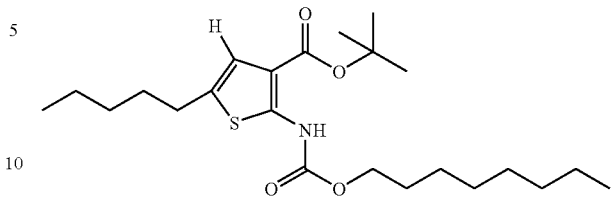

5-Butyl-2-octyloxycarbonylamino-thiophene-3-carboxylic acid tert-butyl ester (20.1): $^1$H NMR (CDCl$_3$, 200 MHz): δ=0.80–1.00 (m, 6H), 1.18–1.49 (m, 12H), 1.50–1.79 (m, 13H), 2.67 (t, J=7.3 Hz, 2H), 4.19 (t, J=6.6 Hz, 2H), 6.74 (t, J=0.9 Hz, 1H), 10.14 (brs, 1H).

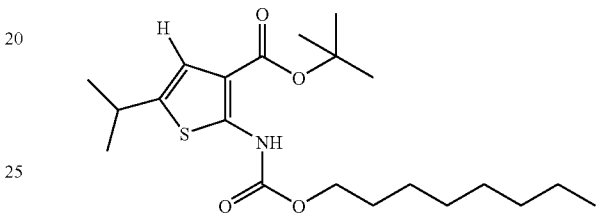

5-Isopropyl-2-octyloxycarbonylamino-thiophene-3-carboxylic acid tert-butyl ester (20.2): $^1$H NMR (CDCl$_3$, 200

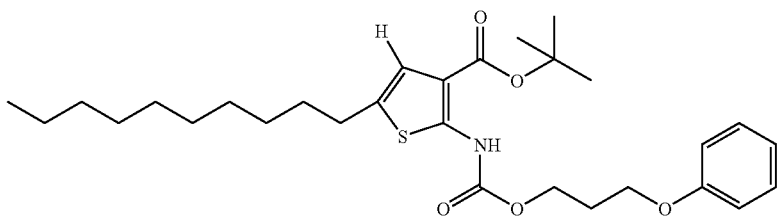

5-Decyl-2-(4-phenyl-butoxycarbonylamino)-thiophene-3-carboxylic acid tert-butyl ester (19.17) pale yellow oil (241 mg, 89% yield) $^1$H NMR (CDCl$_3$, 200 MHz) δ 0.88 (t, 3H, J=6.6 Hz), 1.26–1.38 (m, 14H), 1.56–1.70 (m, 11H), 1.99 (tt, 2H, J=12.6, 6.2 Hz), 2.66 (t, 2H, J=7.5 Hz), 3.58 (t, 2H, J=6.2 Hz), 4.34 (t, 2H, J=6.2 Hz), 4.50 (s, 2H), 6.75 (s, 1H), 7.24–7.34 (m, 5H), 10.16 (s, 1H). $^{13}$C NMR (CDCl$_3$, 50 MHz) δ 14.04, 22.60, 28.26, 28.97, 29.19, 29.23, 29.27, 29.45, 29.48, 29.51, 31.25, 31.82, 63.35, 66.35, 72.96, 81.09, 112.53, 120.60, 127.48, 127.53, 128.28, 133.87, 138.21, 147.97, 152.97, 164.77.

MHz): δ=0.88 (t, J=6.6 Hz, 3H), 1.16–1.46 (m, 16H), 1.50–1.76 (m, 11H), 2.90–3.16 (m, 1H), 4.20 (t, J=6.6 Hz, 2H), 6.75 (d, J=1.0 Hz, 1H), 10.15 (brs, 1H).

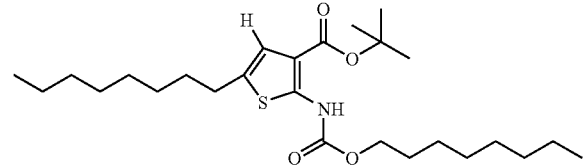

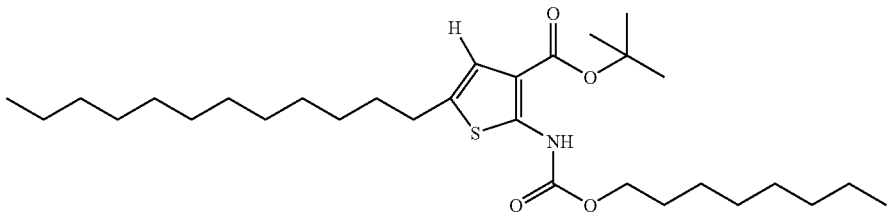

5-Octyl-2-octyloxycarbonylamino-thiophene-3-carboxylic acid tert-butyl ester (20.3): ¹H NMR (CDCl₃, 200 MHz): δ=0.79–0.98 (m, 6H), 1.18–1.46 (m, 20H), 1.51–1.78 (m, 13H), 2.66 (td, J=0.8, 7.5 Hz, 2H), 4.19 (t, J=6.6 Hz, 2H), 6.74 (t, J=1.1 Hz, 1H), 10.14 (brs, 1H).

5-Dodecyl-2-octyloxycarbonylamino-thiophene-3-carboxylic acid tert-butyl ester (20.4): ¹H NMR (CDCl₃, 200 MHz): δ=0.80–0.98 (m, 6H), 1.15–1.46 (m, 28H), 1.52–1.78 (m, 13H), 2.66 (t, J=7.3 Hz, 2H), 4.20 (t, J=6.8 Hz, 2H), 6.74 (s, 1H), 10.14 (brs, 1H).

mL) and then diphosgene (0.25 mL, 2.07 mmol) dropwise. The mixture was allowed to stir vigorously at ambient temperature for 45 min, and aminothiophene 18.4 (283 mg, 0.83 mmol) was added in one portion. After stirring vigorously for 2 h, the reaction mixture was diluted with Et₂O (100 mL), and the organic layer was washed with saturated NaHCO₃ (2×20 mL), and brine (40 mL). The organic layer was dried over Na₂SO₄ and then filtered. The filtrate was concentrated and the resulting residue was purified by flash column chromatography (40:1 Hexanes/EtOAc) to give tert-butyl ester 20.6 as a light yellow oil (416 mg, 95%).

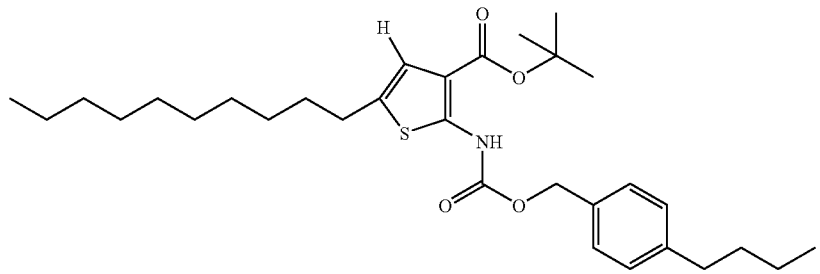

2-(4-Butylbenzyloxycarbonylamino)-5-decyl-thiophene-3-carboxylic acid tert-butyl ester (20.6): ¹H NMR (CDCl₃, 200 MHz): δ=0.82–1.00 (m, 6H), 1.18–1.46 (m, 16H), 1.48–1.72 (m, 13H), 2.54–2.73 (m, 4H), 5.20 (s, 2H), 6.73 (s, 1H), 7.13–7.38 (m, 4H), 10.23 (brs, 1H).

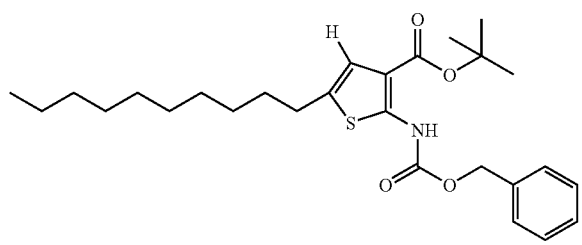

2-Benzyloxycarbonylamino-5-decyl-thiophene-3-carboxylic acid tert-butyl ester (20.5): ¹H NMR (CDCl₃, 200 MHz): δ=0.88 (t, J=6.4 Hz, 3H), 1.18–1.42 (m, 14H), 1.48–1.72 (m, 11H), 2.66 (t, J=7.5 Hz, 2H), 5.24 (s, 2H), 6.74 (s, 1H), 7.31–7.47 (m, 5H), 10.25 (brs, 1H).

General Procedure for the Preparation of tert-butyl Esters 20.6–20.8 from Aminothiophene 18.4 and the Corresponding Commercially Available Alcohols:

To a solution of 4-butylbenzyl alcohol (0.30 mL, 1.76 mmol) in CH₂Cl₂ (10 mL) was added saturated NaHCO₃ (10

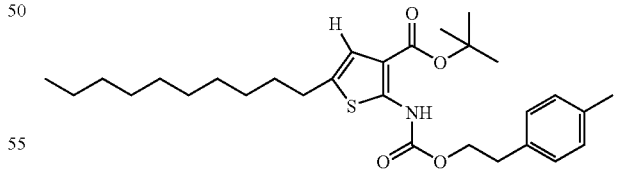

5-Decyl-2-(2-p-tolyl-ethoxycarbonylamino)-thiophene-3-carboxylic acid tert-butyl ester (20.7): ¹H NMR (CDCl₃, 200 MHz): δ=0.88 (t, J=6.4 Hz, 3H), 1.17–1.42 (m, 14H), 1.49–1.72 (m, 11H), 2.32 (s, 3H), 2.66 (t, J=7.3 Hz, 2H), 2.96 (t, J=7.1 Hz, 2H), 4.39 (t, J=7.3 Hz, 2H), 6.74 (s, 1H), 7.08–7.19 (m, 4H), 10.14 (brs, 1H).

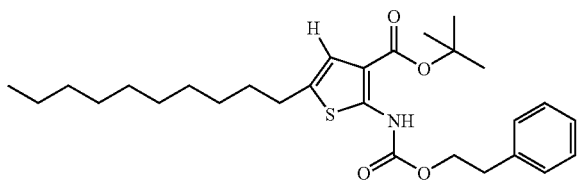

5-Decyl-2-phenethyloxycarbonylamino-thiophene-3-carboxylic acid tert-butyl ester (20.8): $^1$H NMR (CDCl$_3$, 200 MHz): δ=0.88 (t, J=6.4 Hz, 3H), 1.18–1.42 (m, 14H), 1.50–1.72 (m, 11H), 2.66 (t, J=7.3 Hz, 2H), 3.01 (t, J=7.5 Hz, 2H), 4.42 (t, J=7.3 Hz, 2H), 6.74 (s, 1H), 7.18–7.40 (m, 5H), 10.15 (brs, 1H).

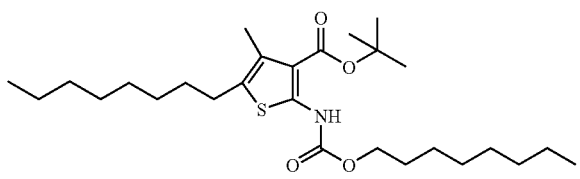

4-Methyl-5-octyl-2-octyloxycarbonylamino-thiophene-3-carboxylic acid tert-butyl ester (20.9): 2.35 g (33%). $^1$H NMR (CDCl$_3$, 200 MHz): δ 0.87 (t, J=6.6 Hz, 3H), 0.88 (t, J=7.6 Hz, 3H), 1.30–1.72 (m, 24H), 1.57 (s, 9H), 2.20 (s, 3H), 2.61 (t, J=7.8 Hz, 2H), 4.18 (t, J=6.6 Hz, 2H), 10.26 (s, 1H); $^{13}$C NMR (CDCl$_3$, 75 MHz): δ 12.3, 12.9, 20.9, 24.0, 24.1, 25.4, 26.7, 27.1, 27.3, 27.4, 27.5, 27.6, 29.6, 30.1, 30.1, 64.5, 79.7, 111.2, 126.2, 127.1, 146.7, 151.5, 164.0.

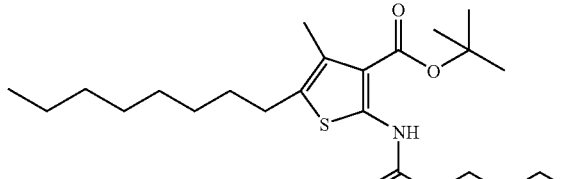

2-Butyloxycarbonylamino-5-octyl-thiophene-3-carboxylic acid tert-butyl ester (20.10): 693 mg (92%). $^1$H NMR (CDCl$_3$, 200 MHz): δ 0.83 (t, J=6.6 Hz, 3H), 0.94 (t, J=7.0 Hz, 3H), 1.20–1.48 (m, 12H), 1.55 (s, 9H), 1.52–1.75 (m, 4H), 2.65 (t, J=7.0 Hz, 2H), 4.20 (t, J=6.6 Hz, 2H), 6.73 (s, 1H), 10.14 (s 1H).

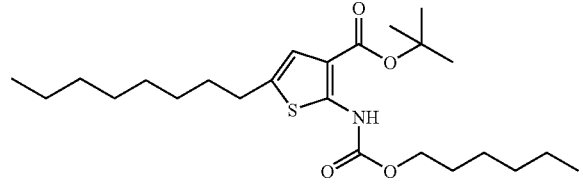

2-Hexyloxycarbonylamino-5-octyl-thiophene-3-carboxylic acid tert-butyl ester (20.11): 760 mg (98%). $^1$H NMR (CDCl$_3$, 200 MHz): δ 0.87 (t, J=6.6 Hz, 3H), 0.89 (t, J=6.6 Hz, 3H), 1.18–1.44 (m, 14H), 1.55 (s, 9H), 1.54–1.76 (m, 4H), 2.65 (t, J=7.0 Hz, 2H), 4.19 (t, J=6.6 Hz, 2H), 6.73 (s, 1H), 10.14 (s, 1H).

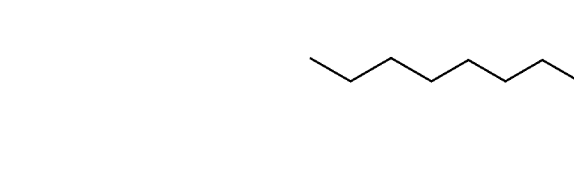

2-Dodecyloxycarbonylamino-5-octyl-thiophene-3-carboxylic acid tert-butyl ester (20.12): 831 mg (88%). $^1$H NMR (CDCl$_3$, 200 MHz): δ 0.87 (t, J=6.6 Hz, 6H), 1.051–0.50 (m, 28H), 1.55 (s, 9H), 1.50–1.75 (m, 4H), 2.65 (t, J=7.2 Hz, 2H), 4.19 (t, J=6.6 Hz, 2H), 6.73 (t, J=1.2 Hz, 1H), 10.14 (s, 1H).

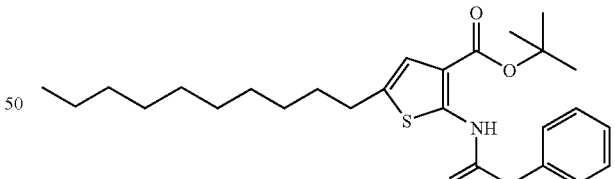

5-Decyl-2-phenyloxycarbonylamino-thiophene-3-carboxylic acid tert-butyl ester (20.13): 696 mg (84%). $^1$H NMR (CDCl$_3$, 200 MHz): 50.88 (t, J=7.0 Hz, 3H), 1.20–1.36 (m, 14H), 1.52–1.66 (m, 2H), 1.59 (s, 9H), 2.67 (dt, J=7.4, 1.2 Hz, 2H), 6.78 (t, J=1.2 Hz, 1H), 7.14–7.48 (m, 5H), 10.55 (s, 1H).

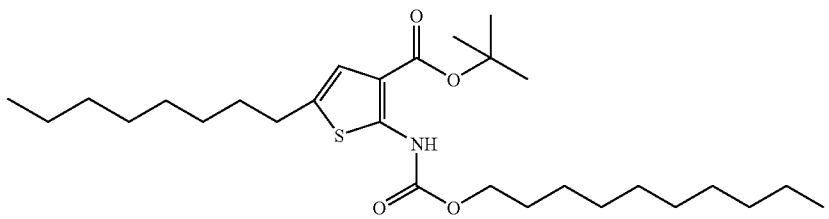

2-Decyloxycarbonylamino-5-octyl-thiophene-3-carboxylic acid tert-butyl ester (20.14): 863 mg (91%). $^1$H NMR (CDCl$_3$, 200 MHz),: δ 0.87 (t, J=6.6 Hz, 6H), 1.14–1.44 (m, 24H), 1.55 (s, 9H), 1.52–1.76 (m, 4H), 2.65 (t, J=7.2 Hz, 2H), 4.19 (t, J=6.6 Hz, 2H), 6.73 (s, 1H), 10.14 (s, 1H).

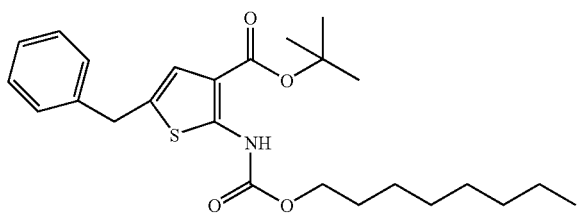

6-Benzyl-2-octyloxycarbonylamino)thiophene-3-carboxylic acid t-butyl ester (20.15)

Light yellow oil in 77% yield.

$^1$H NMR (CDCl$_3$, 200 MHz): δ 10.16 (s, 1H), 7.20–7.40 (m, 5H), 6.82 (s, 1H), 4.17 (t, 2H, J=6.6 Hz), 3.99 (s, 2H), 1.64 (q, 2H, J=6.6 Hz), 1.55 (s, 9H), 1.10–1.50 (m, 10H), 0.88 (t, 3H, J=6.6 Hz).

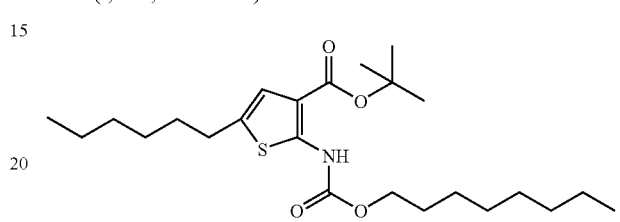

6-Hexyl-2-(octyloxycarbonylamino)thiophene-3-carboxylic acid t-butyl ester (20.16)

Light yellow oil in 86% yield.

$^1$H NMR (CDCl$_3$, 200 MHz): δ 10.14 (brs, 1H), 6.74 (s, 1H), 4.19 (t, 2H, J=6.6 Hz), 2.66 (t, 2H, J=7.6 Hz), 1.60–1.75 (m, 2H), 1.56 (s, 9H), 1.10–1.40 (m, 18H), 0.80–0.95 (m, 6H).

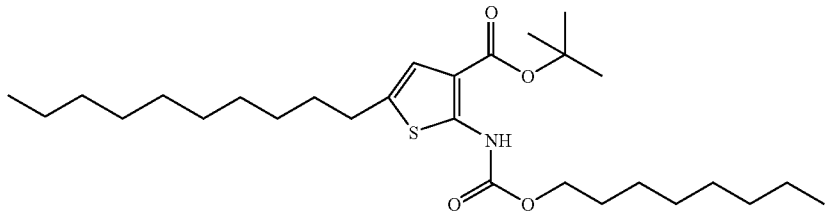

6-Decyl-2-(octyloxycarbonylamino)thiophene-3-carboxylic acid t-butyl ester (20.17)

Light yellow oil in 99% yield.

$^1$H NMR (CDCl$_3$, 200 MHz): δ 10.14 (brs, 1H), 6.74 (s, 1H), 4.19 (t, 2H, J=6.6 Hz), 2.66 (t, 2H, J=8.0 Hz), 1.60–1.75 (m, 2H), 1.56 (s, 9H), 1.08–1.40 (m, 26H), 0.80–0.95 (m, 6H).

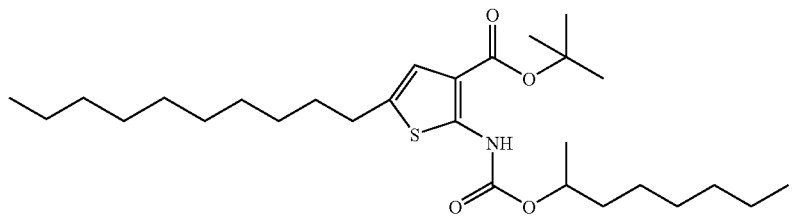

6-Decyl-2-(1-methylheptyloxycarbonylamino)thiophene-3-carboxylic acid t-butyl ester (20.18)

Light yellow oil in 99% yield.

¹H NMR (CDCl₃, 200 MHz): δ 10.10 (brs, 1H), 6.73 (s, 1H), 4.82–5.00 (m, 1H), 2.65 (t, 2H, J=7.4 Hz), 1.50–1.83 (m, 15H), 1.08–1.50 (m, 23H), 0.80–1.00 (m, 6H).

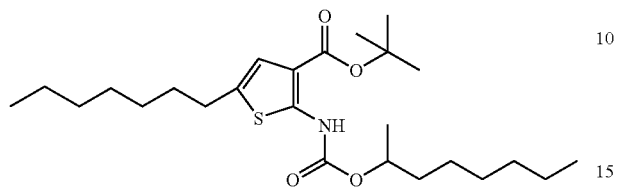

6-Heptyl-2-(1-methylheptyloxycarbonylamino)thiophene-3-carboxylic acid t-butyl ester (20.19)

Light yellow oil in 78% yield.

¹H NMR (CDCl₃, 200 MHz): δ 10.01 (brs, 1H), 6.73 (s, 1H), 4.80–5.00 (m, 1H), 2.65 (t, 2H, J=7.4 Hz), 1.50–1.83 (m, 13H), 1.08–1.50 (m, 17H), 0.80–1.00 (m, 6H).

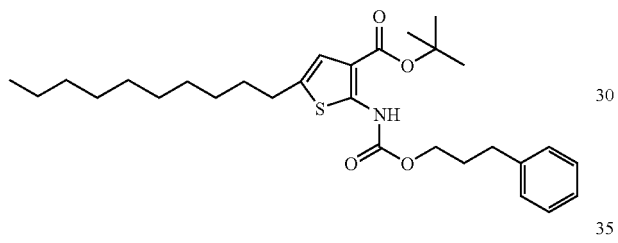

5-Decyl-2-(4-phenylbutoxycarbonylamino)thiophene-3-carboxylic acid t-butyl ester (20.20)

Light brownish oil in 99% yield.

¹H NMR (CDCl₃, 400 MHz): δ 10.12 (s, 1H), 7.26–7.31 (m, 2H), 7.19–7.26 (m, 3H), 6.75 (s, 1H), 4.23 (t, 2H, J=6.4 Hz), 2.73 (t, 2H, J=7.6 Hz), 2.66 (t, 2H, J=7.2 Hz), 1.98–2.07 (m, 2H), 1.59–1.65 (m, 2H), 1.52–1.57 (m, 11H), 1.26–1.30 (m, 12H), 0.88 (t, 3H, J=6.4 Hz).

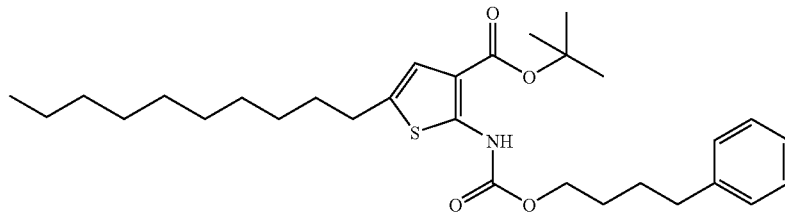

5-Decyl-2-(4-phenylbutoxycarbonylamino)thiophene-3-carboxylic acid t-butyl ester (20.21)

Light brownish oil in 98% yield.

¹H NMR (CDCl₃, 400 MHz): δ 10.11 (s, 1H), 7.26–7.31 (m, 2H), 7.18–7.26 (m, 3H), 6.74 (s, 1H), 4.26 (brs, 2H), 2.67–2.70 (m, 4H), 1.70–1.80 (m, 4H), 1.50–1.70 (m, 11H), 1.18–1.40 (m, 16H), 0.88 (t, 3H, J=6.8 Hz).

EXAMPLE 21

Acid Intermediates

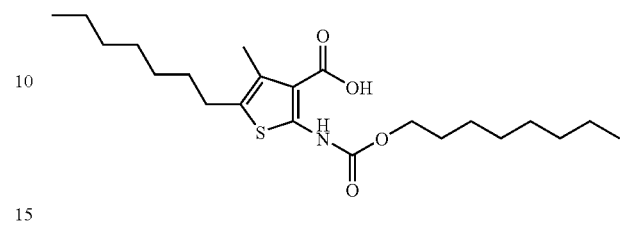

5-Heptyl-4-methyl-2-octyloxycarbonylamino-thiophene-3-carboxylic acid (21.1): May contain ~10% other isomer; ¹H NMR (CDCl₃) δ 0.82–0.94 (m, 6H), 1.20–1.46 (m, 18H), 1.50–1.66 (m, 2H), 1.66–1.80 (m, 2H), 2.28 (s, 3H), 2.64 (t, 2H, J=7.2 Hz), 4.22 (t, 2H, J=7.0 Hz). There was another peak at 2.79 (t, J=7.0 Hz), which may be from other isomer; MS (EI): cal'd 411.61, exp, did not ionize.

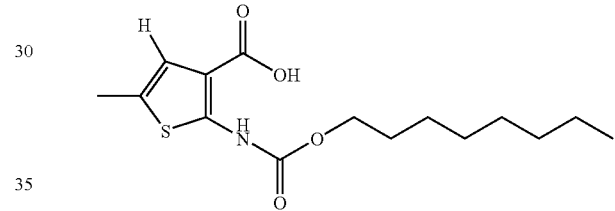

5-Methyl-2-octyloxycarbonylamino-thiophene-3-carboxylic acid (21.2): ¹H NMR (CDCl₃) δ 0.88 (t, 3H, J=7.2 Hz), 1.20–1.45 (m, 10H), 1.65–1.75 (m, 2H), 2.37 (s, 3H), 4.23 (t, 2H, J=6.8 Hz), 6.84 (s, 1H), 9.89 (s, 1H); MS (EI): cal'd 313.41, exp.

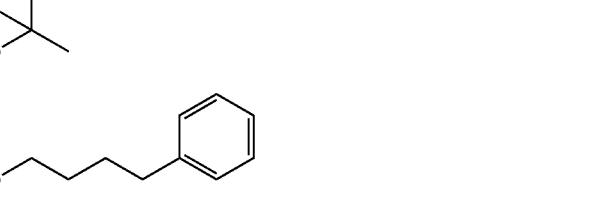

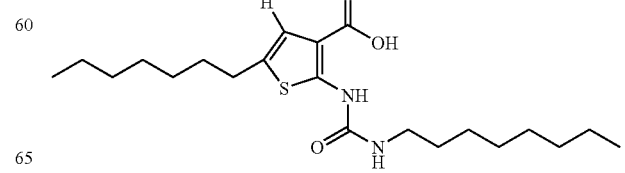

5-Heptyl-2-(3-octyl-ureido)-thiophene-3-carboxylic acid (21.3) tan solid (51 mg, 80% yield): $^1$H NMR (CDCl$_3$, 200 MHz) δ 0.87 (t, 6H, J=5.7 Hz), 1.26 (bs, 18H), 1.54–1.61 (m, 4H), 2.63 (t, 2H, J=7.5 Hz), 3.26 (dt, 2H, J=7.0, 7.0 Hz), 5.95 (bs, 1H), 6.77 (s, 1H), 10.10 (s, 1H), 11.36 (bs, 1H). $^{13}$C NMR (CDCl$_3$, 50 MHz) δ 14.0, 22.6, 26.8, 29.0, 29.2, 29.3, 29.4, 29.7, 31.1, 31.7, 31.8, 41.0, 88.4, 108.9, 119.6, 134.2, 151.9, 154.1, 169.9.

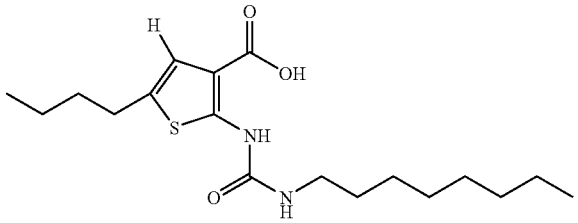

5-Butyl-2-(3-octyl-ureido)-thiophene-3-carboxylic acid (21.4) purple oil (308 mg, 100% yield): $^1$H NMR (CDCl$_3$, 200 MHz) δ 0.87 (t, 6H, J=5.7 Hz), 1.26 (bs, 18H), 1.54–1.61 (m, 4H), 2.63 (t, 2H, J=7.5 Hz), 3.26 (dt, 2H, J=7.0, 7.0 Hz), 5.95 (bs, 1H), 6.77 (s, 1H), 10.10 (s, 1H), 11.36 (bs, 1H).

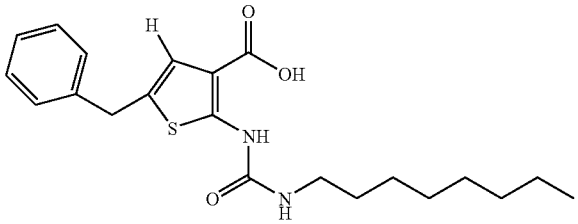

5-Benzyl-2-(3-octyl-ureido)-thiophene-3-carboxylic acid (21.5) tan solid (450 mg): $^1$H NMR (CDCl$_3$, 200 MHz) δ 0.87 (t, 3H, J=6.4 Hz), 1.26 (bs, 10H), 1.51 (tt, 2H, J=12.2, 6.5 Hz), 3.21 (dt, 2H, J=6.6, 6.0 Hz), 3.96 (s, 2H), 6.33 (bs, 1H), 6.82 (s, 1H), 7.14–7.32 (m, 5H), 10.16 (bs, 1H).

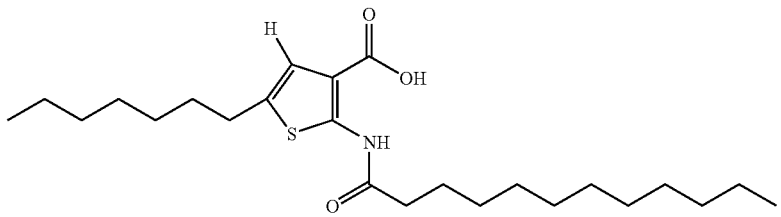

2-Dodecanoylamino-5-heptyl-thiophene-3-carboxylic acid (21.6) dark brown solid (185 mg, 100% yield): $^1$H NMR (CDCl$_3$, 200 MHz) δ 0.85–0.90 (m, 6H), 1.26–1.40 (m, 24H), 1.54–1.79 (m, 4H), 2.52 (t, 2H, J=7.5 Hz), 2.71 (t, 2H, J=7.5 Hz), 6.91 (s, 1H), 10.53 (bs, 1H), 10.75 (s, 1H). MS (ES−) 421.86 (M−1).

5-Heptyl-2-octyloxycarbonylamino-thiophene-3-carboxylic acid (21.7) pale yellow solid (76 mg, 54% yield): $^1$H NMR (CDCl$_3$, 200 MHz) δ 0.85–0.91 (m, 6H), 1.30 (bs, 18H), 1.58–1.75 (m, 4H), 2.69 (t, 2H, J=7.5 Hz), 4.24 (t, 2H, J=6.6 Hz), 6.86 (s, 1H), 9.90 (s, 1H). MS (ES−) 395.93 (M−1).

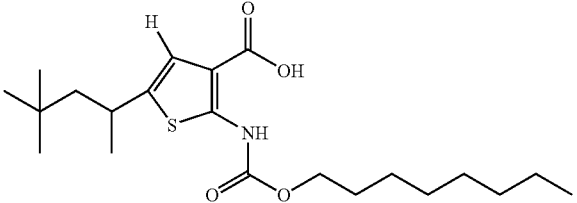

2-Octyloxycarbonylamino-5-(1,3,3-trimethyl-butyl)-thiophene-3-carboxylic acid (21.8) waxy tan solid (190 mg, 100% yield): $^1$H NMR (CDCl$_3$, 200 MHz) δ 0.88–0.89 (m, 12H), 1.28–1.76 (m, 17H), 2.90–3.09 (m, 1H), 4.24 (t, 2H, J=6.6 Hz), 6.87 (s, 1H), 9.85 (s, 1H), 10.34 (bs, 1H).

2-(2-Benzyloxy-ethoxycarbonylamino)-5-decyl-thiophene-3-carboxylic acid (21.9) tan solid (142 mg): $^1$H NMR (CDCl$_3$, 200 MHz) δ 0.89 (t, 3H, J=6.5 Hz), 1.23–1.27 (m, 14H), 1.58–1.69 (m, 2H), 2.69 (t, 2H, J=7.3 Hz), 3.76 (t, 2H, J=4.6 Hz), 4.43 (t, 2H, J=4.6 Hz), 4.61 (s, 2H), 6.88 (s, 1H), 7.28–7.38 (m, 5H), 9.99 (s, 1H), 10.48 (bs, 1H). MS (ES−) 460.06 (M−1).

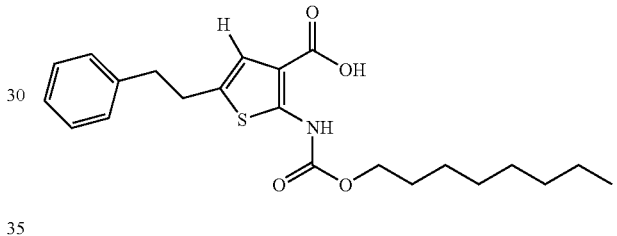

2-Octyloxycarbonylamino-5-phenethyl-thiophene-3-carboxylic acid (21.10) white solid (203 mg, 97% yield): $^1$H NMR (CDCl$_3$, 200 MHz) δ 0.88 (t, 3H, J=6.8 Hz), 1.28 (brs, 10H), 2.98 (s, 4H), 4.23 (t, 2H, J=7.0 Hz), 6.84 (s, 1H), 7.22 (m, 5H), 9.96 (s, 1H)

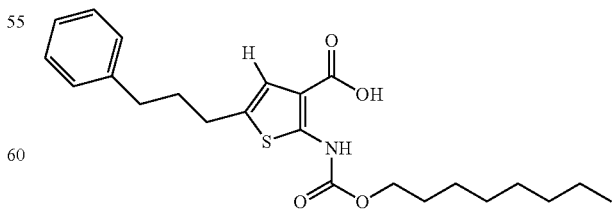

2-Octyloxycarbonylamino-5-(3-phenyl-propyl)-thiophene-3-carboxylic acid (21.11) yellow solid (175 mg, 99% yield): $^1$H NMR (CDCl$_3$, 200 MHz) δ 0.88 (t, 3H, J=6.8 Hz), 1.28

(brs, 10H), 1.68 (m, 2H), 1.98 (tt, 2H, J=7.8 Hz, 7.2 Hz), 4.23 (t, 2H, J=7.0 Hz), 6.87 (s, 1H), 7.26 (m, 5H), 9.93 (1H)

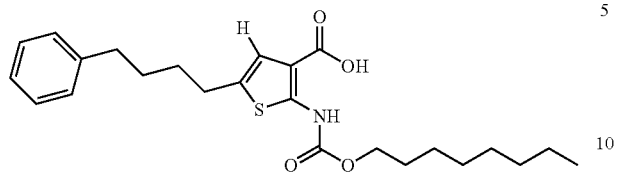

2-Octyloxycarbonylamino-5-(4-phenyl-butyl)-thiophene-3-carboxylic acid (21.12) white waxy solid (303 mg, 92% yield): ¹H NMR (CD₃OD, 400 MHz) δ 0.90 (bt, 3H, J=6.8 Hz), 1.21–1.48 (m, 12H), 1.57–1.76 (m, 6H), 2.57–2.77 (m, 4H), 4.20 (t, 2H, J=6.4 Hz), 6.82 (s, 1H), 7.08–7.32 (m, 5H). MS (ES) 430.35 (M−1), $t_R$(method D)=7.74 min

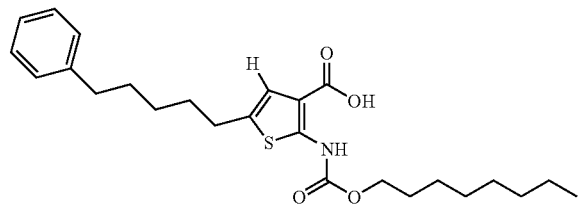

2-Octyloxycarbonylamino-5-(5-phenyl-pentyl)-thiophene-3-carboxylic acid (21.13) off-white solid (331 mg, 90% yield): ¹H NMR (CD₃OD, 400 MHz) δ 0.90 (bt, 3H, J=6.4 Hz), 1.23–1.45 (m, 14H), 1.58–1.75 (m, 6H), 2.59 (t, 2H, J=7.6 Hz), 2.68 (t, 2H, J=7.2 Hz), 4.20 (t, 2H, 6.8 Hz), 6.81 (bs, 1H), 7.07–7.18 (m, 3H), 7.19–7.27 (m, 2H). MS (ES) 443.58 (M−1), $t_R$(method D)=8.58 min

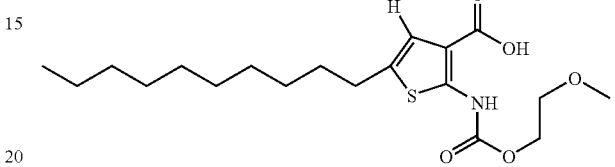

5-Decyl-2-(2-methoxy-ethoxycarbonylamino)-thiophene-3-carboxylic acid (21.14) off-white solid (256 mg, 95% yield): ¹H NMR (CDCl₃, 200 MHz) δ 0.88 (bt, 3H, J=6.2 Hz), 1.11–1.44 (m, 14H), 1.47–1.73 (m, 2H), 2.69 (t, 2H, J=7.8 Hz), 3.43 (s, 3H), 3.62–3.75 (m, 2H), 4.31–4.47 (m, 2H), 6.86 (s, 1H), 10.00 (s, 1H). MS (ES) 384.52 (M−1), $t_R$(method D)=6.28 min.

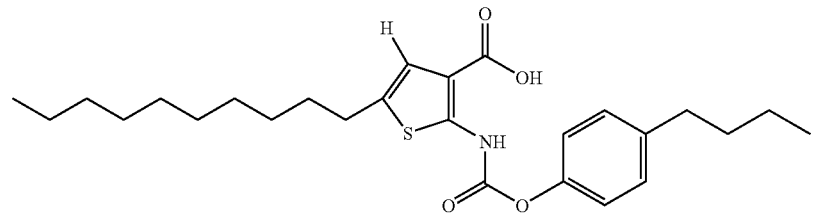

2-(4-Butyl-phenoxycarbonylamino)-5-decyl-thiophene-3-carboxylic acid (21.15) tan solid (214 mg, 97% yield) ¹H NMR (CD₃OD, 400 MHz) δ 0.891 (bt, 3H, J=6.8 Hz), 0.949 (t, 3H, J=7.2 Hz), 1.21–1.43 (m, 16H), 1.54–1.71 (m, 4H), 2.63 (t, 2H, J=7.6 Hz), 2.70 (t, 2H, J=7.2 Hz), 6.87 (s, 1H), 7.12 (d, 2H, J=8.4 Hz), 7.23 (d, 2H, J=8.8 Hz); MS (ES) no ionization (M−1), $t_R$(method D)=no peak

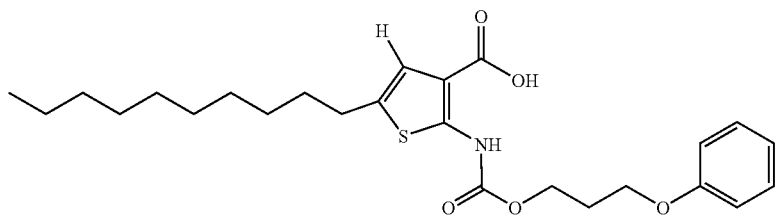

2-(3-phenoxy-propoxycarbonylamino)-5-decyl-thiophene-3-carboxylic acid (21.16) off-white solid (137 mg, 80% yield): $^1$H NMR (CDCl$_3$, 200 MHz) δ 0.88 (t, 3H, J=6.4 Hz), 1.26–1.38 (m, 14H), 1.64 (tt, 2H, J=12.4, 7.0 Hz), 2.02 (tt, 2H, J=12.4, 6.2 Hz), 2.68 (t, 2H, J=7.3 Hz), 3.60 (t, 2H, J=6.2 Hz), 4.37 (t, 2H, J=6.2 Hz), 4.53 (s, 2H), 6.87 (s, 1H), 7.25–7.34 (m, 5H); 9.88 (s, 1H), 10.85 (bs, 1H).

2-(4-Benzyloxy-butoxycarbonylamino)-5-decyl-thiophene-3-carboxylic acid (21.17) off-white solid (55 mg, 55% yield): $^1$H NMR (CDCl$_3$, 200 MHz) δ 0.88 (t, 3H, J=6.3 Hz), 1.26–1.38 (m, 14H), 1.61–1.82 (m, 6H), 2.68 (t, 2H, J=7.4 Hz), 3.53 (t, 2H, J=5.8 Hz), 4.27 (t, 2H, J=5.8 Hz), 4.50 (s, 2H), 6.86 (s, 1H), 7.25–7.33 (m, 5H), 9.92 (s, 1H).

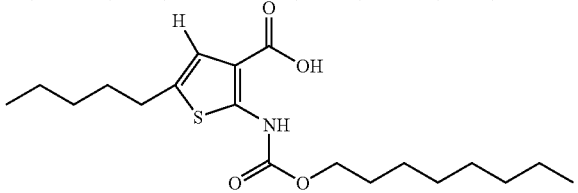

5-Pentyl-2-octyloxycarbonylamino-thiophene-3-carboxylic acid (21.18): $^1$H NMR (CDCl$_3$, 200 MHz): δ=0.78–1.02 (m, 6H), 1.14–1.50 (m, 12H), 1.52–1.82 (m, 4H), 2.69 (t, J=7.5 Hz, 2H), 4.23 (t, J=6.8 Hz, 2H), 6.59 (s, 1H), 9.88 (brs, 1H).

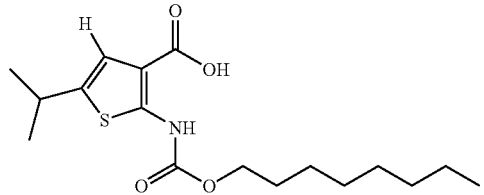

5-Isopropyl-2-octyloxycarbonylamino-thiophene-3-carboxylic acid (21.19): $^1$H NMR (CDCl$_3$, 200 MHz): δ=0.88 (t, J=6.4 Hz, 3H), 1.16–1.50 (m, 16H), 1.60–1.82 (m, 2H), 2.90–3.18 (m, 1H), 4.24 (t, J=6.8 Hz, 2H), 6.87 (d, J=1.2 Hz, 1H), 9.81 (brs, 1H), 9.86 (brs, 1H).

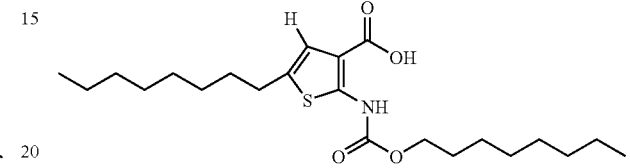

5-Octyl-2-octyloxycarbonylamino-thiophene-3-carboxylic acid (21.20): $^1$H NMR (CDCl$_3$, 200 MHz): δ=0.78–1.00 (m, 6H), 1.12–1.49 (m, 20H), 1.54–1.82 (m, 4H), 2.68 (t, J=7.3 Hz, 2H), 4.23 (t, J=6.6 Hz, 2H), 6.86 (s, 1H), 9.89 (brs, 1H).

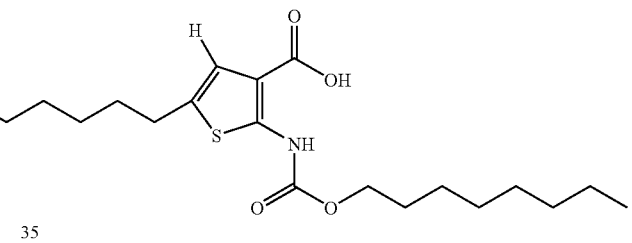

5-Dodecyl-2-octyloxycarbonylamino-thiophene-3-carboxylic acid (21.21): $^1$H NMR (CDCl$_3$, 200 MHz): δ=0.78–0.96 (m, 6H), 1.12–1.46 (m, 28H), 1.52–1.78 (m, 4H), 2.68 (t, J=7.3 Hz, 2H), 4.23 (t, J=6.8 Hz, 2H), 6.85 (s, 1H), 9.90 (brs, 1H).

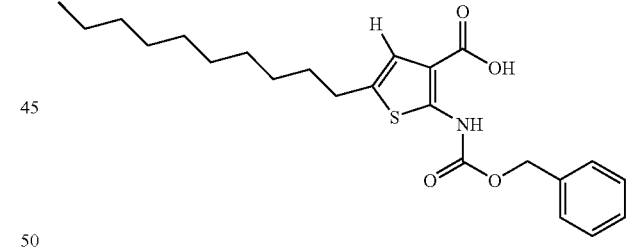

2-Benzyloxycarbonylamino-5-decyl-thiophene-3-carboxylic acid (21.22): $^1$H NMR (CDCl$_3$, 200 MHz): δ=0.88 (t, J=6.4 Hz, 3H), 1.14–1.44 (m, 14H), 1.50–1.74 (m, 2H), 2.68 (t, J=7.1 Hz, 2H), 5.26 (s, 2H), 6.85 (s, 1H), 7.33–7.49 (m, 5H), 9.95 (brs, 1H).

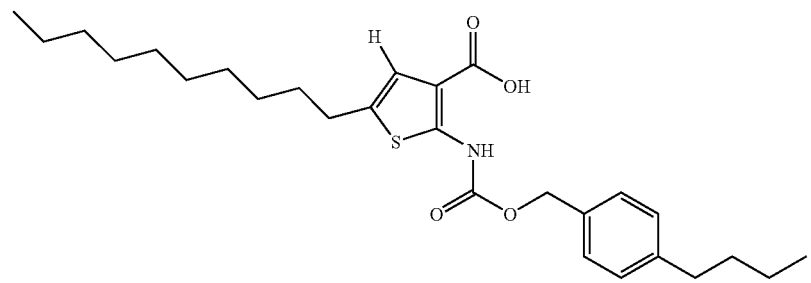

2-(4-Butylbenzyloxycarbonylamino)-5-decyl-thiophene-3-carboxylic acid (21.23): ¹H NMR (CDCl₃, 200 MHz): δ=0.78–1.02 (m, 6H), 1.10–1.46 (m, 16H), 1.48–1.76 (m, 4H), 2.52–2.80 (m, 4H), 5.23 (s, 2H), 6.84 (s, 1H), 7.13–7.40 (m, 4H), 9.93 (brs, 1H).

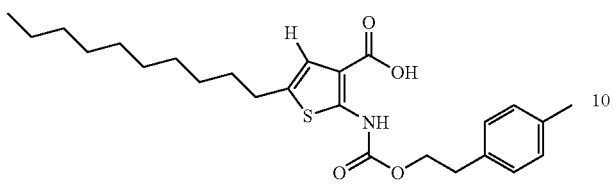

5-Decyl-2-(2-p-tolyl-ethoxycarbonylamino)-thiophene-3-carboxylic acid (21.24): ¹H NMR (CDCl₃, 200 MHz): δ=0.88 (t, J=6.4 Hz, 3H), 1.16–1.46 (m, 14H), 1.52–1.78 (m, 2H), 2.33 (s, 3H), 2.69 (t, J=7.5 Hz, 2H), 3.00 (t, J=7.3 Hz, 2H), 4.43 (t, J=7.3 Hz, 2H), 6.87 (s, 1H), 7.08–7.22 (m, 4H), 9.91 (brs, 1H).

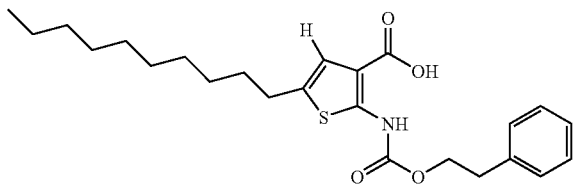

5-Decyl-2-phenethyloxycarbonylamino-thiophene-3-carboxylic acid (21.25): ¹H NMR (CDCl₃, 200 MHz): δ=0.88 (t, J=6.4 Hz, 3H), 1.16–1.46 (m, 14H), 1.52–1.76 (m, 2H), 2.69 (t, J=7.3 Hz, 2H), 3.05 (t, J=7.3 Hz, 2H), 4.46 (t, J=7.5 Hz, 2H), 6.87 (s, 1H), 7.18–7.42 (m, 5H), 9.92 (brs, 1H).

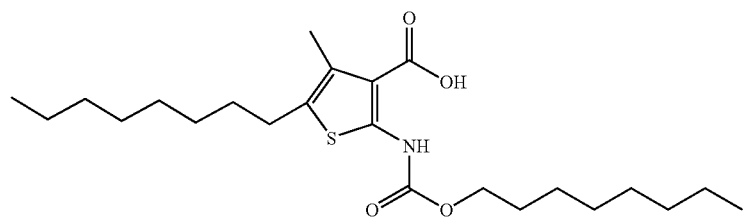

4-Methyl-5-octyl-2-octyloxycarbonylamino-thiophene-3-carboxylic acid (21.26): 520 mg (69%). ¹H NMR (CDCl₃, 200 MHz): δ 0.87 (t, J=6.6 Hz, 6H), 1.16–1.62 (m, 24), 2.28 (s, 3H), 2.64 (t, J=7.2 Hz, 2H), 4.18 (t, J=6.6 Hz, 2H), 10.26 (s, 1H).

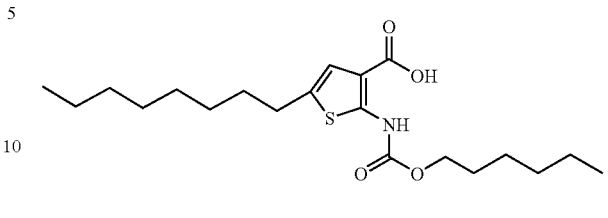

2-Butyloxycarbonylamino-5-octyl-thiophene-3-carboxylic acid (21.27): 366 mg (67%). ¹H NMR (CDCl₃, 200 MHz): δ 0.87 (t, J=6.6 Hz, 3H), 0.96 (t, J=7.4 Hz, 3H), 1.14–1.82 (m, 16H), 2.67 (t, J=7.4 Hz, 2H), 4.24 (t, J=6.6 Hz, 2H), 6.85 (s, 1H), 9.89 (s, 1H).

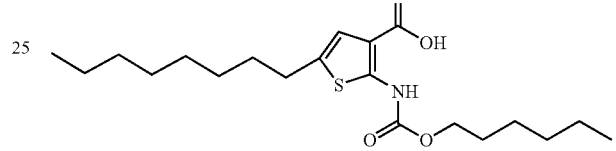

2-Hexyloxycarbonylamino-5-octyl-thiophene-3-carboxylic acid (21.28): 395 mg (60%). ¹H NMR (CDCl₃, 200 MHz): δ 0.87 (t, J=7.0 Hz, 3H), 0.90 (t, J=6.4 Hz, 3H), 1.12–1.52 (m, 16H), 1.50–1.82 (m, 4H), 2.68 (t, J=7.2 Hz, 2H), 4.23 (t, J=7.0 Hz, 2H), 6.68 (s, 1H), 9.88 (s, 1H).

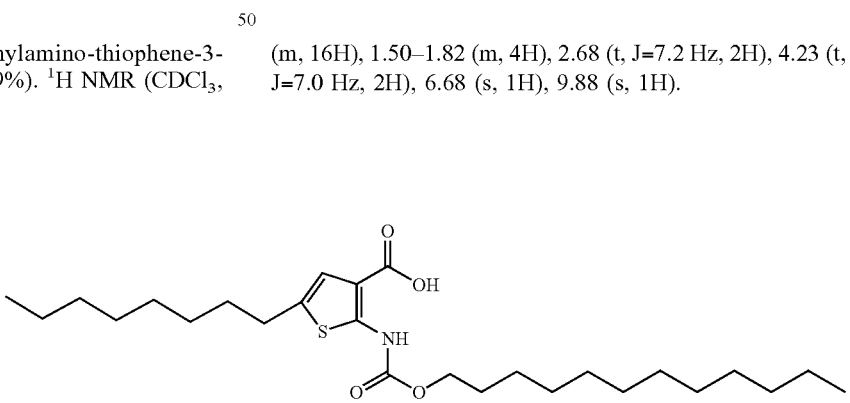

2-Dodecyloxycarbonylamino-5-octyl-thiophene-3-carboxylic acid (21.29): 541 mg (80%). ¹H NMR (CDCl₃, 200 MHz): δ 0.87 (t, J=6.4 Hz, 6H), 1.12–1.50 (m, 28H), 1.50–1.80 (m, 4H), 2.68 (t, J=7.4 Hz, 2H), 4.23 (t, J=6.6 Hz, 2H), 6.85 (s, 1H), 9.89 (s, 1H).

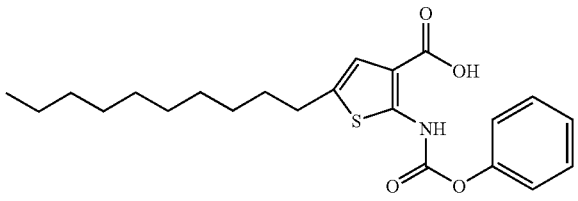

5-Decyl-2-phenyloxycarbonylamino-thiophene-3-carboxylic acid (21.30): 469 mg (80%). ¹H NMR (CDCl₃, 200 MHz): δ 0.87 (t, J=6.6 Hz, 3H), 1.18–1.44 (m, 14H), 1.54–1.76 (m, 2H), 2.70 (t, J=7.2 Hz, 2H), 6.91 (s, 2H), 7.17–7.48 (m, 5H), 10.27 (s, 1H).

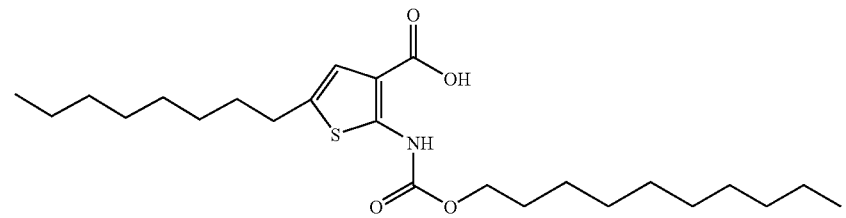

2-Decyloxycarbonylamino-5-octyl-thiophene-3-carboxylic acid (21.31): 603 mg (86%). ¹H NMR (CDCl₃, 200 MHz): δ 0.87 (t, J=6.2 Hz, 6H), 1.32–1.50 (m, 24H), 1.52–1.82 (m, 4H), 2.67 (t, J=7.4 Hz, 2H), 4.23 (t, J=6.6 Hz, 2H), 6.85 (s, 1H), 9.89 (s, 1H).

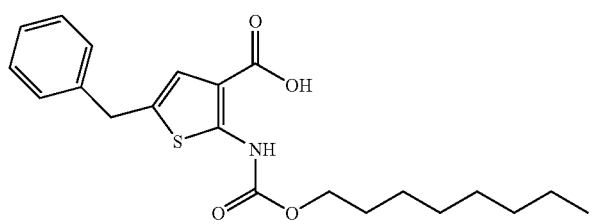

6-Benzyl-2-octyloxycarbonylamino)thiophene-3-carboxylic acid (21.32)

Light yellow solid in 100% yield.

¹H NMR (CDCl₃, 200 MHz): δ 9.86 (s, 1H), 7.22–7.34 (m, 5H), 7.00 (brs, 1H), 6.87 (t, 1H, J=1.0 Hz), 4.21 (t, 2H, J=6.6 Hz), 4.01 (s, 2H), 1.67 (q, 2H, J=7.0 Hz), 1.15–1.45 (m, 10H), 0.88 (t, 3H, J=7.0 Hz).

6-Hexyl-2-(octyloxycarbonylamino)thiophene-3-carboxylic acid (21.33)

Light yellow oil in 74% yield.

¹H NMR (CDCl₃, 200 MHz): δ 10.87 (brs, 1H), 9.83 (s, 1H), 6.86 (s, 1H), 4.24 (t, 2H, J=6.6 Hz), 2.68 (t, 2H, J=7.2 Hz), 1.60–1.80 (m, 4H), 1.10–1.45 (m, 20H), 0.80–0.95 (m, 6H).

6-Decyl-2-(octyloxycarbonylamino)thiophene-3-carboxylic acid (21.34)

Light yellow solid in 100% yield.

¹H NMR (CDCl₃, 200 MHz): δ 9.89 (brs, 1H), 8.00 (brs, 1H), 6.85 (s, 1H), 4.23 (t, 2H, J=6.6 Hz), 2.68 (t, 2H, J=7.0 Hz), 1.60–1.80 (m, 4H), 1.08–1.40 (m, 24H), 0.80–0.95 (m, 6H).

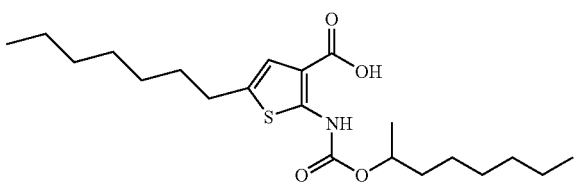

6-Decyl-2-(1-methylheptyloxycarbonylamino)thiophene-3-carboxylic acid (21.35)

Light yellow solid in 98% yield.

$^1$H NMR (CDCl$_3$, 200 MHz): δ 9.80 (brs, 1H), 8.24 (brs, 1H), 6.73 (s, 1H), 4.82–5.00 (m, 1H), 2.65 (t, 2H, J=7.4 Hz), 1.50–1.83 (m, 15H), 1.08–1.50 (m, 23H), 0.80–1.00 (m, 6H).

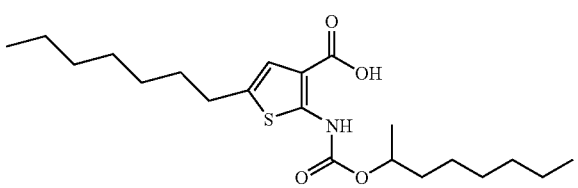

6-Heptyl-2-(1-methylheptyloxycarbonylamino)thiophene-3-carboxylic acid (21.36)

Light yellow oil in 100% yield.

$^1$H NMR (CDCl$_3$, 200 MHz): δ 9.80 (brs, 1H), 8.24 (brs, 1H), 6.85 (s, 1H), 4.90–5.00 (m, 1H), 2.68 (t, 2H, J=7.6 Hz), 1.50–1.83 (m, 4H), 1.08–1.50 (m, 20H), 0.80–1.00 (m, 6H).

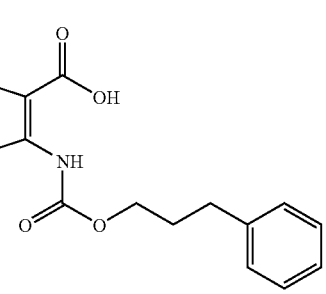

5-Decyl-2-(4-phenylpropoxycarbonylamino)thiophene-3-carboxylic acid (21.37)

Light brownish solid in 100% yield.

$^1$H NMR (CDCl$_3$, 400 MHz): δ 10.4 (brs, 1H), 9.88 (s, 1H), 7.26–7.31 (m, 2H), 7.18–7.21 (m, 3H), 6.87 (s, 1H), 4.27 (t, 2H, J=6.4 Hz), 2.74 (t, 2H, J=8.0 Hz), 2.68 (t, 2H, J=7.6 Hz), 2.02–2.07 (m, 2H), 1.59–1.66 (m, 2H), 1.18–1.40 (m, 14H), 0.88 (t, 3H, J=6.0 Hz).

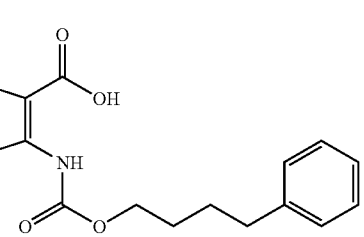

5-Decyl-2-(4-phenylbutoxycarbonylamino)thiophene-3-carboxylic acid (21.38)

Light brownish solid in 100% yield.

$^1$H NMR (CDCl$_3$, 400 MHz): δ 12.0 (brs, 1H), 9.90 (s, 1H), 7.26–7.31 (m, 2H), 7.17–7.21 (m, 3H), 6.87 (s, 1H), 4.26 (t, 2H, J=6.4 Hz), 2.67–2.70 (m, 4H), 1.70–1.80 (m, 4H), 1.50–1.70 (m, 2H), 1.18–1.40 (m, 16H), 0.88 (t, 3H, J=6.8 Hz).

EXAMPLE 22

Thienoxazinones

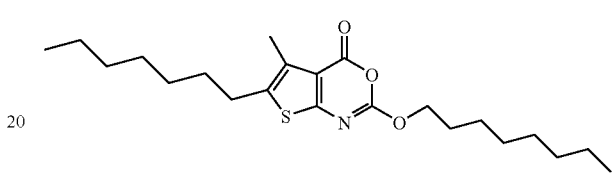

6-Heptyl-5-methyl-2-octyloxy-thieno[2,3-d][1,3]oxazin-4-one (74) (May contain ~10% other isomer); Mp 29–31° C.; $^1$H NMR (CDCl$_3$) δ 0.82–0.96 (m, 6H), 1.20–1.50 (m, 18H), 1.50–1.68 (m, 2H), 1.68–1.86 (m, 2H), 2.36 (s, 3H), 2.70 (t, 2H, J=6.8 Hz), 4.38 (t, 2H, J=6.6 Hz) Another peak at 2.83 (t, J=6.7 Hz), which may be from other isomer; MS (EI): cal'd 393.59, exp, did not ionize.

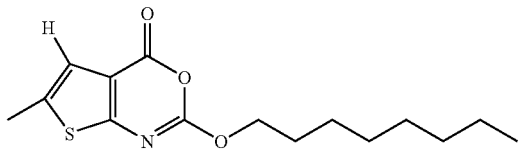

6-Methyl-2-octyloxy-thieno[2,3-d][1,3]oxazin-4-one (22.1): ¹H NMR (CDCl₃) δ 0.88 (t, 3H, J=7.2 Hz), 1.20–1.45 (m, 10H), 1.55 (s, 9H), 1.70–1.84 (m, 2H), 2.46 (s, 3H), 4.39 (t, 2H, J=6.6 Hz), 6.93 (s, 1H); MS (EI): cal'd 295.5, exp.

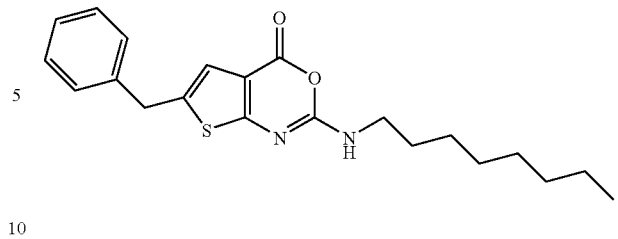

6-Benzyl-2-octylamino-thieno[2,3-d][1,3]oxazin-4-one (62): off-white solid (182 mg, 55% 2-step yield): mp 123.0–124.0° C. ¹H NMR (CDCl₃, 200 MHz) δ 0.87 (t, 3H, J=6.4 Hz), 1.26–1.28 (m, 10H), 1.51 (tt, 2H, J=13.6, 6.5 Hz), 3.36 (dt, 2H, J=7.0, 6.6 Hz), 4.02 (s, 2H), 5.81 (bs, 1H), 6.85 (s, 1H), 7.20–7.35 (m, 5H). MS (ES+) 371.18 (M+1).

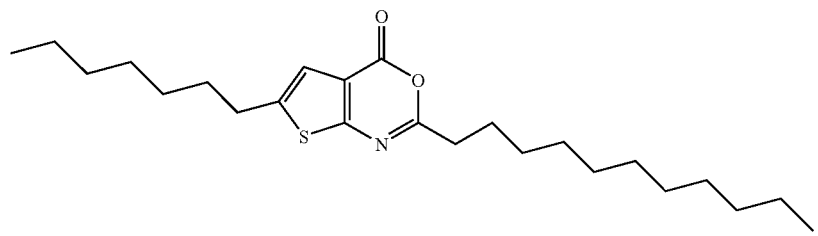

6-Heptyl-2-undecyl-thieno[2,3-d][1,3]oxazin-4-one (67): yellow oil (97 mg, 55% yield): ¹H NMR (CDCl₃, 200 MHz) δ 0.85–0.91 (m, 6H), 1.26–1.32 (m, 24H), 1.66–1.83 (m, 4H), 2.69 (t, 2H, J=7.7 Hz), 2.82 (t, 2H, J=7.5 Hz), 7.06 (s, 1H). ¹³C NMR (CDCl₃, 50 MHz) δ 14.0, 14.1, 22.5, 22.6, 26.2, 28.8, 28.9, 29.0, 29.2, 29.3, 29.4, 29.5, 30.4, 31.0, 31.7, 31.9, 34.7, 117.8, 118.6, 144.3, 155.6, 162.2, 165.2.

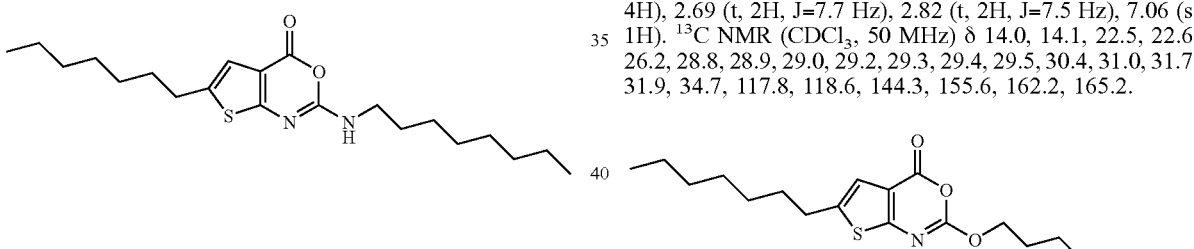

6-Heptyl-2-octylamino-thieno[2,3-d][1,3]oxazin-4-one (61): off-white solid (38 mg, 801% yield): ¹H NMR (CDCl₃, 200 MHz) δ 0.87 (t, 6H, J=6.4 Hz), 1.27–1.30 (m, 18H), 1.58–1.67 (m, 4H), 2.71 (t, 2H, J=7.3 Hz), 3.38 (dt, 2H, J=7.0, 6.2 Hz), 5.45 (bs, 1H), 6.84 (s, 1H).

6-Heptyl-2-octyloxy-thieno[2,3-d][1,3]oxazin-4-one (68): yellow oil (36 mg, 50% yield): ¹H NMR (CDCl₃, 200 MHz) δ 0.85–0.93 (m, 6H), 1.29–1.48 (m, 18H), 1.61–1.87 (m, 4H), 2.77 (t, 2H, J=7.5 Hz), 4.41 (t, 2H, J=6.6 Hz), 6.97 (t, 1H, J=1.1 Hz).

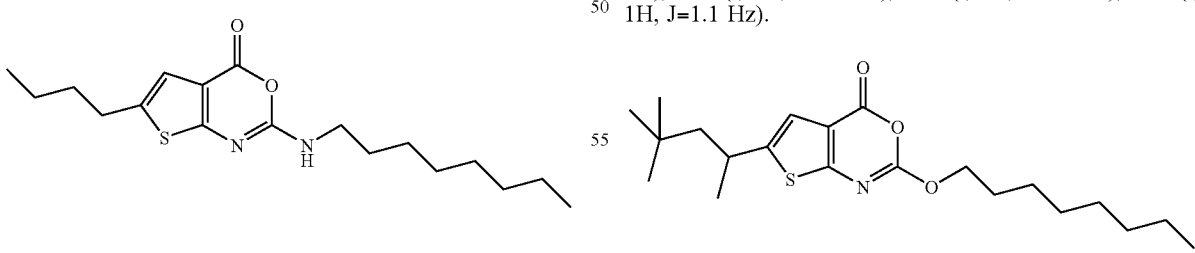

6-Butyl-2-octylamino-thieno[2,3-d][1,3]oxazin-4-one (63): off-white solid (162 mg, 55% yield): mp 93.0–94.0° C. ¹H NMR (CDCl₃, 200 MHz) δ 0.88 (t, 3H, J=6.4 Hz), 0.93 (t, 3H, J=7.3 Hz), 1.27–1.48 (m, 12H), 1.56–1.71 (m, 4H), 2.72 (t, 2H, J=7.5 Hz), 3.39 (dt, 2H, J=7.0, 6.2 Hz), 5.73 (bs, 1H), 6.85 (t, 1H, J=1.1 Hz). MS (ES+) 337.23 (M+1).

2-Octyloxy-6-(1,3,3-trimethyl-butyl)-thieno[2,3-d][1,3]oxazin-4-one (78): colorless oil (92 mg, 51% yield): ¹H NMR (CDCl₃, 200 MHz) δ 0.88–0.89 (m, 12H), 1.30–1.83 (m, 17H), 3.04–3.13 (m, 1H), 4.41 (t, 2H, J=6.6 Hz), 6.98 (s, 1H). ¹³C NMR (CDCl₃, 50 MHz) δ 14.0, 22.6, 25.6, 26.2, 28.3, 29.1, 29.8, 31.3, 31.7, 32.8, 52.6, 70.5, 113.2, 116.5, 149.4, 154.5, 156.9, 165.3. MS (ES+) 380.01 (M+1).

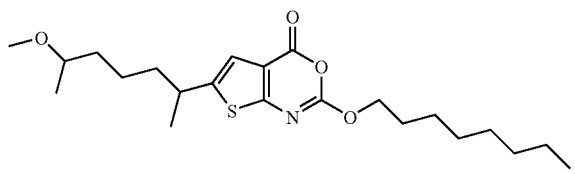

6-(5-Methoxy-1,5-dimethyl-hexyl)-2-octyloxy-thieno[2,3-d][1,3]oxazin-4-one (83): pale yellow oil (3 mg): ¹H NMR (CDCl₃, 200 MHz) δ 0.89 (t, 3H, J=6.6 Hz), 1.11 (s, 6H), 1.26–1.67 (m, 19H), 1.77 (dt, 2H, J=7.0, 6.6 Hz), 2.96 (dq, 1H, J=7.2, 7.0 Hz), 3.15 (s, 3H), 4.40 (t, 2H, J=6.6 Hz), 6.98 (s, 1H). MS (ES+) 424.03 (M+1).

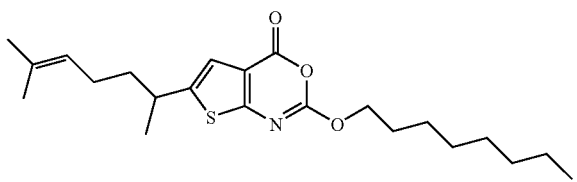

6-(1,5-Dimethyl-hex-4-enyl)-2-octyloxy-thieno[2,3-d][1,3]oxazin-4-one and 6-(1,5-Dimethyl-hex-5-enyl)-2-octyloxy-thieno[2,3-d][1,3]oxazin-4-one (2:1 mixture of isomers) (81): colorless oil (16 mg): MS (ES+) 391.95, 391.97 (M+1).

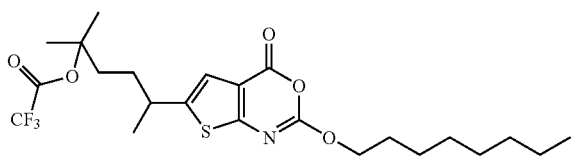

Trifluoro-acetic acid 1,1-dimethyl-5-(2-octyloxy-4-oxo-4H-thieno[2,3-d][1,3]oxazin-6-yl)-hexyl ester (82): colorless oil (61 mg): ¹H NMR (CDCl₃, 200 MHz) δ 0.89 (t, 3H, J=6.6 Hz), 1.26–1.69 (m, 8H), 1.76–1.88 (m, 4H), 2.97 (dq, 1H, J=7.0, 6.8 Hz), 4.41 (t, 2H, J=6.6 Hz), 6.98 (s, 1H). ¹³C NMR (CDCl₃, 100 MHz) δ 14.2, 21.5, 22.7, 22.8, 25.7, 25.8, 28.5, 29.3, 31.9, 35.8, 38.7, 40.3, 70.8, 89.1, 113.6, 114.6 (q, CF3, J=285.9 Hz), 117.3, 117.4, 146.8, 154.7, 156.4 (q, COCF₃, J=40.9 Hz), 157.3, 165.8. MS (ES+) 505.93 (M+1).

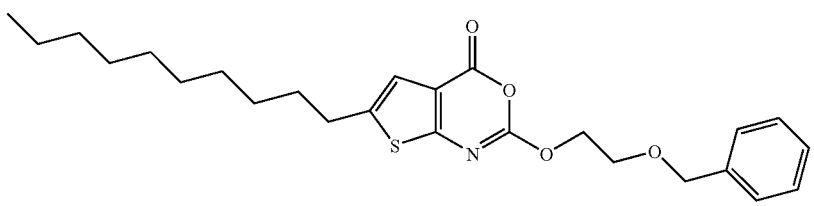

2-(2-Benzyloxy-ethoxy)-6-decyl-thieno[2,3-d][1,3]oxazin-4-one (97): yellow oil (68 mg, 50% yield): ¹H NMR (CDCl₃, 400 MHz) δ 0.88 (t, 3H, J=6.8 Hz), 1.26–1.32 (m, 14H), 1.66 (tt, 2H, J=14, 7.6 Hz), 2.76 (t, 2H, J=7.6 Hz), 3.81 (t, 2H, J=4.4 Hz), 4.57 (t, 2H, J=4.6 Hz), 4.60 (s, 2H), 6.95 (s, 1H), 7.25–7.34 (m, 5H). ¹³C NMR (CDCl₃, 100 MHz) δ 14.0, 22.6, 28.8, 29.2, 29.3, 29.4, 29.5, 30.2, 30.9, 31.8, 67.1, 69.3, 73.3, 113.7, 118.2, 127.6, 127.7, 128.4, 137.6, 141.3, 154.2, 156.7, 165.2.

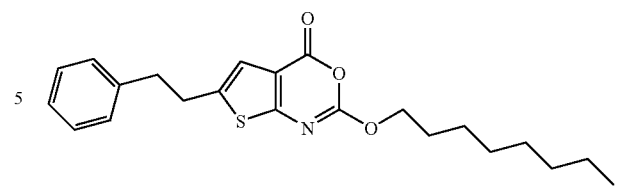

2-Octyloxy-6-phenethyl-thieno[2,3-d][1,3]oxazin-4-one (103): clear oil (84 mg, 88% yield) ¹H NMR (CDCl₃, 200 MHz) δ 0.89 (t, 3h, J=6.8 Hz), 1.28–1.43 (m, 10H), 1.79 (tt, 2H, J=7.6 Hz, J=7.2 Hz), 2.98 (t, 2H, J=7.2 Hz), 3.10 (t, 2H, J=7.6 Hz), 4.39 (t, 2H, J=6.8 Hz), 6.95 (s, 1H), 7.17–7.31 (m, 5H).

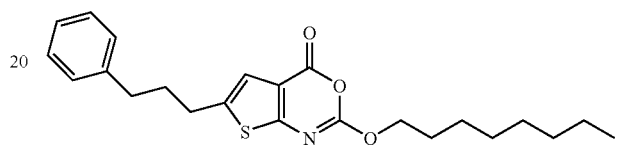

2-Octyloxy-6-(3-phenyl-propyl)-thieno[2,3-d][1,3]oxazin-4-one (104): white solid (72 mg, 75% yield) ¹H NMR (CDCl₃, 200 MHz) δ 0.88 (t, 3H, J=6.6 Hz), 1.21–1.50 (m, 10H), 1.79 (tt, 2H, J=7.0 Hz, J=6.6 Hz), 2.01 (tt, 2H, J=7.8 Hz, J=7.2 Hz), 2.69 (t, 2H, J=7.6 Hz), 2.80 (t, 2H, J=7.2 Hz), 4.40 (t, 2H, J=6.6 Hz), 6.98 (s, 1H), 7.16–7.35 (m, 5H).

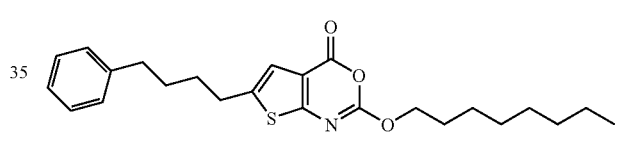

2-Octyloxy-6-(4-phenyl-butyl)-thieno[2,3-d][1,3]oxazin-4-one (92): pale yellow oil (218 mg, 78% yield) ¹H NMR (CDCl₃, 200 MHz) δ 0.887 (bt, 3H, 6.2 Hz), 1.08–1.52 (m, 10H), 1.60–1.90 (m, 6H), 2.54–2.72 (m, 2H), 2.72–2.88 (m, 2H), 4.40 (t, 2H, J=6.6 Hz), 6.95 (s, 1H), 7.09–7.38 (m, 5H); MS (ES) 414.59 (M+1), t_R(method D)=9.71 min.

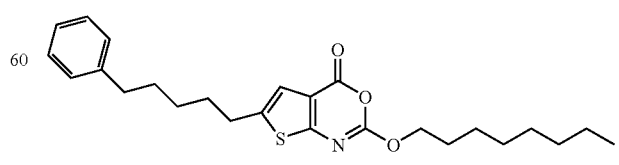

2-Octyloxy-6-(5-phenyl-pentyl)-thieno[2,3-d][1,3]oxazin-4-one (93): Pale yellow oil (223 mg, 94% yield) ¹H NMR (CDCl₃, 200 MHz) δ 0.887 (bt, 3H, J=6.2 Hz), 1.20–1.50 (m, 12H), 1.57–1.88 (m, 6H), 2.61 (t, 2H, J=7.4 Hz), 2.76 (t, 2H, J=6.8 Hz), 4.40 (t, 2H, J=6.6 Hz), 6.95 (t, 1H, J=1 Hz), 7.08–7.35 (m, 5H); MS (ES) 428.62 (M+1), $t_R$(method D)=10.69 min.

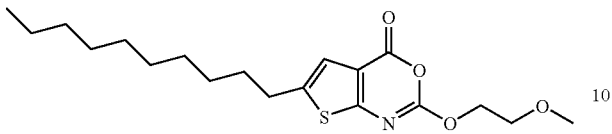

6-Decyl-2-(2-methoxy-ethoxy)-thieno[2,3-d][1,3]oxazin-4-one (96): off-white waxy solid (195 mg, 83% yield); m.p.= 38–41° C.; ¹H NMR (CDCl₃, 200 MHz) δ 0.879 (bt, 3H, J=6.2 Hz), 1.06–1.43 (m, 14H), 1.52–1.78 (m, 2H), 2.76 (t, 3H, J=7.0 Hz), 3.43 (s, 3H), 3.62–3.82 (m, 2H), 4.44–4.64 (m, 2H), 6.96 (s, 1H); MS (ES) 368.52 (M+1), $t_R$(method D)=8.00 min.

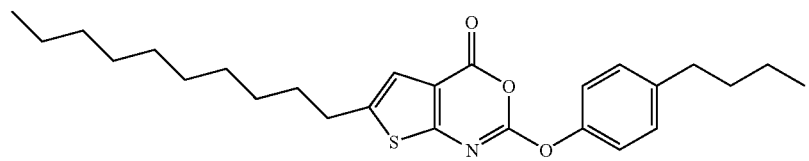

2-(4-Butyl-phenoxy)-6-decyl-thieno[2,3-d][1,3]oxazin-4-one (102): light yellow solid (145 mg, 79% yield); m.p.= 55–58° C.; ¹H NMR (CDCl₃, 400 MHz) δ 0.878 (t, 3H, J=6.0 Hz), 0.946 (t, 3H, J=7.6 Hz), 1.18–1.45 (m, 18H), 1.55–1.71 (m, 4H), 2.64 (t, 2H, J=7.6 Hz), 2.76 (t, 2H, J=7.6 Hz), 6.99 (s, 1H), 7.15 (d, 2H, J=8.4 Hz), 7.24 (d, 2H, J=8.4 Hz); MS (ES) 442.64 (M+1), $t_R$(method D)=12.19 min.

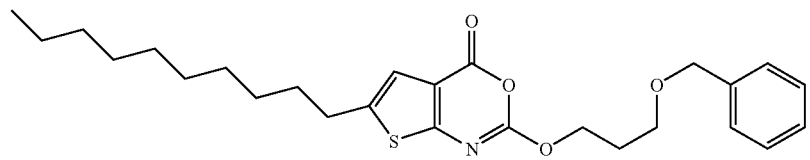

2-(3-Benzyloxy-propoxy)-6-decyl-thieno[2,3-d][1,3]oxazin-4-one (109): colorless oil (115 mg, 87% yield): ¹H NMR (CDCl₃, 200 MHz) δ 0.88 (t, 3H, J=6.6 Hz), 1.26–1.38 (m, 14H), 1.67 (tt, 2H, J=14.4, 7.4 Hz), 2.09 (tt, 2H, J=12.4, 6.2 Hz), 2.76 (t, 2H, J=7.4 Hz), 3.62 (t, 2H, J=6.2 Hz), 4.51 (s, 2H), 4.53 (t, 2H, J=6.4 Hz), 6.96 (t, 1H, J=1.1 Hz), 7.24–7.33 (m, 5H). ¹³C NMR (CDCl₃, 100 MHz) δ 14.04, 22.61, 28.78, 28.83, 29.22, 29.23, 29.44, 29.50, 30.25, 30.90, 31.82, 65.93, 67.46, 73.06, 113.59, 118.14, 127.60, 128.31, 138.09, 141.18, 154.30, 156.73, 165.54.

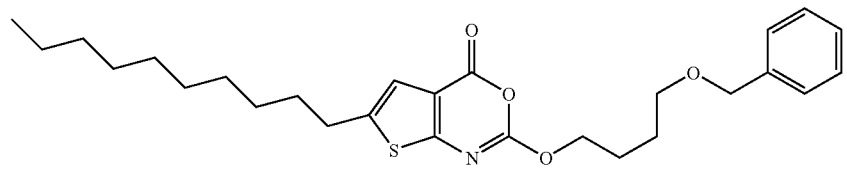

2-(3-Benzyloxy-butyloxy)-6-decyl-thieno[2,3-d][1,3]oxazin-4-one (111): colorless oil (19 mg, 36% yield): ¹H NMR (CDCl₃, 200 MHz) δ 0.88 (t, 3H, J=6.4 Hz), 1.26–1.38 (m, 14H), 1.63–1.99 (m, 14H), 2.76 (t, 2H, J=7.7 Hz), 3.54 (t, 2H, J=6.2 Hz), 4.44 (t, 2H, J=6.2 Hz), 4.51 (s, 2H), 6.96 (t, 1H, J=1.0 Hz), 7.28–7.35 (m, 5H).

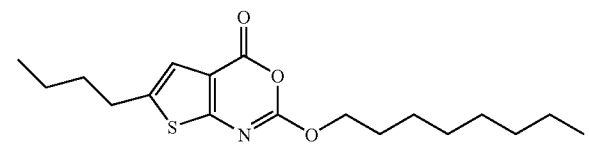

6-Butyl-2-octyloxy-thieno[2,3-d][1,3]oxazin-4-one (75): MS (ES/SIR): m/z 338.49 [MH⁺]. ¹H NMR (CDCl₃, 200 MHz): δ=0.78–1.03 (m, 6H), 1.15–1.53 (m, 12H), 1.54–1.90 (m, 4H), 2.77 (t, J=7.5 Hz, 2H), 4.40 (t, J=6.6 Hz, 2H), 6.96 (t, J=0.8 Hz, 1H).

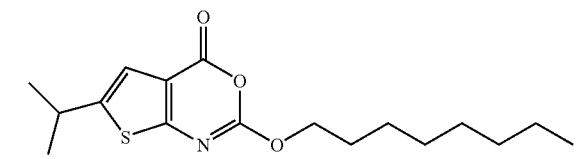

6-Isopropyl-2-octyloxy-thieno[2,3-d][1,3]oxazin-4-one (76): MS (ES/SIR): m/z 324.46 [MH+]. ¹H NMR (CDCl₃, 200 MHz): δ=0.88 (t, J=6.6 Hz, 3H), 1.18–1.52 (m, 16H), 1.70–1.88 (m, 2H), 2.98–3.22 (m, 1H), 4.40 (t, J=6.6 Hz, 2H), 6.98 (d, J=1.0 Hz, 1H).

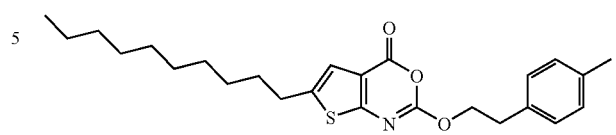

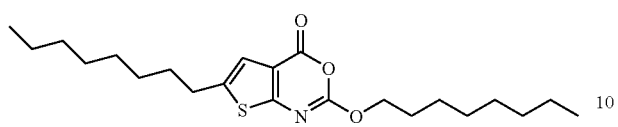

6-Octyl-2-octyloxy-thieno[2,3-d][1,3]oxazin-4-one (85): ¹H NMR (CDCl₃, 200 MHz): δ=0.80–1.00 (m, 6H), 1.12–1.52 (m, 20H), 1.57–1.90 (m, 4H), 2.76 (td, J=1.0, 7.6 Hz, 2H), 4.40 (t, J=6.6 Hz, 2H), 6.95 (t, J=1.1 Hz, 1H).

6-Decyl-2-(2-p-toly-ethoxy)-thieno[2,3-d][1,3]oxazin-4-one (107): ¹H NMR (CDCl₃, 200 MHz): δ=0.88 (t, J=6.6 Hz, 3H), 1.14–1.46 (m, 14H), 1.56–1.78 (m, 2H), 2.32 (s, 3H), 2.76 (t, J=7.4 Hz, 2H), 3.06 (t, J=7.0 Hz, 2H), 4.58 (t, J=7.0 Hz, 2H), 6.95 (t, J=1.1 Hz, 1H), 7.07–7.22 (m, 4H).

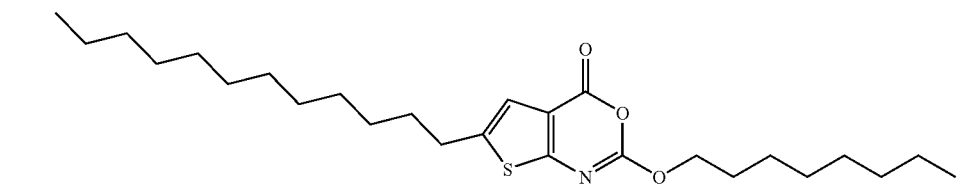

6-Dodecyl-2-octyloxy-thieno[2,3-d][1,3]oxazin-4-one (88): ¹H NMR (CDCl₃, 200 MHz): δ=0.80–0.98 (m, 6H), 1.16–1.52 (m, 28H), 1.58–1.88 (m, 4H), 2.76 (t, J=7.2 Hz, 2H), 4.40 (t, J=6.6 Hz, 2H), 6.95 (s, 1H).

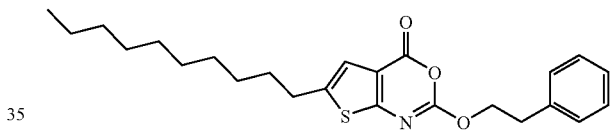

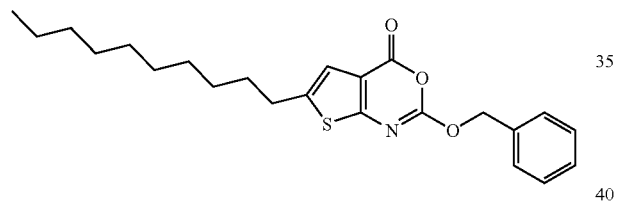

2-Benzyloxy-6-Decyl-thieno[2,3-d][1,3]oxazin-4-one (105): MS (ES/SIR): m/z 400.56 [MH+]. ¹H NMR (CDCl₃, 400 MHz): δ=0.88 (t, J=6.8 Hz, 3H), 1.17–1.42 (m, 14H), 1.67 (quint., J=7.4 Hz, 2H), 2.77 (t, J=7.1 Hz, 2H), 5.44 (s, 2H), 6.96 (s, 1H), 7.33–7.49 (m, 5H).

6-Decyl-2-phenethyloxy-thieno[2,3-d][1,3]oxazin-4-one (108): ¹H NMR (CDCl₃, 200 MHz): δ=0.88 (t, J=6.4 Hz, 3H), 1.14–1.46 (m, 14H), 1.56–1.76 (m, 2H), 2.76 (t, J=7.2 Hz, 2H), 3.11 (t, J=7.0 Hz, 2H), 4.60 (t, J=7.0 Hz, 2H), 6.95 (s, 1H), 7.18–7.42 (m, 5H).

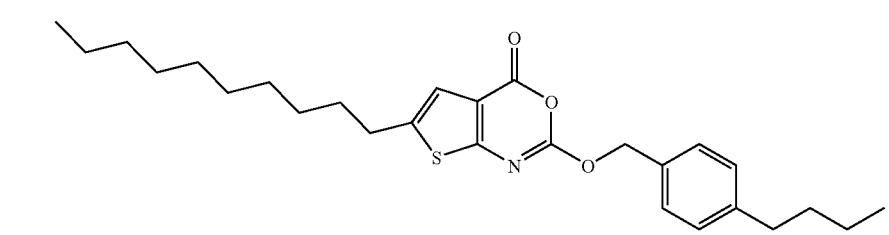

2-(4-Butylbenzyloxy)-6-Decyl-thieno[2,3-d][1,3]oxazin-4-one (106): ¹H NMR (CDCl₃, 200 MHz): δ=0.78–1.02 (m, 6H), 1.12–1.47 (m, 16H), 1.50–1.77 (m, 4H), 2.62 (t, J=7.5 Hz, 2H), 2.77 (t, J=7.6 Hz, 2H), 5.40 (s, 2H), 6.96 (s, 1H), 7.20 (d, J=8.0 Hz, 2H), 7.36 (d, J=8.2 Hz, 2H).

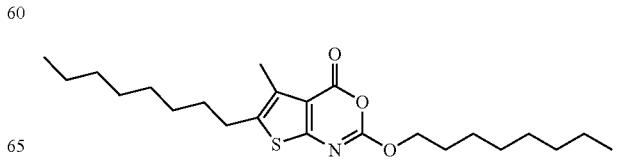

3-Methyl-6-octyl-2-octyloxy-5H-thieno[2,3-b]pyridin-4-one (87): 51 mg (60%). m.p. 36° C. ¹H NMR (CDCl₃, 200 MHz): δ 0.88 (t, J=6.6 Hz, 6H0, 1.10–1.94 (m, 24H), 2.35 (s, 3H), 2.69 (t, J=7.2 Hz, 2H), 4.38 (t, J=7.0 Hz, 2H); ¹³C NMR (CDCl₃, 75 MHz): δ 11.1, 12.3, 20.9, 23.9, 25.7, 26.6, 27.3, 27.4, 27.5, 27.6, 29.4, 30.0, 30.1, 68.6, 11.5, 126.9, 132.0, 153.1, 155.1, 162.9.

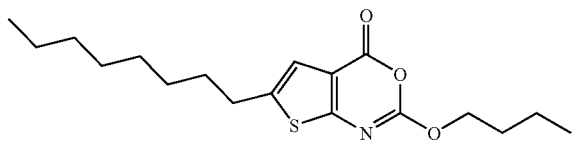

2-Butoxy-6-octyl-5H-thieno[2,3-b]pyridin-4-one (95): 265 mg (93%). ¹H NMR (CDCl₃, 200 MHz): δ 0.86 (t, J=6.6 Hz, 3H), 0.96 (t, J=7.2 Hz, 3H), 1.14–1.88 (m, 16H), 2.74 (t, J=7.4 Hz, 2H), 4.39 (t, J=6.6 Hz, 2H), 6.93 (s, 1H); ¹³C NMR (CDCl₃, 75 MHz): δ 11.9, 12.3, 17.2, 20.9, 27.2, 27.4, 27.5, 28.6, 29.2, 30.1, 68.5, 101.9, 116.5, 139.4, 152.7, 155.2, 164.0; MS (SIR): 338.48 (M+1).

2-Hexyloxy-6-octyl-5H-thieno[2,3-b]pyridin-4-one (94): 312 mg (94%). ¹H NMR (CDCl₃, 200 MHz): δ 0.86 (t, J=6.6 Hz, 3H), 0.89 (t, J=6.6 Hz, 3H), 1.15–1.54 (m, 16H), 1.54–1.88 (m, 4H), 2.74 (t, J=7.0 Hz, 2H), 4.38 (t, J=6.6 Hz, 2H), 6.94 (t, J=1.2 Hz, 1H); ¹³C NMR (CDCl₃, 75 MHz): δ 12.2, 12.3, 20.8, 20.9, 23.6, 26.6, 27.2, 27.4, 27.5, 28.6, 29.2, 29.6, 30.1, 68.8, 101.9, 116.5, 139.4, 152.7, 155.2, 164.0; MS (SIR): 366.55 (M+1).

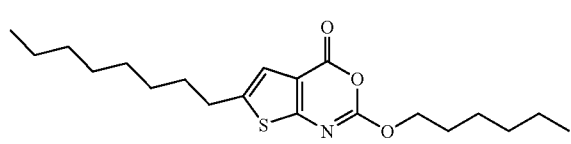

2-Dodecyloxy-6-octyl-5H-thieno[2,3-b]pyridin-4-one (100): 322 mg (91%). ¹H NMR (CDCl₃, 200 MHz): δ 0.87 (t, J=6.2 Hz, 6H), 1.04–1.52 (m, 28H), 1.52–1.90 (m, 4H), 2.75 (t, J=7.0 Hz, 2H), 4.38 (t, J=6.5 Hz, 2H), 6.94 (s, 1H); ¹³C NMR (CDCl₃, 75 MHz): δ 12.3, 12.4, 20.9, 21.0, 23.9, 26.6, 27.2, 27.4, 27.5, 27.6, 27.7, 27.8, 27.9, 28.6, 29.2, 30.1, 30.2, 68.8, 11.9, 116.5, 139.4, 152.7, 155.2, 164.0; MS (SIR): 450.71 (M+1).

6-Decyl-2-phenoxy-5H-thieno[2,3-b]pyridin-4-one (101): 322 mg (86%). ¹H NMR (CDCl₃, 200 MHz): δ 0.87 (t, J=6.6 Hz, 3H), 1.15–1.45 (m, 14H), 1.55–1.75 (m, 2H), 2.75 (t, J=7.0 Hz, 2H), 7.0 (t, J=1 Hz, 1H), 7.22–7.51 (m, 5H); ¹³C NMR (CDCl₃, 75 MHz): δ 12.4, 21.0, 27.2, 27.5, 27.6, 27.6, 27.8, 28.6, 29.2, 30.2, 97.7, 97.7, 102.5, 116.5, 119.4, 124.9, 128.0, 140.7, 149.5, 152.3, 154.5, 163.1; MS (SIR): 358.48 (M+1).

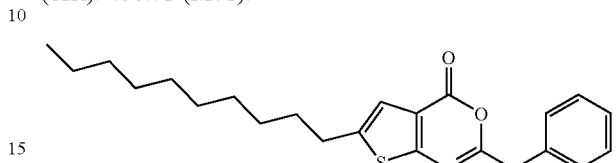

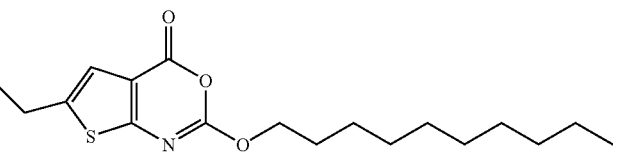

2-Decyloxy-6-octyl-5H-thieno[2,3-b]pyridin-4-one (110): 313 mg (69%). ¹H NMR (CDCl₃, 200 MHz): δ 0.85 (t, J=6.4 Hz, 6H), 1.16–1.50 (m, 24H), 1.50–1.88 (m, 4H), 2.74 (t, J=6.8 Hz, 2H), 4.38 (t, J=6.6 Hz, 2H), 6.93 (s, 1H); ¹³C NMR (CDCl₃, 75 MHz): δ 12.3, 20.9, 20.9, 23.9, 26.6, 27.2, 27.4, 27.5, 27.6, 27.7, 27.8, 28.6, 29.2, 30.1, 30.1, 68.8, 111.9, 116.5, 139.3, 152.6, 155.2, 164.0.

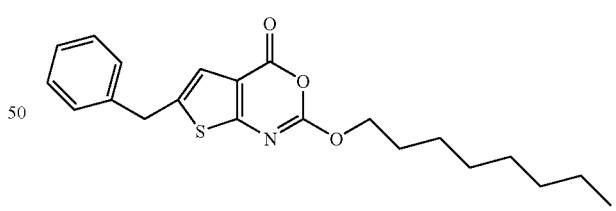

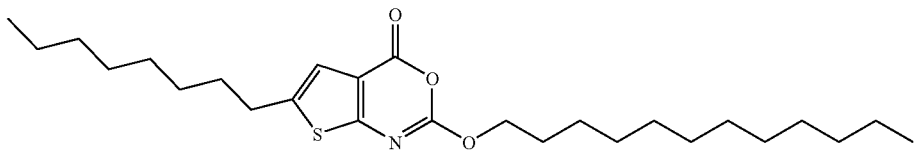

6-Benzyl-2-octyloxythieno[2,3-d][1,3]oxazin-4-one (77)

Light yellow oil in 53% yield.

$^1$H NMR (CDCl$_3$, 200 MHz): δ 7.20–7.40 (m, 5H), 6.98 (t, 1H, J=1.0 Hz), 4.38 (t, 2H, J=6.6 Hz), 4.09 (s, 2H), 1.76 (q, 2H, J=7.2 Hz), 1.10–1.50 (m, 10H), 0.88 (t, 3H, J=7.0 Hz). MS (ES) [M$^+$+1] 372.51.

6-Decyl-2-(1-methylheptyloxy)thieno[2,3-d][1,3]oxazin-4-one (90)

Light yellow oil in 22% yield.

$^1$H NMR (CDCl$_3$, 200 MHz): δ 6.96 (s, 1H), 5.13 (tq, 1H, J=5.8, 6.2 Hz), 2.76 (t, 2H, J=7.6 Hz), 1.58–1.83 (m, 4H), 1.08–1.50 (m, 26H), 0.80–1.00 (m, 6H). MS (ES) [M$^+$+1] 380.57.

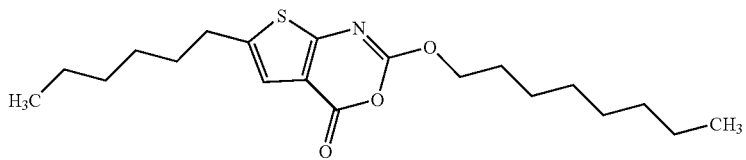

6-Hexyl-2-octyloxythieno[2,3-d][1,3]oxazin-4-one (84)

Light yellow oil in 30% yield.

$^1$H NMR (CDCl$_3$, 200 MHz): δ 6.94 (s, 1H), 4.39 (t, 2H, J=6.6 Hz), 2.76 (t, 2H, J=7.2 Hz), 1.76 (q, 2H, J=7.4 Hz), 1.64 (q, 2H, J=7.6 Hz), 1.08–1.50 (m, 14H), 0.80–0.95 (m, 6H). MS (ES) [M$^+$+1] 366.55.

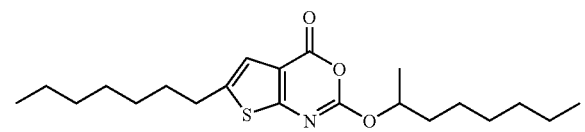

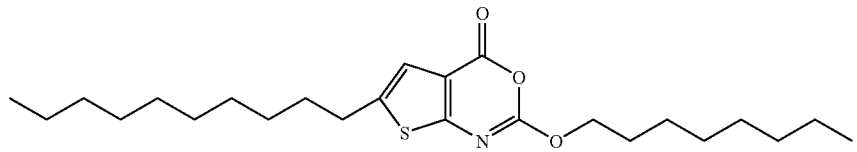

6-Decyl-2-octyloxythieno[2,3-d][1,3]oxazin-4-one (86)

Light yellow oil in 50% yield.

$^1$H NMR (CDCl$_3$, 200 MHz): δ 6.94 (s, 1H), 4.39 (t, 2H, J=6.6 Hz), 2.76 (t, 2H, J=7.2 Hz), 1.76 (q, 2H, J=7.4 Hz), 1.64 (q, 2H, J=7.6 Hz), 1.08–1.50 (m, 20H), 0.80–0.95 (m, 6H). MS (ES) [M$^+$+1] 422.56

6-Heptyl-2-(1-methylheptyloxy)thieno[2,3-d][1,3]oxazin-4-one (91)

Light yellow oil in 28% yield.

$^1$H NMR (CDCl$_3$, 200 MHz): δ 6.96 (s, 1H), 5.13 (tq, 1H, J=6.2, 6.6 Hz), 2.76 (t, 2H, J=7.6 Hz), 1.58–1.83 (m, 4H), 1.08–1.50 (m, 20H), 0.80–1.00 (m, 6H). MS (ES) [M$^+$+1] 422.65

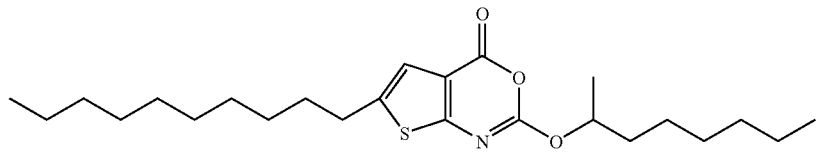

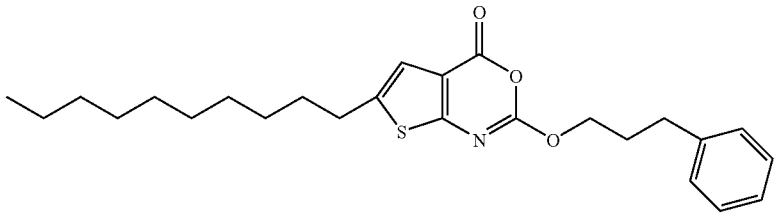

6-Decyl-2-(4-phenylpropoxy)thieno[2,3-d][1,3]oxazin-4-one (99)

Light yellow oil in 28% yield.

$^1$H NMR (CDCl$_3$, 200 MHz): δ 7.17–7.38 (m, 5H), 6.96 (s, 1H), 4.42 (t, 2H, J=6.6 Hz), 2.72–2.85 (m, 4H), 2.05–2.20 (m, 2H), 1.50–1.75 (m, 2H), 1.20–1.40 (m, 16H), 0.88 (t, 3H, J=6.6 Hz). MS (ES) [M$^+$+1] 428.62.

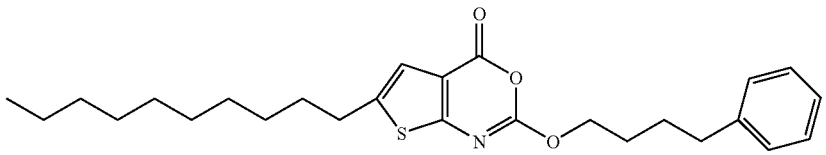

6-Decyl-2-(4-phenylbutoxy)thieno[2,3-d][1,3]oxazin-4-one (98)

Light yellow oil in 25% yield.

$^1$H NMR (CDCl$_3$, 200 MHz): δ 7.10–7.38 (m, 5H), 6.96 (s, 1H), 4.42 (t, 2H, J=6.4 Hz), 2.60–2.80 (m, 4H), 1.75–1.83 (m, 4H), 1.50–1.70 (m, 2H), 1.18–1.40 (m, 16H), 0.88 (t, 3H, J=6.4 Hz).

EXAMPLE 23

Pancreatic Lipase Assay

The use of a pancreatic lipase assay has been described in the literature (Hadvary, P. et al. *Biochem. J.* (1988) 256: 357–361; Hadvary, P. et al. *Biochem. J.* (1991) 266:2021–2027). Pancreatic lipase activity was measured using a 718 Stat Titrino (Brinkmann) programmed to maintain a pH of 8.0 using 0.1 N NaOH. The substrate mixture (pH 8) contained 1 mM taurochenodeoxycholate (Sigma), 9 mM taurodeoxycholate (Sigma), 0.1 mM cholesterol (Sigma), 1 mM phosphatidylcholine (Sigma), 1.5% BSA, 2 mM Tris base, 100 mM NaCl, 10 mM CaCl$_2$, and 3% triolein (Sigma). The mixture (5 mL) was emulsified via sonication at room temperature, and added to the titration vessel with rapid stirring. The Stat Titrino was turned on and lipase (7.0 nM type VI-S porcine pancreatic lipase (Sigma) dissolved in PBS) was added to the vessel. After 10 min, inhibitor (700 nM dissolved in 100% DMSO) was added and the reaction continued for an additional 12.5 min. The k values were determined for the 12.5 min after the addition of the inhibitor using a one phase exponential association equation, Y=Ymax*(1−exp(−k*X)), k values for lipase alone were 0.0004±0.0001 sec. The k values for compounds disclosed herein are >0.0004±0.0001 sec.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound having the structure:

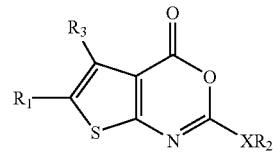

wherein,

Y is O;

XR$_2$ is
—N([CH$_2$]$_7$CH$_3$)C(O)NH(CH$_2$)$_7$CH$_3$,
—N([CH$_2$]$_6$CH$_3$)C(O)NH(CH$_2$)$_6$CH$_3$,
—NH(CH$_2$)$_q$CH$_3$,
—NH(C$_6$H$_4$)O(C$_6$H$_5$),
—N(CH$_3$)(CH$_2$)$_5$CH$_3$,
—NHCH[(CH$_2$)$_3$CH$_3$]$_2$,
—NHCH(CH$_3$)[(CH$_2$)$_5$CH$_3$, or
—N([CH$_2$]$_7$CH$_3$)$_2$;

q is an integer from 6 to 15;

R$_1$ is H, substituted C$_1$–C$_{15}$ alkyl, or unsubstituted C$_2$–C$_{15}$ alkyl, C$_1$–C$_8$ alkylaryl, —C(O)OR$_4$, —C(O)NR$_4$R$_5$, —CR$_6$R$_6$,OR$_4$, —CR$_6$R$_6$,OC(O)R$_4$, —CR$_6$R$_6$,OC(O)NHR$_7$, —C(O)NR$_8$R$_9$NR$_8$R$_9$, —N(R$_5$)C(O)NHR$_5$, or CH$_2$R$_4$;

$R_3$ is H, —$CH_3$, —$CH_2OCH_3$ or $C_3$–$C_{10}$ cycloalkyl, wherein
$R_4$ is H or a substituted or unsubstituted, straight chain or branched, $C_6$–$C_{30}$ alkyl, aryl, —$CH_2$-aryl, aryl —$C_1$–$C_{30}$ alkyl, heteroaryl-$C_1$–$C_{30}$ alkyl or $C_3$–$C_{10}$ cycloalkyl;
$R_6$ and $R_{6'}$ are each independently H, substituted or unsubstituted $C_1$–$C_6$ alkyl, dialkyl or $C_3$–$C_{10}$ cycloalkyl or together form a 3–7 membered cycloalkyl or aryl group;
$R_7$ is H or substituted or unsubstituted $C_1$–$C_{12}$ alkyl or $C_3$–$C_{10}$ cycloalkyl; and
$R_8$ and $R_9$ are each independently H, substituted or unsubstituted $C_1$–$C_6$ alkyl, $C_1$–$C_6$ alkoxy, $C_1$–$C_6$ alkylaryl, or $NR_8R_9$ together form a substituted piperazine or piperidine ring or a dihydro-1H-isoquinoline ring system, or a specific enantiomer thereof, or a specific tautomer, or a pharmaceutically acceptable salt thereof.

2. The compound of claim 1 having the structure:

wherein,
$R_1$ is H,
—$(CH_2)_rCH_3$,
—$CH(CH_3)_2$,
—$CH(CH_3)CH_2C(CH_3)_3$,
—$CH(CH_3)(CH_2)_3C(=CH_2)CH_3$,
—$CH(CH_3)(CH_2)_3C(CH_3)_2OC(O)CH_3$,
—$CH(CH_3)[CH_2]_3C(CH_3)_2OCH_3$,
—$CH_s(C_6H_5)$,
—$C(O)OH$,
—$C(O)NH(CH_2)_tCH_3$,
—$C(O)O(CH_2)_uCH_3$,
—$C(O)OCH[(CH_2)_3CH_3]_2$,
—$C(O)NH(CH_2)_vCH_3$,
—$C(O)N(CH_3)_2$,
—$C(O)NHCH_2(C_6H_5)$,
—$C(O)NHCH_2(C_5H_4N)$,
—$C(O)N[(CH_2)_3CH_3]_2$,
—$C(O)N[(CH_2)_5CH_3]_2$,
—$C(O)N[(CH_2)_7CH_3]_2$,
—$C(O)NH(C_6H_{11})$,
—$C(O)(NC_4H_8N)CH_2(C_6H_5)$,
—$C(O)(NC_5H_9)CH_2(C_6H_5)$,
—$C(O)NH(CH_2)_3O(C_6H_5)$,
—$C(O)NHCH[(CH_2)_3CH_3]_2$,
—$C(O)NH(CH_2)_3N(CH_3)_2$,
—$C(O)NHCH_2C(O)OCH_2(C_6H_5)$,
—$C(O)N(CH_3)CH_2(C_5H_3N[CH_3])$,
—$C(O)NH(CH_2)_2(C_5H_4N)$,
—$C(O)N(CH_2CH_3)(CH_2)_2(C_5H_4N)$,
—$C(O)NHCH_2(C_4H_3O)$,
—$C(O)(NC_4H_8N)[CH_2]_2(NC_5H_{10})$,
—$C(O)NHCH_2CH(CH_3)_2$,
—$C(O)NHCH_2(C_5H_4N)$,
—$C(O)NHCH_2C(CH_3)_3$,
—$C(O)(NC_4H_8N)CH_2C(O)NHCH(CH_3)_2$,
—$C(O)(NC_9H_8)[OCH_3]_2$,
—$C(O)NHCH_2(C_6H_3[OCH_3]_2)$,
—$C(O)NHCH_2(C_7H_5O_2)$,
—$C(O)NH(CH_2)_2O(C_6H_5)$,
—$C(O)NH(CH_2)_2OCH_3$,
—$C(O)NH(CH_2)_3OCH_3$,
—$C(O)NH(CH_2)_4(C_6H_5)$, or
—$C(O)NH(CH_2)_3(C_6H_5)$;
$r$ is an integer from 1 to 15;
$s$ is an integer from 0 to 6;
$t$ is an integer from 0 to 6;
$u$ is an integer from 3 to 8;
$v$ is an integer from 5 to 15;
$XR_2$ is
—$N([CH_2]_7CH_3)C(O)NH(CH_2)_7CH_3$,
—$N([CH_2]_6CH_3)C(O)NH(CH_2)_6CH_3$,
—$NH(CH_2)_qCH_3$,
—$NH(C_6H_4)O(C_6H_5)$,
—$N(CH_3)(CH_2)_5CH_3$,
—$NHCH[(CH_2)_3CH_3]_2$,
—$NHCH(CH_3)[CH_2]_5CH_3$, or
—$N([CH_2]_7CH_3)_2$;
$q$ is an integer from 6 to 15; and
$R_3$ is H, —$CH_3$, —$CH_2OCH_3$ or $C_3$–$C_{10}$ cycloalkyl.

3. The compound of claim 2, having the structure:

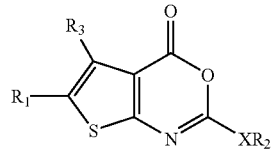

wherein,
$R_1$ is H,
—$(CH_2)_3CH_3$,
—$(CH_2)_5CH_3$,
—$(CH_2)_6CH_3$,
—$(CH_2)_7CH_3$,
—$(CH_2)_9CH_3$,
—$(CH_2)_{11}CH_3$,
—$CH(CH_3)_2$,
—$CH(CH_3)CH_2C(CH_3)_3$,
—$CH(CH_3)(CH_2)_3C(=CH_2)CH_3$,
—$CH(CH_3)(CH_2)_3C(CH_3)_2OC(O)CH_3$,
—$CH(CH_3)[CH_2]_3C(CH_3)_2OCH_3$,
—$CH_2(C_6H_5)$,
—$(CH_2)_2(C_6H_5)$,
—$(CH_2)_3(C_6H_5)$,
—$(CH_2)_4(C_6H_5)$,
—$(CH_2)_5(C_6H_5)$,
—$C(O)OH$,
—$C(O)NHCH_3$,
—$C(O)NHCH_2CH_3$,
—$C(O)NH(CH_2)_3CH_3$,
—$C(O)OCH_2(C_6H_5)$,
—$C(O)O(CH_2)_5CH_3$,
—$C(O)O(CH_2)_6CH_3$,
—$C(O)O(CH_2)_7CH_3$,
—$C(O)OCH[(CH_2)_3CH_3]_2$,
—$C(O)NH(CH_2)_5CH_3$,
—$C(O)NH(CH_2)_7CH_3$,
—$C(O)NH(CH_2)_9CH_3$,
—$C(O)NH(CH_2)_{11}CH_3$,
—$C(O)NH(CH_2)_{15}CH_3$,
—$C(O)N(CH_3)_2$,
—$C(O)NHCH_2(C_6H_5)$,
—$C(O)NHCH_2(C_5H_4N)$,
—$C(O)N[(CH_2)_3CH_3]_2$,
—$C(O)N[(CH_2)_5CH_3]_2$, —C(O)N[(CH$_2$)$_7$CH$_3$]$_2$,
—C(O)NH(C$_6$H$_{11}$),
—C(O)(NC$_4$H$_8$N)CH$_2$(C$_6$H$_5$),
—C(O)(NC$_5$H$_9$)CH$_2$(C$_6$H$_5$),
—C(O)NH(CH$_2$)$_3$O(C$_6$H$_5$),
—C(O)NHCH[(CH$_2$)$_3$CH$_3$]$_2$,
—C(O)NH(CH$_2$)$_3$N(CH$_3$)$_2$,
—C(O)NHCH$_2$C(O)OCH$_2$(C$_6$H$_5$),
—C(O)N(CH$_3$)CH$_2$(C$_5$H$_3$N[CH$_3$]),
—C(O)NH(CH$_2$)$_2$(C$_5$H$_4$N),
—C(O)N(CH$_2$CH$_3$)(CH$_2$)$_2$(C$_5$H$_4$N),
—C(O)NHCH$_2$(C$_4$H$_3$O),
—C(O)(NC$_4$H$_8$N)[CH$_2$]$_2$(NC$_5$H$_{10}$),
—C(O)NHCH$_2$CH(CH$_3$)$_2$,
—C(O)NHCH$_2$(C$_5$H$_4$N),
—C(O)NHCH$_2$C(CH$_3$)$_3$,
—C(O)(NC$_4$H$_8$N)CH$_2$C(O)NHCH(CH$_3$)$_2$,
—C(O)(NC$_9$H$_8$)[OCH$_3$]$_2$,
—C(O)NHCH$_2$(C$_6$H$_3$[OCH$_3$]$_2$),
—C(O)NHCH$_2$(C$_7$H$_5$O$_2$),
—C(O)NH(CH$_2$)$_2$O(C$_6$H$_5$),
—C(O)NH(CH$_2$)$_2$OCH$_3$,
—C(O)NH(CH$_2$)$_3$OCH$_3$,
—C(O)NH(CH$_2$)$_4$(C$_6$H$_5$), or
—C(O)NH(CH$_2$)$_3$(C$_6$H$_5$);
XR$_2$ is —N([CH$_2$]$_7$CH$_3$)C(O)NH(CH$_2$)$_7$CH$_3$,
—N([CH$_2$]$_6$CH$_3$)C(O)NH(CH$_2$)$_6$CH$_3$,
—NH(CH$_2$)$_6$CH$_3$,
—NH(CH$_2$)$_7$CH$_3$,
—NH(CH$_2$)$_{11}$CH$_3$,
—NH(CH$_2$)$_{13}$CH$_3$,
—NH(CH$_2$)$_{15}$CH$_3$,
—NH(C$_6$H$_4$)O(C$_6$H$_5$),
—N(CH$_3$)(CH$_2$)$_5$CH$_3$,
—NHCH[(CH$_2$)$_3$CH$_3$]$_2$,
—NHCH(CH$_3$)[CH$_2$]$_5$CH$_3$, or
—N([CH$_2$]$_7$CH$_3$)$_2$; and
R$_3$ is H, —CH$_3$ or —CH$_2$OCH$_3$.

4. A process of manufacturing a compound having the structure:

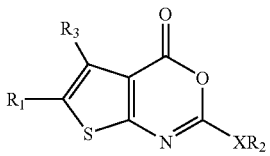

wherein,
XR$_2$ is
—N([CH$_2$]$_7$CH$_3$)C(O)NH(CH$_2$)$_7$CH$_3$,
—N([CH$_2$]$_6$CH$_3$)C(O)NH(CH$_2$)$_6$CH$_3$,
—NH(CH$_2$)$_q$CH$_3$,
—NH(C$_6$H$_4$)O(C$_6$H$_5$),
—N(CH$_3$)(CH$_2$)$_5$CH$_3$,
—NHCH[(CH$_2$)$_3$CH$_3$]$_2$,
—NHCH(CH$_3$)[CH$_2$]$_5$CH$_3$, or
—N([CH$_2$]$_7$CH$_3$)$_2$;
q is an integer from 6 to 15;
R$_1$ is H, substituted or unsubstituted C$_1$–C$_{15}$ alkyl, or unsubstituted C$_2$–C$_{15}$ alkyl, C$_1$–C$_8$ alkylaryl, —C(O)OR$_4$, —C(O)NR$_4$R$_5$, —CR$_6$R$_6'$OR$_4$, —CR$_6$R$_6'$OC(O)R$_4$, —CR$_6$R$_6'$OC(O)NHR$_7$, —C(O)NR$_8$R$_9$, NR$_8$R$_9$NR$_8$R$_9$, —N(R$_5$)C(O)NHR$_5$, or CH$_2$R$_4$;
R$_2$ is a substituted or unsubstituted, straight chain C$_1$–C$_{30}$ alkyl or branched C$_3$–C$_{30}$ alkyl, aryl, alkylaryl, arylalkyl, heteroarylalkyl or cycloalkyl;
R$_3$ is H or substituted or unsubstituted C$_1$–C$_6$ alkyl-CH$_3$, —CH$_2$OCH$_3$ or cycloalkyl;
R$_4$ is H or a substituted or unsubstituted, straight chain or branched, C$_6$–C$_{30}$ alkyl, aryl, —CH$_2$-aryl, arylalkyl, heteroarylalkyl or cycloalkyl;
R$_5$ is H or a substituted or unsubstituted, straight chain or branched, C$_6$–C$_{30}$ alkyl, aryl, arylalkyl, heteroarylalkyl or cycloalkyl;
R$_6$ and R$_6'$ are each independently H, substituted or unsubstituted C$_1$–C$_6$ alkyl, dialkyl or cycloalkyl or together form a 3–7 membered cycloalkyl or aryl group ring system;
R$_7$ is H or substituted or unsubstituted C$_1$–C$_{12}$ alkyl or cycloalkyl;
R$_8$ and R$_9$ are each independently H, substituted or unsubstituted C$_1$–C$_6$ alkyl, C$_1$–C$_6$ alkoxy, C$_1$–C$_6$ alkylaryl, or NR$_8$R$_9$ together form a substituted piperazine or piperidine ring or a dihydro-1H-isoquinoline ring system,
comprising
(a) reacting

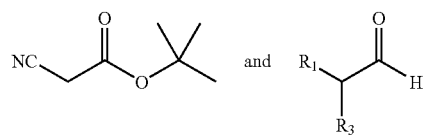

in the presence of sulfur, a base and solvent to produce:

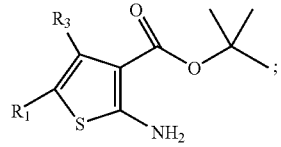

(b) reacting the product of step (a) with

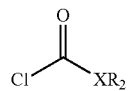

in the presence of a base to produce:

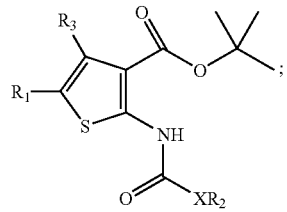

(c) reacting the product of step (b) with trifluoroacetic acid (TFA) in the presence of solvent to produce:

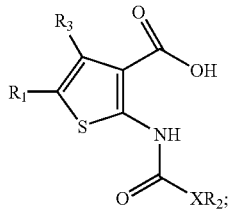

(d) reacting the product of step (c) with SOCl$_2$ in the presence of solvent to produce the compound.

5. A compound having the structure:

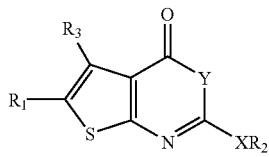

wherein,

X is O, S, or CH$_2$;

Y is O;

R$_1$ is H, substituted C$_1$–C$_{15}$ alkyl, unsubstituted C$_2$–C$_{15}$ alkyl, C$_1$–C$_8$ alkylaryl, —C(O)OR$_4$, —C(O)NR$_4$R$_5$, —CR$_6$R$_6'$OR$_4$, —CR$_6$R$_6'$OC(O)R$_4$, —CR$_6$R$_6'$OC(O)NHR$_7$, —C(O)NR$_8$R$_9$ NR$_8$R$_9$, —N(R$_5$)C(O)NHR$_5$, or CH$_2$R$_4$;

R$_2$ is a substituted or unsubstituted, straight chain C$_1$–C$_{30}$ alkyl or branched C$_3$–C$_{30}$ alkyl, aryl, alkylaryl, arylalkyl, heteroarylalkyl or cycloalkyl; and R$_3$ is H, —CH$_3$, —CH$_2$OCH$_3$ or C$_3$–C$_{10}$ cycloalkyl, wherein R$_4$ is H or a substituted or unsubstituted, straight chain or branched, C$_6$–C$_{30}$ alkyl, aryl, —CH$_2$-aryl, aryl —C$_1$–C$_{30}$ alkyl, heteroaryl-C$_1$–C$_{30}$ alkyl or C$_3$–C$_{10}$ cycloalkyl;

R$_5$ is H or a substituted or unsubstituted, straight chain or branched, C$_6$–C$_{30}$ alkyl, aryl C$_1$–C$_{30}$ alkyl, heteroarylalkyl or cycloalkyl;

R$_6$ and R$_6'$ are each independently H, substituted or unsubstituted C$_1$–C$_6$ alkyl, dialkyl or C$_3$–C$_{10}$ cycloalkyl or together form a 3–7 membered cycloalkyl or aryl group;

R$_7$ is H or substituted or unsubstituted C$_1$–C$_{12}$ alkyl or C$_3$–C$_{10}$ cycloalkyl; and R$_8$ and R$_9$ are each independently H, substituted or unsubstituted C$_1$–C$_6$ alkyl, C$_1$–C$_6$ alkoxy, C$_1$–C$_6$ alkylaryl, or NR$_8$R$_9$ together form a substituted piperazine or piperidine ring or a dihydro-1H-isoquinoline ring system, or a specific enantiomer thereof, or a specific tautomer, or a pharmaceutically acceptable salt thereof.

6. The compound of claim 1, having the structure:

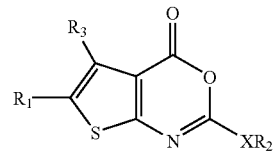

wherein,

X is O or S;

R$_1$ is H, —C(O)OR$_4$, —C(O)NR$_4$R$_5$, —CR$_6$R$_6'$OR$_4$, —CR$_6$R$_6'$OC(O)R$_4$, —CR$_6$R$_6'$OC(O)NHR$_7$, or CH$_2$R$_4$;

R$_2$ is a substituted or unsubstituted, straight chain or branched C$_6$–C$_{30}$ alkyl, arylalkyl, heteroarylalkyl or cycloalkyl; and R$_3$ is H, —CH$_3$, —CH$_2$OCH$_3$ or C$_3$–C$_{10}$ cycloalkyl, wherein, R$_4$ is H or a substituted or unsubstituted, straight chain or branched, C$_6$–C$_{30}$ alkyl, arylalkyl, heteroarylalky or cycloalkyl;

R$_5$ is H or a substituted or unsubstituted, straight chain or branched, C$_6$–C$_{30}$ alkyl, arylalkyl, heteroarylalkyl or cycloalkyl;

R$_6$ and R$_6'$ are each independently H, substituted or unsubstituted C$_1$–C$_6$ alkyl, dialkyl or cycloalkyl or together form a 3–7 membered cycloalkyl or aryl group; and R$_7$ is H or substituted or unsubstituted C$_1$–C$_{12}$ alkyl or cycloalkyl.

7. The compound of claim 6, wherein

X is O;

R$_1$ is —C(O)O—(C$_6$–C$_{30}$) alkyl, —C(O)NH—(C$_6$–C$_{30}$) alkyl or —C(O)OCH$_2$(C$_6$H$_5$);

R$_2$ is C$_6$–C$_{30}$ alkyl; and

R$_3$ is —CH$_3$ or —CH$_2$OCH$_3$.

8. The compound of claim 6, wherein R$_3$ is H or —CH$_3$.

9. The compound of claim 8, wherein X is O.

10. The compound of claim 9, wherein R$_3$ is methyl.

11. The compound of claim 1, having the structure:

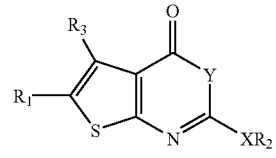

wherein,

Y is O;

R$_1$ is

H,

—(CH$_2$)$_r$CH$_3$,

—CH(CH$_3$)$_2$,

—CH(CH$_3$)CH$_2$C(CH$_3$)$_3$,

—CH(CH$_3$)(CH$_2$)$_3$C(=CH$_2$)CH$_3$,

—CH(CH$_3$)(CH$_2$)$_3$C(CH$_3$)$_2$OC(O)CH$_3$,

—CH(CH$_3$)[CH$_2$]$_3$C(CH$_3$)$_2$OCH$_3$,

—CH$_s$(C$_6$H$_5$),

—C(O)OH,

—C(O)NH(CH$_2$)$_t$CH$_3$,

—C(O)O(CH$_2$)$_u$CH$_3$,

—C(O)OCH[(CH$_2$)$_3$CH$_3$]$_2$,

—C(O)NH(CH$_2$)$_v$CH$_3$,

—C(O)N(CH$_3$)$_2$,

197

—C(O)NHCH$_2$(C$_6$H$_5$),
—C(O)NHCH$_2$(C$_5$H$_4$N),
—C(O)N[(CH$_2$)$_3$CH$_3$]$_2$,
—C(O)N[(CH$_2$)$_5$CH$_3$]$_2$,
—C(O)N[(CH$_2$)$_7$CH$_3$]$_2$,
—C(O)NH(C$_6$H$_{11}$),
—C(O)(NC$_4$H$_8$N)CH$_2$(C$_6$H$_5$),
—C(O)(NC$_5$H$_9$)CH$_2$(C$_6$H$_5$),
—C(O)NH(CH$_2$)$_3$O(C$_6$H$_5$),
—C(O)NHCH[(CH$_2$)$_3$CH$_3$]$_2$,
—C(O)NH(CH$_2$)$_3$N(CH$_3$)$_2$,
—C(O)NHCH$_2$C(O)OCH$_2$(C$_6$H$_5$),
—C(O)N(CH$_3$)CH$_2$(C$_5$H$_3$N[CH$_3$]),
—C(O)NH(CH$_2$)$_2$(C$_5$H$_4$N),
—C(O)N(CH$_2$CH$_3$)(CH$_2$)$_2$(C$_5$H$_4$N),
—C(O)NHCH$_2$(C$_4$H$_3$O),
—C(O)(NC$_4$H$_8$N)[CH$_2$]$_2$(NC$_5$H$_{10}$),
—C(O)NHCH$_2$CH(CH$_3$)$_2$,
—C(O)NHCH$_2$(C$_5$H$_4$N),
—C(O)NHCH$_2$C(CH$_3$)$_3$,
—C(O)(NC$_4$H$_8$N)CH$_2$C(O)NHCH(CH$_3$)$_2$,
—C(O)(NC$_9$H$_8$)[OCH$_3$]$_2$,
—C(O)NHCH$_2$(C$_6$H$_3$[OCH$_3$]$_2$),
—C(O)NHCH$_2$(C$_7$H$_5$O$_2$),
—C(O)NH(CH$_2$)$_2$O(C$_6$H$_5$),
—C(O)NH(CH$_2$)$_2$OCH$_3$,
—C(O)NH(CH$_2$)$_3$OCH$_3$,
—C(O)NH(CH$_2$)$_4$(C$_6$H$_5$), or
—C(O)NH(CH$_2$)$_3$(C$_6$H$_5$);
   r is an integer from 1 to 15;
   s is an integer from 0 to 6;
   t is an integer from 0 to 6;
   u is an integer from 3 to 8;
   v is an integer from 5 to 15;
XR$_2$ is
   —(CH$_2$)$_n$CH$_3$,
   —O(CH$_2$)$_m$CH$_3$,
   —OCH(CH$_3$)$_2$,
   —OCH(CH$_3$)(CH$_2$)$_5$CH$_3$,
   —OCH$_2$CH(CH$_3$)$_2$,
   —O(CH$_2$)$_2$OCH$_3$,
   —O(CH$_2$)$_2$OCH$_2$(C$_6$H$_5$),
   —O(CH$_2$)$_p$(C$_6$H$_5$),
   —OCH$_2$(C$_6$H$_4$[(CH$_2$)$_3$CH$_3$]),
   —O(C$_6$H$_4$[(CH$_2$)$_3$CH$_3$]),
   —O(CH$_2$)$_2$(C$_6$H$_4$[CH$_3$]),
   —O(CH$_2$)$_3$OCH$_2$(C$_6$H$_5$), or
   —O(CH$_2$)$_4$OCH$_2$(C$_6$H$_5$),
   n is an integer from 6 to 15;
   m is an integer from 1 to 15;
   p is an integer from 0 to 6; and
R$_3$ is H, —CH$_3$ or —CH$_2$OCH$_3$.

12. The compound of claim 11, having the structure:

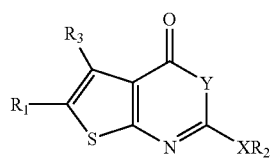

wherein,
Y is O;
R$_1$ is H,
   —(CH$_2$)$_3$CH$_3$,
   —(CH$_2$)$_5$CH$_3$,

198

—(CH$_2$)$_6$CH$_3$,
   —(CH$_2$)$_7$CH$_3$,
   —(CH$_2$)$_9$CH$_3$,
   —(CH$_2$)$_{11}$CH$_3$,
   —CH(CH$_3$)$_2$,
   —CH(CH$_3$)CH$_2$C(CH$_3$)$_3$,
   —CH(CH$_3$)(CH$_2$)$_2$C(=CH$_2$)CH$_3$,
   —CH(CH$_3$)(CH$_2$)$_2$C(CH$_3$)$_2$OC(O)CH$_3$,
   —CH(CH$_3$)[CH$_2$]$_3$C(CH$_3$)$_2$OCH$_3$,
   —CH$_2$(C$_6$H$_5$),
   —(CH$_2$)$_2$(C$_6$H$_5$),
   —(CH$_2$)$_3$(C$_6$H$_5$),
   —(CH$_2$)$_4$(C$_6$H$_5$),
   —(CH$_2$)$_5$(C$_6$H$_5$),
   —C(O)OH,
   —C(O)NHCH$_3$,
   —C(O)NHCH$_2$CH$_3$,
   —C(O)NH(CH$_2$)$_3$CH$_3$,
   —C(O)OCH$_2$(C$_6$H$_5$),
   —C(O)O(CH$_2$)$_5$CH$_3$,
   —C(O)O(CH$_2$)$_6$CH$_3$,
   —C(O)O(CH$_2$)$_7$CH$_3$,
   —C(O)OCH[(CH$_2$)$_3$CH$_3$]$_2$,
   —C(O)NH(CH$_2$)$_5$CH$_3$,
   —C(O)NH(CH$_2$)$_7$CH$_3$,
   —C(O)NH(CH$_2$)$_9$CH$_3$,
   —C(O)NH(CH$_2$)$_{11}$CH$_3$,
   —C(O)NH(CH$_2$)$_{15}$CH$_3$,
   —C(O)N(CH$_3$)$_2$,
   —C(O)NHCH$_2$(C$_6$H$_5$),
   —C(O)NHCH$_2$(C$_5$H$_4$N),
   —C(O)N[(CH$_2$)$_3$CH$_3$]$_2$,
   —C(O)N[(CH$_2$)$_5$CH$_3$]$_2$,
   —C(O)N[(CH$_2$)$_7$CH$_3$]$_2$,
   —C(O)NH(C$_6$H$_{11}$),
   —C(O)(NC$_4$H$_8$N)CH$_2$(C$_6$H$_5$),
   —C(O)(NC$_5$H$_9$)CH$_2$(C$_6$H$_5$),
   —C(O)NH(CH$_2$)$_3$O(C$_6$H$_5$),
   —C(O)NHCH[(CH$_2$)$_3$CH$_3$]$_2$,
   —C(O)NH(CH$_2$)$_3$N(CH$_3$)$_2$,
   —C(O)NHCH$_2$C(O)OCH$_2$(C$_6$H$_5$),
   —C(O)N(CH$_3$)CH$_2$(C$_5$H$_3$N[CH$_3$]),
   —C(O)NH(CH$_2$)$_2$(C$_5$H$_4$N),
   —C(O)N(CH$_2$CH$_3$)(CH$_2$)$_2$(C$_5$H$_4$N),
   —C(O)NHCH$_2$(C$_4$H$_3$O),
   —C(O)(NC$_4$H$_8$N)[CH$_2$]$_2$(NC$_5$H$_{10}$),
   —C(O)NHCH$_2$CH(CH$_3$)$_2$,
   —C(O)NHCH$_2$(C$_5$H$_4$N),
   —C(O)NHCH$_2$C(CH$_3$)$_3$,
   —C(O)(NC$_4$H$_8$N)CH$_2$C(O)NHCH(CH$_3$)$_2$,
   —C(O)(NC$_9$H$_8$)[OCH$_3$]$_2$,
   —C(O)NHCH$_2$(C$_6$H$_3$[OCH$_3$]$_2$),
   —C(O)NHCH$_2$(C$_7$H$_5$O$_2$),
   —C(O)NH(CH$_2$)$_2$O(C$_6$H$_5$),
   —C(O)NH(CH$_2$)$_2$OCH$_3$,
   —C(O)NH(CH$_2$)$_3$OCH$_3$,
   —C(O)NH(CH$_2$)$_4$(C$_6$H$_5$), or
   —C(O)NH(CH$_2$)$_3$(C$_6$H$_5$);
XR$_2$ is —(CH$_2$)$_6$CH$_3$,
   —(CH$_2$)$_{10}$CH$_3$,
   —(CH$_2$)$_{14}$CH$_3$,
   —O(CH$_2$)$_3$CH$_3$,
   —O(CH$_2$)$_5$CH$_3$,
   —O(CH$_2$)$_6$CH$_3$,
   —O(CH$_2$)$_7$CH$_3$,
   —O(CH$_2$)$_9$CH$_3$,
   —O(CH$_2$)$_{11}$CH$_3$,

—O(CH$_2$)$_{15}$CH$_3$,
—OCH(CH$_3$)$_2$,
—OCH(CH$_3$)(CH$_2$)$_5$CH$_3$,
—OCH$_2$CH(CH$_3$)$_2$,
—O(CH$_2$)$_2$OCH$_3$,
—O(CH$_2$)$_2$OCH$_2$(C$_6$H$_5$),
—O(CH$_2$)$_4$(C$_6$H$_5$),
—O(CH$_2$)$_3$(C$_6$H$_5$),
—O(CH$_2$)$_2$(C$_6$H$_5$),
—O(C$_6$H$_5$),
—OCH$_2$(C$_6$H$_5$),
—OCH$_2$(C$_6$H$_4$[(CH$_2$)$_3$CH$_3$]),
—O(C$_6$H$_4$[(CH$_2$)$_3$CH$_3$]),
—O(CH$_2$)$_2$(C$_6$H$_4$[CH$_3$]),
—O(CH$_2$)$_3$OCH$_2$(C$_6$H$_5$), or
—O(CH$_2$)$_4$OCH$_2$(C$_6$H$_5$), and R$_3$ is H, —CH$_3$ or —CH$_2$OCH$_3$.

13. The compound of claim 1, wherein the compound is selected from the group consisting of:

6-Heptyl-2-octyloxy-thieno[2,3-d][1,3]oxazin-4-one;
6-Hexyl-2-octyloxy-thieno[2,3-d][1,3]oxazin-4-one;
2-Octyloxy-6-(1,3,3-trimethyl-butyl)-thieno[2,3-d][1,3]oxazin-4-one;
6-Butyl-2-octyloxy-thieno[2,3-d][1,3]oxazin-4-one;
6-Heptyl-2-octylamino-thieno[2,3-d][1,3]oxazin-4-one;
6-Butyl-2-octylamino-thieno[2,3-d][1,3]oxazin-4-one;
6-Benzyl-2-octylamino-thieno[2,3-d][1,3]oxazin-4-one;
6-Heptyl-2-undecyl-thieno[2,3-d][1,3]oxazin-4-one;
6-(5-Methoxy-1,5-dimethyl-hexyl)-2-octyloxy-thieno[2,3-d][1,3]oxazin-4-one;
6-(1,5-Dimethyl-hex-4-enyl)-2-octyloxy-thieno[2,3-d][1,3]oxazin-4-one;
6-(1,5-Dimethyl-hex-5-enyl)-2-octyloxy-thieno[2,3-d][1,3]oxazin-4-one;
Trifluoro-acetic acid 1,1-dimethyl-5-(2-octyloxy-4-oxo-4H-thieno[2,3-d][1,3]oxazin-6-yl)-hexyl ester;
2-(2-Benzyloxy-ethoxy)-6-decyl-thieno[2,3-d][1,3]oxazin-4-one;
6-Heptyl-5-methyl-2-octyloxy-thieno[2,3-d][1,3]oxazin-4-one;
6-Methyl-2-octyloxy-thieno[2,3-d][1,3]oxazin-4-one;
2-Octyloxy-6-phenethyl-thieno[2,3-d][1,3]oxazin-4-one;
2-Octyloxy-6-(3-phenyl-propyl)-thieno[2,3-d][1,3]oxazin-4-one;
2-Octyloxy-6-(4-phenyl-butyl)-thieno[2,3-d][1,3]oxazin-4-one;
2-Octyloxy-6-(5-phenyl-pentyl)-thieno[2,3-d][1,3]oxazin-4-one;
6-Decyl-2-(2-methoxy-ethoxy)-thieno[2,3-d][1,3]oxazin-4-one;
2-(4-Butyl-phenoxy)-6-decyl-thieno[2,3-d][1,3]oxazin-4-one;
2-(3-Benzyloxy-propoxy)-6-decyl-thieno[2,3-d][1,3]oxazin-4-one;
2-(3-Benzyloxy-butyloxy)-6-decyl-thieno[2,3-d][1,3]oxazin-4-one;
6-Isopropyl-2-octyloxy-thieno[2,3-d][1,3]oxazin-4-one;
6-Octyl-2-octyloxy-thieno[2,3-d][1,3]oxazin-4-one;
6-Dodecyl-2-octyloxy-thieno[2,3-d][1,3]oxazin-4-one;
2-Benzyloxy-6-Decyl-thieno[2,3-d][1,3]oxazin-4-one;
2-(4-Butylbenzyloxy)-6-Decyl-thieno[2,3-d][1,3]oxazin-4-one;
6-Decyl-2-(2-p-tolyl-ethoxy)-thieno[2,3-d][1,3]oxazin-4-one;
6-Decyl-2-phenethyloxy-thieno[2,3-d][1,3]oxazin-4-one;
6-Benzyl-2-octyloxythieno[2,3-d][1,3]oxazin-4-one;
6-Decyl-2-octyloxythieno[2,3-d][1,3]oxazin-4-one;
6-Decyl-2-(1-methylheptyloxy)thieno[2,3-d][1,3]oxazin-4-one;
6-Heptyl-2-(1-methylheptyloxy)thieno[2,3-d][1,3]oxazin-4-one;
6-Decyl-2-(4-phenylpropoxy)thieno[2,3-d][1,3]oxazin-4-one; and
6-Decyl-2-(4-phenylbutoxy)thieno[2,3-d][1,3]oxazin-4-one.

14. A method for treating obesity in a subject in need of such treatment, comprising administering to the subject a therapeutically effective amount of the compound of any one of claims 1, 6, 11, 12, 1, 2 or 3 so as to thereby treat obesity in the subject.

15. A method for treating diabetes arising from obesity in a subject in need of such treatment, comprising administering to the subject a therapeutically effective amount of the compound of any one of claims 1, 6, 11, 12, 1, 2 or 3 so as to thereby treat diabetes arising from obesity in the subject.

16. A method of inhibiting the hydrolytic activity of pancreatic lipase enzymes in a cell, comprising contacting the cell with an amount of the compound of any one of claims 1, 6, 11, 12, 1, 2 or 3 which is effective in inhibiting the hydrolytic activity of pancreatic lipase enzymes.

17. A pharmaceutical composition comprising the compound of claim 1, 6, 11, 12, 1, 2 or 3 and a pharmaceutically acceptable carrier.

18. The pharmaceutical composition of claim 17, formulated for oral, topical, parenteral, or nasal administration.

19. A process for the manufacture of a pharmaceutical composition comprising admixing the compound of claim 1, 6, 11, 12, 1, 2 or 3 with a pharmaceutically acceptable carrier.

20. An article of manufacture comprising packaging material; the pharmaceutical composition of claim 17, and instructions for use of the pharmaceutical composition in the treatment of obesity.

21. A process of manufacturing a compound having the structure:

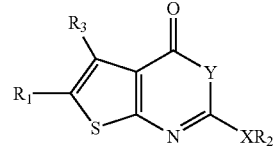

wherein,

X is O, S, or CH$_2$;

R$_1$ is H, substituted C$_1$–C$_{15}$ alkyl, unsubstituted C$_2$–C$_{15}$ alkyl, C$_1$–C$_8$ alkylaryl, —C(O)OR$_4$, —C(O)NR$_4$R$_5$, —CR$_6$R$_6$OR$_4$,
CR$_6$R$_6$OC(O)R$_4$, —CR$_6$R$_6$OC(O)NHR$_7$, —C(O)NR$_8$R$_9$, —C(O)NR$_8$R$_9$NR$_8$R$_9$, —N(R$_5$)C(O)NHR$_5$, or CH$_2$R$_4$;

R$_2$ is a substituted or unsubstituted, straight chain C$_1$–C$_{30}$ alkyl or branched C$_3$–C$_{30}$ alkyl, aryl, alkylaryl, arylalkyl, heteroarylalkyl or cycloalkyl;

R$_3$ is H, —CH$_3$, —CH$_2$OCH$_3$ or cycloalkyl;

R$_4$ is H or a substituted or unsubstituted, straight chain or branched, C$_6$–C$_{30}$ alkyl, aryl, —CH$_2$-aryl, arylalkyl, heteroarylalkyl or cycloalkyl;

$R_5$ is H or a substituted or unsubstituted, straight chain or branched, $C_6$–$C_{30}$ alkyl, arylalkyl, heteroarylalkyl or cycloalkyl;

$R_6$ and $R_{6'}$ are each independently H, substituted or unsubstituted $C_1$–$C_6$ alkyl, dialkyl or cycloalkyl or together form a 3–7 membered cycloalkyl or aryl group;

$R_7$ is H or substituted or unsubstituted $C_1$–$C_{12}$ alkyl or cycloalkyl;

$R_8$ and $R_9$ are each independently H, substituted or unsubstituted $C_1$–$C_6$ alkyl, $C_1$–$C_6$ alkoxy, $C_1$–$C_6$ alkylaryl, or $NR_8R_9$ together form a substituted piperazine or piperidine ring or a dihydro-1H-isoquinoline ring system, comprising (a) reacting

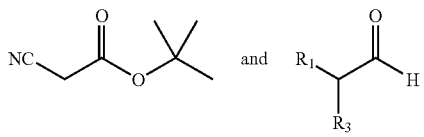

in the presence of sulfur, a base and solvent to produce:

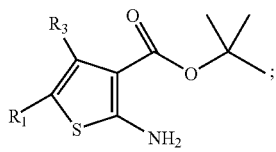

(b) reacting the product of step (a) with

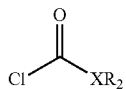

in the presence of a base to produce:

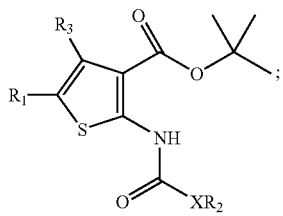

c) reacting the product of step (b) with trifluoroacetic acid (TFA) in the presence of solvent to produce:

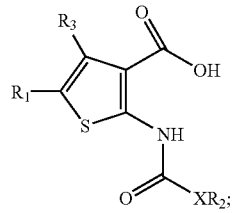

(d) reacting the product of step (c) with $SOCl_2$ in the presence of solvent to produce the compound.

22. The process of claim 21, wherein the base in step (a) is triethyl amine and the solvent is dimethylformamide (DMF).

23. The process of claim 22, wherein the solvent in step (c) is dichloromethane.

24. The process of claim 23, wherein the solvent in step (d) is pyridine:$CH_2Cl_2$.

25. A compound produced by the process of claim 21.

26. The compound of claim 5 or 1, wherein a cycloalkyl or heteroaryl ring, if present, is a piperazine, piperidine, (1,4)diazepan, pyrazine, pyridine, pyrrolidine, pyrazole, pyrimidine, thiophene, imidazole, azetidine, pyrrole, benzothiazole, benzodioxolane, dithiolane, oxathiine, imidazolidine, quinoline, isoquinoline, dihydroisoquinoline, indole, isoindole, triazaspiro[4.5]decane, morpholine, furan or an isothiazole ring.

27. The compound of any one of claims 1, 6, 10, 1, 2 or 3 wherein any substituent, if present, is halogen, hydroxyl, straight chain ($C_1$–$C_{30}$)alkyl, branched chain ($C_3$–$C_{30}$)alkyl, ($C_3$–$C_{10}$)cycloalkyl, straight chain ($C_1$–$C_{30}$) alkylcarbonyloxy, branched chain ($C_3$–$C_{30}$) alkylcarbonyloxy, arylcarbonyloxy, straight chain($C_1$–$C_{30}$) alkoxycarbonyloxy, branched chain ($C_3$–$C_{30}$) alkoxycarbonyloxy, aryloxycarbonyloxy, carboxylate, straight chain($C_1$–$C_{30}$)alkylcarbonyl, branched chain ($C_3$–$C_{30}$)alkylcarbonyl, straight chain ($C_1$–$C_{30}$) alkoxycarbonyl, branched chain ($C_3$–$C_{30}$)alkoxycarbonyl, aminocarbonyl, straight chain ($C_1$–$C_{30}$)alkylthiocarbonyl, branched chain ($C_3$–$C_{30}$)alkylthiocarbonyl, straight chain ($C_1$–$C_{30}$)alkoxyl, branched chain ($C_1$–$C_{30}$)alkoxyl, phosphate, phosphonato, cyano, amino, straight chain ($C_1$–$C_{30}$)alkylamino, branched chain ($C_3$–$C_{30}$)alkylamino, straight chain ($C_1$–$C_{30}$)dialkylamino, branched chain ($C_3$–$C_{30}$)dialkylamino, arylamino, diarylamino, straight chain ($C_1$–$C_{30}$)alkylarylamino, branched chain ($C_3$–$C_{30}$) alkylarylamino, acylamino, straight chain ($C_1$–$C_{30}$) alkylcarbonylamino, branched chain ($C_3$–$C_{30}$) alkylcarbonylamino, arylcarbonylamino, carbamoyl, ureido, amidino, imino, sulfhydryl, straight chain ($C_1$–$C_{30}$) alkylthio, branched chain ($C_3$–$C_{30}$)alkylthio, arylthio, thiocarboxylate, sulfates, sulfonato, sulfamoyl, sulfonamido, nitro, trifluoromethyl, azido, 4–10 membered heterocyclyl, straight chain ($C_1$–$C_{30}$)alkylaryl, branched chain ($C_3$–$C_{30}$)alkylaryl, benzo(1,3)dioxole, or an aromatic or 5–6 membered heteroaromatic moiety, which substituent may be further substituted by any of the above.

\* \* \* \* \*